United States Patent
Comita-Prevoir et al.

(10) Patent No.: US 11,046,694 B2
(45) Date of Patent: Jun. 29, 2021

(54) COMPOUNDS AND METHODS FOR TREATING BACTERIAL INFECTIONS

(71) Applicant: Entasis Therapeutics, Inc., Waltham, MA (US)

(72) Inventors: Janelle Comita-Prevoir, Northborough, MA (US); Thomas Francois Durand-Reville, Belmont, MA (US); Satenig Guler, Waltham, MA (US); Jan Romero, Arlington, MA (US); Mark Sylvester, Waltham, MA (US); Ruben Tommasi, Stow, MA (US); Camilo Velez-Vega, Waltham, MA (US); Xiaoyun Wu, Westborough, MA (US); Jing Zhang, Sudbury, MA (US)

(73) Assignee: Entasis Therapeutics, Inc., Waltham, MA (US)

( * ) Notice: Subject to any disclaimer, the term of this patent is extended or adjusted under 35 U.S.C. 154(b) by 0 days.

(21) Appl. No.: 16/611,065

(22) PCT Filed: May 8, 2018

(86) PCT No.: PCT/US2018/031593
§ 371 (c)(1),
(2) Date: Nov. 5, 2019

(87) PCT Pub. No.: WO2018/208769
PCT Pub. Date: Nov. 15, 2018

(65) Prior Publication Data
US 2020/0165251 A1    May 28, 2020

Related U.S. Application Data

(60) Provisional application No. 62/502,867, filed on May 8, 2018.

(51) Int. Cl.
*C07D 471/18* (2006.01)
*A61P 31/04* (2006.01)

(52) U.S. Cl.
CPC .......... *C07D 471/18* (2013.01); *A61P 31/04* (2018.01)

(58) Field of Classification Search
CPC .................................................. C07D 471/18
See application file for complete search history.

(56) References Cited

U.S. PATENT DOCUMENTS

| | | |
|---|---|---|
| 7,112,592 B2 | 9/2006 | Lampilas et al. |
| 7,612,087 B2 | 11/2009 | Aszodi et al. |
| 9,309,245 B2 | 4/2016 | McGuire et al. |
| 9,623,014 B2 | 4/2017 | Mcguire et al. |
| 9,968,593 B2 | 5/2018 | DeJonge et al. |
| 10,376,499 B2 | 8/2019 | DeJonge et al. |
| 10,800,778 B2 | 10/2020 | Comita-Prevoir et al. |
| 2004/0157826 A1 | 8/2004 | Lampilas et al. |
| 2005/0020572 A1 | 1/2005 | Aszodi et al. |
| 2005/0245505 A1 | 11/2005 | Aszodi et al. |
| 2006/0046995 A1 | 3/2006 | Lampilas et al. |
| 2009/0018329 A1 | 1/2009 | Lampilas et al. |
| 2010/0087648 A1 | 4/2010 | Lampilas et al. |
| 2010/0092443 A1 | 4/2010 | Levasseur et al. |
| 2010/0093784 A1 | 4/2010 | Ledoussal et al. |
| 2010/0137355 A1 | 6/2010 | Lampilas et al. |
| 2011/0046102 A1 | 2/2011 | Ledoussal et al. |
| 2013/0225554 A1 | 8/2013 | Maiti et al. |
| 2013/0289012 A1 | 10/2013 | Gu et al. |
| 2013/0296555 A1 | 11/2013 | Gu et al. |
| 2014/0094447 A1 | 4/2014 | Bhagwat et al. |
| 2019/0202832 A1 | 7/2019 | Basarab et al. |

FOREIGN PATENT DOCUMENTS

| | | |
|---|---|---|
| CN | 1655781 A | 8/2005 |
| EP | 2135959 A1 | 12/2009 |
| JP | 2004-505088 A | 2/2004 |
| JP | 2005-518333 A | 6/2005 |
| JP | 2005-523897 A | 8/2005 |
| JP | 2006-512335 A | 4/2006 |
| JP | 2011-510012 A | 3/2011 |
| WO | 1995/18129 A1 | 7/1995 |
| WO | 2002/010172 A1 | 2/2002 |
| WO | 2009/091856 A2 | 7/2009 |
| WO | 2009/133442 A1 | 11/2009 |
| WO | 2011/042560 A1 | 4/2011 |
| WO | 2013/014497 A1 | 1/2013 |
| WO | 2013/30733 A1 | 3/2013 |
| WO | 2013/30735 A1 | 3/2013 |
| WO | 2013/38330 A1 | 3/2013 |
| WO | 2013/122888 A2 | 8/2013 |
| WO | 2013/149121 A1 | 10/2013 |
| WO | 2013/149136 A1 | 10/2013 |
| WO | 2013/150296 A1 | 10/2013 |
| WO | 2013/180197 A1 | 12/2013 |

(Continued)

OTHER PUBLICATIONS

Akova, Sulbactam-containing beta-lactamase inhibitor combinations. Clin Microbiol Infect. 2008;14(Suppl. 1):185-188.

(Continued)

*Primary Examiner* — Susanna Moore
(74) *Attorney, Agent, or Firm* — McCarter & English, LLP; Steven G. Davis; Michael J. DeGrazia

(57) ABSTRACT

Provided herein are antibacterial compounds represented by Formula I, or a pharmaceutically acceptable salt thereof, wherein X, Y, $R^4$, $R^5$, and $R^6$ are as defined herein. Also provided are pharmaceutical compositions comprising the compounds of Formula I.

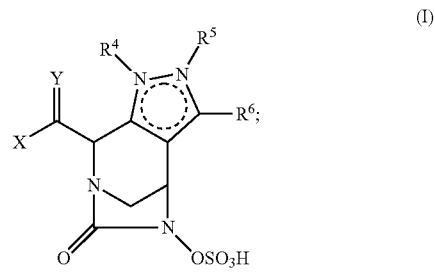

(I)

26 Claims, 2 Drawing Sheets

(56) References Cited

FOREIGN PATENT DOCUMENTS

| WO | 2014/33560 A1 | 3/2014 |
|---|---|---|
| WO | 2014/033561 A1 | 3/2014 |
| WO | 2014/122468 A1 | 8/2014 |
| WO | 2014/141132 A1 | 9/2014 |
| WO | 2016/081452 A1 | 5/2016 |

OTHER PUBLICATIONS

Aszodi et al., Design and synthesis of bridged gamma-lactams as analogues of beta-lactam antibiotics. Bioorg Med Chem Lett. May 17, 2004;14(10):2489-92.

Bonnefoy et al., In vitro activity of AVE1330A, an innovative broad-spectrum non-beta-lactam beta-lactamase inhibitor. J Antimicrob Chemother. Aug. 2004;54(2):410-7.

Kanematsu et al., Significance of beta-Lactamase Inhibitor in the Treatment of Urinary Tract Infection. Chemotherapy. 1984;32(suppl. 4):494-503.

Sawai et al., Mechanism of beta-lactamase inhibition: differences between sulbactam and other inhibitors. Diagn Microbiol Infect Dis. Jul.-Aug. 1989;12(4 Suppl):121S-129S.

Shlaes et al., New beta-lactam-beta-lactamase inhibitor combinations in clinical development. Ann N Y Acad Sci. Jan. 2013;1277:105-14.

Copending U.S. Appl. No. 16/451,498, filed Jun. 25, 2019.

U.S. Appl. No. 14/389,854, filed Jul. 9, 2015, U.S. Publication No. 2015-0073011, U.S. Pat. No. 9,309,245, Issued.

U.S. Appl. No. 15/056,090, filed Feb. 29, 2016, U.S. Publication No. 2016-0175290, U.S. Pat. No. 9,623,014, Issued.

U.S. Appl. No. 15/435,481, filed Feb. 17, 2017, Abandoned.

U.S. Appl. No. 15/527,091, filed May 16, 2017, U.S. Publication No. 2018-0000800, U.S. Pat. No. 9,968,593, Issued.

U.S. Appl. No. 15/947,959, filed Apr. 9, 2018, U.S. Publication No. 2018-0289681, U.S. Pat. No. 10,376,499, Issued.

U.S. Appl. No. 16/451,498, filed Jun. 25, 2019, Abandoned.

U.S. Appl. No. 16/333,900, filed Mar. 15, 2019, U.S. Publication No. 2019-0202832, U.S. Pat. No. 10,800,778, Issued.

U.S. Appl. No. 16/999,935, filed Aug. 21, 2020, Pending.

STN Registry No. 1055320-07-4, 1 page, Sep. 30, 2008.

STN Registry No. 1057653-58-3, 1 page, Oct. 6, 2008.

STN Registry No. 1062174-54-7, 1 page, Oct. 16, 2008.

Copending U.S. Appl. No. 16/999,935, filed Aug. 21, 2020; Entasis Therapeutics Ltd.

COMPOUNDS AND METHODS FOR TREATING BACTERIAL INFECTIONS

RELATED APPLICATIONS

This application is a 35 U.S.C. § 371 national stage filing of International Application No. PCT/US2018/031593, filed May 8, 2018, which claims priority to U.S. Provisional Application No. 62/502,867, filed May 8, 2017, the entire contents of each of which are incorporated herein by reference.

STATEMENT REGARDING FEDERALLY SPONSORED RESEARCH AND DEVELOPMENT

This invention was made with government support under grant No. IDSEP160030 awarded by the U.S. Department of Health & Human Services Office of the Assistant Secretary for Preparedness and Response. The Government has certain rights in the invention.

BACKGROUND

According to the Center for Disease Control and Prevention (CDC) an estimated 51,000 healthcare-associated *P. aeruginosa* infections occur each year in the United States alone with more than 6,000 (13%) of these infections being derived from multi-drug resistant strains. This has led to, on average, about 400 deaths per year. The European Center for Disease Control and Prevention has even higher values with an estimate in 2009 of approximately 800,000 extra hospital days and 10,000 extra deaths caused by resistant *P. aeruginosa* strains. Currently the multi-drug resistant rate is about 20% for *P. aeruginosa* and is expected to rise to about 30% by the year 2040.

Present treatments against *P. aeruginosa* include β-lactam antibiotics. Although some β-lactam antibiotics show promise in vitro, most, if not all, are plagued by high resistance in clinical settings. Due to the continued resistance and estimated increase for infection, the development of new antibacterials, particularly those which are not, or weakly, affected by the resistance mechanisms currently observed in the clinic, is an important medical need.

SUMMARY

Provided herein are antibacterial compounds which are useful for, among other uses, the treatment of bacterial infections. Such compounds are represented by Formula I,

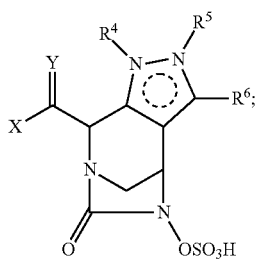

or pharmaceutically acceptable salts thereof, wherein X, Y, $R^4$, $R^5$, and $R^6$ are as defined herein. Also provided are pharmaceutical compositions comprising the compounds of Formula I.

The disclosed compounds act as Penicillin-Binding Protein 3 (PBP3) inhibitors, and in some instances, also PBP1 inhibitors, and show antibacterial activity. See e.g., Tables 6 and 7.

The disclosed PBP3 inhibitors also have substantial in vivo improvement over known PBP2 inhibitors. See e.g., the "in vivo profiling for *P. aeruginosa* PBP inhibitors" in the exemplification section as well as FIGS. 1 and 2, where Example 40 of the subject application was compared with a PBP2 inhibitor (Comparator 1). The only structural difference between Example 40 and Comparator 1 is the replacement of an amino methyl for an N-methyl-amidoxime group. Yet, Comparator 1 was not active against a *P. aeruginosa* clinical isolate in a neutropenic murine thigh model (did not achieve stasis in this study even with exposures of 100% Time above the MIC), whereas Example 40 of the subject application showed robust efficacy (more than 2 Log(CFU/g) reduction with an exposure of 57% Time above the MIC).

It has also been found that the replacement of a carbonyl for an oxime provides an improvement in PBP3 biochemical activity and a decrease in MIC across Gram-negative pathogens. See e.g., the data in Tables 5-7, comparing the results from Comparator 2 with oximes of the present disclosure.

DETAILED DESCRIPTION

1. General Description of Compounds

Figure 1:
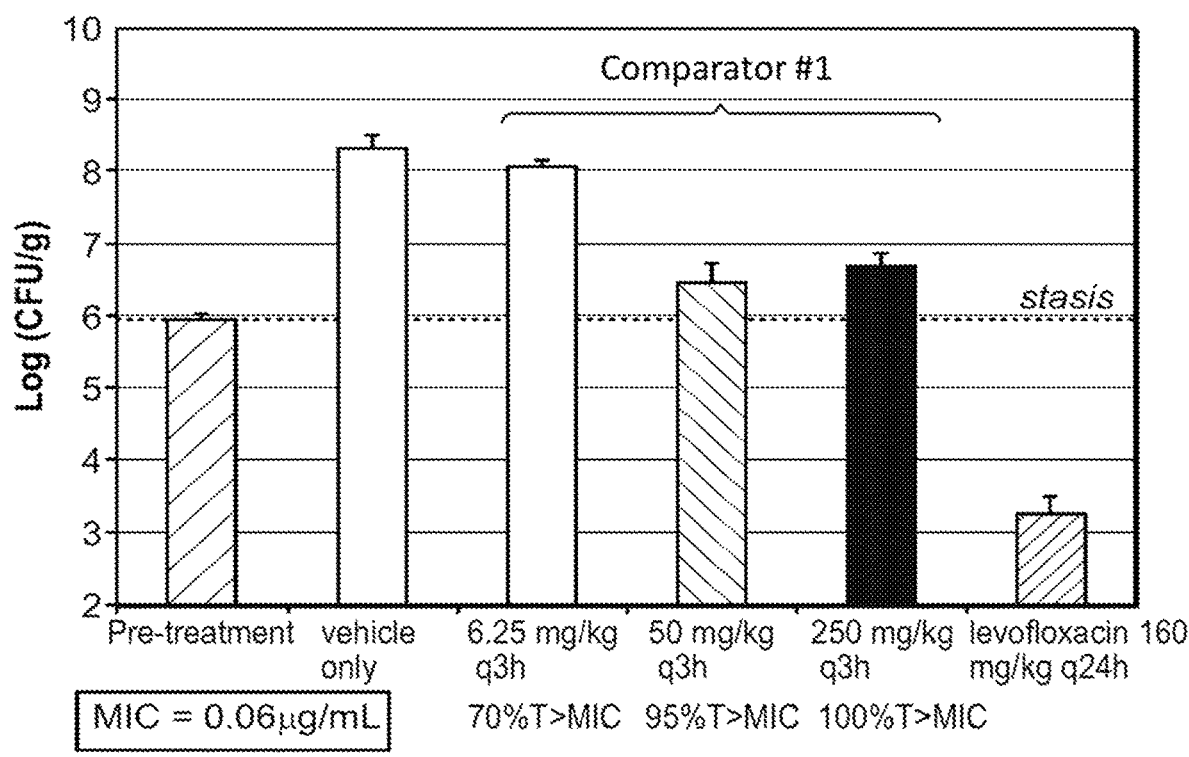
FIG. 1 shows the in vivo efficacy of a PBP2 compound (Comparator 1) against a *P. aeruginosa* clinical isolate (ARC6347, AmpC+, PoxB+) in a neutropenic murine thigh model.

In certain embodiments, the present disclosure provides a compound of Formula I:

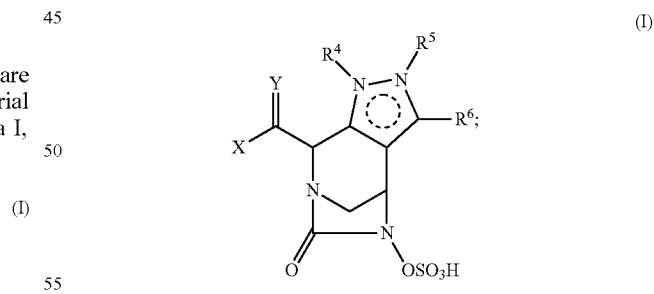

or a pharmaceutically acceptable salt thereof, wherein
X is H, CN, C(O)NR$^1$R$^2$, NR$^1$R$^2$ or (C$_1$-C$_6$)alkyl optionally substituted with NHC(O)R$^g$ or NHS(O)NH$_2$;
Y is NOR$^3$; or R$^3$ and X taken together with the atoms to which they are attached form a 4- to 6-membered heterocyclyl or 5- to 6-membered heteroaryl, each of which is optionally substituted with one or more groups selected from (C$_1$-C$_6$)alkyl, C=O, C(O)OH, and C(O)O(C$_1$-C$_6$)alkyl, wherein said (C$_1$-C$_6$)alkyl is optionally substituted with one or more groups selected from OH, (C$_1$-C$_6$)alkoxy, phenyl, and 5- to 6-membered heteroaryl, wherein said 5- to 6-membered heteroaryl is optionally substituted with $NH_2$, $NH(C_1\text{-}C_6)$alkyl, and $N((C_1\text{-}C_6)\text{alkyl})_2$;

$R^1$ and $R^2$ are each independently hydrogen, cyano, $C(O)NH_2$, $NH_2$, OH, $(C_1\text{-}C_6)$alkoxy, or $(C_1\text{-}C_6)$alkyl optionally substituted with one or more $R^7$;

$R^3$ is hydrogen, $C(O)O(C_1\text{-}C_6)$alkyl, $C(O)NR^dR^e$, $SO_2NH_2$, $SO_2OH$, or $(C_1\text{-}C_6)$alkyl optionally substituted with one or more $R^7$;

$R^4$, $R^5$, and $R^6$ are each independently hydrogen, $(C_1\text{-}C_6)$alkyl, or $C(O)NR^aR^b$, wherein said $(C_1\text{-}C_6)$alkyl for $R^4$, $R^5$, and $R^6$ is optionally substituted with one or more $R^7$, provided that at least one of $R^4$ and $R^5$ is not hydrogen and provided that $R^4$ and $R^5$ are not present when the corresponding nitrogen atom to which $R^4$ and $R^5$ are bound is connected to an adjacent ring atom via a double bond;

each $R^7$ is independently selected from halo, OH, $OR^c$, $(C_1\text{-}C_6)$alkoxy, CN, 4- to 6-membered heterocyclyl, 5- to 6-membered heteroaryl, phenyl, $C(=NH)NH_2$, NHC$(=NH)NH_2$, $NR^dR^e$, $C(O)OH$, $C=NO(C_1\text{-}C_6)$alkyl$NH_2$, $NHC(O)(C_1\text{-}C_6)$alkyl, $C(O)NR^dR^e$, $SO_2R^f$, and $S(O)R^f$, wherein said 5- to 6-membered heteroaryl is optionally substituted with $NH_2$ and said phenyl is optionally substituted with $NH_2$;

$R^a$, $R^b$, $R^d$, and $R^e$ are each independently hydrogen, OH, $(C_1\text{-}C_6)$alkyl, $(C_1\text{-}C_6)$alkoxy, phenyl, $OSO_2OH$, 4- to 6-membered cycloalkyl, 4- to 6-membered heterocyclyl or 5- to 6-membered heteroaryl, wherein each of said $(C_1\text{-}C_6)$alkyl and $(C_1\text{-}C_6)$alkoxy for $R^a$, $R^b$, $R^d$, and $R^e$ are optionally and independently substituted with one or more groups selected from OH, $NH_2$, $C(O)OH$, $C(O)O(C_1\text{-}C_6)$alkyl, $NHC(O)NH_2$, $NHC(O)NH(C_1\text{-}C_6)$alkyl, $C(O)NH_2$, $NHC(O)N((C_1\text{-}C_6)\text{alkyl})_2$, $NHC(O)(C_1\text{-}C_6)$alkyl, $NHC(O)$halo$(C_1\text{-}C_6)$alkyl, 4- to 6-membered heterocyclyl, 5- to 6-membered heteroaryl, $NH(C_1\text{-}C_6)$alkyl, and $N((C_1\text{-}C_6)\text{alkyl})_2$, wherein each of said phenyl, 4- to 6-membered heterocyclyl, 4- to 6-membered cycloalkyl, and 5- to 6-membered heteroaryl for $R^a$, $R^b$, $R^d$, and $R^e$, and said 5- to 6-membered optional heteroaryl group for $(C_1\text{-}C_6)$alkyl and $(C_1\text{-}C_6)$alkoxy for $R^a$, $R^b$, $R^d$, and $R^e$ are optionally and independently substituted with one or more groups selected from $(C_1\text{-}C_6)$alkyl, $NH_2$, $NH(C_1\text{-}C_6)$alkyl, and $-N((C_1\text{-}C_6)\text{alkyl})_2$;

$R^c$ is phenyl optionally substituted with one or more groups selected from $C(=NH)NH_2$, $C(=NH)NH(5\text{-}$ to 6-membered heterocyclyl), $C(=NH)NH(C_1\text{-}C_6)$alkyl, NHC$(=NH)NH_2$, $-NR^dR^e$, $C(O)NR^dR^e$, $SO_2R^f$, and $SOR^f$, wherein said $(C_1\text{-}C_6)$alkyl in the group $C(=NH)NH(C_1\text{-}C_6)$alkyl is optionally substituted with one or more groups selected from $NH_2$, $NH(C_1\text{-}C_6)$alkyl, and $N((C_1\text{-}C_6)\text{alkyl})_2$;

$R^f$ is hydrogen or $(C_1\text{-}C_6)$alkyl; and $R^g$ is 4- to 6-membered heterocyclyl optionally substituted with one or more groups selected from $C=O$ and $(C_1\text{-}C_6)$alkyl.

2. Definitions

When used in connection to describe a chemical group that may have multiple points of attachment, a hyphen (-) designates the point of attachment of that group to the variable to which it is defined. For example, $-NR^dR^e$ means that the point of attachment for this group occurs on the nitrogen atom.

The terms "halo" and "halogen" as used herein refer to an atom selected from fluorine (fluoro, F), chlorine (chloro, Cl), bromine (bromo, Br), and iodine (iodo, I).

The term "alkyl" used alone or as part of a larger moiety, such as "alkoxy", "haloalkyl", and the like, means saturated straight-chain or branched monovalent hydrocarbon radical. Unless otherwise specified, an alkyl group typically has 1-6 carbon atoms, i.e., $(C_1\text{-}C_6)$alkyl. As used herein, a "$(C_1\text{-}C_6)$ alkyl" group means a radical having from 1 to 6 carbon atoms in a linear or branched arrangement.

The term "haloalkyl" includes mono, poly, and perhaloalkyl groups where the halogens are independently selected from fluorine, chlorine, bromine, and iodine.

"Alkoxy" means an alkyl radical attached through an oxygen linking atom, represented by —O-alkyl. For example, "$(C_1\text{-}C_4)$alkoxy" includes methoxy, ethoxy, propoxy, and butoxy.

Unless otherwise specified, the term "heteroaryl" refers to a 5- to 12-membered aromatic radical containing 1-4 heteroatoms selected from N, O, and S. In some instances, nitrogen atoms in a heteroaryl may be quaternized. The term "heteroaryl" may be used interchangeably with the terms "heteroaryl ring", "heteroaryl group", or "heteroaromatic". A heteroaryl group may be mono- or bi-cyclic. Monocyclic heteroaryl includes, for example, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, etc. Bi-cyclic heteroaryls include groups in which a monocyclic heteroaryl ring is fused to one or more aryl or heteroaryl rings. Nonlimiting examples include indolyl, benzooxazolyl, benzooxodiazolyl, indazolyl, benzimidazolyl, benzthiazolyl, quinolyl, quinazolinyl, quinoxalinyl, pyrrolopyridinyl, pyrrolopyrimidinyl, pyrrolopyridinyl, thienopyridinyl, thienopyrimidinyl, indolizinyl, purinyl, naphthyridinyl, and pteridinyl. It will be understood that when specified, optional substituents on a heteroaryl group may be present on any substitutable position and, include, e.g., the position at which the heteroaryl is attached.

Unless otherwise specified, the term "heterocyclyl" means a 4- to 12-membered saturated or partially unsaturated heterocyclic ring containing 1 to 4 heteroatoms independently selected from N, O, and S. The terms "heterocycle", "heterocyclyl", "heterocyclyl ring", "heterocyclic group", "heterocyclic moiety", and "heterocyclic radical", are used interchangeably herein. A heterocyclyl ring can be attached to its pendant group at any heteroatom or carbon atom that results in a stable structure. A heterocyclyl group may be mono- or bicyclic. Examples of monocyclic saturated or partially unsaturated heterocyclic radicals include, without limitation, tetrahydrofuranyl, tetrahydrothienyl, tetrahydropyranyl, pyrrolidinyl, pyrrolidonyl, piperidinyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, tetrahydropyrimidinyl, dihydrooxadiazolyl, and dihydroisoxazolyl. Bi-cyclic heterocyclyl groups include, e.g., unsaturated heterocyclic radicals fused to another unsaturated heterocyclic radical, cycloalkyl, aryl, or heteroaryl ring, such as for example, benzodioxolyl, dihydrobenzodioxinyl, dihydrobenzofuranyl, and the like. It will be understood that when specified, optional substituents on a heterocyclyl group may be present on any substitutable position and, include, e.g., the position at which the heterocyclyl is attached.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable.

Diastereomers are stereoisomers that contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms.

"Racemate" or "racemic mixture" means a compound of equimolar quantities of two enantiomers, wherein such mixtures exhibit no optical activity, i.e., they do not rotate the plane of polarized light.

"Geometric isomer" means isomers that differ in the orientation of substituent atoms in relationship to e.g., a carbon-carbon double bond, to an oxime, to an oxime ether, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "syn," "anti," "cis," and "trans," indicate configurations relative to the core molecule. When a disclosed compound is named or depicted by structure without indicating a particular geometric isomer form, it is to be understood that the name or structure encompasses one geometric isomer free of other geometric isomers, mixtures of geometric isomers, or mixtures of all geometric isomers. For oximes and oxime ethers, the designation of "Z" or "E" and "syn" or "anti" may be used.

When depicted by structure only, in instances where the N—O bond of the oxime is drawn by a solid bond, it means that the depicted geometrical isomer is at least 60%, 70%, 80%, 90%, 99% or 99.9% by weight pure relative to all of the other isomers. Percent by weight pure relative to all of the other isomers is the ratio of the weight of one isomer over the weight of the other isomers. Similarly, in instances where the geometrical isomer of the N—O bond of the oxime is named (i.e., by E or Z), it means that the named geometrical isomer is at least 60%, 70%, 80%, 90%, 99% or 99.9% by weight pure relative to all of the other isomers. In the case of the disclosed oximes, a wavy bond (v r) indicates that the structure encompasses one geometric isomer free of other geometric isomers, mixtures of geometric isomers, or mixtures of all geometric isomers. Similarly, in instances where the geometrical isomer of the N—O bond of the oxime is not named, the compound encompasses one geometric isomer free of other geometric isomers, mixtures of geometric isomers, or mixtures of all geometric isomers.

The compounds of the herein may be prepared as individual enantiomers by either enantio-specific synthesis or resolved from an enantiomerically enriched mixture. Conventional resolution techniques include forming the salt of a free base of each isomer of an enantiomeric pair using an optically active acid (followed by fractional crystallization and regeneration of the free base), forming the salt of the acid form of each enantiomer of an enantiomeric pair using an optically active amine (followed by fractional crystallization and regeneration of the free acid), forming an ester or amide of each of the enantiomers of an enantiomeric pair using an optically pure acid, amine or alcohol (followed by chromatographic separation and removal of the chiral auxiliary), or resolving an enantiomeric mixture of either a starting material or a final product using various well known chromatographic methods. Additionally, the compounds can be prepared as individual enantiomers by separating a racemic mixture using conventional chiral chromatography techniques.

When the stereochemistry of a disclosed compound is named or depicted by structure, the named or depicted stereoisomer is at least 60%, 70%, 80%, 90%, 99% or 99.9% by weight pure relative to all of the other stereoisomers. Percent by weight pure relative to all of the other stereoisomers is the ratio of the weight of one stereoisomer over the weight of the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomer is at least 60%, 70%, 80%, 90%, 99% or 99.9% by weight pure relative to all of the other stereoisomers. The stereoisomeric purity in this case is determined by dividing the total weight in the mixture of the stereoisomers encompassed by the name or structure by the total weight in the mixture of all of the stereoisomers.

When a disclosed compound is named or depicted by structure without indicating the stereochemistry, and the compound has one chiral center, it is to be understood that the name or structure encompasses one enantiomer of compound free from the corresponding optical isomer, a racemic mixture of the compound, or mixtures enriched in one enantiomer relative to its corresponding optical isomer.

When a disclosed compound is named or depicted by structure without indicating the stereochemistry and e.g., the compound has more than one chiral center (e.g., at least two chiral centers), it is to be understood that the name or structure encompasses one stereoisomer free of other stereoisomers, mixtures of stereoisomers, or mixtures of stereoisomers in which one or more stereoisomers is enriched relative to the other stereoisomer(s). For example, the name or structure may encompass one stereoisomer free of other diastereomers, mixtures of stereoisomers, or mixtures of stereoisomers in which one or more diastereomers is enriched relative to the other diastereomer(s).

All stereoisomers in the present disclosure are relative (i.e., are trans racemic), unless the R and S designations are followed by an asterisk (*) as in Int-29, Int-30, Example 40, and Example 41. For example, the name "(4R,8S)-8-((Z)—N'-hydroxy-N-methylcarbamimidoyl)-1-methyl-6-oxo-4,8-dihydro-1H-4,7-methanopyrazolo[3,4-e][1,3]diazepin-5 (6H)-yl hydrogen sulfate" in Example 1 means that the compound is trans racemic. In contrast, the name "sodium (4R*,8S*)-8-((Z)—N'-hydroxy-N-methylcarbamimidoyl)-1-methyl-6-oxo-4,8-dihydro-1H-4,7-methanopyrazolo[3,4-e][1,3]diazepin-5(6H)-yl hydrogen sulfate" in Example 40 means that the stereochemistry at the chiral centers is absolute.

All stereoisomers in the present disclosure are relative (i.e., are trans racemic), unless the stereocenters of the compound, when drawn, are labeled by R and S such as in Int-29, Int-30, Example 40, and Example 41. For example,

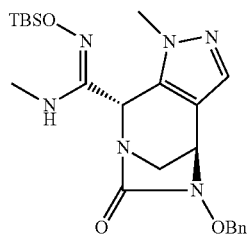 [SMILES: CN/C(=N\O[Si](C)(C)C(C)(C)C)[C@@H]1c2c(cnn2C)[C@@H]2CN1C(=O)N2OCc1ccccc1]

means that the stereochemistry is relative and the compound is trans racemic, whereas

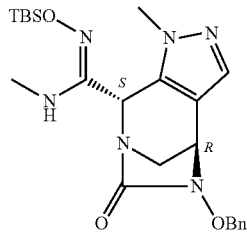

means that the stereochemistry is absolute as 4R*,8S*.

Unless otherwise stated, all tautomeric forms of the compounds described herein are within the scope of the invention.

The compounds of the herein may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

The terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

The term "inhibit," "inhibition" or "inhibiting" includes a decrease in the baseline activity of a biological activity or process.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of exposure to a particular organism, or other susceptibility factors), i.e., prophylactic treatment. Treatment may also be continued after symptoms have resolved, for example to prevent or delay their recurrence.

The term "effective amount" or "therapeutically effective amount" includes an amount of the compound described herein that will elicit a biological or medical response of a subject, for example, the reduction or inhibition of enzyme or protein activity related to a bacterial infection, amelioration of symptoms of a bacterial infection, or the slowing or delaying of progression of a bacterial infection. In some embodiments, the language "effective amount" includes the amount of a compound described herein, that when administered to a subject, is effective to at least partially alleviate, inhibit, and/or ameliorate a bacterial infection or inhibit PBP3, and/or reduce or inhibit the bacterial growth, replication or bacterial load of a bacteria in a subject.

The term "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, organic or inorganic carriers, excipients or diluents suitable for pharmaceutical applications.

3. Description of Exemplary Compounds

In a first embodiment, the present disclosure provides a compound of Formula I:

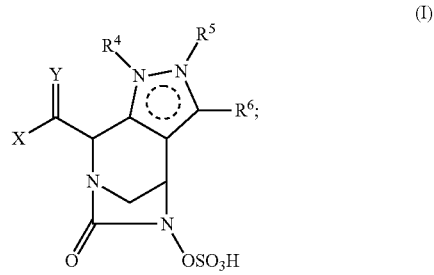

or a pharmaceutically acceptable salt thereof, wherein the variables are as described above.

In a second embodiment, Y is $NOR^3$ in the compound of Formula I and $R^3$ and X are taken together with the atoms to which they are attached to form a 4- to 6-membered heterocyclyl optionally substituted with one or more groups selected from $(C_1-C_6)$alkyl, C=O, or C(O)OH, wherein said $(C_1-C_6)$alkyl is optionally substituted with OH, phenyl, or 5- to 6-membered heteroaryl, wherein said 5- to 6-membered heteroaryl is optionally substituted with $NH_2$, and wherein the remaining variables are as described above for Formula I. Alternatively, Y is $NOR^3$ in the compound of Formula I and $R^3$ and X are taken together with the atoms to which they are attached to form a 4,5-dihydro-1,2,4-oxadiazole or 4,5-dihydroisoxazole, each of which are optionally substituted with one or more groups selected from $(C_1-C_4)$alkyl, C=O, or C(O)OH, wherein said $(C_1-C_4)$alkyl is optionally substituted with OH, phenyl, or thiazolyl, wherein said thiazolyl is optionally substituted with $NH_2$, wherein the remaining variables are as described above for Formula I.

In a third embodiment, said 4- to 6-membered cycloalkyl for $R^a$, $R^b$, $R^d$, and $R^e$ in the compound of Formula I is cyclohexyl and said 4- to 6-membered heterocyclyl for $R^g$ is piperazinyl, wherein the remaining variables are as described above for Formula I or the second embodiment.

In a fourth embodiment, the compound of Formula I is of the Formula Ia:

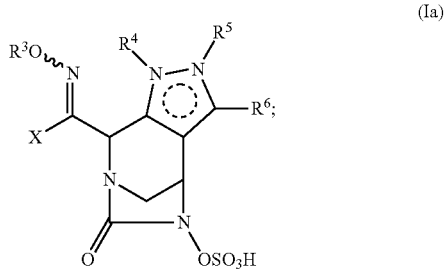

or a pharmaceutically acceptable salt thereof, wherein
X is H, CN, C(O)NR$^1$R$^2$, NR$^1$R$^2$ or $(C_1-C_6)$alkyl;
$R^1$ and $R^2$ are each independently hydrogen, cyano, or $(C_1-C_6)$alkyl optionally substituted with one or more $R^7$;

R³ is hydrogen or (C₁-C₆)alkyl optionally substituted with one or more R⁷;

R⁴, R⁵, and R⁶ are each independently hydrogen, (C₁-C₆) alkyl, or C(O)NRᵃRᵇ, wherein said (C₁-C₆)alkyl for R⁴, R⁵, and R⁶ is optionally substituted with one or more R⁷, provided that at least one of R⁴ and R⁵ is not hydrogen and provided that R⁴ and R⁵ are not present when the corresponding nitrogen atom to which R⁴ and R⁵ are bound is connected to an adjacent ring atom via a double bond;

each R⁷ is independently selected from halo, OH, ORᵉ, (C₁-C₆)alkoxy, CN, 4- to 6-membered heterocyclyl, 5- to 6-membered heteroaryl, phenyl, C(=NH)NH₂, NHC(=NH)NH₂, NRᵈRᵉ, C(O)NRᵈRᵉ, SO₂Rᶠ, and S(O)Rᶠ;

Rᵃ, Rᵇ, Rᵈ, and Rᵉ are each independently hydrogen, (C₁-C₆)alkyl, (C₁-C₆)alkoxy, phenyl, 4- to 6-membered heterocyclyl or 5- to 6-membered heteroaryl, wherein each of said (C₁-C₆)alkyl and (C₁-C₆)alkoxy for Rᵃ, Rᵇ, Rᵈ, and Rᵉ are optionally and independently substituted with one or more groups selected from NH₂, NH(C₁-C₆)alkyl, and N((C₁-C₆)alkyl)₂, and wherein each of said phenyl, 4- to 6-membered heterocyclyl, and 5- to 6-membered heteroaryl for Rᵃ, Rᵇ, Rᵈ, and Rᵉ are optionally and independently substituted with one or more groups selected from (C₁-C₆) alkyl, NH₂, NH(C₁-C₆)alkyl, and N((C₁-C₆)alkyl)₂;

Rᶜ is phenyl optionally substituted with one or more groups selected from C(=NH)NH₂, C(=NH)NH(C₁-C₆) alkyl, NHC(=NH)NH₂, NRᵈRᵉ, C(O)NRᵈRᵉ, SO₂Rᶠ, and SORᶠ, wherein said (C₁-C₆)alkyl in the group C(=NH)NH (C₁-C₆)alkyl is optionally substituted with one or more groups selected from NH₂, NH(C₁-C₆)alkyl, and N((C₁-C₆) alkyl)₂; and Rᶠ is hydrogen or (C₁-C₆)alkyl.

In a fifth embodiment, the compound of Formula I is of the Formula II:

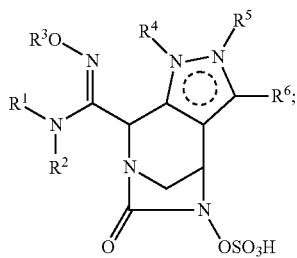

(II)

or a pharmaceutically acceptable salt thereof, wherein the variables are as described above for Formula I or Ia.

In a sixth embodiment, the compound of Formula I is of the Formula III:

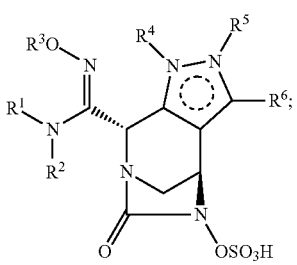

(III)

or a pharmaceutically acceptable salt thereof, wherein the variables are as described above for Formula I or Ia.

In a seventh embodiment, R³ in any one of Formulae I, Ia, II, or III is hydrogen or (C₁-C₆)alkyl optionally substituted with amino, wherein the remaining variables are as described above for Formula I or Ia. In an alternative, R³ in any one of Formulae I, Ia, II, or III is hydrogen, wherein the remaining variables are as described above for Formula I or Ia.

In an eighth embodiment, R¹ in any one of Formulae I, Ia, II, or III is hydrogen and R² is (C₁-C₆)alkyl, wherein the remaining variables are as described above for Formula I or Ia or the seventh embodiment. In an alternative, R¹ in any one of Formulae I, Ia, II, or III is hydrogen and R² is methyl, wherein the remaining variables are as described above for Formula I or Ia or the seventh embodiment.

In a ninth embodiment, R¹ and R² in any one of Formulae I, Ia, II, or III are each (C₁-C₆)alkyl, wherein the remaining variables are as described above for Formula I or Ia or the seventh embodiment. In an alternative, R¹ and R² in any one of Formulae I, Ia, II, or III are each methyl, wherein the variables are as described above for Formula I or Ia or the seventh embodiment.

In a tenth embodiment, the compound of Formula I or Ia is of the Formula IV or V:

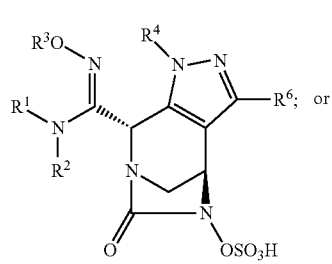

(IV)

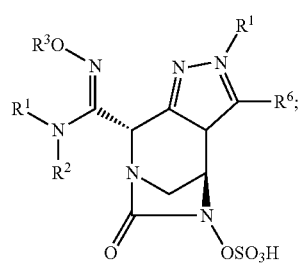

(V)

or a pharmaceutically acceptable salt thereof, wherein the variables are as described above for Formula I or Ia or the seventh, eighth, or ninth embodiment.

In an eleventh embodiment, R⁶ in any one of Formulae I, Ia, II, III, IV, or V is hydrogen, —C(O)NRᵃRᵇ, or (C₁-C₆) alkyl optionally substituted with ORᶜ, wherein the remaining variables are as described above for Formula I or Ia or the seventh, eighth, or ninth embodiment.

In a twelfth embodiment, Rᵃ in any one of Formulae I, Ia, II, III, IV, or V is hydrogen; Rᵇ is 5- to 6-membered heteroaryl optionally substituted with one or more (C₁-C₆) alkyl, or (C₁-C₆)alkyl optionally substituted with —ORᶜ; and Rᶜ is phenyl optionally substituted with —C(=NH)NH (C₁-C₆)alkylNH₂, wherein the remaining variables are as described above for Formula I or Ia or the seventh, eighth, ninth, or eleventh embodiment. In an alternative, Rᵃ in any one of Formulae I, Ia, II, III, IV, or V is hydrogen and Rᵇ is pyrazolyl optionally substituted with one or more (C₁-C₆) alkyl, wherein the remaining variables are as described above for Formula I or Ia or the seventh, eighth, ninth, or eleventh embodiment.

In a thirteenth embodiment, the compound of Formula I or Ia is of the Formula VI:

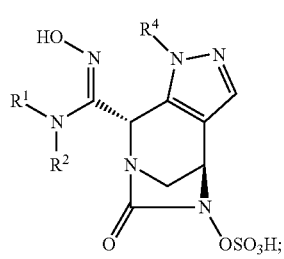

(VI)

or a pharmaceutically acceptable salt thereof, wherein the variables are as described above for Formula I or Ia or the eighth or ninth embodiment.

In a fourteenth embodiment, $R^4$ in any one of Formulae I, Ia, II, III, IV, V, or VI is $C(O)NR^aR^b$ or $(C_1-C_6)$alkyl optionally substituted with $NH_2$; $R^a$ is hydrogen; and $R^b$ is $(C_1-C_6)$alkyl optionally substituted with $NH_2$, wherein the remaining variables are as described above for Formula I or Ia or the eighth or ninth embodiment. In an alternative, $R^4$ in any one of Formulae I, Ia, II, III, IV, V, or VI is $(C_1-C_6)$alkyl, wherein the remaining variables are as described above for Formula I or Ia or the eighth or ninth embodiment. In another alternative, $R^4$ in any one of Formulae I, Ia, II, III, IV, V, or VI is methyl, wherein the remaining variables are as described above for Formula I or Ia or the eighth or ninth embodiment.

In a fifteenth embodiment, the compound of Formula I or Ia is of the Formula VII:

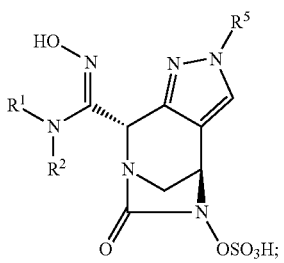

(VII)

or a pharmaceutically acceptable salt thereof, wherein the variables are as described above for Formula I or Ia or the eighth or ninth embodiment.

In a sixteenth embodiment, $R^5$ in any one of Formulae I, Ia, II, III, IV, VI, or VII is $C(O)NR^aR^b$ or $(C_1-C_6)$alkyl optionally substituted with $NH_2$; $R^a$ is hydrogen; and $R^b$ is $(C_1-C_6)$alkyl optionally substituted with $NH_2$, wherein the remaining variables are as described above for Formula I or Ia or the eighth or ninth embodiment. In an alternative, $R^5$ in any one of Formulae I, Ia, II, III, IV, VI, or VII is $(C_1-C_6)$alkyl, wherein the remaining variables are as described above for Formula I or Ia or the eighth or ninth embodiment. In another alternative, $R^5$ in any one of Formulae I, Ia, II, III, IV, VI, or VII is methyl, wherein the remaining variables are as described above for Formula I or Ia or the eighth or ninth embodiment.

Specific examples of compounds are provided in the EXEMPLIFICATION. Pharmaceutically acceptable salts as well as the neutral forms of these compounds are included herein.

4. Uses, Formulation and Administration

The compounds described herein can be used to treat bacterial infections caused by one or more species of Gram-negative, or atypical bacteria. Gram-negative bacteria include, but are not limited, to *Haemophilus influenzae, Acinetobacter baumannii, Burkholderia* spp. *Citrobacter* spp., *Escherichia coli, Enterobacter* spp., *Pseudomonas aeruginosa, Klebsiella* spp., *Stenotrophomonas maltophila, Francisella tularensis, Yersinia* spp., *Salmonella* spp., *Shigella* spp., *Legionella* spp. and *Neisseria gonorrhoeae*. Atypical bacteria include, but are not limited to, *Mycoplasma pneumoniae, Chlamydophila pneumoniae,* and *Legionella pneumophila*.

In some aspects, the bacteria are resistant to one or more antibacterials other than the compounds described herein. The language "resistance" and "antibacterial resistance" refers to bacteria that are able to survive exposure to one or more antibacterials. In one aspect, the compounds described herein can be used to treat bacterial infections caused by Gram-negative bacteria or resistant Gram-negative bacteria. In another aspect, the compounds described herein can be used to treat bacterial infections caused by Enterobacteriaceae such as *E. coli, K. pneumoniae,* and *Acinetobacter* spp. In yet a further aspect, the compounds described herein can be used to treat bacterial infections caused by *P. aeruginosa, A. baumannii,* or Enterobacteriaceae, as well as antibacterial-resistant forms. In yet a further aspect, the compounds described herein can be used to treat bacterial infections caused by *P. aeruginosa,* as well as antibacterial-resistant forms. For example, resistance mechanisms in Gram-negative bacteria include, but are not limited to, extended-spectrum j-lactamase expression, metallo-β-lactamase expression, carbapenemase expression, DNA gyrase mutation, porin mutation, efflux system overexpression, lipopolysaccharide modification, and 16S rRNA methylase expression.

In one aspect, the bacterial infection treated by the present compounds is caused by a Gram-negative bacteria. In another aspect, the bacterial infection treated by the present compounds is caused by *P. aeruginosa, A. baumannii, E. coli,* or *K. pneumoniae* and other Enterobacteriaceae. In a further aspect, the bacterial infection treated by the present compounds is caused by *P. aeruginosa*. In another aspect, the bacterial infection treated by the present compounds is caused by an antibacterial-resistant Gram-negative bacteria. In yet another aspect, the bacterial infection treated by the present compounds is caused by an antibacterial-resistant strain of *P. aeruginosa*. In yet another aspect, the bacterial infection treated by the present compounds is caused by Enterobacteriaceae. In yet another aspect, the bacterial infection treated by the present compounds is caused by *E. coli, K. pneumoniae,* or *Acinetobacter* spp. In yet another aspect, the bacterial infection treated by the present compounds is caused by a pathogen selected from *Burkholderia* spp., *B. anthracis, Y. pestis,* and *F. tularensis*.

Bacterial infections treated by the present compounds include, but are not limited to, respiratory (e.g., pneumonia), blood stream (e.g., bacteremia), heart (e.g., endocarditis), CNS (e.g., meningitis, brain abscess), ear (e.g., otitis externa), eye (e.g., bacterial keratitis, endophthalmitis), GI tract (diarrhea, enteritis, enterocolitis), urinary tract, skin, intraabdominal, nosocomial and wound/burn infections.

In one aspect, the compounds described herein inhibit penicillin-binding protein 3 (PBP3). Thus, in one aspect, the present disclosure provides a method of inhibiting bacterial PBP3, comprising administering to a subject in need thereof one or more of the compounds described herein, or a pharmaceutically acceptable salt thereof.

In another aspect, the compounds described herein inhibit penicillin-binding protein 1 (e.g., PBP1a and/or PBP1b). Thus, in one aspect, the present disclosure provides a method of inhibiting bacterial PBP1, comprising administering to a subject in need thereof one or more of the compounds described herein, or a pharmaceutically acceptable salt thereof. In another aspect, the present disclosure provides a method of inhibiting bacterial PBP1 (e.g., PBP1a and/or PBP1b) and bacterial PBP3, comprising administering to a subject in need thereof one or more of the compounds described herein, or a pharmaceutically acceptable salt thereof.

In yet another aspect, the compounds described herein are not specific inhibitors of penicillin binding protein 2 (PBP2).

According to other aspect, the present disclosure provides pharmaceutically acceptable compositions comprising a compound described herein; and a pharmaceutically acceptable carrier. These compositions can be used to treat one or more of the bacterial infections described above, as well as inhibit PBP3.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Liquid dosage forms, injectable preparations, solid dispersion forms, and dosage forms for topical or transdermal administration of a compound are included herein.

The amount of provided compounds that may be combined with carrier materials to produce a composition in a single dosage form will vary depending upon the patient to be treated and the particular mode of administration.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound in the composition will also depend upon the particular compound in the composition.

EXEMPLIFICATION

As depicted in the Examples below, in certain exemplary embodiments, compounds are prepared according to the following general procedures. It will be appreciated that, although the general methods depict the synthesis of certain compounds herein, the following general methods, and other methods known to one of ordinary skill in the art, can be applied to all compounds and subclasses and species of each of these compounds, as described herein.

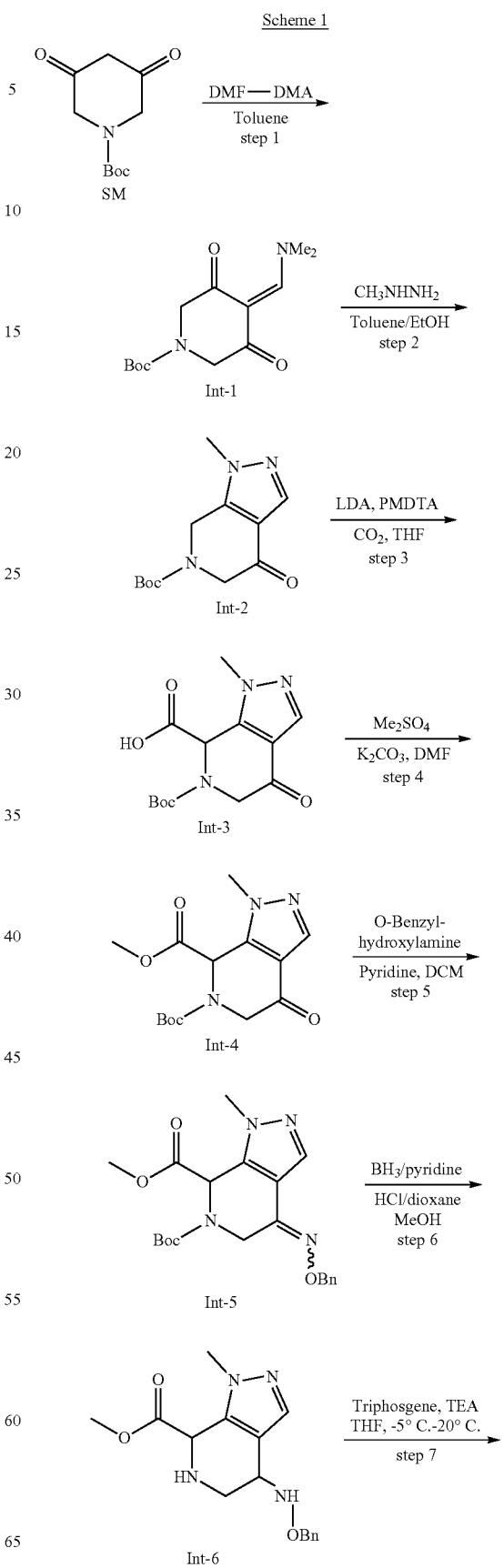

Scheme 1

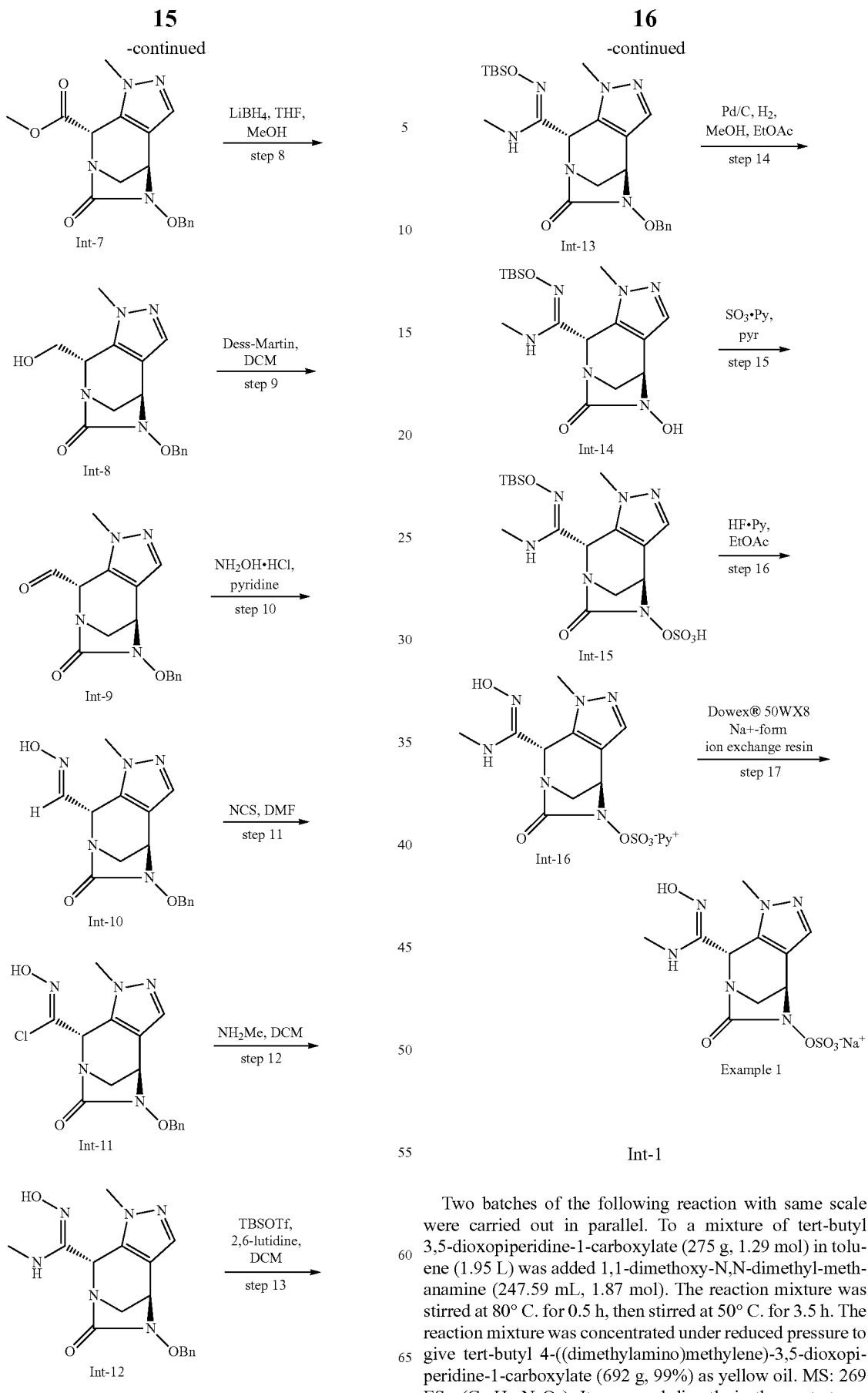

Two batches of the following reaction with same scale were carried out in parallel. To a mixture of tert-butyl 3,5-dioxopiperidine-1-carboxylate (275 g, 1.29 mol) in toluene (1.95 L) was added 1,1-dimethoxy-N,N-dimethyl-methanamine (247.59 mL, 1.87 mol). The reaction mixture was stirred at 80° C. for 0.5 h, then stirred at 50° C. for 3.5 h. The reaction mixture was concentrated under reduced pressure to give tert-butyl 4-((dimethylamino)methylene)-3,5-dioxopiperidine-1-carboxylate (692 g, 99%) as yellow oil. MS: 269 ES+ ($C_{13}H_{20}N_2O_4$). It was used directly in the next step.

Int-2

Two batches of the following reaction on the same scale were carried out in parallel. To a solution of tert-butyl 4-((dimethylamino)methylene)-3,5-dioxopiperidine-1-carboxylate (346 g, 1.29 mol) in ethanol (1.90 L) and toluene (1.90 L) was added methylhydrazine (168.1 mL, 3.21 mol). The mixture was stirred at 25° C. for 3 hours. The reaction mixture was concentrated under reduced pressure to give a residue. The residue was purified by column chromatography (SiO$_2$, DCM/Ethyl acetate=1:0 to 1:1) to give tert-butyl 1-methyl-4-oxo-1,4,5,7-tetrahydro-6H-pyrazolo[3,4-c]pyridine-6-carboxylate (540 g, 83%) as a yellow solid. $^1$H NMR (400 MHz, CDCl$_3$) δ: 1.51-1.43 (m, 9H); 3.85 (s, 3H); 4.14 (s, 2H); 4.73 (br s, 2H); 7.88 (s, 1H).

Int-3

Tert-butyl 1-methyl-4-oxo-1,4,5,7-tetrahydro-6H-pyrazolo[3,4-c]pyridine-6-carboxylate (50 g, 0.199 mmol) was dissolved in THF (500 mL) and placed under N$_2$ atmosphere. The reaction mixture was cooled down to −78° C. and LDA (2M, 397.96 mL) was added. The reaction mixture was stirred at −78° C. for 40 minutes. Carbon dioxide in excess was introduced over 1 h, and then the mixture was left to return to ambient temperature and stir for 12 h. The reaction mixture was quenched by addition of 10% H$_2$SO$_4$ to pH=2.5, and extracted with ethyl acetate (3×500 ml). Aqueous saturated sodium bicarbonate solution was added to the combined organic layers until pH >7. The aqueous phase was separated and acidified by adding citric acid solution (10%). It was then extracted with ethyl acetate (4×500 mL). The organic extracts were combined, dried over anhydrous sodium sulfate and concentrated under reduced pressure to give 6-(tert-butoxycarbonyl)-1-methyl-4-oxo-4,5,6,7-tetrahydro-1H-pyrazolo[3,4-c]pyridine-7-carboxylic acid (58 g, 95%) as a white solid. It was used directly in the next step. $^1$H NMR (400 MHz, CDCl$_3$) δ: 1.48 (s, 9H); 4.02 (s, 3H); 4.12 (m, 1H); 4.65-4.52 (m, 1H); 6.16 (s, 1H); 7.90 (s, 1H).

Int-4

To a solution of 6-(tert-butoxycarbonyl)-1-methyl-4-oxo-4,5,6,7-tetrahydro-1H-pyrazolo[3,4-c]pyridine-7-carboxylic acid (58 g, 196.42 mmol) in DMF (300 mL) was added dimethyl sulfate (196.42 mL, 245.52 mmol) and stirred at 25° C. for 2 h. Potassium carbonate (10.86 g, 78.57 mmol) and dimethyl sulfate (196.42 mL, 39.28 mmol) were added and stirred at 25° C. for 12 h. Additional potassium carbonate (5.43 g, 39.28 mmol) was added and the reaction mixture was stirred for another hour. Water (500 mL) was added to the reaction mixture, and extracted with DCM (3×500 mL). The combined organic layers were washed with 0.1N HCl (300 mL), followed by H$_2$O (300 mL), dried over anhydrous sodium sulfate, filtered and concentrated under reduced pressure to give 6-(tert-butyl) 7-methyl 1-methyl-4-oxo-1,4,5,7-tetrahydro-6H-pyrazolo[3,4-c]pyridine-6,7-dicarboxylate (50 g, 82%) as a yellow oil. It was used directly in the next step. $^1$H NMR (400 MHz, CDCl$_3$) δ: 1.49 (s, 9H); 3.03-2.82 (m, 1H); 3.80 (s, 3H); 4.02 (s, 3H); 4.59 (d, J=18.4 Hz, 1H); 6.16 (s, 1H); 7.91 (s, 1H).

Int-5

To a solution of 6-(tert-butyl) 7-methyl 1-methyl-4-oxo-1,4,5,7-tetrahydro-6H-pyrazolo[3,4-c]pyridine-6,7-dicarboxylate (50 g, 161.64 mmol) in DCM (500 mL) was added pyridine (25.57 g, 323.28 mmol) and O-benzylhydroxylamine hydrochloride (25.80 g, 161.64 mmol). The reaction mixture was stirred at 20° C. for 12 hours. 10% tartaric acid (200 mL) was added. The organic layer was separated and washed with 2% tartaric acid (200 mL). The combined aqueous layers were washed with DCM (500 mL). The combined organics were washed with brine (200 mL), dried over anhydrous sodium sulfate, filtered and concentrated under reduced pressure to give 6-(tert-butyl) 7-methyl (Z)-4-((benzyloxy)imino)-1-methyl-1,4,5,7-tetrahydro-6H-pyrazolo[3,4-c]pyridine-6,7-dicarboxylate (70 g, 104%) as a yellow oil. It was used directly in the next step without further purification.

Int-6

To a solution of 6-(tert-butyl) 7-methyl (Z)-4-((benzyloxy)imino)-1-methyl-1,4,5,7-tetrahydro-6H-pyrazolo[3,4-c]pyridine-6,7-dicarboxylate (60 g, 144.77 mmol) in MeOH (240 mL) was added HCl/dioxane (4N, 36.16 mL, 144.77 mmol) at 0° C. The reaction mixture was stirred for 30 minutes. Borane pyridine complex (13.45 g, 144.77 mmol) was added at 0-2° C. and stirred for 1.5 h, followed by HCl/dioxane (4M, 180.96 mL, 723.84 mmol). The reaction mixture was stirred at 25° C. for 12 hours. HCl (31.67 g, 868.62 mmol) gas was bubbled through the reaction mixture. Acetonitrile (500 mL) was added and stirred for 40 minutes. The reaction mixture was filtered, the cake was washed with acetonitrile (300 mL), then MTBE (300 ml). The filter cake was dissolved in ethyl acetate (500 mL) and saturated aqueous sodium bicarbonate was added to adjust pH >7. The aqueous was extracted with ethyl acetate (3×500 mL). The combined organic layers were dried over anhydrous sodium sulfate and concentrated to give methyl 4-((benzyloxy)amino)-1-methyl-4,5,6,7-tetrahydro-1H-pyrazolo[3,4-c]pyridine-7-carboxylate (37 g, 81%) as a brown oil. $^1$H NMR (400 MHz, CDCl$_3$) δ: 2.01-1.70 (m, 1H); 2.88 (dd, J=2.8, 13.6 Hz, 1H); 3.32 (d, J=13.4 Hz, 1H); 3.76 (s, 3H); 3.82-3.78 (m, 3H); 3.94 (br s, 1H); 4.56 (s, 1H); 4.70 (s, 2H); 7.38-7.25 (m, 5H); 7.42 (s, 1H).

Int-7

Two batches of the following reaction with same scale were carried out in parallel. To a solution methyl 4-((benzyloxy)amino)-1-methyl-4,5,6,7-tetrahydro-1H-pyrazolo[3,4-c]pyridine-7-carboxylate (18.5 g, 58.48 mmol) and trimethylamine (130.4 mL, 935.68 mmol) in THF (360 mL) at 0° C. was added a solution of triphosgene (6.94 g, 23.39 mmol) in THF (80 mL). The mixture was stirred at 0° C. and allowed to warm to 25° C. for 12 hours. The reaction mixture was filtered, the filter cake was dissolved in DCM (200 mL) and adjusted to pH<7 with 1N HCl solution, then extracted with DCM (3×200 mL). The combined organic layers were dried over anhydrous sodium sulfate, filtered and concentrated under reduced pressure to give methyl (4R,8S)-5-(benzyloxy)-1-methyl-6-oxo-4,5,6,8-tetrahydro-1H-4,7-methanopyrazolo[3,4-e][1,3]diazepine-8-carboxylate (12.00 g) as a white solid. The reaction mixture filtrate was concentrated and the residue was purified by column chromatography (SiO$_2$, petroleum ether/ethyl acetate/DCM=5/1/0 to 1/1/0.5) to give additional methyl (4R,8S)-5-(benzyloxy)-1-methyl-6-oxo-4,5,6,8-tetrahydro-1H-4,7-methanopyrazolo[3,4-e][1,3]diazepine-8-carboxylate (13.00 g) as a white solid. The two batches (25.00 g, 62%) were combined and used directly in the next step.

¹H NMR (400 MHz, CDCl₃) δ: 3.23 (d, J=11.2 Hz, 1H); 3.43 (dd, J=2.9, 11.5 Hz, 1H); 3.77 (s, 3H); 3.86 (s, 3H); 3.98 (d, J=2.4 Hz, 1H); 4.86 (d, J=11.8 Hz, 1H); 5.04-4.95 (m, 1H); 5.21 (s, 1H); 7.48-7.32 (m, 6H).

Int-8

A solution of lithium borohydride (2N in THF, 146.04 mL, 292.1 mmol) was added to a solution of methyl (4R,8S)-5-(benzyloxy)-1-methyl-6-oxo-4,5,6,8-tetrahydro-1H-4,7-methanopyrazolo[3,4-e][1,3]diazepine-8-carboxylate (20 g, 58.42 mmol) in methanol (960 mL) and THF (480 mL) at −10° C. The resulting mixture was stirred at −5° C. for 1.5 hours. It was then quenched with saturated aqueous ammonium chloride solution. Most of the solvent was removed under reduced pressure. The crude material was re-dissolved in DCM (1000 mL) and water (500 mL) was added. Organic layer was separated, dried over anhydrous sodium sulfate and concentrated. The resulting residue was triturated with ethyl acetate to give (4R,8S)-5-(benzyloxy)-8-(hydroxymethyl)-1-methyl-1,4,5,8-tetrahydro-6H-4,7-methanopyrazolo[3,4-e][1,3]diazepin-6-one (12.5 g, 68%) as a white solid. It was used directly in the next step. MS: 315 ES+ ($C_{17}H_{18}N_4O_4$)

Int-9

To a solution of (4R,8S)-5-(benzyloxy)-8-(hydroxymethyl)-1-methyl-1,4,5,8-tetrahydro-6H-4,7-methanopyrazolo[3,4-e][1,3]diazepin-6-one (12.36 g, 39.36 mmol) in dichloromethane (500 mL) at ambient temperature was added Dess-Martin periodinane (20.06 g, 47.23 mmol). The reaction mixture was stirred for 1 hour. Aqueous sodium thiosulfate solution (1N, 300 mL) and aqueous saturated sodium bicarbonate solution (200 mL) were added to the reaction mixture and stirred for 15 minutes. The biphasic mixture was separated and the aqueous extracted with dichloromethane (500 mL). The combined organics were dried over anhydrous magnesium sulfate, filtered and concentrated to give the crude product. Flash chromatography (120 g silica gel, 0%-100% ethyl acetate/hexanes) afforded (4R,8S)-5-(benzyloxy)-1-methyl-6-oxo-4,5,6,8-tetrahydro-1H-4,7-methanopyrazolo[3,4-e][1,3]diazepine-8-carbaldehyde (9.72 g, 79%) as a white solid. MS: 313 ES+ ($C_{16}H_{16}N_4O_3$)

Int-10

To a solution of (4R,8S)-5-(benzyloxy)-1-methyl-6-oxo-4,5,6,8-tetrahydro-1H-4,7-methanopyrazolo[3,4-e][1,3]diazepine-8-carbaldehyde (8.62 g, 27.6 mmol) in pyridine (120 mL) at ambient temperature was added hydroxylamine hydrochloride (2.11 g, 30.36 mmol). The reaction mixture was stirred for 20 minutes. Aqueous ammonium chloride solution (500 mL) and ethyl acetate (500 mL) were added. The organic layer was separated, dried over anhydrous sodium sulfate and concentrated to give (E)-5-(benzyloxy)-1-methyl-6-oxo-4,5,6,8-tetrahydro-1H-4,7-methanopyrazolo[3,4-e][1,3]diazepine-8-carbaldehyde oxime (9.03 g, 99%) as a white solid. It was used directly in the next step. MS: 328 ES+ ($C_{16}H_{17}N_5O_3$)

Int-11

To a solution of (E)-5-(benzyloxy)-1-methyl-6-oxo-4,5,6,8-tetrahydro-1H-4,7-methanopyrazolo[3,4-e][1,3]diazepine-8-carbaldehyde oxime (9.03 g, 27.6 mmol) in DMF (300 mL) at room temperature was added N-chlorosuccinimide (4.05 g, 30.36 mmol). The reaction mixture was stirred at 40° C. for 2 hours, then left at ambient temperature overnight. Ice water (500 mL) and ethyl acetate (500 mL) were added. The organic layer was separated, dried over anhydrous sodium sulfate and concentrated to give ((4R,8S,Z)-5-(benzyloxy)-N-hydroxy-1-methyl-6-oxo-4,5,6,8-tetrahydro-1H-4,7-methanopyrazolo[3,4-e][1,3]diazepine-8-carbimidoyl chloride (9.98 g, 99%) as a light yellow solid. It was used directly in the next step. MS: 362 ES+ ($C_{16}H_{16}ClN_5O_3$)

Int-12

To a solution of ((4R,8S,Z)-5-(benzyloxy)-N-hydroxy-1-methyl-6-oxo-4,5,6,8-tetrahydro-1H-4,7-methanopyrazolo[3,4-e][1,3]diazepine-8-carbimidoyl chloride (9.98 g, 27.6 mmol) in DCM (360 mL) at room temperature was added methylamine (2N in THF, 2.02 mL, 56.05 mmol). The reaction mixture was stirred at ambient temperature for 30 minutes. Saturated aqueous ammonium chloride solution (300 mL) and DCM (200 mL) were added. The organic layer was separated, dried over anhydrous sodium sulfate and concentrated to give the crude product. The crude product was triturated with a mixture of DCM and acetone and filtered to give (Z)-5-(benzyloxy)-N'-hydroxy-N,1-dimethyl-6-oxo-4,5,6,8-tetrahydro-1H-4,7-methanopyrazolo[3,4-e][1,3]diazepine-8-carboximidamide (7.27 g, 74%) as a white solid. It was used directly in the next step. MS: 357 ES+ ($C_{17}H_{20}N_6O_3$)

Int-13

To a solution of (Z)-5-(benzyloxy)-N'-hydroxy-N,1-dimethyl-6-oxo-4,5,6,8-tetrahydro-1H-4,7-methanopyrazolo[3,4-e][1,3]diazepine-8-carboximidamide (6.88 g, 19.31 mmol) in DCM (500 mL) at room temperature was added tert-butyldimethylsilyl trifluoromethanesulfonate (4.88 mL, 21.24 mmol) and 2,6-lutidine (2.7 mL, 23.17 mmol). The reaction mixture was stirred at 30° C. for 2 hours. DCM (300 mL) and saturated aqueous ammonium chloride solution (300 mL) were added. The organic layer was separated, dried over anhydrous sodium sulfate and concentrated to give the crude product. The crude product was triturated with a mixture of hexanes and ethyl acetate and filtered to give (4R,8S,Z)-5-(benzyloxy)-N'-((tert-butyldimethylsilyl)oxy)-N,1-dimethyl-6-oxo-4,5,6,8-tetrahydro-1H-4,7-methanopyrazolo[3,4-e][1,3]diazepine-8-carboximidamide (9.17 g, 99%) as a white solid. MS: 471 ES+ ($C_{23}H_{34}N_6O_3Si$)

Int-14

A solution of (4R,8S,Z)-5-(benzyloxy)-N'-((tert-butyldimethylsilyl)oxy)-N,1-dimethyl-6-oxo-4,5,6,8-tetrahydro-1H-4,7-methanopyrazolo[3,4-e][1,3]diazepine-8-carboximidamide (1.3 g, 2.76 mmol) in MeOH (60 mL) and ethyl acetate (150 mL) was purged with nitrogen 3 times, and 10% Pd/C (294 mg, 0.28 mmol) was added. The reaction mixture was purged with nitrogen 3 times and then stirred under hydrogen atmosphere at ambient temperature for 1 hour. The reaction mixture was filtered through Celite. The filtrate was concentrated to give (4R,8S,Z)—N'-((tert-butyldimethylsilyl)oxy)-5-hydroxy-N,1-dimethyl-6-oxo-4,5,6,8-tetrahydro-1H-4,7-methanopyrazolo[3,4-e][1,3]diazepine-8-carboximidamide (1.02 g, 97%) as a white solid. MS: 381 ES+ ($C_{16}H_{28}N_6O_3Si$)

Int-15

To a solution of (4R,8S,Z)—N'-((tert-butyldimethylsilyl)oxy)-5-hydroxy-N,1-dimethyl-6-oxo-4,5,6,8-tetrahydro-1H-4,7-methanopyrazolo[3,4-e][1,3]diazepine-8-carboximidamide (400 mg, 1.05 mmol) in pyridine (20 mL) at ambient temperature was added sulfur trioxide pyridine complex (1338 mg, 8.41 mmol). The reaction mixture was stirred overnight, then concentrated under reduced pressure to give the crude product. The material was purified on a short silica pad, eluting with hexanes (100 mL), followed by ethyl acetate/hexanes (1:1, 100 mL), ethyl acetate (100 mL) and acetone (200 mL). Fractions containing the product were pooled and concentrated to give (4R,8S)-8-((Z)—N'-((tert-butyldimethylsilyl)oxy)-N-methylcarbamimidoyl)-1-methyl-6-oxo-4,8-dihydro-1H-4,7-methanopyrazolo[3,4-e][1,3]diazepin-5(6H)-yl hydrogen sulfate (400 mg, 83%) as a white solid. MS: 461 ES+ ($C_{16}H_{28}N_6O_6SSi$)

Int-16

To a solution of (4R,8S)-8-((Z)—N'-((tert-butyldimethylsilyl)oxy)-N-methylcarbamimidoyl)-1-methyl-6-oxo-4,8-dihydro-1H-4,7-methanopyrazolo[3,4-e][1,3]diazepin-5(6H)-yl hydrogen sulfate (130 mg, 0.28 mmol) in ethyl acetate (15 mL) at ambient temperature was added HF.Pyridine (0.01 mL, 0.31 mmol). The reaction mixture was stirred for 2 hours, then concentrated. The resulting solid was purified by reverse phase chromatography (Sepabeads, 100% water) to afford the pyridium salt of (4R,8S)-8-((Z)—N'-hydroxy-N-methylcarbamimidoyl)-1-methyl-6-oxo-4,8-dihydro-1H-4,7-methanopyrazolo[3,4-e][1,3]diazepin-5(6H)-yl hydrogen sulfate (71 mg, 59%) as a white solid. MS: 345 ES− ($C_{10}H_{14}N_6O_6S$)

Example 1

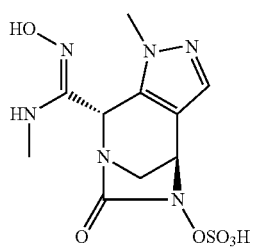

The pyridium salt of (4R,8S)-8-((Z)—N'-hydroxy-N-methylcarbamimidoyl)-1-methyl-6-oxo-4,8-dihydro-1H-4,7-methanopyrazolo[3,4-e][1,3]diazepin-5(6H)-yl hydrogen sulfate (71 mg, 0.17 mmol) was dissolved in water (2 mL) and eluted through a Dowex® 50WX8 Na+-form ion exchange resin cartridge with water as the eluent. Fractions containing the product were pooled and lyophilized to afford sodium (4R,8S)-8-((Z)—N'-hydroxy-N-methylcarbamimidoyl)-1-methyl-6-oxo-4,8-dihydro-1H-4,7-methanopyrazolo[3,4-e][1,3]diazepin-5(6H)-yl sulfate (55 mg, 88%) as a white solid. MS: 345 ES− ($C_{10}H_{14}N_6O_6S$) $^1$H NMR (300 MHz, $D_2O$) δ: 3.08 (s, 3H); 3.46 (m, 1H); 3.57 (m, 1H); 3.61 (s, 3H); 4.92 (m, 1H); 5.75 (s, 1H); 7.60 (s, 1H).

Example 2

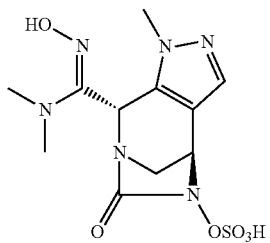

(4R,8S)-8-((Z)—N'-hydroxy-N,N-dimethylcarbamimidoyl)-1-methyl-6-oxo-4,8-dihydro-1H-4,7-methanopyrazolo[3,4-e][1,3]diazepin-5(6H)-yl hydrogen sulfate was synthesized by following similar reaction sequence as shown for Example 1, using a solution of dimethyl amine in THF in step 12. Example 2 was purified and submitted as the free sulfate in step 16. MS: 359 ES− ($C_{11}H_{16}N_6O_6S$) $^1$H NMR (300 MHz, $D_2O$) δ: 3.01 (s, 6H); 3.49 (m, 2H); 3.60 (s, 3H); 4.90 (m, 1H); 5.64 (s, 1H); 7.57 (s, 1H).

Example 3

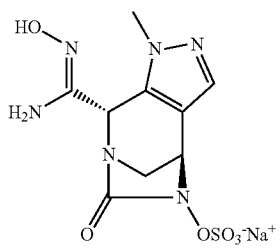

Sodium (4R,8S)-8-((Z)—N'-hydroxycarbamimidoyl)-1-methyl-6-oxo-4,8-dihydro-1H-4,7-methanopyrazolo[3,4-e][1,3]diazepin-5(6H)-yl sulfate was synthesized by following a similar reaction sequence as shown for Example 1, using a solution of ammonia in THF in step 12 MS: 331 ES− ($C_9H_{12}N_6O_6S$) $^1$H NMR (300 MHz, $D_2O$) δ: 3.17 (m, 2H); 3.64 (s, 1H); 4.96 (m, 1H); 5.38 (s, 1H); 7.59 (s, 1H).

Scheme 2

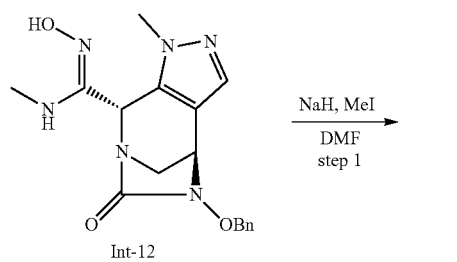
Int-12

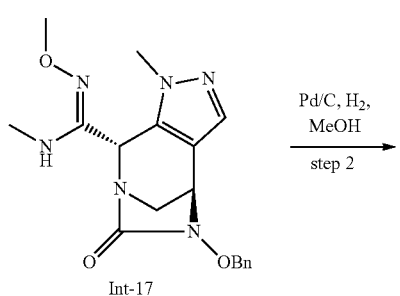
Int-17

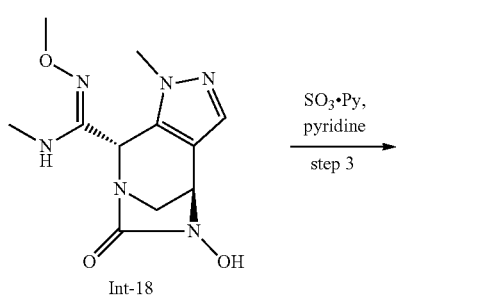
Int-18

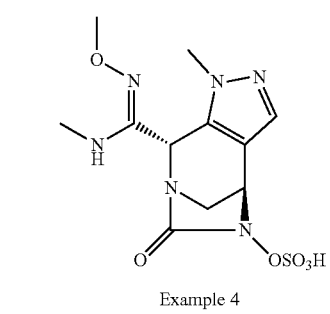
Example 4

Int-17

To a solution of (4R,8S,Z)-5-(benzyloxy)-N-hydroxy-N,1-dimethyl-6-oxo-4,5,6,8-tetrahydro-1H-4,7-methanopyrazolo[3,4-e][1,3]diazepine-8-carboximidamide (Int-12, 15 mg, 0.042 mmol) in DMF (2 mL) at 0° C. was added NaH (2.53 mg, 0.063 mmol, 60%). After the reaction mixture was stirred at 0° C. for 10 minutes, methyl iodide (7.17 mg, 0.050 mmol) was added. It was then warmed up to room temperature and stirred at room temperature for 10 minutes. Ethyl acetate and saturated ammonium chloride solution were added. Organic layer was separated, washed with water, brine, dried over anhydrous sodium sulfate, and concentrated to give the crude product. It was purified by flash chromatography (0-100% Acetone in DCM) to afford (4R,8S,Z)-5-(benzyloxy)-N'-methoxy-N,1-dimethyl-6-oxo-4,5,6,8-tetrahydro-1H-4,7-methanopyrazolo[3,4-e][1,3]diazepine-8-carboximidamide (8 mg, yield, 51.3%) as a white solid. MS: 371 ES+ ($C_{18}H_{22}N_6O_3$).

Int-18

A solution of (4R,8S,Z)-5-(benzyloxy)-N'-methoxy-N,1-dimethyl-6-oxo-4,5,6,8-tetrahydro-1H-4,7-methanopyrazolo[3,4-e][1,3]diazepine-8-carboximidamide (Int-17, 8 mg, 0.0216 mmol) in MeOH (3 mL) was purged with nitrogen 3 times, and 10% Pd/C (4.58 mg, 0.0043 mmol) was added. The reaction mixture was purged with nitrogen 3 times and then stirred under hydrogen atmosphere at room temperature for 2 hours. The reaction mixture was filtered through Celite. The filtrate was concentrated to give (4R,8S,Z)-5-hydroxy-N'-methoxy-N,1-dimethyl-6-oxo-4,5,6,8-tetrahydro-1H-4,7-methanopyrazolo[3,4-e][1,3]diazepine-8-carboximidamide (4.5 mg, 74.3%) as a white solid. MS: 281 ES+ ($C_{11}H_{16}N_6O_3$).

Example 4

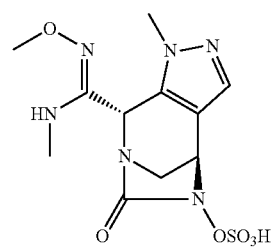

To a solution of (4R,8S,Z)-5-hydroxy-N'-methoxy-N,1-dimethyl-6-oxo-4,5,6,8-tetrahydro-1H-4,7-methanopyrazolo[3,4-e][1,3]diazepine-8-carboximidamide (Int-18, 4.5 mg, 0.016 mmol) in pyridine (2 mL) at room temperature was added sulfur trioxide pyridine complex (25.5 mg, 0.16 mmol). The reaction mixture was stirred for 16 hours, then concentrated under reduced pressure to give the crude product. It was triturated with DCM and filtered to remove solids. The filtrate was concentrated and purified by reversed phase chromatography (Sepabeads, 12 g, ACN/water 0-50%) to afford (4R,8S)-8-((Z)—N'-methoxy-N-methylcarbamimidoyl)-1-methyl-6-oxo-4,8-dihydro-1H-4,7-methanopyrazolo[3,4-e][1,3]diazepin-5(6H)-yl hydrogen sulfate (2.2 mg, 30.4%) as a white solid. MS: 359 ES– ($C_{11}H_{16}N_6O_6S$) $^1$H NMR (300 MHz, $D_2O$-$d_2$) δ: 3.07 (s, 3H); 3.52-3.66 (m, 2H); 3.69 (m, 6H); 4.96 (s, 1H); 5.73 (s, 1H); 7.64 (s, 1H).

Analytical Data for Additional Examples

Example 6 and 7 were synthesized by following a similar synthetic sequence as shown for Example 4. The other examples in Table 1 were synthesized in a manner similar to Scheme 1 using similar reactions easily known to a person skilled in the art. All compounds were isolated as trans racemic.

TABLE 1

| Ex. # | Structure | Calc. MW | MS | 1H NMR |
|---|---|---|---|---|
| 5 | 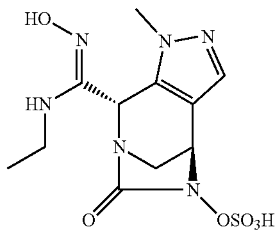 | 360.34 | ES − 359<br>ES + 242<br>(TBA salt) | $^1$H NMR TBA salt (300 MHz, D$_2$O-d$_2$) δ: 0.90 (m, 9H); 1.21 (m, 3H); 1.31 (m, 6H); 1.62 (m, 6H); 3.22 (m, 6H); 3.52 (m, 4H); 3.60 (s, 3H); 4.91 (s, 1H), 5.63 (s, 1H); 7.57 (s, 1H). |
| 6 | 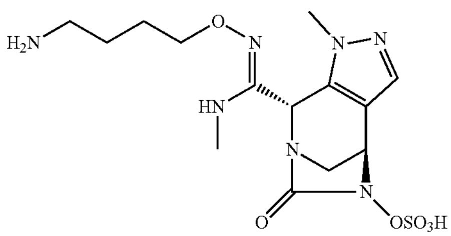 | 417.4 | ES + 418 | $^1$H NMR (300 MHz, D$_2$O-d$_2$) δ: 1.72 (m, 4H); 3.01 (m, 2H); 3.11 (s, 3H); 3.50-3.66 (m, 2H); 3.67 (s, 3H); 3.91 (m, 2H); 4.97 (s, 1H); 5.75 (s, 1H), 7.66 (s, 1H). |
| 7 | 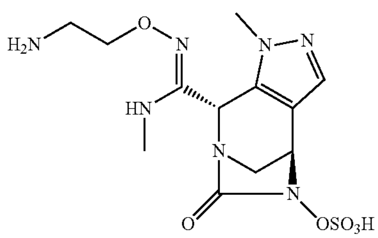 | 389.4 | ES + 390 | $^1$H NMR (300 MHz, D$_2$O-d$_2$) δ: 3.11 (s,3H); 3.26 (m, 2H); 3.57-3.68 (m, 2H); 3.70 (s, 3H); 4.12 (m, 2H); 4.99 (s, 1H); 5.77 (s, 1H), 7.64 (s, 1H). |
| 8 | 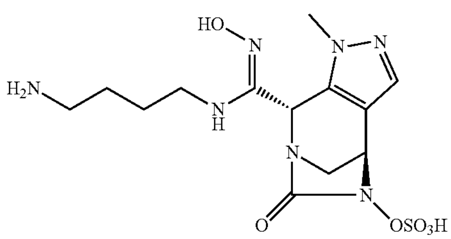 | 403.4 | ES − 402 | $^1$H NMR (300 MHz, D$_2$O-d$_2$) δ: 1.77 (m, 4H): 3.01 (m, 2H); 3.43-3.63 (m, 4H); 3.67 (s, 3H); 4.93 (s, 1H); 5.80 (s, 1H); 7.63 (s, 1H). |
| 9 | 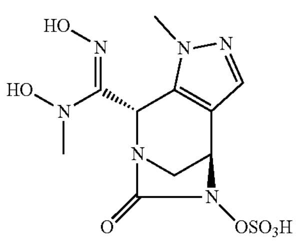 | 362.32 | ES + 363 | (300 MHz, D$_2$O) δ: 3.24 (s, 3H); 3.50-3.73 (m, 5H); 4.98 (m, 1H); 5.99 (s, 1H); 7.65 (s, 1H) |
| 10 | 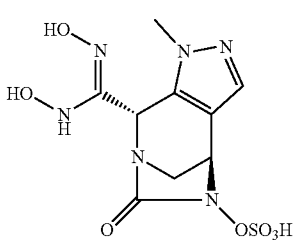 | 348.29 | ES − 347 | (300 MHz, D$_2$O) δ: 3.48-3.81 (m, 5H); 4.98 (m, 1H); 5.92 (s, 1H); 7.65 (s, 1H) |

TABLE 1-continued
| Ex. # | Structure | Calc. MW | MS | 1H NMR |
|---|---|---|---|---|
| 11 | 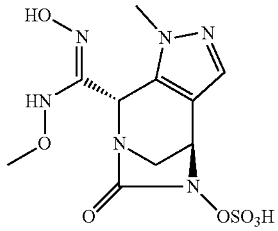 | 362.32 | ES + 363 | (300 MHz, D$_2$O) δ: 3.46-4.00 (m, 8H); 4.98 (m, 1H); 5.91 (s, 1H); 7.66 (s, 1H); 8.07 (m, 1.12H); 8.60 (m, 0.56H); 8.81 (m, 1.12H) Compound/pyridine ratio (1:0.56) |
| 12 | 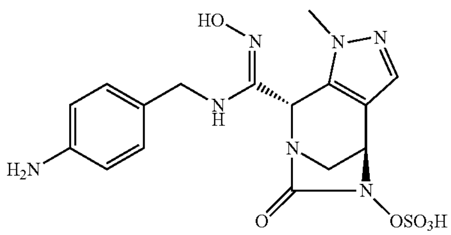 | 437.43 | ES + 438 | (300 MHz, D$_2$O) δ: 3.36 (s, 3H); 3.45 (s, 2H); 4.66 (m, 2H); 4.87 (m, 1H); 5.36 (m, 1H); 7.37 (m, 2H); 7.54 (m, 3H). |
| 13 | 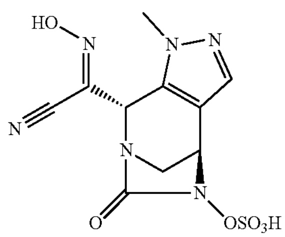 | 342.29 | ES − 341 | (300 MHz, DMSO-d$_6$) δ: 3.04 (m, 1H); 3.42 (m, 1H); 3.62 (s, 3H); 4.71 (m, 1H); 5.77 (s, 1H); 7.42 (s, 1H); 7.69 (m, 2.6H); 8.13 (m, 1.3H); 8.73 (m, 2.6H); 13.78 (s, 1H). compound/pyridine ratio (1:1.3) |
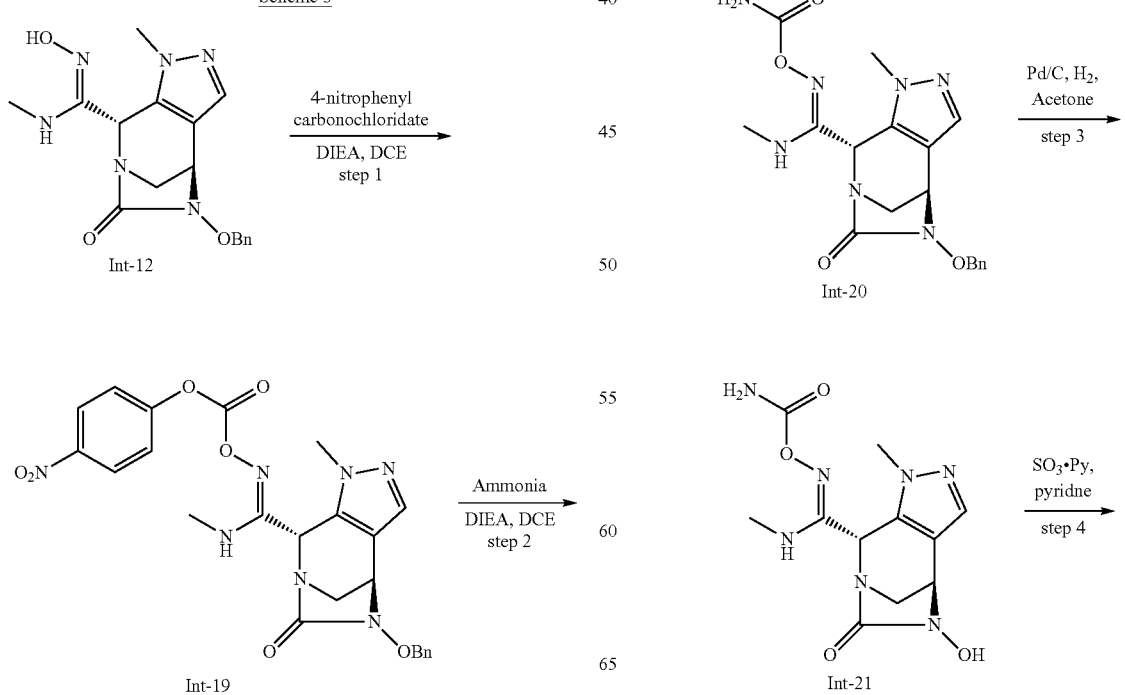
Scheme 3

-continued

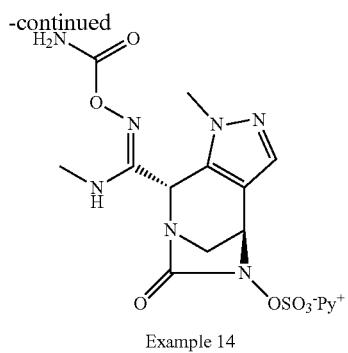

Example 14

Int-19 and Int 20

To a solution of (4R,8S,Z)-5-(benzyloxy)-N'-hydroxy-N,1-dimethyl-6-oxo-4,5,6,8-tetrahydro-1H-4,7-methanopyrazolo[3,4-e][1,3]diazepine-8-carboximidamide (Int-12, 229 mg, 0.64 mmol) in DCE (15 mL) at room temperature was added DIEA (0.11 mL, 0.64 mmol) and (4-nitrophenyl)carbonochloridate (129.52 mg, 0.64 mmol). The reaction mixture was stirred at room temperature for 2 hours to afford a solution of (4R,8S,Z)-5-(benzyloxy)-N,1-dimethyl-N'-(((4-nitrophenoxy)carbonyl)oxy)-6-oxo-4,5,6,8-tetrahydro-1H-4,7-methanopyrazolo[3,4-e][1,3]diazepine-8-carboximidamide (Int 19).

To the solution of Int-19 described above at room temperature was added DIEA (0.11 mL, 0.64 mmol) and a solution of ammonia in THF (0.64 mL, 0.64 mmol). The reaction mixture was stirred at room temperature for 1 hour. Solvent was removed to give the crude product. It was purified by flash chromatography (20 g silica gel, 0%-100% ethyl acetate/hexanes) to afford (4R,8S,Z)-5-(benzyloxy)-N'-(carbamoyloxy)-N,1-dimethyl-6-oxo-4,5,6,8-tetrahydro-1H-4,7-methanopyrazolo[3,4-e][1,3]diazepine-8-carboximidamide (87 mg, 34%) as a white solid. MS: 400 ES+ ($C_{18}H_{21}N_7O_4$).

Int-21

A solution of (4R,8S,Z)-5-(benzyloxy)-N'-(carbamoyloxy)-N,1-dimethyl-6-oxo-4,5,6,8-tetrahydro-1H-4,7-methanopyrazolo[3,4-e][1,3]diazepine-8-carboximidamide (Int-20, 87 mg, 0.22 mmol) in Acetone (10 mL) was purged with nitrogen 3 times, and 10% Pd/C (23 mg, 0.022 mmol) was added. The reaction mixture was purged with nitrogen 3 times and then stirred under hydrogen atmosphere at ambient temperature for 2 hours. The reaction mixture was filtered through Celite. The filtrate was concentrated to afford ((4R,8S,Z)—N'-(carbamoyloxy)-5-hydroxy-N,1-dimethyl-6-oxo-4,5,6,8-tetrahydro-1H-4,7-methanopyrazolo[3,4-e][1,3]diazepine-8-carboximidamide (66 mg, 67%) as a white solid. MS: 310 ES+ ($C_{11}H_{15}N_7O_4$).

Example 14

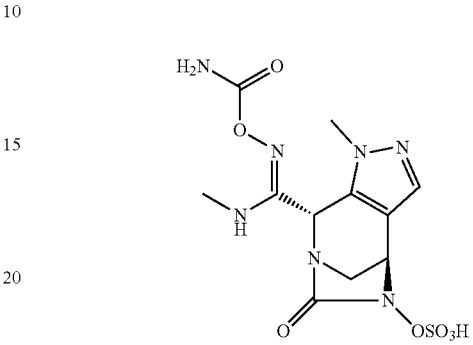

To a solution of ((4R,8S,Z)—N'-(carbamoyloxy)-5-hydroxy-N, 1-dimethyl-6-oxo-4,5,6,8-tetrahydro-1H-4,7-methanopyrazolo[3,4-e][1,3]diazepine-8-carboximidamide (Int-21, 66 mg, 0.21 mmol) in pyridine (5 mL) at ambient temperature was added sulfur trioxide pyridine complex (271 mg, 1.71 mmol). The reaction mixture was stirred overnight, then concentrated under reduced pressure to give the crude product. It was purified on a short silica pad, eluting with hexanes (50 mL), followed by ethyl acetate/hexanes (1:1, 50 mL), ethyl acetate (50 mL) and acetone (100 mL) to afford pyridium (4R,8S)-8-((Z)—N'-(carbamoyloxy)-N-methylcarbamimidoyl)-1-methyl-6-oxo-4,8-dihydro-1H-4,7-methanopyrazolo[3,4-e][1,3]diazepin-5(6H)-yl hydrogen sulfate (13 mg, 14%) as a white solid. MS: 388 ES– ($C_{11}H_{15}N_7O_7S$) $^1$H NMR (300 MHz, $D_2O$) δ: 3.57-3.63 (m, 5H); 4.90 (m, 1H); 5.72 (m, 1H); 7.58 (s, 1H); 8.01 (m, 2H); 8.58 (m, 1H); 8.74 (m, 2H) compound/pyridine ratio (1:1).

Analytical Data for Additional Examples

All compounds in Table 2 were synthesized according to Scheme 3 or using similar reactions easily known to a person skilled in the art. All compounds were isolated as trans racemic.

TABLE 2

| Example # | Structure | Calc. MW | MS | $^1$H NMR |
|---|---|---|---|---|
| 15 | (structure shown) | 483.46 | ES + 484 | (300 MHz, DMSO-d6) δ 2.98 (d, 3H); 3.33 (s, 2H); 3.59 (s, 3H); 3.77 (s, 3H); 4.02 (m, 2H); 4.68 (d, 1H); 5.61 (s, 1H); 6.76 (bs, 2H); 7.26 (s, 1H); 7.35 (s, 1H); 7.48 (s, 1H) |

TABLE 2-continued

| Example # | Structure | Calc. MW | MS | ¹H NMR |
|---|---|---|---|---|
| 16 | 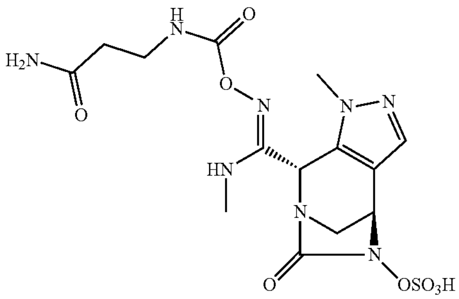 | 460.42 | ES + 461 | (300 MHz, DMSO-d6) δ 2.13 (t, 2H); 2.92 (d, 3H); 3.09 (m, 4H); 3.56 (s, 3H); 4.63 (d, 1H); 5.52 (s, 1H); 6.47 (t, 1H); 6.74 (bs, 2H); 7.28 (bs, 1H); 7.27 (s, 1H) |
| 17 | 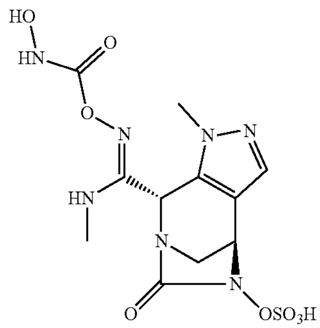 | 405.07 | ES − 404 | (300 MHz, D₂O) δ: 3.05 (s, 3H); 3.58 (m, 2H); 3.64 (s, 3H); 4.91 (m, 1H); 5.72 (m, 1H); 7.58 (s, 1H): 8.15 (m, 2H); 8.35 (m, 1H); 8.73 (m, 2H) compound/ pyridine ratio (1:1) |
| 18 | 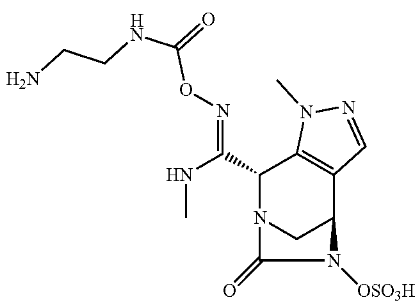 | 432.12 | ES + 433 | (300 MHz, D₂O) δ: 3.10 (m, 5H); 3.41 (m, 2H); 3.62 (m, 2H); 3.67 (s, 3H); 4.94 (m, 1H); 5.76 (m, 1H); 7.62 (s, 1H) compound/TFA ratio (1:1) |
| 19 | 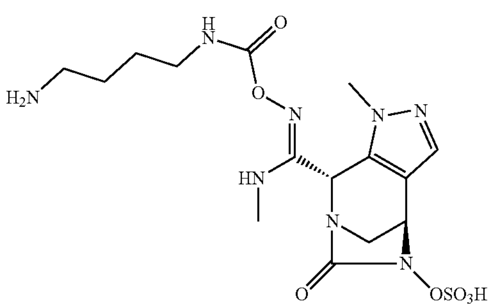 | 460.15 | ES + 461 | (300 MHz, D₂O) δ: 1.35-1.60 (m, 6H); 2.95 (m, 2H); 2.98 (s, 3H); 3.12 (m, 1H); 3.60 (m, 1H); 3.67 (s, 3H); 4.94 (m, 1H); 5.76 (m, 1H); 7.63 (s, 1H) compound/TFA ratio (1:1) |
| 20 | 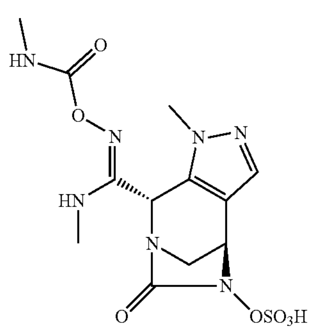 | 403.09 | ES − 402 | (300 MHz, D₂O) δ: 2.68 (s, 3H); 3.09 (s, 3H); 3.61 (m, 2H); 3.66 (s, 3H); 4.95 (m, 1H); 5.75 (m, 1H); 7.63 (s, 1H); 8.01 (m, 2H); 8.35 (m, 1H); 8.75 (m, 2H) compound/ pyridine ratio (1:1) |

TABLE 2-continued

| Example # | Structure | Calc. MW | MS | ¹H NMR |
|---|---|---|---|---|
| 21 | 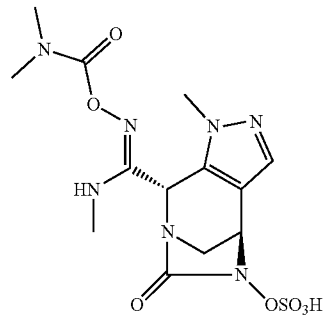 | 417.17 | ES − 416 | (300 MHz, D$_2$O) δ: 2.91 (m, 6H); 3.08 (s, 3H); 3.62 (m, 2H); 3.69 (s, 3H); 4.94 (m, 1H); 5.76 (m, 1H); 7.60 (s, 1H); 8.01 (m, 2H); 8.58 (m, 1H); 8.75 (m, 2H) compound/pyridine ratio (1:1) |
| 22 | 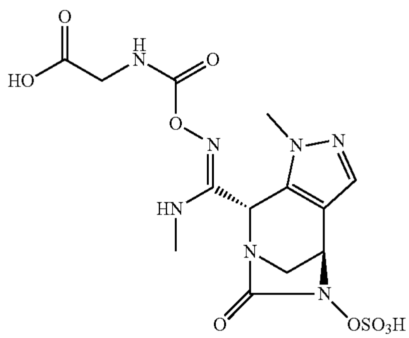 | 447.38 | ES + 448 | (300 MHz, DMSO-d$_6$) δ: 3.01 (s, 3H); 3.35 (m, 2H); 3.64 (s 3H); 3.72 (m, 2H); 4.69 (s, 1H); 5.62 (s, 1H); 6.74 (m, 1H); 6.86 (m, 1H); 7.35 (s, 1H) |
| 23 | 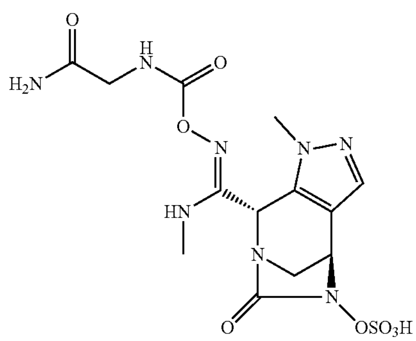 | 446.4 | ES + 447 | (300 MHz, D$_2$O) δ: 3.09 (s, 3H); 3.62 (d, 2H); 3.67 (s, 3H); 3.83 (s, 2H); 4.94 (s, 1H); 5.76 (s, 1H); 7.62 (s, 1H) |
| 24 | 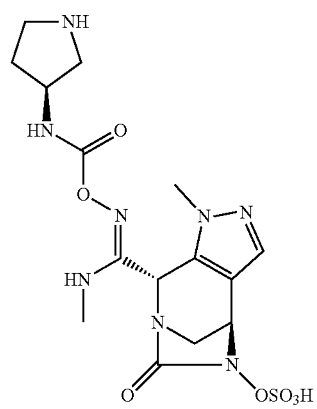 | 458.45 | ES + 459 | (300 MHz, DMSO-d$_6$) δ: 1.71 (m, 1H); 2.04 (m, 1H); 2.94 (m, 3H); 2.98 (m, 1H); 3.15 (m, 2H); 3.27 (m, 2H); 3.58 (d, 3H); 4.05 (m, 1H); 4.64 (m, 1H); 5.56 (m, 1H); 6.62 (m, 1H); 6.94 (m, 1H); 7.27 (m, 1H); 8.57 (bs, 2H) |

TABLE 2-continued

| Example # | Structure | Calc. MW | MS | $^1$H NMR |
|---|---|---|---|---|
| 25 | 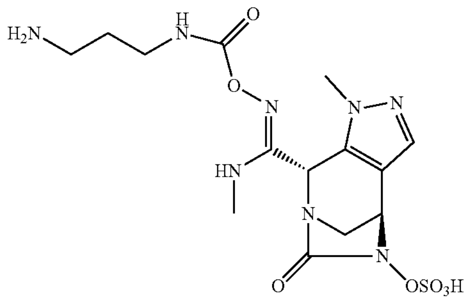 | 446.13 | ES + 447 | (300 MHz, D$_2$O) δ: 1.84 (m, 2H); 2.93 (m, 2H); 3.08 (s, 3H); 3.21 (m, 2H); 3.61 (m, 2H); 3.66 (s, 3H); 4.94 (m, 1H); 5.76 (m, 1H); 7.63 (s, 1H) compound/TFA ratio (1:1) |
| 26 | 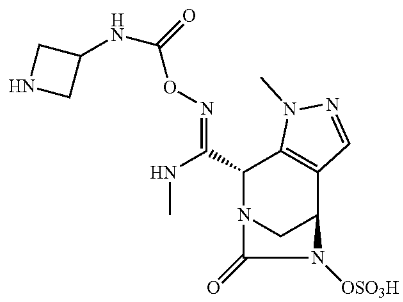 | 444.12 | ES + 445 | (300 MHz, D$_2$O) δ: 3.09 (s, 3H); 3.61 (m, 2H); 3.67 (s, 3H); 4.17 (m, 2H); 4.33 (m, 2H); 4.54 (m, 1H); 4.94 (m, 1H); 5.76 (m, 1H): 7.61 (s, 1H) compound/TFA ratio (1:1) |
| 27 | 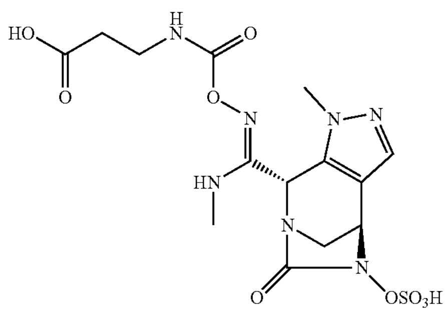 | 461.41 | ES + 462 | (300 MHz, DMSO-d$_6$) δ: 2.36 (t, 2H); 2.43 (m, 1H); 2.99 (d, 3H); 3.21 (m, 2H); 3.62 (s, 3H); 4.70 (s, 1H); 5.60 (s, 1H); 6.58 (bs, 1H); 6.82 (bs, 1H); 7.34 (s, 1H) |
| 28 | 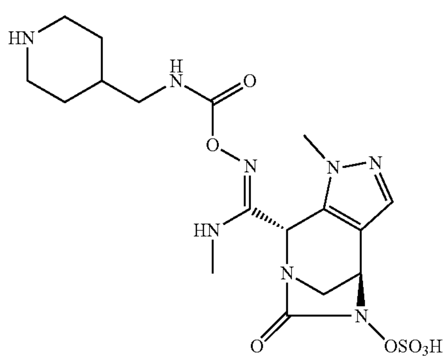 | 486.50 | ES + 487 | (300 MHz, DMSO-d$_6$) δ: 1.18 (m, 3H); 1.65 (m, 3H); 2.79 (t, 2H); 2.89 (m, 3H); 3.00 (d, 3H); 3.21 (m, 2H); 3.35 (m, 2H); 3.64 (s, 3H); 4.71 (s, 1H); 5.63 (s, 1H); 6.64 (bs, 1H); 6.76 (bs, 1H); 7.36 (s, 1H); 8.03 (bs, 1H) |
| 29 | 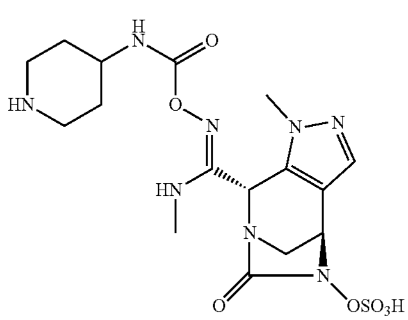 | 472.48 | ES + 473 | (300 MHz, DMSO-d$_6$) δ: 1.49 (m, 2H); 1.91 (bs, 2H); 2.92 (d, 3H); 3.01 (d, 3H); 3.18 (m, 2H); 3.55 (m, 1H); 3.65 (s, 3H); 4.71 (s, 1H); 5.64 (s, 1H); 6.71 (bs, 2H); 7.36 (s, 1H); 8.17 (bs, 1H) |

TABLE 2-continued

| Example # | Structure | Calc. MW | MS | $^1$H NMR |
|---|---|---|---|---|
| 30 | 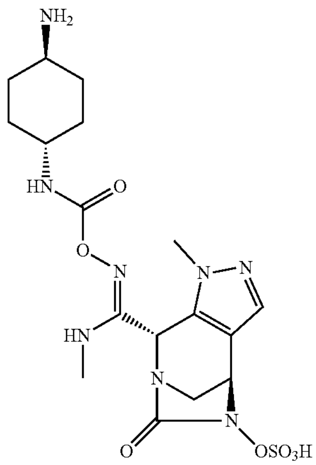 | 486.5 | ES + 487 | (300 MHz, DMSO-d$_6$) δ: 1.20 (m, 4H); 1.80 (m, 4H); 2.93 (m, 4H); 3.16 (m, 1H); 3.24 (m, 1H); 3.57 (s, 3H); 4.64 (m, 1H); 5.56 (s, 1H); 6.31 (m, 1H); 6.68 (m, 1H); 7.29 (s, 1H); 7.62 (bs, 3H) |
| 31 | 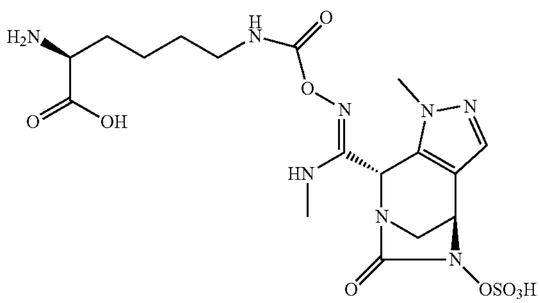 | 518.15 | ES − 517 | (300 MHz, D$_2$O) δ: 1.31-1.48 (m, 4H); 1.85 (m, 2H); 3.15 (m, 5H); 3.56 (m, 2H); 3.72 (s, 3H); 3.78 (m, 1H); 4.68 (m, 1H); 5.71 (m, 1H); 7.59 (s, 1H); 8.01 (m, 0.5H); 8.58 (m, 0.25H); 8.78 (m, 0.5H) compound/Pyridine ratio (4:1) |
| 32 | 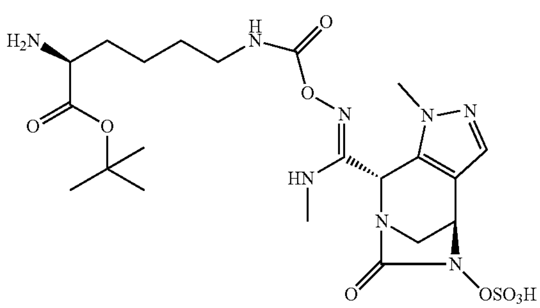 | 574.22 | ES − 573 | (300 MHz, D$_2$O) δ: 1.31 (m, 11H); 1.89 (m, 2H); 3.15-3.18 (m, 5H); 3.58-3.62 (m, 6H); 3.90 (m, 2H); 4.94 (m, 1H); 5.75 (m, 1H); 7.62 (s, 1H) |
| 33 | 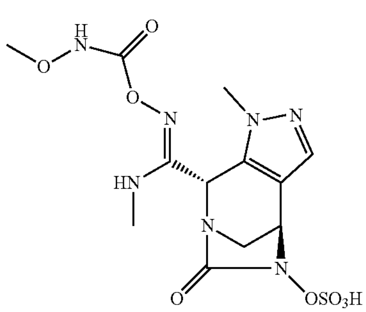 | 419.09 | ES − 418 | (300 MHz, D$_2$O) δ: 3.08 (s, 3H); 3.60 (m, 2H); 3.67 (m, 6H); 4.94 (m, 1H); 5.76 (m, 1H); 7.62 (s, 1H); 8.05 (m, 1H); 8.61 (m, 0.5H); 8.77 (m, 1H) compound/pyridine ratio (2:1) |

TABLE 2-continued

| Example # | Structure | Calc. MW | MS | 1H NMR |
|---|---|---|---|---|
| 34 | 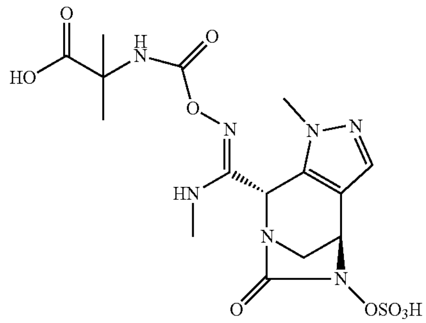 | 475.11 | ES − 474 | (300 MHz, D$_2$O) δ: 1.43-1.53 (m, 6H); 3.08 (s, 3H); 3.60 (m, 2H); 3.67 (s, 3H); 4.93 (m, 1H); 5.75 (m, 1H); 7.60 (s, 1H); 8.01 (m, 1H); 8.60 (m, 0.5H); 8.78 (m, 1H) compound/ pyridine ratio (2:1) |

Scheme 4

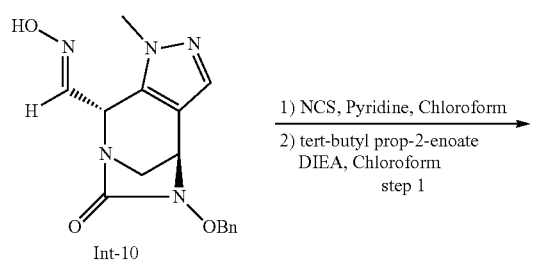

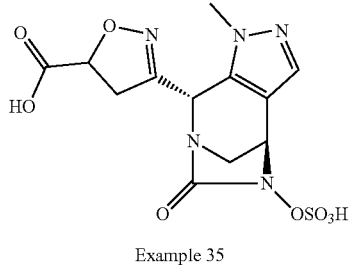

Example 35

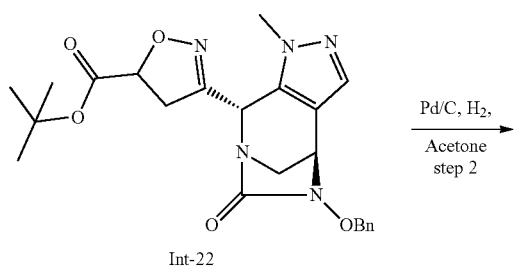

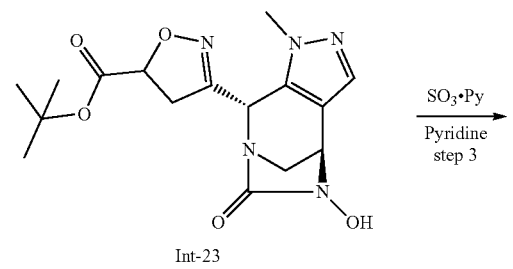

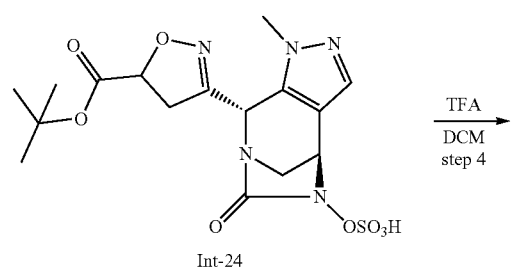

Int-22

To a solution of (E)-5-(benzyloxy)-1-methyl-6-oxo-4,5,6, 8-tetrahydro-1H-4,7-methanopyrazolo[3,4-e][1,3]diazepine-8-carbaldehyde oxime (Int-10, 88 mg, 0.27 mmol) in Chloroform (10 mL) at room temperature was added NCS (52 mg, 0.30 mmol) and Pyridine (0.02 mL, 0.27 mmol). It was stirred at 40° C. for 1 hours and cooled to room temperature. Tert-butyl prop-2-enoate (0.04 mL, 0.30 mmol) and DIEA (0.06 mL, 0.32 mmol) were added and stirred at room temperature for 30 minutes DCM (10 mL) and saturated ammonium chloride solution (10 mL) were added. The organic layer was separated, dried over anhydrous sodium sulfate and concentrated to give the crude product. It was purified by flash chromatography (12 g silica gel, 0-100% EtOAc in Hexane) to afford tert-butyl 3-((4R,8S)-5-(benzyloxy)-1-methyl-6-oxo-4,5,6,8-tetrahydro-1H-4,7-methanopyrazolo[3,4-e][1,3]diazepin-8-yl)-4,5-dihydroisoxazole-5-carboxylate (51 mg, 41%) as a white solid. MS: 454 ES+ (C$_{23}$H$_{27}$N$_5$O$_5$).

Int-23

A solution of tert-butyl 3-((4R,8S)-5-(benzyloxy)-1-methyl-6-oxo-4,5,6,8-tetrahydro-1H-4,7-methanopyrazolo[3,4-e][1,3]diazepin-8-yl)-4,5-dihydroisoxazole-5-carboxylate (Int-22, 41 mg, 0.094 mmol) in Acetone (10 mL) was purged with nitrogen 3 times, and 10% Pd/C (1 mg, 0.001 mmol) was added. The reaction mixture was purged with nitrogen 3 times and then stirred under hydrogen atmosphere at ambient temperature for 2 hours. The reaction mixture was filtered through Celite. The filtrate was concentrated to afford tert-butyl 3-((4R,8S)-5-hydroxy-1-methyl-6-oxo-4,5,6,8-tetrahydro-1H-4,7-methanopyrazolo[3,4-e][1,3]diazepin-8-yl)-4,5-dihydroisoxazole-5-carboxylate (32 mg, 97%) as a white solid. MS: 364 ES+ ($C_{16}H_{21}N_5O_5$).

Int-24

To a solution of tert-butyl 3-((4R,8S)-5-hydroxy-1-methyl-6-oxo-4,5,6,8-tetrahydro-1H-4,7-methanopyrazolo[3,4-e][1,3]diazepin-8-yl)-4,5-dihydroisoxazole-5-carboxylate (Int-23, 32 mg, 0.088 mmol) in pyridine (5 mL) at ambient temperature was added sulfur trioxide pyridine complex (112 mg, 0.70 mmol). The reaction mixture was stirred overnight, then concentrated under reduced pressure to give the crude product. It was purified by reversed phase chromatography (Sepabeads, 20 g, Acetonitrile/water=0/100 to 1/5) to afford tert-butyl 3-((4R,8S)-1-methyl-6-oxo-5-(sulfooxy)-4,5,6,8-tetrahydro-1H-4,7-methanopyrazolo[3,4-e][1,3]diazepin-8-yl)-4,5-dihydroisoxazole-5-carboxylate (17 mg, 43%) as a white solid. MS: 442 ES– ($C_{16}H_{21}N_5O_8S$).

Example 35

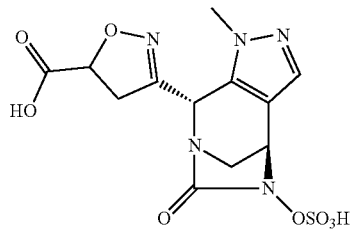

To a solution of tert-butyl 3-((4R,8S)-1-methyl-6-oxo-5-(sulfooxy)-4,5,6,8-tetrahydro-1H-4,7-methanopyrazolo[3,4-e][1,3]diazepin-8-yl)-4,5-dihydroisoxazole-5-carboxylate (Int-24, 17 mg, 0.038 mmol) in DCM (1 mL) at 0° C. was added TFA (1 mL, 13.05 mmol). The reaction mixture was stirred at 0° C. for 2 hours. Solvent was removed to give the crude product. It was dissolved in water and purified by reversed phase chromatography (Sepabeads, 12 g, 100% water) to afford the 3-((4R,8S)-1-methyl-6-oxo-5-(sulfooxy)-4,5,6,8-tetrahydro-1H-4,7-methanopyrazolo[3,4-e][1,3]diazepin-8-yl)-4,5-dihydroisoxazole-5-carboxylic acid (12 mg, 64%) as a white solid. MS: 386 ES– ($C_{12}H_{13}N_5O_8S$) $^1$H NMR (300 MHz, $D_2O$) δ: 3.26-3.34 (m, 2H); 2.52-3.68 (m, 5H); 4.72 (m, 1H); 4.85-5.02 (m, 1H); 5.55 (m, 1H); 7.53 (s, 1H).

Analytical Data for Additional Examples

All compounds in Table 3 were synthesized according to scheme 4 or using similar reactions easily known to a person skilled in the art. All compounds were isolated as trans racemic.

TABLE 3

| Ex. # | Structure | Calc. MW | MS | $^1$H NMR |
|---|---|---|---|---|
| 36 | Isomer 1 | 433.44 | ES + 434 | (300 MHz, DMSO-$d_6$) δ: 2.90 (m, 4H); 3.14 (m, 1H); 3.25 (m, 1H); 3.46 (s, 3H); 4.62 (m, 1H); 4.85 (m, 1H); 5.38 (s, 1H); 1.22 (m, 6H). |
| 37 | Isomer 2 | 433.44 | ES + 434 | (300 MHz, DMSO-$d_6$) δ: 2.82 (m, 2H); 3.02 (m, 1H); 3.22 (m, 1H); 3.50 (s, 3H); 4.54 (m, 1H); 4.93 (m, 1H); 5.36 (s, 1H); 7.23 (m, 6H). |

Scheme 5

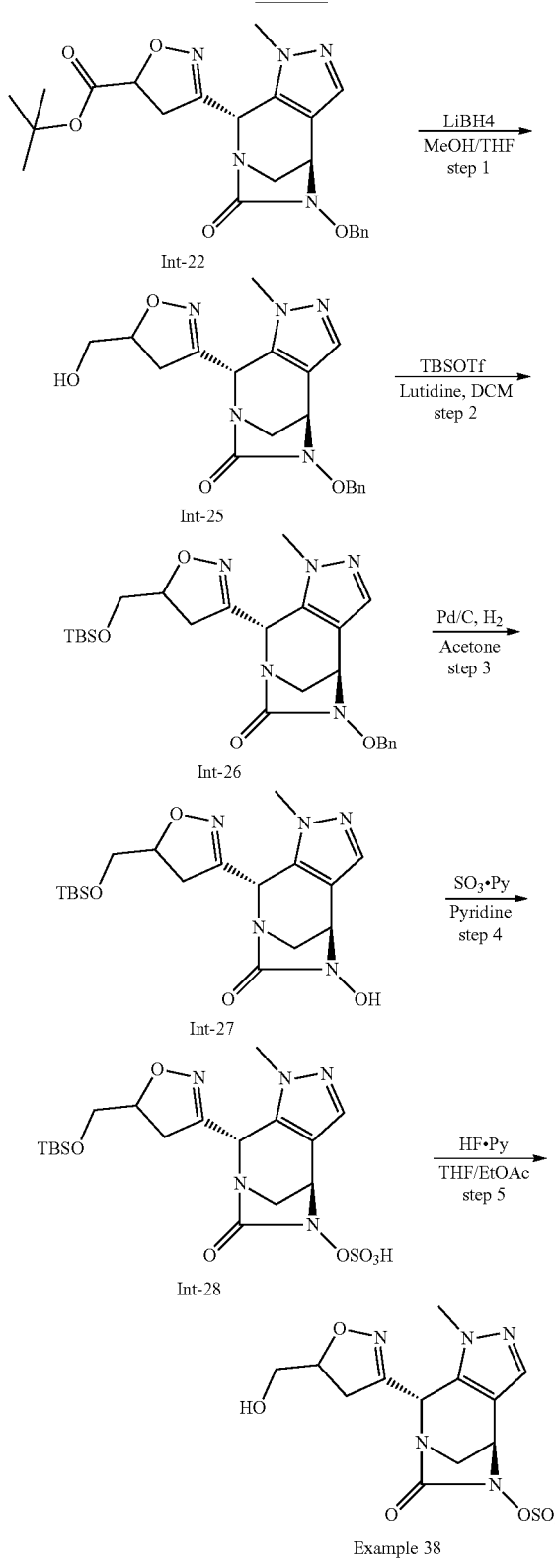

Int-25

To a solution of tert-butyl 3-((4R,8S)-5-(benzyloxy)-1-methyl-6-oxo-4,5,6,8-tetrahydro-1H-4,7-methanopyrazolo[3,4-e][1,3]diazepin-8-yl)-4,5-dihydroisoxazole-5-carboxylate (Int-22, 90 mg, 0.198 mmol) in MeOH (3 mL) and THF (6 mL) at −10° C. was added a solution of LiBH$_4$ (5.94 mL, 5.94 mmol) in THF (1 N). The reaction mixture was stirred at −10° C. for 2 hours. DCM (50 mL) and saturated ammonium chloride solution (50 mL) were added. The organic layer was separated, dried over anhydrous sodium sulfate and concentrated to give the crude product. It was purified by flash chromatography (12 g silica gel, 0-100% EtOAc in Hexane) to afford (4R,8S)-5-(benzyloxy)-8-(5-(hydroxymethyl)-4,5-dihydroisoxazol-3-yl)-1-methyl-1,4,5,8-tetrahydro-6H-4,7-methanopyrazolo[3,4-e][1,3]diazepin-6-one (40 mg, 52%) as a white solid. MS: 384 ES+ ($C_{19}H_{21}N_5O_4$).

Int 26

To a solution of (4R,8S)-5-(benzyloxy)-8-(5-(hydroxymethyl)-4,5-dihydroisoxazol-3-yl)-1-methyl-1,4,5,8-tetrahydro-6H-4,7-methanopyrazolo[3,4-e][1,3]diazepin-6-one (Int-25, 40 mg, 0.10 mmol) in DCM (10 mL) at room temperature was added 2,6-lutidine (0.01 mL, 0.13 mmol) and tert-butyldimethylsilyl trifluoromethanesulfonate (0.03 mL, 0.11 mmol). The reaction mixture was stirred at 35° C. for 2 hours. DCM (10 mL) and saturated ammonium chloride solution (10 mL) were added. The organic layer was separated, dried over anhydrous sodium sulfate and concentrated to give the crude product. It was purified by flash chromatography (12 g silica gel, 0-100% EtOAc in Hexane) to afford (4R,8S)-5-(benzyloxy)-8-(5-(((tert-butyldimethylsilyl)oxy)methyl)-4,5-dihydroisoxazol-3-yl)-1-methyl-1,4,5,8-tetrahydro-6H-4,7-methanopyrazolo[3,4-e][1,3]diazepin-6-one (50 mg, 96%) as a white solid. MS: 498 ES+ ($C_{25}H_{35}N_5O_4Si$).

Int 27

A solution of (4R,8S)-5-(benzyloxy)-8-(5-(((tert-butyldimethylsilyl)oxy)methyl)-4,5-dihydroisoxazol-3-yl)-1-methyl-1,4,5,8-tetrahydro-6H-4,7-methanopyrazolo[3,4-e][1,3]diazepin-6-one (Int-26, 50 mg, 0.10 mmol) in Acetone (10 mL) was purged with nitrogen 3 times, and 10% Pd/C (1 mg, 0.001 mmol) was added. The reaction mixture was purged with nitrogen 3 times and then stirred under hydrogen atmosphere at ambient temperature for 2 hours. The reaction mixture was filtered through Celite. The filtrate was concentrated to afford (4R,8S)-8-(5-(((tert-butyldimethylsilyl)oxy)methyl)-4,5-dihydroisoxazol-3-yl)-5-hydroxy-1-methyl-1,4,5,8-tetrahydro-6H-4,7-methanopyrazolo[3,4-e][1,3]diazepin-6-one (40 mg, 97%) as a white solid. MS: 408 ES+ ($C_{18}H_{29}N_5O_4Si$).

Int-28

To a solution of (4R,8S)-8-(5-(((tert-butyldimethylsilyl)oxy)methyl)-4,5-dihydroisoxazol-3-yl)-5-hydroxy-1-methyl-1,4,5,8-tetrahydro-6H-4,7-methanopyrazolo[3,4-e][1,3]diazepin-6-one (Int-27, 40 mg, 0.098 mmol) in pyridine (5 mL) at ambient temperature was added sulfur trioxide pyridine complex (125 mg, 0.785 mmol). The reaction mixture was stirred overnight, then concentrated under reduced pressure to give the crude product. It was purified by flash chromatography (silica gel, 4 g, 0-100% EtOAc in Hexane) to afford (4R,8S)-8-(5-(((tert-butyldimethylsilyl)oxy)methyl)-4,5-dihydroisoxazol-3-yl)-1-methyl-6-oxo-4, 8-dihydro-1H-4,7-methanopyrazolo[3,4-e][1,3]diazepin-5 (6H)-yl hydrogen sulfate (5 mg, 10%) as a white solid. MS: 486 ES– ($C_{18}H_{29}N_5O_7SiS$).

Example 38

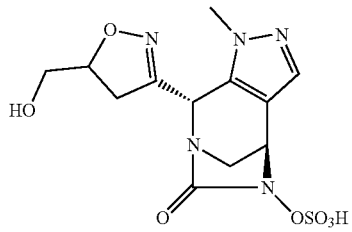

To a solution of (4R,8S)-8-(5-(((tert-butyldimethylsilyl) oxy)methyl)-4,5-dihydroisoxazol-3-yl)-1-methyl-6-oxo-4, 8-dihydro-1H-4,7-methanopyrazolo[3,4-e][1,3]diazepin-5 (6H)-yl hydrogen sulfate (Int-28, 5 mg, 0.0103 mmol) in ethyl acetate (2 mL) and THF (1 mL) at ambient temperature was added HF.Pyridine (0.001 mL, 0.09 mmol). The reaction mixture was stirred for 2 hours, then concentrated. The resulting solid was dissolved in water and purified by reversed phase chromatography (Sepabeads, 4 g, 100% water) to afford (4R,8S)-8-(5-(hydroxymethyl)-4,5-dihydroisoxazol-3-yl)-1-methyl-6-oxo-4,8-dihydro-1H-4,7-methanopyrazolo[3,4-e][1,3]diazepin-5(6H)-yl hydrogen sulfate (0.8 mg, 19%) as a white solid. MS: 372 ES– ($C_{12}H_{15}N_5O_7S$) $^1$H NMR (300 MHz, $D_2O$) δ: (300 MHz, $D_2O$) δ: 3.25-3.30 (m, 3H); 3.59-3.65 (m, 5H); 3.62-3.79 (m, 1H); 4.93 (m, 2H); 5.60 (m, 1H); 7.60 (s, 1H); 7.98 (m, 1H); 8.48 (m, 0.5H); 8.72 (m, 1H) compound/pyridine ratio (2:1).

Example 39

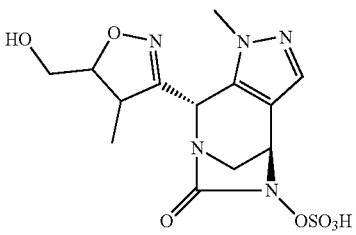

Pyridium (4R,8S)-8-(5-(hydroxymethyl)-4-methyl-4,5-dihydroisoxazol-3-yl)-1-methyl-6-oxo-4,8-dihydro-1H-4,7-methanopyrazolo[3,4-e][1,3]diazepin-5(6H)-yl hydrogen sulfate was synthesized by following similar a reaction sequence as shown for Example 38, using methyl (E)-but-2-enoate and KF.2H$_2$O in step 1 of Scheme 4. MS: 386 ES– ($C_{13}H_{17}N_5O_7S$) $^1$H NMR (300 MHz, $D_2O$) δ: 1.42 (d, 3H); 3.25 (m, 1H); 3.56 (m, 1H); 3.60 (m, 2H); 3.65 (s, 3H); 3.81 (m, 1H); 4.50 (m, 1H); 4.93 (m, 1H); 5.65 (m, 1H); 7.61 (s, 1H); 8.04 (m, 2H); 8.61 (m, 1H); 8.77 (m, 2H) compound/pyridine ratio (1:1).

Scheme 6

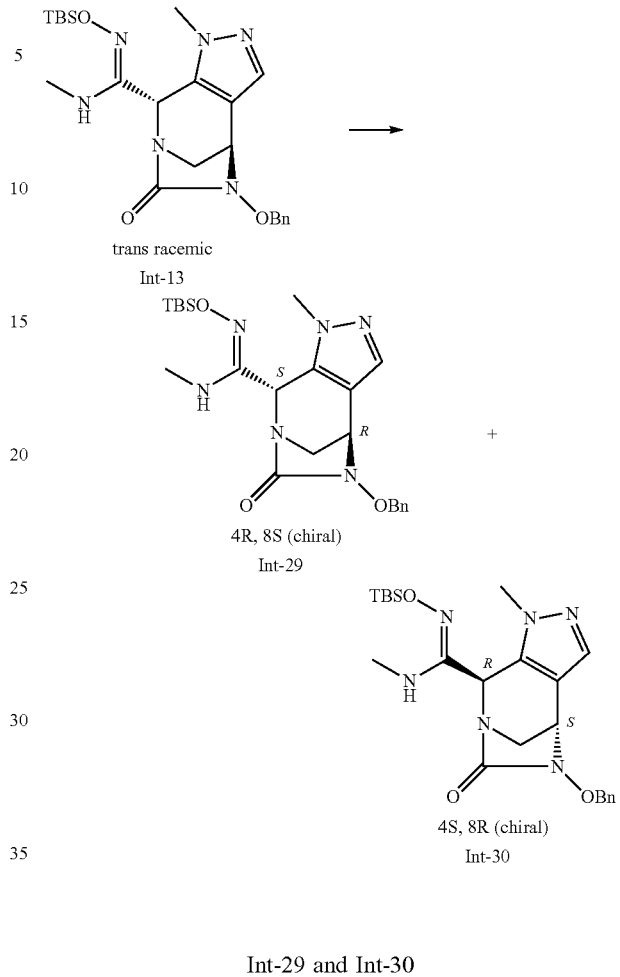

Int-29 and Int-30

Trans racemic (Z)-5-(benzyloxy)-N'-((tert-butyldimethylsilyl)oxy)-N,1-dimethyl-6-oxo-4,5,6,8-tetrahydro-1H-4,7-methanopyrazolo[3,4-e][1,3]diazepine-8-carboximidamide (Int-13, 8 g) was separated by SFC using a Chiralpak AD-H column, 25% isopropanol as $CO_2$ co-solvent at 75 g/min, system pressure 120 bar, column temperature 25° C. to afford:

Int-29: (4R*,8S*,Z)-5-(benzyloxy)-N'-((tert-butyldimethylsilyl)oxy)-N,1-dimethyl-6-oxo-4,5,6,8-tetrahydro-1H-4, 7-methanopyrazolo[3,4-e][1,3]diazepine-8-carboximidamide (Chiral, 3.06 g, 34%). MS: 471 ES+ ($C_{23}H_{34}N_6O_3Si$) $^1$H NMR (300 MHz, MeOD) δ: 0.01 (s, 6H); 0.81 (s, 9H); 3.07 (s, 3H); 3.32 (m, 1H); 3.47 (m, 1H); 3.62 (s, 3H); 4.31 (m, 1H); 4.95 (m, 2H); 5.48 (m, 1H); 7.35-7.44 (m, 6H). ee >99%.

Int-30: (4S*,8R*,Z)-5-(benzyloxy)-N'-((tert-butyldimethylsilyl)oxy)-N,1-dimethyl-6-oxo-4,5,6,8-tetrahydro-1H-4, 7-methanopyrazolo[3,4-e][1,3]diazepine-8-carboximidamide (Chiral, 2.38 g, 26%). MS: 471 ES+ ($C_{23}H_{34}N_6O_3Si$) $^1$H NMR (300 MHz, MeOD) δ: 0.01 (s, 6H); 0.81 (s, 9H); 3.07 (s, 3H); 3.32 (m, 1H); 3.47 (m, 1H); 3.62 (s, 3H); 4.31 (m, 1H); 4.95 (m, 2H); 5.48 (m, 1H); 7.35-7.44 (m, 6H). ee >99%.

Example 40

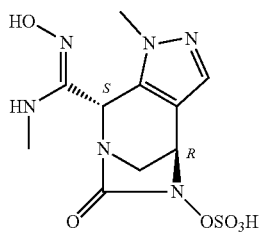

Sodium (4R*,8S*)-8-((Z)—N'-hydroxy-N-methylcarbamimidoyl)-1-methyl-6-oxo-4,8-dihydro-1H-4,7-methanopyrazolo[3,4-e][1,3]diazepin-5(6H)-yl hydrogen sulfate (chiral) was synthesized by following a similar reaction sequence as shown for Example 1, using Int-29 in step 14 of Scheme 1. MS: 345 ES– ($C_{10}H_{14}N_6O_6S$) $^1$H NMR (300 MHz, $D_2O$) δ: 3.08 (s, 3H); 3.52 (m, 2H); 3.61 (s, 3H); 4.93 (m, 1H); 5.69 (s, 1H); 7.60 (s, 1H). Absolute stereochemistry was confirmed by crystallography.

Example 41

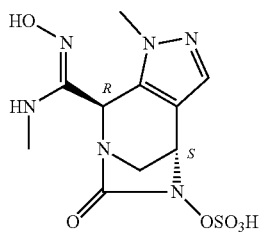

Sodium (4S*,8R*)-8-((Z)—N'-hydroxy-N-methylcarbamimidoyl)-1-methyl-6-oxo-4,8-dihydro-1H-4,7-methanopyrazolo[3,4-e][1,3]diazepin-5(6H)-yl hydrogen sulfate (chiral) was synthesized by following a similar reaction sequence as shown for Example 1, using Int-30 in step 14 of Scheme 1. MS: 345 ES– ($C_{10}H_{14}N_6O_6S$) $^1$H NMR (300 MHz, $D_2O$) δ: 3.05 (s, 3H); 3.52 (m, 2H); 3.60 (s, 3H); 4.92 (m, 1H); 5.68 (s, 1H); 7.58 (s, 1H).

Example 42

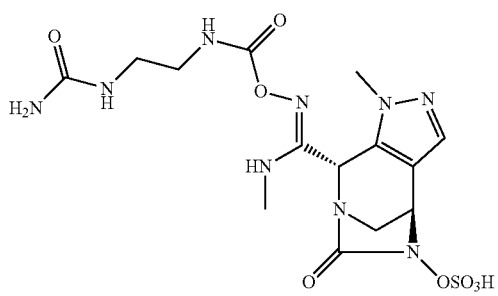

To a solution of (4R,8S)-8-((Z)—N'-(((2-aminoethyl)carbamoyl)oxy)-N-methylcarbamimidoyl)-1-methyl-6-oxo-4,8-dihydro-1H-4,7-methanopyrazolo[3,4-e][1,3]diazepin-5(6H)-yl hydrogen sulfate (Example 18, 8.3 mg, 0.0192 mmol) in Pyridine (0.5 mL) at 0° C. was added trimethylsilylisocyanate (2.35 mg, 0.0192 mmol). The reaction mixture was stirred at 0° C. for 2 hours. Solvent was removed to give the crude product. It was dissolved in water and purified by reversed phase chromatography (Sepabeads, 4 g, 100% water) to afford (4R,8S)-1-methyl-8-((Z)—N-methyl-N'-(((2-ureidoethyl)carbamoyl)oxy)carbamimidoyl)-6-oxo-4,8-dihydro-1H-4,7-methanopyrazolo[3,4-e][1,3]diazepin-5(6H)-yl hydrogen sulfate (2 mg, 19%) as a white solid. MS: 474 ES– ($C_{14}H_{21}N_9O_8S$) $^1$H NMR (300 MHz, $D_2O$) δ: 3.05 (s, 3H); 3.14 (m, 4H); 3.57 (m, 2H); 3.63 (s, 3H); 4.90 (m, 1H); 5.72 (m, 1H); 7.59 (s, 1H).

Example 43

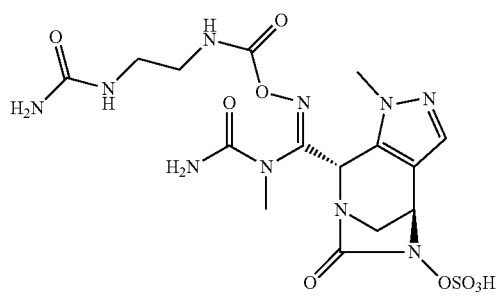

Example 43 was synthesized by following similar reaction conditions as in Example 42. Taking (4R,8S)-8-((Z)—N'-(((2-aminoethyl)carbamoyl)oxy)-N-methylcarbamimidoyl)-1-methyl-6-oxo-4,8-dihydro-1H-4,7-methanopyrazolo[3,4-e][1,3]diazepin-5(6H)-yl hydrogen sulfate (Example 18, 8.3 mg, 0.0192 mmol) as the substrate, to afford (4R,8S)-8-((Z)—N-carbamoyl-N-methyl-N'-(((2-ureidoethyl)carbamoyl)oxy)carbamimidoyl)-1-methyl-6-oxo-4,8-dihydro-1H-4,7-methanopyrazolo[3,4-e][1,3]diazepin-5(6H)-yl hydrogen sulfate (0.7 mg, 6%) as a white solid. MS: 517 ES– ($C_{15}H_{22}N_{10}O_9S$) $^1$H NMR (300 MHz, $D_2O$) δ: 3.05 (s, 3H); 3.24 (m, 4H); 3.56 (m, 2H); 3.62 (s, 3H); 4.90 (m, 1H); 5.71 (m, 1H); 7.58 (s, 1H).

Example 44

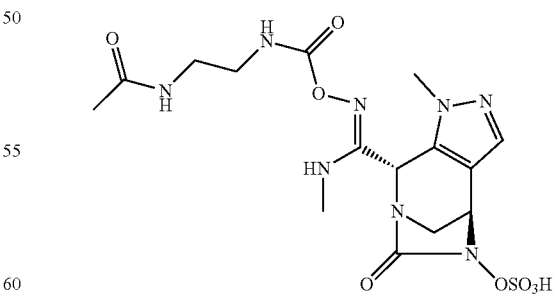

Example 44 was synthesized by following similar reaction conditions as shown for Example 42. Taking (4R,8S)-8-((Z)—N'-(((2-aminoethyl)carbamoyl)oxy)-N-methylcarbamimidoyl)-1-methyl-6-oxo-4,8-dihydro-1H-4,7-methanopyrazolo[3,4-e][1,3]diazepin-5(6H)-yl hydrogen sulfate (Example 18, 8 mg, 0.0185 mmol) as the substrate, and acetyl chloride (0.001 mL, 0.0185 mmol) as reagent to afford (4R,8S)-8-((Z)—N'-(((2-acetamidoethyl)carbamoyl)oxy)-N-methylcarbamimidoyl)-1-methyl-6-oxo-4,8-dihydro-1H-4,7-methanopyrazolo[3,4-e][1,3]diazepin-5(6H)-yl hydrogen sulfate (4 mg, 41%) as a white solid. MS: 473 ES− (C$_{15}$H$_{22}$N$_8$O$_8$S) $^1$H NMR (300 MHz, D$_2$O) δ: 1.88 (s, 3H); 3.05 (2, 3H); 3.19 (m, 4H); 3.57 (m, 2H); 3.62 (s, 3H); 4.90 (m, 1H); 5.71 (m, 1H); 7.59 (s, 1H); 8.01 (m, 1H); 8.55 (m, 0.5H); 8.72 (m, 1H) compound/pyridine ratio (2:1).

Example 45

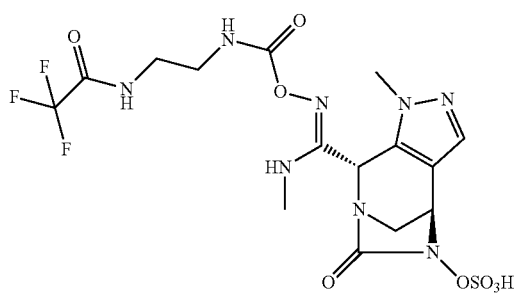

To a solution of (4R,8S)-8-((Z)—N'-(((4-aminobutyl)carbamoyl)oxy)-N-methylcarbamimidoyl)-1-methyl-6-oxo-4,8-dihydro-1H-4,7-methanopyrazolo[3,4-e][1,3]diazepin-5(6H)-yl hydrogen sulfate (Int-19, 70 mg, 0.125 mmol) in DCM (10 mL) at 0° C. was added TFA (0.956 mL, 12.48 mmol), The reaction mixture was stirred at 0° C. for 2 hours. Solvent was removed. The residue was dissolved in water and purified by reversed phase chromatography (40 g Sepabeads, 100% water) to afford (4R,8S)-1-methyl-8-((Z)—N-methyl-N'-(((4-(2,2,2-trifluoroacetamido)butyl)carbamoyl)oxy)carbamimidoyl)-6-oxo-4,8-dihydro-1H-4,7-methanopyrazolo[3,4-e][1,3]diazepin-5(6H)-yl hydrogen sulfate (48 mg, 59%) as a white solid. MS: 555 ES− (C$_{17}$H$_{23}$F$_3$N$_8$O$_8$S) $^1$H NMR (300 MHz, D$_2$O) δ: 1.47 (m, 4H); 3.05-3.25 (m, 7H); 3.57-3.69 (m, 5H); 4.95 (m, 1H); 5.75 (m, 1H); 7.59 (s, 1H).

Scheme 7

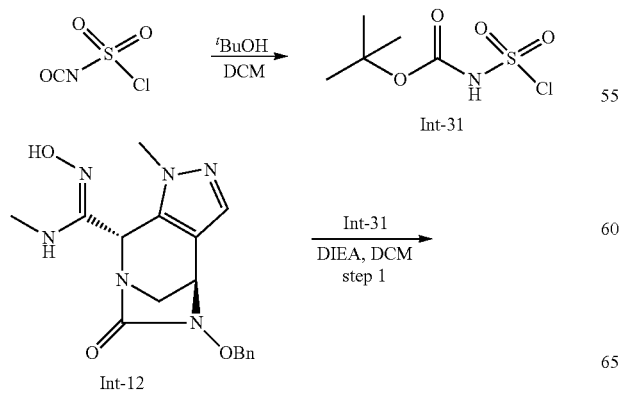

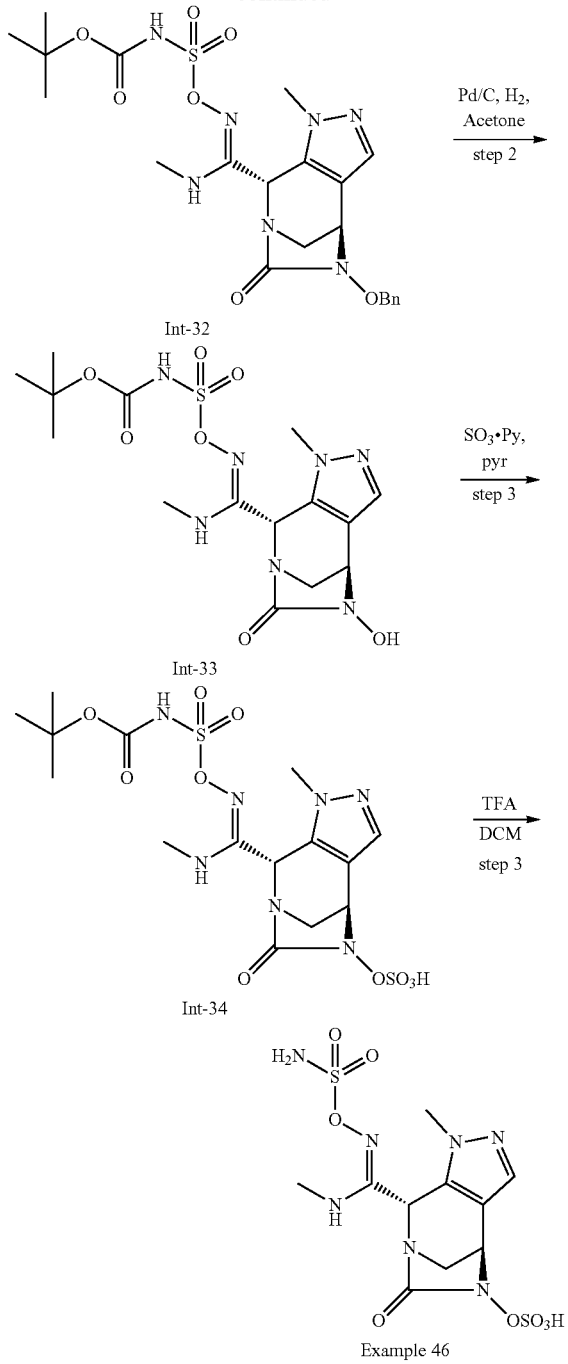

Int-31

To a stirred solution of tert-butanol (1.9 mL, 20 mmol) in DCM (12 mL) at 0° C. was added chlorosulfonyl isocyanate (1.4 mL, 15 mmol) dropwise over the course of 10 minutes. After stirring at 0° C. for 5 minutes, the reaction mixture was warmed up to room temperature and stirred for 20 minutes. It was concentrated in vacuo to one-third volume. The flask was placed back into the 0° C. bath, and the product crystallized out of solution. After 50 min, the product was filtered and washed with hexanes (20 mL) to afford tert-butyl (chlorosulfonyl)carbamate (1.41 g, 40%) as a white solid. It was used immediately in the next step.

Int-32

To a stirred solution of (4R,8S,Z)-5-(benzyloxy)-N'-hydroxy-N,1-dimethyl-6-oxo-4,5,6,8-tetrahydro-1H-4,7-methanopyrazolo[3,4-e][1,3]diazepine-8-carboximidamide (Int-12, 248 mg, 0.696 mmol) in DCM (30 mL) at 0° C. was added tert-butyl (chlorosulfonyl)carbamate (Int-31, 225 mg, 1.044 mmol), followed by DIEA (0.36 mL, 2.09 mmol). The reaction mixture was stirred at 0° C. for 16 hours. Saturated ammonium chloride solution (20 mL) and DCM (20 mL) were added to the reaction mixture. The organic layer was separated, dried over anhydrous sodium sulfate, and concentrated to give the crude product. It was purified by flash chromatography (4 g, 0-100% EtOAc in Hexanes) to afford tert-butyl (((((Z)-((4R,8S)-5-(benzyloxy)-1-methyl-6-oxo-4,5,6,8-tetrahydro-1H-4,7-methanopyrazolo[3,4-e][1,3]diazepin-8-yl)(methylamino)methylene)amino)oxy)sulfonyl)carbamate (88 mg, 24%) as a white solid. MS: 536 ES+ ($C_{22}H_{29}N_7O_7S$).

Int-33

A solution of tert-butyl (((((Z)-((4R,8S)-5-(benzyloxy)-1-methyl-6-oxo-4,5,6,8-tetrahydro-1H-4,7-methanopyrazolo[3,4-e][1,3]diazepin-8-yl)(methylamino)methylene)amino)oxy)sulfonyl)carbamate (Int-32, 88 mg, 0.164 mmol) in Acetone (20 mL) was purged with nitrogen 3 times, and 10% Pd/C (1.7 mg, 0.0016 mmol) was added. The reaction mixture was purged with nitrogen 3 times and then stirred under hydrogen atmosphere at ambient temperature for 2 hours. The reaction mixture was filtered through Celite. The filtrate was concentrated to afford tert-butyl (((((Z)-((4R,8S)-5-hydroxy-1-methyl-6-oxo-4,5,6,8-tetrahydro-1H-4,7-methanopyrazolo[3,4-e][1,3]diazepin-8-yl)(methylamino)methylene)amino)oxy)sulfonyl)carbamate (60 mg, 82%) as a white solid. MS: 446 ES+ ($C_{15}H_{23}N_7O_7S$).

Int-34

To a solution of tert-butyl (((((Z)-((4R,8S)-5-hydroxy-1-methyl-6-oxo-4,5,6,8-tetrahydro-1H-4,7-methanopyrazolo[3,4-e][1,3]diazepin-8-yl)(methylamino)methylene)amino)oxy)sulfonyl)carbamate (Int-33, 60 mg, 0.135 mmol) in pyridine (10 mL) at ambient temperature was added sulfur trioxide pyridine complex (172 mg, 1.078 mmol). The reaction mixture was stirred overnight, then concentrated under reduced pressure to give the crude product. It was purified by flash chromatography (silica gel, 4 g, 0-100% EtOAc in Hexane, then Acetone) to afford (4R,8S)-8-((Z)—N'—((N-(tert-butoxycarbonyl) sulfamoyl)oxy)-N-methylcarbamimidoyl)-1-methyl-6-oxo-4,8-dihydro-1H-4,7-methanopyrazolo[3,4-e][1,3]diazepin-5(6H)-yl hydrogen sulfate (70 mg, 99%) as a white solid. MS: 524 ES– ($C_{15}H_{23}N_7O_{10}S_2$).

Example 46

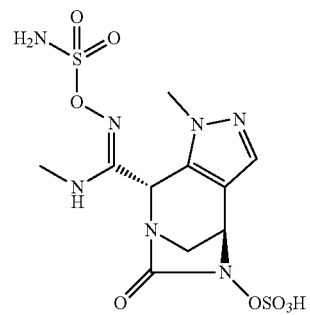

To a stirred solution of (4R,8S)-8-((Z)—N'—((N-(tert-butoxycarbonyl) sulfamoyl)oxy)-N-methylcarbamimidoyl)-1-methyl-6-oxo-4,8-dihydro-1H-4,7-methanopyrazolo[3,4-e][1,3]diazepin-5(6H)-yl hydrogen sulfate (Int-34, 50 mg, 0.095 mmol) in DCM (0.5 mL) at 0° C. was added TFA (2.7 mL, 36.3 mmol). The reaction mixture was stirred at 0° C. for 2 hours. Solvent was removed to give the crude product. It was dissolved in water and purified by reversed phase chromatography (Sepabeads, 12 g, 100% water) to afford (4R,8S)-1-methyl-8-((Z)—N-methyl-N'-(sulfamoyloxy)carbamimidoyl)-6-oxo-4,8-dihydro-1H-4,7-methanopyrazolo[3,4-e][1,3]diazepin-5(6H)-yl hydrogen sulfate (8 mg, 17%) as a white solid. MS: 424 ES– ($C_{10}H_{15}N_7O_8S_2$) $^1$H NMR (300 MHz, $D_2O$) δ: (300 MHz, $D_2O$) δ: 3.14 (s, 3H); 3.65-3.76 (m, 5H); 4.98 (m, 1H); 5.85 (m, 1H); 7.67 (s, 1H); 8.11 (m, 4H); 8.63 (m, 2H); 8.82 (m, 4H) compound/pyridine/TFA ratio (1:2:1).

Scheme 8

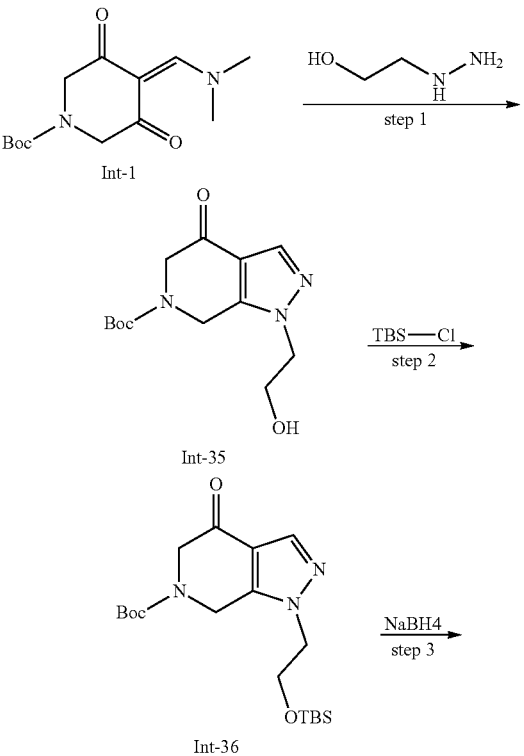

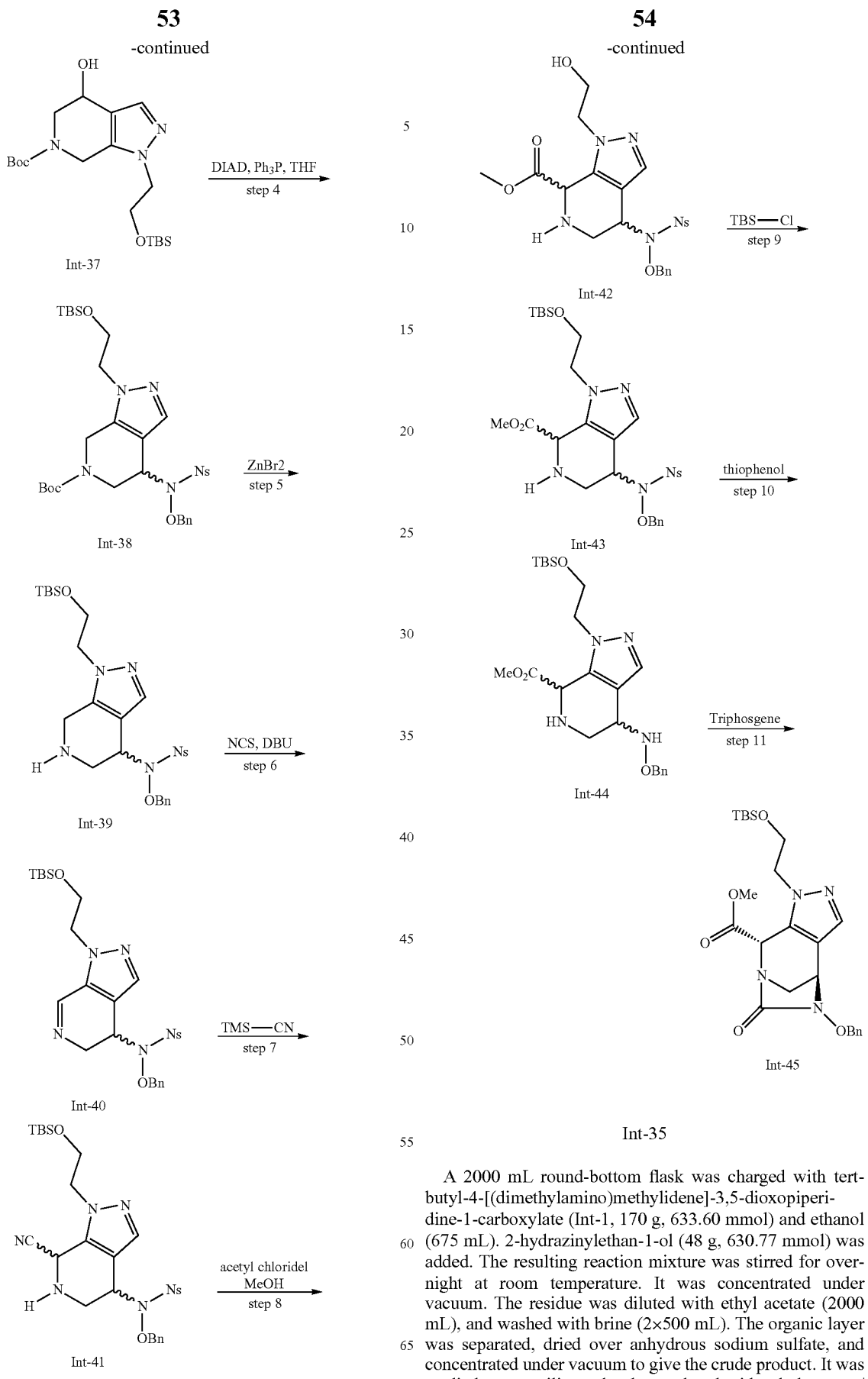

Int-35

A 2000 mL round-bottom flask was charged with tert-butyl-4-[(dimethylamino)methylidene]-3,5-dioxopiperidine-1-carboxylate (Int-1, 170 g, 633.60 mmol) and ethanol (675 mL). 2-hydrazinylethan-1-ol (48 g, 630.77 mmol) was added. The resulting reaction mixture was stirred for overnight at room temperature. It was concentrated under vacuum. The residue was diluted with ethyl acetate (2000 mL), and washed with brine (2×500 mL). The organic layer was separated, dried over anhydrous sodium sulfate, and concentrated under vacuum to give the crude product. It was applied onto a silica gel column eluted with ethyl acetate/ petroleum ether to afford tert-butyl 1-(2-hydroxyethyl)-4-oxo-1,4,5,7-tetrahydro-6H-pyrazolo[3,4-c]pyridine-6-carboxylate (95 g, 53%) as a light yellow oil. MS: 282 ES+ ($C_{13}H_{19}N_3O_4$).

Int-36

A 2000-mL round-bottom flask was charged with 1-(2-hydroxyethyl)-4-oxo-1,4,5,7-tetrahydro-6H-pyrazolo[3,4-c]pyridine-6-carboxylate (Int-35, 95 g, 337.71 mmol), imidazole (46 g, 676.47 mmol), and DCM (1000 mL) at 0° C. A solution of tert-butyl(chloro)dimethylsilane (66 g, 437.89 mmol) in DCM (100 mL) was added dropwise. The reaction mixture was stirred for overnight at room temperature. The resulting mixture was washed with brine (2×500 mL). The organic layer was separated, dried over anhydrous sodium sulfate and concentrated under vacuum. The residue was applied onto a silica gel column and eluted with ethyl acetate/petroleum ether to afford tert-butyl 1-(2-((tert-butyldimethylsilyl)oxy)ethyl)-4-oxo-1,4,5,7-tetrahydro-6H-pyrazolo[3,4-c]pyridine-6-carboxylate (130 g, 97%) as a white solid. MS: 396 ES+ ($C_{19}H_{33}N_3O_4Si$).

Int-37

A 2000-mL round-bottom flask was charged with tert-butyl 1-(2-((tert-butyldimethylsilyl)oxy)ethyl)-4-oxo-1,4,5,7-tetrahydro-6H-pyrazolo[3,4-c]pyridine-6-carboxylate (Int-36, 73 g, 184.54 mmol), MeOH (365 mL), and THF (730 mL) at 0° C. NaBH$_4$ (7 g, 185 mmol) was added. The resulting reaction mixture was stirred for 2 hours at 0° C. It was then quenched by the addition of water (1000 mL). The resulting solution was extracted with EtOAc (3×1000 mL). The combined organic layer was washed with brine (2×500 mL), separated, dried over anhydrous sodium sulfate, and concentrated under vacuum to afford tert-butyl 1-(2-((tert-butyldimethylsilyl)oxy)ethyl)-4-hydroxy-1,4,5,7-tetrahydro-6H-pyrazolo[3,4-c]pyridine-6-carboxylate (77.5 g, quantitative yield) as light yellow oil. MS: 398 ES+ ($C_{19}H_{35}N_3O_4Si$).

Int-38

A 2000-mL round-bottom flask was charged with tert-butyl 1-(2-((tert-butyldimethylsilyl)oxy)ethyl)-4-hydroxy-1,4,5,7-tetrahydro-6H-pyrazolo[3,4-c]pyridine-6-carboxylate (Int-37, 51 g, 128 mmol), N-(benzyloxy)-2-nitrobenzene-1-sulfonamide (59 g, 191 mmol), PPh3 (67 g, 255 mmol) and THF (1000 mL) at 0° C. A solution of DIAD (52 g, 255 mmol) in THF (100 mL) was added dropwise. The resulting reaction mixture was stirred for overnight at room temperature and concentrated under vacuum. The residue was applied onto a silica gel column and eluted with ethyl acetate/petroleum ether to afford tert-butyl 4-((N-(benzyloxy)-4-nitrophenyl) sulfonamido)-1-(2-((tert-butyldimethylsilyl)oxy)ethyl)-1,4,5,7-tetrahydro-6H-pyrazolo[3,4-c]pyridine-6-carboxylate (68 g, 77%) as a light yellow oil. MS: 688 ES+ ($C_{32}H_{45}N_5O_8SSi$).

Int-39

A 2000-mL round-bottom flask was charged with tert-butyl 4-((N-(benzyloxy)-4-nitrophenyl) sulfonamido)-1-(2-((tert-butyldimethylsilyl)oxy)ethyl)-1,4,5,7-tetrahydro-6H-pyrazolo[3,4-c]pyridine-6-carboxylate (Int-38, 68 g, 98.85 mmol), DCM (680 mL), and ZnBr$_2$ (67 g, 296.55 mmol). The reaction mixture was stirred for 2 days at room temperature. The solids were filtered out. The reaction was then quenched by the addition of saturated ammonium chloride solution (500 mL) and extracted with DCM (3×500 mL). The organic layers were combined, dried over anhydrous sodium sulfate, and concentrated under vacuum. The residue was applied onto a silica gel column and eluted with ethyl acetate/petroleum ether to afford N-(benzyloxy)-N-(1-(2-((tert-butyldimethylsilyl)oxy)ethyl)-4,5,6,7-tetrahydro-1H-pyrazolo[3,4-c]pyridin-4-yl)-4-nitrobenzenesulfonamide (55 g, 94.7%) as light yellow oil. MS: 588 ES+ ($C_{27}H_{37}N_5O_6SSi$).

Int-40

A 2000-mL round-bottom flask was charged with N-(benzyloxy)-N-(1-(2-((tert-butyldimethylsilyl)oxy)ethyl)-4,5,6,7-tetrahydro-1H-pyrazolo[3,4-c]pyridin-4-yl)-4-nitrobenzenesulfonamide (Int-39, 53 g, 90.17 mmol) and DCM (530 mL) at 0° C. NCS (15.7 g, 117.22 mmol) was added. The reaction mixture was stirred for 1.5 hours at room temperature and then cooled to 0° C. DBU (20.6 g, 135.25 mmol) was added, the reaction mixture was allowed to warm to room temperature and stirred for an additional 3 hours. The resulting solution was used in next reaction without further purification. MS: 586 ES+ ($C_{27}H_{35}N_5O_6SSi$).

Int-41

TMSCN (35.7 g, 360.7 mmol) was added to the solution of N-(benzyloxy)-N-(1-(2-((tert-butyldimethylsilyl)oxy)ethyl)-4,5-dihydro-1H-pyrazolo[3,4-c]pyridin-4-yl)-4-nitrobenzenesulfonamide (Int-40). The reaction mixture was stirred for overnight at room temperature. It was diluted with saturated aqueous sodium bicarbonate solution (500 mL) and extracted with DCM (2×500 mL). The organic extracts were combined, dried over anhydrous sodium sulfate, and concentrated under vacuum. The residue was applied onto a silica gel column and eluted with ethyl acetate/petroleum ether to afford N-(benzyloxy)-N-(1-(2-((tert-butyldimethylsilyl)oxy)ethyl)-7-cyano-4,5,6,7-tetrahydro-1H-pyrazolo[3,4-c]pyridin-4-yl)-4-nitrobenzenesulfonamide (46 g, 83%) as light brown oil. MS: 613 ES+ ($C_{28}H_{36}N_6O_6SSi$).

Int-42

A 1000-mL round-bottom flask was charged with N-(benzyloxy)-N-(1-(2-((tert-butyldimethylsilyl)oxy)ethyl)-7-cyano-4,5,6,7-tetrahydro-1H-pyrazolo[3,4-c]pyridin-4-yl)-4-nitrobenzenesulfonamide (Int-41, 44.7 g, 72.95 mmol) and methanol (450 mL) at 0° C. Acetyl chloride (148 g, 1896 mmol) was added dropwise. The resulting reaction mixture was stirred for 1 hour at room temperature, and then 2 hours at 55° C. It was cooled to room temperature. The pH value of the reaction mixture was adjusted to 9 with saturated aqueous sodium bicarbonate solution and extracted with ethyl acetate (3×50 mL). The organic extracts were combined, dried over anhydrous sodium sulfate, and concentrated under vacuum to afford methyl 4-((N-(benzyloxy)-4-nitrophenyl)sulfonamido)-1-(2-hydroxyethyl)-4,5,6,7-tetrahydro-1H-pyrazolo[3,4-c]pyridine-7-carboxylate (38 g, 98%) as brown oil. MS: 532 ES+ ($C_{23}H_{25}N_5O_8S$).

Int-43

A 1000-mL round-bottom flask was charged with methyl 4-((N-(benzyloxy)-4-nitrophenyl) sulfonamido)-1-(2-hydroxyethyl)-4,5,6,7-tetrahydro-1H-pyrazolo[3,4-c]pyridine-7-carboxylate (Int-42, 38 g, 71.49 mmol), DCM (380 mL), and imidazole (9.7 g, 142.98 mmol) at 0° C. A solution of TBSCl (14 g, 92.94 mmol) in DCM (50 mL) was added dropwise. The resulting reaction mixture was stirred for overnight at room temperature. It was washed with brine (2×500 mL). The organic extract was dried over anhydrous sodium sulfate and concentrated under vacuum. The residue was applied onto a silica gel column and eluted with ethyl acetate/petroleum ether to afford methyl 4-((N-(benzyloxy)-4-nitrophenyl) sulfonamido)-1-(2-((tert-butyldimethylsilyl)oxy)ethyl)-4,5,6,7-tetrahydro-1H-pyrazolo[3,4-c]pyridine-7-carboxylate (39 g, 85%) as yellow oil. MS: 646 ES+ ($C_{29}H_{39}N_5O_8SSi$).

Int-44

A 250 mL round-bottom flask was charged with 4-((N-(benzyloxy)-4-nitrophenyl) sulfonamido)-1-(2-((tert-butyldimethylsilyl)oxy)ethyl)-4,5,6,7-tetrahydro-1H-pyrazolo[3,4-c]pyridine-7-carboxylate (Int-43, 10 g, 15.48 mmol)), DMF (100 mL), thioglycolic acid (3.56 g, 30.96 mmol) and LiOH (1.86 g, 77.40 mmol). The reaction mixture was stirred for 1 hour at room temperature, and diluted with EtOAc (200 mL). It was washed with brine (200 mL). The aqueous layer was extracted with EtOAc (100 mL) and the organic layers combined. The organic extract was washed with brine (5×100 mL), dried over anhydrous sodium sulfate, and concentrated under vacuum. The residue was applied onto a silica gel column and eluted with ethyl acetate/petroleum ether to afford methyl 4-((benzyloxy)amino)-1-(2-((tert-butyldimethylsilyl)oxy)ethyl)-4,5,6,7-tetrahydro-1H-pyrazolo[3,4-c]pyridine-7-carboxylate (5.4 g, 76%) as yellow oil. MS: 461 ES+ ($C_{23}H_{36}N_4O_4Si$).

Int-45

A 2000-mL round-bottom flask was charged with methyl 4-((benzyloxy)amino)-1-(2-((tert-butyldimethylsilyl)oxy)ethyl)-4,5,6,7-tetrahydro-1H-pyrazolo[3,4-c]pyridine-7-carboxylate (Int-44, 27 g, 58.61 mmol), Acetonitrile (540 mL), DIEA (30 g, 234.44 mmol) at 0° C. A solution of triphosgene (7 g, 23.44 mmol) in Acetonitrile (100 mL) was added dropwise to the reaction mixture with stirring in 2 hours, followed by 4-dimethylaminopyridine (1.4 g, 11.72 mmol). The resulting reaction mixture was stirred for overnight at room temperature, and concentrated under vacuum. It was diluted with EtOAc (500 mL) and washed with brine (2×100 mL). The organic layer was separated, dried over anhydrous sodium sulfate, and concentrated to give the crude product. It was applied onto a silica gel column, eluted with ethyl acetate/petroleum ether, to afford methyl (4R,8S)-5-(benzyloxy)-1-(2-((tert-butyldimethylsilyl)oxy)ethyl)-6-oxo-4,5,6,8-tetrahydro-1H-4,7-methanopyrazolo[3,4-e][1,3]diazepine-8-carboxylate (16 g, 56%). MS: 487 ES+ ($C_{24}H_{34}N_4O_5Si$).

Scheme 9

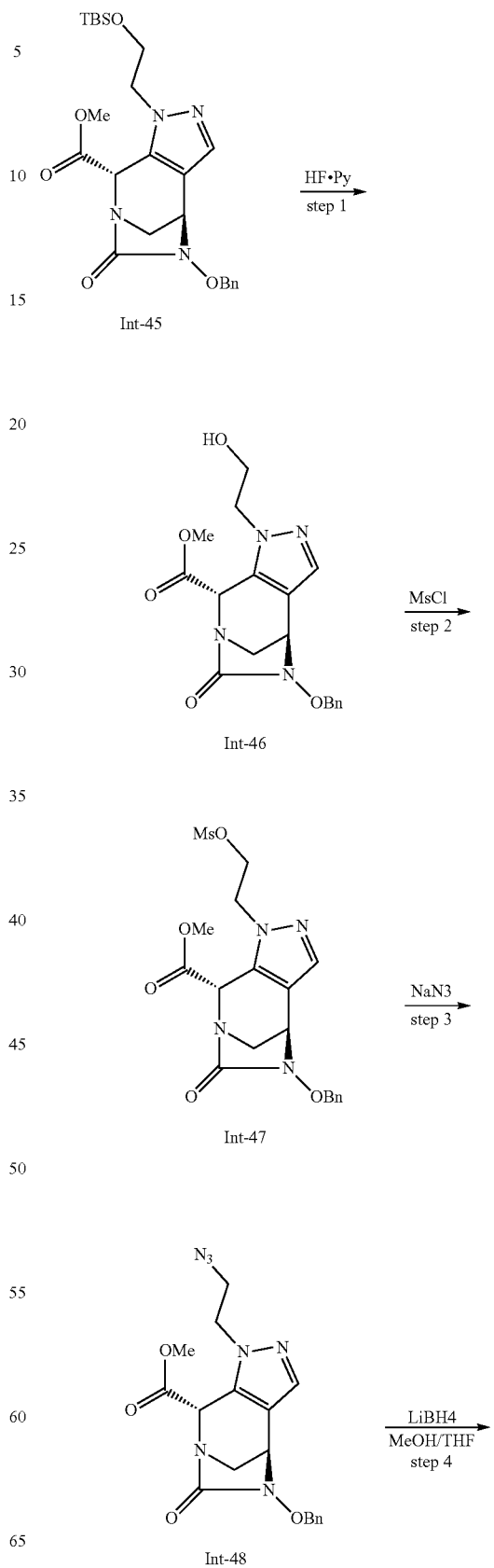

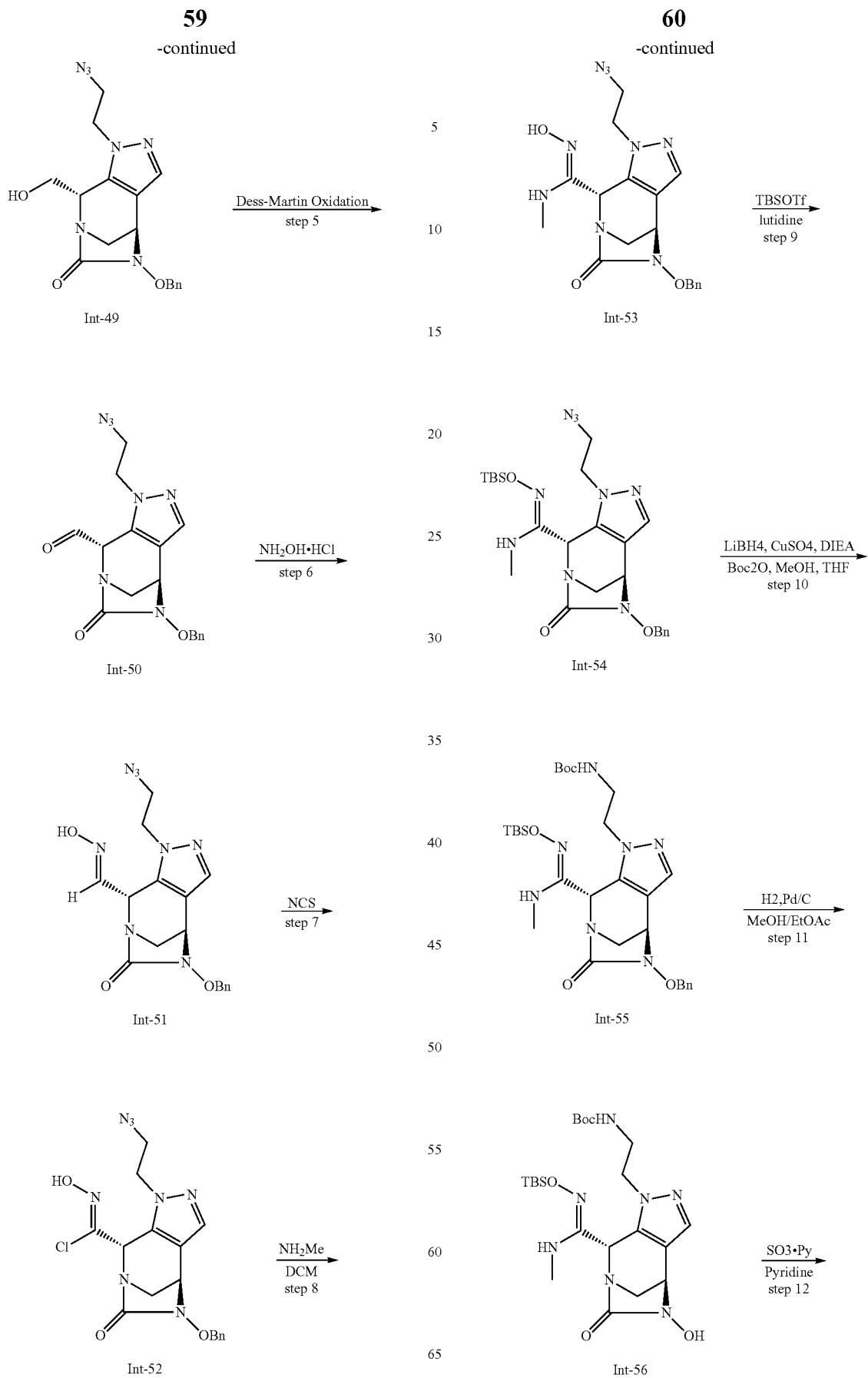

-continued

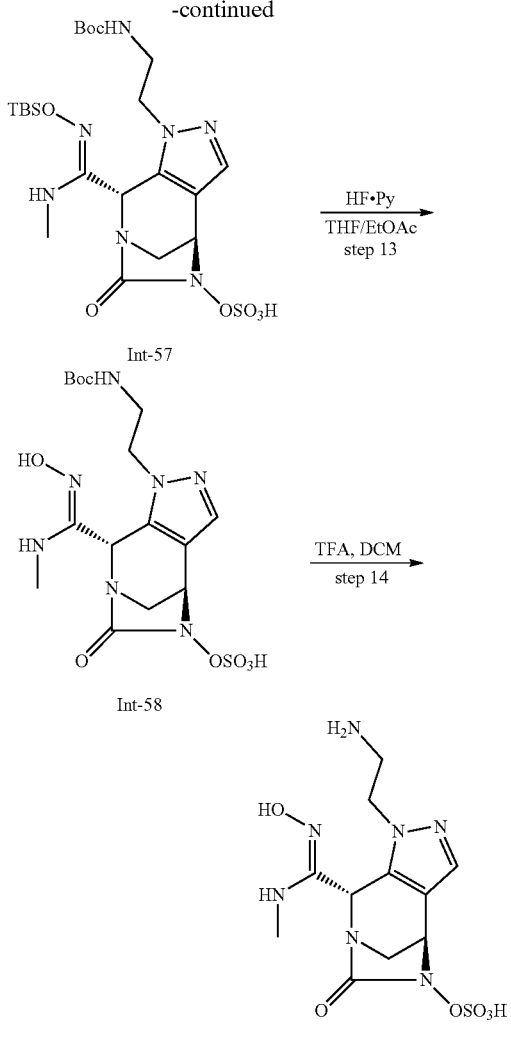

Int 46

A 250-mL round-bottom flask was charged with methyl (4R,8S)-5-(benzyloxy)-1-(2-((tert-butyldimethylsilyl)oxy)ethyl)-6-oxo-4,5,6,8-tetrahydro-1H-4,7-methanopyrazolo[3,4-e][1,3]diazepine-8-carboxylate (Int-45, 3820 mg, 7.85 mmol), HF.Pyridine (0.32 mL, 8.63 mmol), and EtOAc (100 mL). The reaction mixture was stirred at room temperature for 3 hours. Saturated aqueous ammonium chloride solution (100 mL) and EtOAc (100 mL) were added. The organic layer was separated, dried over anhydrous sodium sulfate and concentrated to give the crude product. It was triturated with EtOAc (20 mL). Precipitate was filtered and washed with EtOAc (5 mL) to afford methyl (4R,8S)-5-(benzyloxy)-1-(2-hydroxyethyl)-6-oxo-4,5,6,8-tetrahydro-1H-4,7-methanopyrazolo[3,4-e][1,3]diazepine-8-carboxylate (2724 mg, 93%) as a white solid. MS: 373 ES+ ($C_{18}H_{20}N_4O_5$).

Int-47

A 100-mL round-bottom flask was charged with methyl (4R,8S)-5-(benzyloxy)-1-(2-hydroxyethyl)-6-oxo-4,5,6,8-tetrahydro-1H-4,7-methanopyrazolo[3,4-e][1,3]diazepine-8-carboxylate (Int-46, 1910 mg, 5.13 mmol), DCM (30 mL) at 0° C. A solution of methanesulfonyl chloride (0.48 mL, 6.16 mmol) in DCM (5 mL) was added, followed by DIEA (1.34 mL, 7.69 mmol). The reaction mixture was stirred at 0° C. for 20 minutes Water (100 mL) was added. pH of the mixture was adjusted to around 3 by adding 0.5N HCl solution. The mixture as extracted with EtOAc (3×100 mL). The organic extracts were pooled, dried over anhydrous sodium sulfate, and concentrated to afford methyl (4R,8S)-5-(benzyloxy)-1-(2-((methylsulfonyl)oxy)ethyl)-6-oxo-4,5,6,8-tetrahydro-1H-4,7-methanopyrazolo[3,4-e][1,3]diazepine-8-carboxylate (2070 mg, 89%) as a white sticky foam. MS: 451 ES+ ($C_{19}H_{22}N_4O_7S$).

Int-48

A 100-mL round-bottom flask was charged with methyl (4R,8S)-5-(benzyloxy)-1-(2-((methylsulfonyl)oxy)ethyl)-6-oxo-4,5,6,8-tetrahydro-1H-4,7-methanopyrazolo[3,4-e][1,3]diazepine-8-carboxylate (Int-47, 2070 mg, 4.6 mmol) and DMF (50 mL). Sodium azide (3584 mg, 55.14 mmol) was added, the reaction mixture was stirred at 40° C. for 4 hours, and then at room temperature for overnight. The reaction mixture was partitioned between water (200 mL) and EtOAc (200 mL). The organic layer was separated, washed with water (100 mL), brine (100 mL), dried over anhydrous sodium sulfate, and concentrated to give the crude product. It was purified with flash chromatography (40 g, eluting with EtOAc/hexane) to afford methyl (4R,8S)-1-(2-azidoethyl)-5-(benzyloxy)-6-oxo-4,5,6,8-tetrahydro-1H-4,7-methanopyrazolo[3,4-e][1,3]diazepine-8-carboxylate (1810 mg, 99%) as an off-white solid. MS: 398 ES+ ($C_{18}H_{19}N_7O_4$).

Int-49

To a solution of methyl (4R,8S)-1-(2-azidoethyl)-5-(benzyloxy)-6-oxo-4,5,6,8-tetrahydro-1H-4,7-methanopyrazolo[3,4-e][1,3]diazepine-8-carboxylate (Int-48, 354 mg, 0.89 mmol) in Methanol (60 mL) and THF (30 mL) at −10° C. was added a solution of LiBH$_4$ (4.46 mL, 8.90 mmol) in THF. The resulting mixture was stirred at −10° C. for 2 hours. DCM (100 mL) and saturated aqueous ammonium chloride solution (100 mL) were added. The organic layer was separated, dried over anhydrous sodium sulfate, and concentrated to give the crude product. It was purified by flash chromatography (40 g silica gel, 0-100% EtOAc in Hexanes, then 100% Acetone) to afford (4R,8S)-1-(2-azidoethyl)-5-(benzyloxy)-8-(hydroxymethyl)-1,4,5,8-tetrahydro-6H-4,7-methanopyrazolo[3,4-e][1,3]diazepin-6-one (310 mg, 94%) as a white solid. MS: 370 ES+ ($C_{17}H_{19}N_7O_3$).

Int-50

To a solution of (4R,8S)-1-(2-azidoethyl)-5-(benzyloxy)-8-(hydroxymethyl)-1,4,5,8-tetrahydro-6H-4,7-methanopyrazolo[3,4-e][1,3]diazepin-6-one (Int-49, 310 mg, 0.84 mmol) in DCM (60 mL) at room temperature was added Dess-Martin Periodinane (427 mg, 1.01 mmol). The reaction mixture was stirred for 2 hours. Water (10 mL), saturated aqueous sodium bicarbonate solution (30 mL), and 2N Na$_2$S$_2$O$_3$ solution (50 mL) were added and stirred for 5 minutes. The biphasic mixture was separated and the aqueous extracted with DCM (100 mL). The combined organics were dried over anhydrous magnesium sulfate, filtered and concentrated to afford (4R,8S)-1-(2-azidoethyl)-5-(benzyloxy)-6-oxo-4,5,6,8-tetrahydro-1H-4,7-methanopyrazolo[3, 4-e][1,3]diazepine-8-carbaldehyde (300 mg, 97%) as a colorless oil. MS: 368 ES+ ($C_{17}H_{17}N_7O_3$).

Int-51

Int-51 was synthesized by following similar reaction conditions as shown for Int-10 (Scheme 1, step 10), using (4R,8S)-1-(2-azidoethyl)-5-(benzyloxy)-6-oxo-4,5,6,8-tetrahydro-1H-4,7-methanopyrazolo[3,4-e][1,3]diazepine-8-carbaldehyde (Int-50, 300 mg, 0.816 mmol) as substrate, and afford (E)-1-(2-azidoethyl)-5-(benzyloxy)-6-oxo-4,5,6,8-tetrahydro-1H-4,7-methanopyrazolo[3,4-e][1,3]diazepine-8-carbaldehyde oxime (283 mg, 91%) as a white solid. MS: 383 ES+ ($C_{17}H_{18}N_8O_3$).

Int-52

Int-52 was synthesized by following similar reaction conditions as shown for Int-11 (Scheme 1, step 11), using (E)-1-(2-azidoethyl)-5-(benzyloxy)-6-oxo-4,5,6,8-tetrahydro-1H-4,7-methanopyrazolo[3,4-e][1,3]diazepine-8-carbaldehyde oxime (Int-51, 283 mg, 0.74 mmol) as substrate, and afford (4R,8S,Z)-1-(2-azidoethyl)-5-(benzyloxy)-N-hydroxy-6-oxo-4,5,6,8-tetrahydro-1H-4,7-methanopyrazolo[3,4-e][1,3]diazepine-8-carbimidoyl chloride (308 mg, 99%) as a yellow solid. MS: 417 ES+ ($C_{17}H_{17}ClN_8O_3$).

Int-53

Int-53 was synthesized by following similar reaction conditions as shown for Int-12 (Scheme 1, step 12), using (4R,8S,Z)-1-(2-azidoethyl)-5-(benzyloxy)-N-hydroxy-6-oxo-4,5,6,8-tetrahydro-1H-4,7-methanopyrazolo[3,4-e][1,3]diazepine-8-carbimidoyl chloride (Int-52, 308 mg, 0.74 mmol) as substrate, and afford (4R,8S,Z)-1-(2-azidoethyl)-5-(benzyloxy)-N'-hydroxy-N-methyl-6-oxo-4,5,6,8-tetrahydro-1H-4,7-methanopyrazolo[3,4-e][1,3]diazepine-8-carboximidamide (247 mg, 81%) as a white solid. MS: 412 ES+ ($C_{18}H_{21}N_9O_3$).

Int-54

Int-54 was synthesized by following similar reaction conditions as shown for Int-13 (Scheme 1, step 13), using (4R,8S,Z)-1-(2-azidoethyl)-5-(benzyloxy)-N'-hydroxy-N-methyl-6-oxo-4,5,6,8-tetrahydro-1H-4,7-methanopyrazolo[3,4-e][1,3]diazepine-8-carboximidamide (Int-53, 247 mg, 0.60 mmol) as substrate, and afford (4R,8S,Z)-1-(2-azidoethyl)-5-(benzyloxy)-N'-((tert-butyldimethylsilyl)oxy)-N-methyl-6-oxo-4,5,6,8-tetrahydro-1H-4,7-methanopyrazolo[3,4-e][1,3]diazepine-8-carboximidamide (308 mg, 97%) as a white solid. MS: 526 ES+ ($C_{24}H_{35}N_9O_3Si$).

Int-55

To a solution of (4R,8S,Z)-1-(2-azidoethyl)-5-(benzyloxy)-N'-((tert-butyldimethylsilyl)oxy)-N-methyl-6-oxo-4,5,6,8-tetrahydro-1H-4,7-methanopyrazolo[3,4-e][1,3]diazepine-8-carboximidamide (Int-54, 308 mg, 0.586 mmol) in Methanol (20 mL) and THF (10 mL) at −10° C. was added a solution of LiBH$_4$ (1.46 mL, 2.93 mmol) and CuSO$_4$ (93.52 mg, 0.59 mmol). It was stirred at −10° C. for 1 hour. Boc$_2$O (127.87 mg, 0.59 mmol) and DIEA (0.1 mL, 0.59 mmol) were added and stirred at 0° C. for 2 hours. Saturated ammonium chloride solution (20 mL) was added and stirred for 5 minutes. Most of organic solvent was removed. DCM (100 mL) and saturated ammonium chloride solution (100 mL) were added. The organic layer was separated, dried over anhydrous sodium sulfate, and concentrated to give the crude product. It was purified by flash chromatography (20 g silica gel, 0-50% EtOAc in Hexane) to afford tert-butyl (2-((4R,8S)-5-(benzyloxy)-8-((Z)—N'-((tert-butyldimethylsilyl)oxy)-N-methylcarbamimidoyl)-6-oxo-4,5,6,8-tetrahydro-1H-4,7-methanopyrazolo[3,4-e][1,3]diazepin-1-yl)ethyl)carbamate (86 mg, 24%) as a colorless oil. MS: 600 ES+ ($C_{29}H_{45}N_7O_5Si$).

Int-56

Int-56 was synthesized by following similar reaction conditions as shown for Int-14 (Scheme 1, step 14), using tert-butyl (2-((4R,8S)-5-(benzyloxy)-8-((Z)—N'-((tert-butyldimethylsilyl)oxy)-N-methylcarbamimidoyl)-6-oxo-4,5,6,8-tetrahydro-1H-4,7-methanopyrazolo[3,4-e][1,3]diazepin-1-yl)ethyl)carbamate (Int-55, 86 mg, 0.14 mmol) as substrate, and afford tert-butyl (2-((4R,8S)-8-((Z)—N'-((tert-butyldimethylsilyl)oxy)-N-methylcarbamimidoyl)-5-hydroxy-6-oxo-4,5,6,8-tetrahydro-1H-4,7-methanopyrazolo[3,4-e][1,3]diazepin-1-yl)ethyl)carbamate (68 mg, 93%) as a white solid. MS: 510 ES+ ($C_{22}H_{39}N_7O_5Si$).

Int-57

Int-57 was synthesized by following similar reaction conditions as shown for Int-15 (Scheme 1, step 15), using tert-butyl (2-((4R,8S)-8-((Z)—N'-((tert-butyldimethylsilyl)oxy)-N-methylcarbamimidoyl)-5-hydroxy-6-oxo-4,5,6,8-tetrahydro-1H-4,7-methanopyrazolo[3,4-e][1,3]diazepin-1-yl)ethyl)carbamate (Int-56, 68 mg, 0.13 mmol) as substrate, and afford (4R,8S)-1-(2-((tert-butoxycarbonyl)amino)ethyl)-8-((Z)—N'-((tert-butyldimethylsilyl)oxy)-N-methylcarbamimidoyl)-6-oxo-4,8-dihydro-1H-4,7-methanopyrazolo[3,4-e][1,3]diazepin-5(6H)-yl hydrogen sulfate (78 mg, 99%) as a white solid. MS: 588 ES− ($C_{22}H_{39}N_7O_8SSi$).

Int-58

Int-58 was synthesized by following similar reaction conditions as shown for Int-16 (Scheme 1, step 16), using (4R,8S)-1-(2-((tert-butoxycarbonyl)amino)ethyl)-8-((Z)—N'-((tert-butyldimethylsilyl)oxy)-N-methylcarbamimidoyl)-6-oxo-4,8-dihydro-1H-4,7-methanopyrazolo[3,4-e][1,3]diazepin-5(6H)-yl hydrogen sulfate (Int-57, 78 mg, 0.13 mmol) as substrate, and afford (4R,8S)-1-(2-((tert-butoxycarbonyl)amino)ethyl)-8-((Z)—N'-hydroxy-N-methylcarbamimidoyl)-6-oxo-4,8-dihydro-1H-4,7-methanopyrazolo[3,4-e][1,3]diazepin-5(6H)-yl hydrogen sulfate (31 mg, 49%) as a white solid. MS: 474 ES− ($C_{16}H_{25}N_7O_8S$).

Example 47

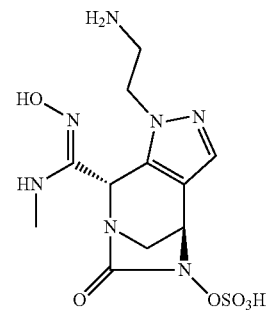

To a solution of (4R,8S)-1-(2-((tert-butoxycarbonyl)amino)ethyl)-8-((Z)—N'-hydroxy-N-methylcarbamimidoyl)-6-oxo-4,8-dihydro-1H-4,7-methanopyrazolo[3,4-e][1,3]diazepin-5(6H)-yl hydrogen sulfate (Int-58, 31 mg, 0.07 mmol) in DCM (10 mL) at 0° C. was added TFA (0.25 mL, 3.28 mmol). The reaction mixture was stirred at 0° C. for 6 hours and concentrated under reduced pressure. The crude material was dissolved in water and purified by reversed phase chromatography (sepabeads 12 g, 100% water) to afford (4R,8S)-1-(2-aminoethyl)-8-((Z)—N'-hydroxy-N-methylcarbamimidoyl)-6-oxo-4,8-dihydro-1H-4,7-methanopyrazolo[3,4-e][1,3]diazepin-5(6H)-yl hydrogen sulfate (7 mg, 25%) as a white solid. MS: 376 ES+ ($C_{11}H_{17}N_7O_6S$) $^1$H NMR (300 MHz, $D_2O$) δ: 3.05 (s, 3H); 3.42 (m, 2H); 3.57 (m, 2H); 4.17 (m, 2H); 4.91 (m, 1H); 5.71 (m, 1H); 7.70 (s, 1H).

Scheme 10

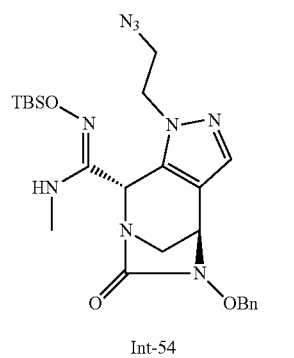

Int-54

LiBH4, CuSO4, DIEA
MeOH, THF
step 1

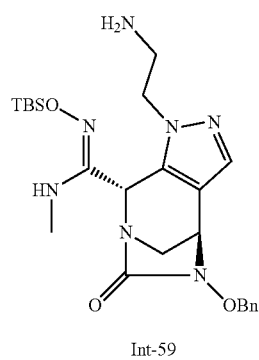

Acetic anhydride
Pyridine
step 2

Int-59

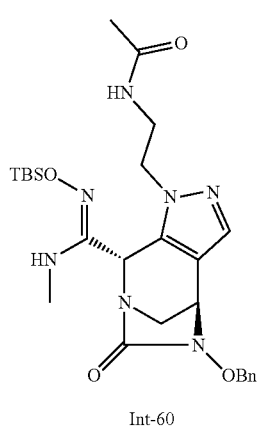

Int-60

H2, Pd/C
MeOH/EtOAc
step 3

-continued

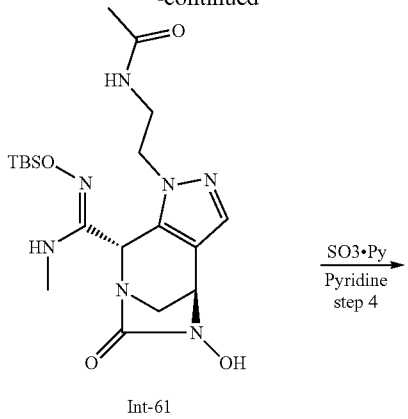

Int-61

SO3•Py
Pyridine
step 4

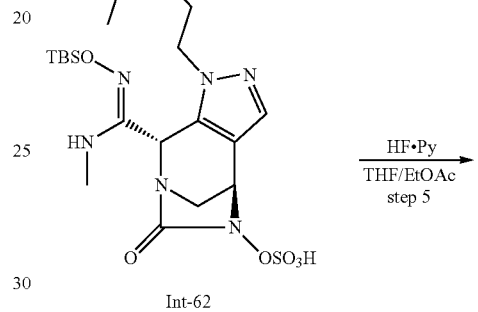

Int-62

HF•Py
THF/EtOAc
step 5

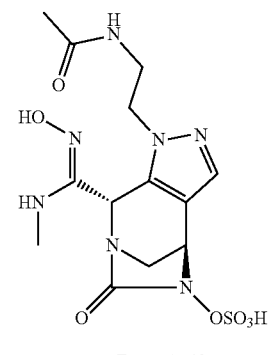

Example 48

Int-59 was synthesized by following similar reaction conditions as shown for Int-55 (Scheme 9, step 10), using (4R,8S,Z)-1-(2-azidoethyl)-5-(benzyloxy)-N'-((tert-butyldimethylsilyl)oxy)-N-methyl-6-oxo-4,5,6,8-tetrahydro-1H-4,7-methanopyrazolo[3,4-e][1,3]diazepine-8-carboximidamide (Int-54, 89 mg, 0.17 mmol) as substrate, and no Boc$_2$O was added, to afford (4R,8S,Z)-1-(2-aminoethyl)-5-(benzyloxy)-N'-((tert-butyldimethylsilyl)oxy)-N-methyl-6-oxo-4,5,6,8-tetrahydro-1H-4,7-methanopyrazolo[3,4-e][1,3]diazepine-8-carboximidamide (84 mg, 99%) as a white solid. MS: 500 ES+ ($C_{24}H_{37}N_7O_3Si$).

Int-60

To a solution of (4R,8S,Z)-1-(2-aminoethyl)-5-(benzyloxy)-N'-((tert-butyldimethylsilyl)oxy)-N-methyl-6-oxo-4,5,6,8-tetrahydro-1H-4,7-methanopyrazolo[3,4-e][1,3]diazepine-8-carboximidamide (Int-59, 84 mg, 0.17 mmol) in Pyridine (5 mL) at −10° C. was added acetic anhydride (0.01 mL, 0.17 mmol). It was stirred at −10° C. for 1 hour.

Saturated ammonium chloride solution (20 mL) and DCM (20 mL) were added. The organic layer was separated, dried over anhydrous sodium sulfate, and concentrated to give the crude product. It was purified by flash chromatography (20 g silica gel, 0-50% EtOAc in Hexane) to afford N-(2-((4R, 8S)-5-(benzyloxy)-8-((Z)—N'-((tert-butyldimethylsilyl)oxy)-N-methylcarbamimidoyl)-6-oxo-4,5,6,8-tetrahydro-1H-4,7-methanopyrazolo[3,4-e][1,3]diazepin-1-yl)ethyl)acetamide (74 mg, 81%) as a colorless sticky oil. MS: 542 ES+ ($C_{26}H_{39}N_7O_4Si$).

Int-61

Int-61 was synthesized by following similar reaction conditions as shown for Int-56 (Scheme 9, step 11), using N-(2-((4R,8S)-5-(benzyloxy)-8-((Z)—N'-((tert-butyldimethylsilyl)oxy)-N-methylcarbamimidoyl)-6-oxo-4,5,6,8-tetrahydro-1H-4,7-methanopyrazolo[3,4-e][1,3]diazepin-1-yl)ethyl)acetamide (Int-60, 74 mg, 0.136 mmol) as substrate, and afford N-(2-((4R,8S)-8-((Z)—N'-((tert-butyldimethylsilyl)oxy)-N-methylcarbamimidoyl)-5-hydroxy-6-oxo-4,5,6,8-tetrahydro-1H-4,7-methanopyrazolo[3,4-e][1,3]diazepin-1-yl)ethyl)acetamide (50 mg, 81%) as a white solid. MS: 452 ES+ ($C_{19}H_{33}N_7O_4Si$).

Int-62

Int-62 was synthesized by following similar reaction conditions as shown for Int-57 (Scheme 9, step 12), using N-(2-((4R,8S)-8-((Z)—N'-((tert-butyldimethylsilyl)oxy)-N-methylcarbamimidoyl)-5-hydroxy-6-oxo-4,5,6,8-tetrahydro-1H-4,7-methanopyrazolo[3,4-e][1,3]diazepin-1-yl)ethyl)acetamide (Int-61, 50 mg, 0.11 mmol) as substrate, and afford (4R,8S)-1-(2-acetamidoethyl)-8-((Z)—N'-((tert-butyldimethylsilyl)oxy)-N-methylcarbamimidoyl)-6-oxo-4,8-dihydro-1H-4,7-methanopyrazolo[3,4-e][1,3]diazepin-5(6H)-yl hydrogen sulfate (57 mg, 97%) as a white solid. MS: 530 ES– ($C_{19}H_{33}N_7O_7SiS$).

Example 48

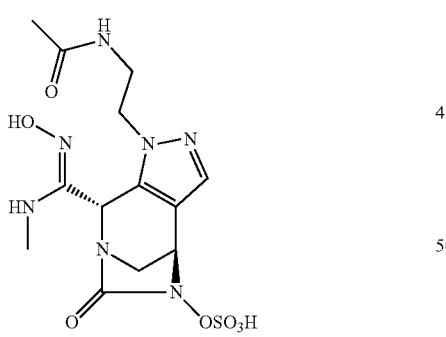

Example 48 was synthesized by following similar reaction conditions as shown for Int-16 (Scheme 1, step 16), using (4R,8S)-1-(2-acetamidoethyl)-8-((Z)—N'-((tert-butyldimethylsilyl)oxy)-N-methylcarbamimidoyl)-6-oxo-4,8-dihydro-1H-4,7-methanopyrazolo[3,4-e][1,3]diazepin-5(6H)-yl hydrogen sulfate (Int-62, 57 mg, 0.107 mmol) as substrate, and afford (4R,8S)-1-(2-acetamidoethyl)-8-((Z)—N'-hydroxy-N-methylcarbamimidoyl)-6-oxo-4,8-dihydro-1H-4,7-methanopyrazolo[3,4-e][1,3]diazepin-5(6H)-yl hydrogen sulfate (10 mg, 20%) as a white solid. MS: 416 ES– ($C_{13}H_{19}N_7O_7S$) $^1$H NMR (300 MHz, $D_2O$) δ: 1.93 (s, 3H); 3.08 (s, 3H); 3.55 (m, 4H); 4.01 (m, 2H); 4.94 (m, 1H); 5.45 (m, 1H); 7.68 (s, 1H); 8.02 (m, 0.5H); 8.61 (m, 0.25H); 8.79 (0.5H) compound/pyridine ratio (1:0.25).

Scheme 11

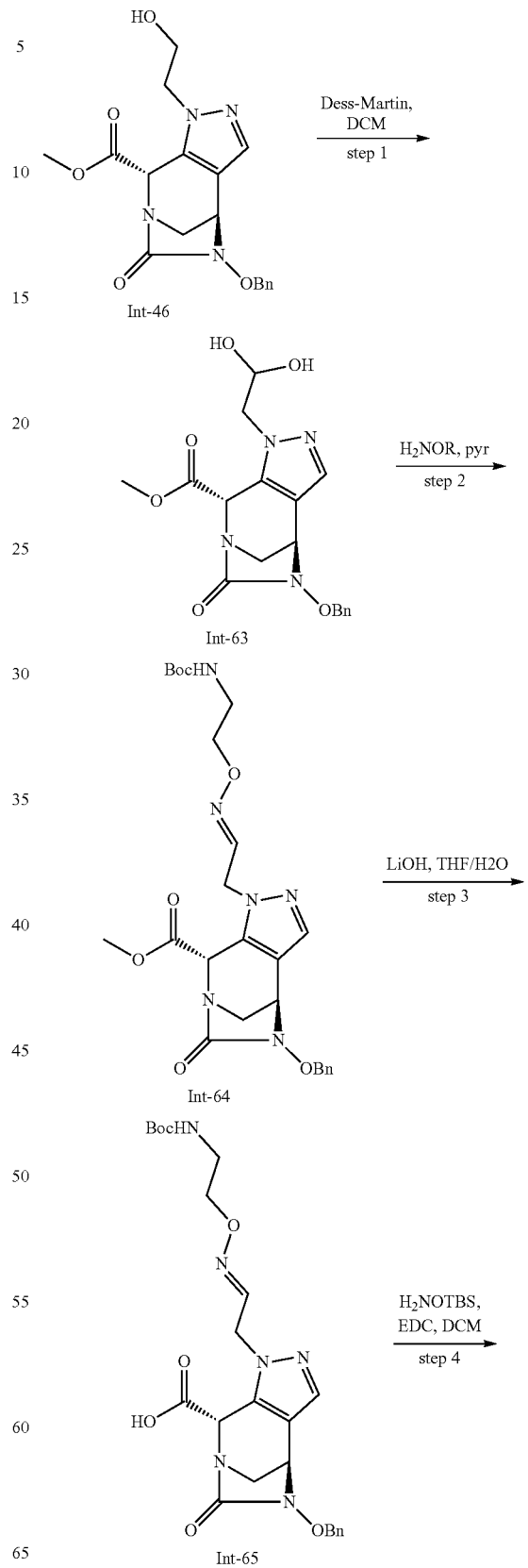

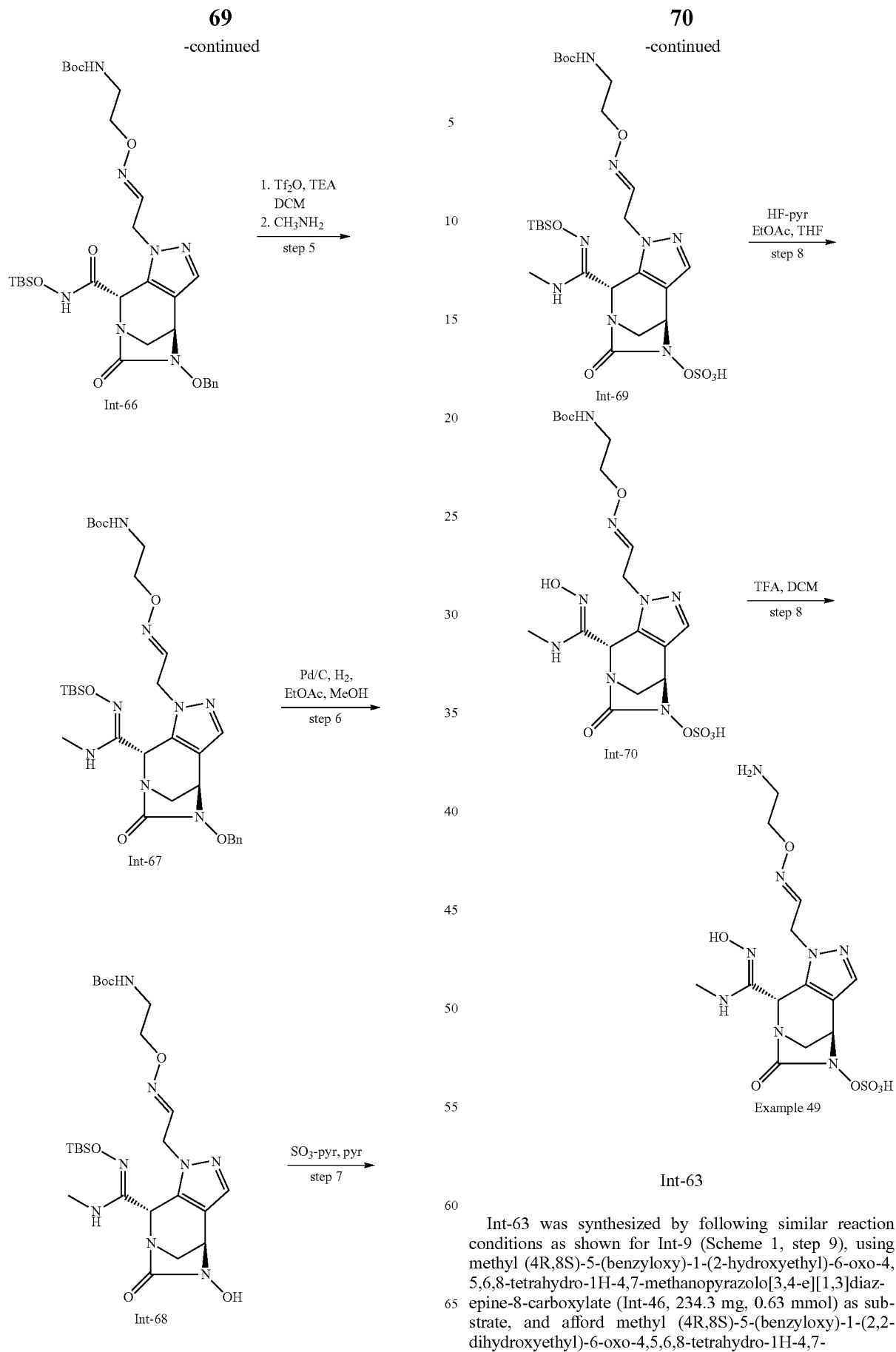
Int-63 was synthesized by following similar reaction conditions as shown for Int-9 (Scheme 1, step 9), using methyl (4R,8S)-5-(benzyloxy)-1-(2-hydroxyethyl)-6-oxo-4,5,6,8-tetrahydro-1H-4,7-methanopyrazolo[3,4-e][1,3]diazepine-8-carboxylate (Int-46, 234.3 mg, 0.63 mmol) as substrate, and afford methyl (4R,8S)-5-(benzyloxy)-1-(2,2-dihydroxyethyl)-6-oxo-4,5,6,8-tetrahydro-1H-4,7- methanopyrazolo[3,4-e][1,3]diazepine-8-carboxylate (244.3 mg, 100%) as a light yellow solid. MS: 389 ES+ ($C_{18}H_{20}N_4O_6$).

Int-64

To a solution of methyl (4R,8S)-5-(benzyloxy)-1-(2,2-dihydroxyethyl)-6-oxo-4,5,6,8-tetrahydro-1H-4,7-methanopyrazolo[3,4-e][1,3]diazepine-8-carboxylate (Int-63, 244.3 mg, 0.63 mmol) in pyridine (0.5 mL) at 0° C. was added tert-butyl (2-(aminooxy)ethyl)carbamate (110.84 mg, 0.63 mmol) in pyridine (0.5 mL). The reaction mixture was warmed to room temperature and stirred for 15 minutes then diluted with ethyl acetate (50 mL) and washed with saturated ammonium chloride (20 mL) and brine (20 mL). The organics were dried over anhydrous sodium sulfate, filtered and concentrated. Silica gel chromatography (0%-80% ethyl acetate/hexanes) afforded methyl (4R,8S)-5-(benzyloxy)-1-((E)-10,10-dimethyl-8-oxo-4,9-dioxa-3,7-diazaundec-2-en-1-yl)-6-oxo-4,5,6,8-tetrahydro-1H-4,7-methanopyrazolo[3,4-e][1,3]diazepine-8-carboxylate (241.1 mg, 73%) as an off-white solid. MS: 529 ES+ ($C_{25}H_{32}N_6O_7$).

Int-65

To a solution of methyl (4R,8S)-5-(benzyloxy)-1-((E)-10,10-dimethyl-8-oxo-4,9-dioxa-3,7-diazaundec-2-en-1-yl)-6-oxo-4,5,6,8-tetrahydro-1H-4,7-methanopyrazolo[3,4-e][1,3]diazepine-8-carboxylate (Int-64, 248.5 mg, 0.47 mmol) in THF (4 mL) and water (1 mL) at 0° C. was added lithium hydroxide (0.66 mL, 0.66 mmol). The reaction mixture was stirred for 15 minutes at 0° C. then neutralized with 1N HCl. The THF was removed and the aqueous was frozen and lyophilized to afford a white solid. The solid was dissolved in water to give a cloudy solution. The pH was adjusted to ~3-4 and the product was extracted with ethyl acetate (2×100 mL). The organics were dried over anhydrous sodium sulfate, filtered and concentrated to afford (4R,8S)-5-(benzyloxy)-1-((E)-10,10-dimethyl-8-oxo-4,9-dioxa-3,7-diazaundec-2-en-1-yl)-6-oxo-4,5,6,8-tetrahydro-1H-4,7-methanopyrazolo[3,4-e][1,3]diazepine-8-carboxylic acid (236.4 mg, 98%) as an off-white foam. MS: 515 ES+ ($C_{24}H_{30}N_6O_7$).

Int-66

To a suspension of (4R,8S)-5-(benzyloxy)-1-((E)-10,10-dimethyl-8-oxo-4,9-dioxa-3,7-diazaundec-2-en-1-yl)-6-oxo-4,5,6,8-tetrahydro-1H-4,7-methanopyrazolo[3,4-e][1,3]diazepine-8-carboxylic acid (Int-65, 236.4 mg, 0.46 mmol) in DCM (4 mL) at room temperature was added O-(tert-butyldimethylsilyl) hydroxylamine (87.98 mg, 0.59 mmol) and EDC (105.63 mg, 0.55 mmol). The reaction mixture was stirred at room temperature for ~2 hours then diluted with dichloromethane and washed once with 1:1 brine:water. The organics were dried over magnesium sulfate, filtered and concentrated. Silica gel chromatography (0%-50% ethyl acetate/hexanes) tert-butyl (2-((((E)-2-((4R,8S)-5-(benzyloxy)-8-(((tert-butyldimethylsilyl)oxy)carbamoyl)-6-oxo-4,5,6,8-tetrahydro-1H-4,7-methanopyrazolo[3,4-e][1,3]diazepin-1-yl)ethylidene)amino)oxy)ethyl)carbamate (148.2 mg, 50%) as a white foam. MS: 644 ES+ ($C_{30}H_{45}N_7O_7Si$).

Int-67

To a solution of tert-butyl (2-((((E)-2-((4R,8S)-5-(benzyloxy)-8-(((tert-butyldimethylsilyl)oxy)carbamoyl)-6-oxo-4,5,6,8-tetrahydro-1H-4,7-methanopyrazolo[3,4-e][1,3]diazepin-1-yl)ethylidene)amino)oxy)ethyl)carbamate (Int-66, 141 mg, 0.22 mmol) and triethylamine (0.06 mL, 0.44 mmol) in DCM (3 mL) at −78° C. was added triflic anhydride (0.07 mL, 0.44 mmol). The reaction mixture was stirred for 5 minutes. To the solution was added methylamine (0.05 mL, 1.31 mmol) dropwise. The reaction mixture was then allowed to warm to room temperature and stir for 1.5 hours. The reaction mixture was diluted with DCM and washed once with saturated ammonium chloride. The organics were dried over magnesium sulfate, filtered and concentrated. Silica gel chromatography (0%-50% ethyl acetate/hexanes) afforded tert-butyl (2-((((E)-2-((4R,8S)-5-(benzyloxy)-8-((Z)—N'-((tert-butyldimethylsilyl)oxy)-N-methylcarbamimidoyl)-6-oxo-4,5,6,8-tetrahydro-1H-4,7-methanopyrazolo[3,4-e][1,3]diazepin-1-yl)ethylidene)amino)oxy)ethyl)carbamate as white foam (60.6 mg, 42%). MS: 657 ES+ ($C_{31}H_{48}N_8O_6Si$).

Int-68

To a solution of tert-butyl (2-((((E)-2-((4R,8S)-5-(benzyloxy)-8-((Z)—N'-((tert-butyldimethylsilyl)oxy)-N-methylcarbamimidoyl)-6-oxo-4,5,6,8-tetrahydro-1H-4,7-methanopyrazolo[3,4-e][1,3]diazepin-1-yl)ethylidene)amino)oxy)ethyl)carbamate (Int-67, 60.6 mg, 0.09 mmol) in ethyl acetate (3 mL) was degassed with nitrogen and Pd/C (9.82 mg, 0.01 mmol) was added. The mixture was degassed again and placed under hydrogen balloon. The reaction mixture was stirred for 2 hours. Trace amount of product observed. The reaction mixture was flushed with nitrogen and methanol was added (1 mL). The reaction mixture was degassed. More Pd/C (9.82 mg, 0.01 mmol) was added and the reaction mixture was degassed and placed under hydrogen balloon again. The reaction mixture was stirred for ~40 minutes then flushed with nitrogen and filtered to remove the catalyst. The filtrate was concentrated to afford tert-butyl (2-((((E)-2-((4R,8S)-8-((Z)—N'-((tert-butyldimethylsilyl)oxy)-N-methylcarbamimidoyl)-5-hydroxy-6-oxo-4,5,6,8-tetrahydro-1H-4,7-methanopyrazolo[3,4-e][1,3]diazepin-1-yl)ethylidene)amino)oxy)ethyl)carbamate (52.28 mg, 100%) as a colorless oil. MS: 567 ES+ ($C_{24}H_{42}N_8O_6Si$).

Int-69

To a solution of tert-butyl (2-((((E)-2-((4R,8S)-8-((Z)—N'-((tert-butyldimethylsilyl)oxy)-N-methylcarbamimidoyl)-5-hydroxy-6-oxo-4,5,6,8-tetrahydro-1H-4,7-methanopyrazolo[3,4-e][1,3]diazepin-1-yl)ethylidene)amino)oxy)ethyl)carbamate (Int-68, 52.2 mg, 0.09 mmol) in pyridine (2 mL) at room temperature was added sulfur trioxide pyridine complex (87.96 mg, 0.55 mmol). The reaction mixture was stirred overnight then diluted with DCM and filtered to remove solids. The filtrate was concentrated and dried under vacuum. The resulting oil was triturated with DCM and acetone, filtered to remove solids. The filtrate was concentrated to afford (4R,8S)-8-((Z)—N'-((tert-butyldimethylsilyl)oxy)-N-methylcarbamimidoyl)-1-((E)-10,10-dimethyl-8-oxo-4,9-dioxa-3,7-diazaundec-2-en-1-yl)-6-oxo-4,8-dihydro-1H-4,7-methanopyrazolo[3,4-e][1,3]diazepin-5(6H)-yl hydrogen sulfate (59.57 mg, 100%) as an off-white foam. MS: 645 ES− ($C_{24}H_{42}N_8O_9SiS$).

Int-70

To a solution of (4R,8S)-8-((Z)—N'-((tert-butyldimethyl-silyl)oxy)-N-methylcarbamimidoyl)-1-((E)-10,10-dimethyl-8-oxo-4,9-dioxa-3,7-diazaundec-2-en-1-yl)-6-oxo-4,8-dihydro-1H-4,7-methanopyrazolo[3,4-e][1,3]diazepin-5(6H)-yl hydrogen sulfate (Int-69, 59.57 mg, 0.09 mmol) in ethyl acetate (2 mL) and THF (1 mL) at room temperature was added HF.pyridine (0.0026 mL, 0.10 mmol). The reaction mixture was stirred for 30 minutes. More HF.pyridine (0.0026 mL, 0.10 mmol) added. After another 30 minutes, an additional HF pyridine (0.0026 mL, 0.10 mmol) was added. After 30 minutes the reaction mixture was concentrated to afford (4R,8S)-1-((E)-10,10-dimethyl-8-oxo-4,9-dioxa-3,7-diazaundec-2-en-1-yl)-8-((Z)—N'-hydroxy-N-methylcarbamimidoyl)-6-oxo-4,8-dihydro-1H-4,7-methanopyrazolo[3,4-e][1,3]diazepin-5(6H)-yl hydrogen sulfate (49 mg, 100%) as a white solid. MS: 533 ES+ ($C_{18}H_{28}N_8O_9S$).

Example 49

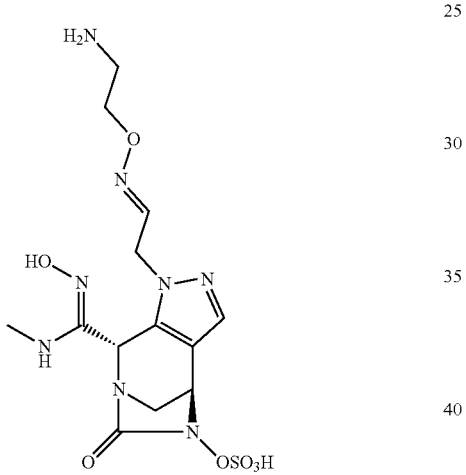

To a suspension of (4R,8S)-1-((E)-10,10-dimethyl-8-oxo-4,9-dioxa-3,7-diazaundec-2-en-1-yl)-8-((Z)—N'-hydroxy-N-methylcarbamimidoyl)-6-oxo-4,8-dihydro-1H-4,7-methanopyrazolo[3,4-e][1,3]diazepin-5(6H)-yl hydrogen sulfate (Int-70, 49 mg, 0.09 mmol) in DCM (2 mL) at 0° C. was added trifluoroacetic acid (0.14 mL, 1.84 mmol). The reaction mixture was stirred for 30 minutes. More trifluoroacetic acid (0.14 mL, 1.84 mmol) was added and the reaction mixture was warmed to room temperature for 15 minutes. The reaction mixture was concentrated with DCM several times to remove excess TFA. The resulting oil was dried under vacuum. Purification by C18 ISCO (100% water, 4 min, 0%-50% ACN/water, 3 min) afforded 1-((E)-2-((2-aminoethoxy)imino)ethyl)-8-((Z)—N'-hydroxy-N-methylcarbamimidoyl)-6-oxo-4,8-dihydro-1H-4,7-methanopyrazolo[3,4-e][1,3]diazepin-5(6H)-yl hydrogen sulfate (14.8 mg, 37%) as a white solid, ~3:2 mixture of E/Z isomers. MS: 431 ES− ($C_{13}H_{20}N_8O_7S$). $^1$H NMR (300 MHz, DMSO-$d_6$) δ: 2.89 (m, 3H); 3.03 (m, 2H); 4.13 (m, 2H); 4.70 (m, 3H); 5.44 (d, 1H); 5.75 (m, 1H); 6.95 (m, 0.4H); 7.35 (m, 1H); 7.51 (m, 0.6H); 7.74 (bs, 3H); 9.45 (m, 1H).

Scheme 12

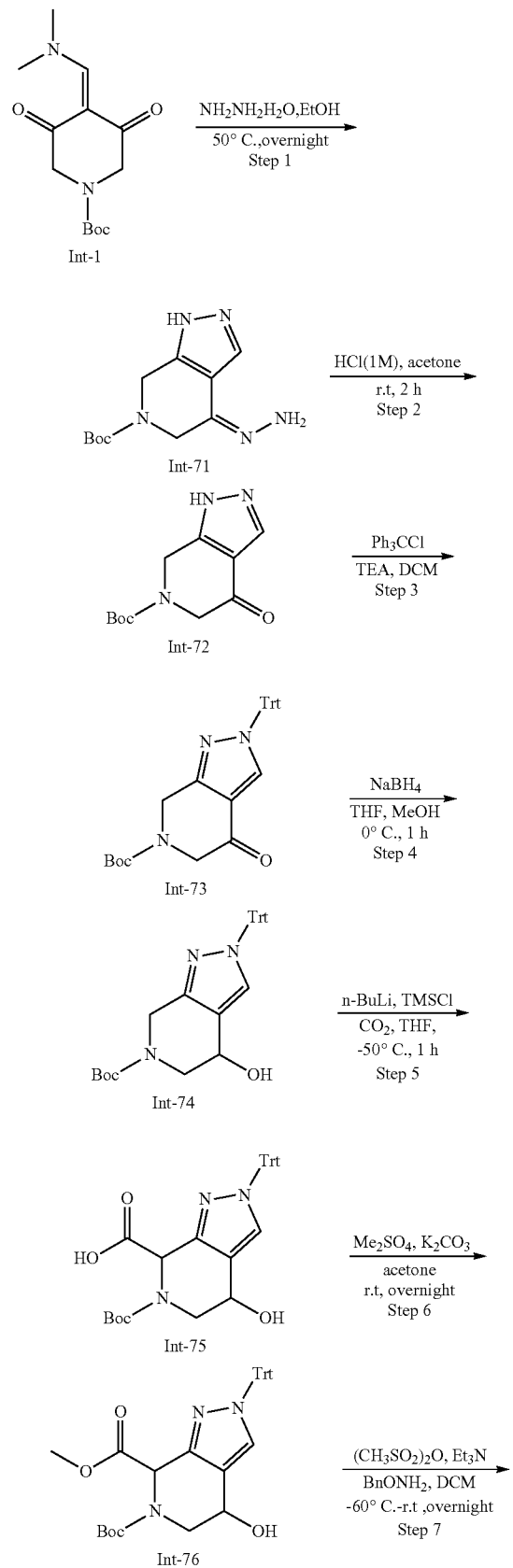

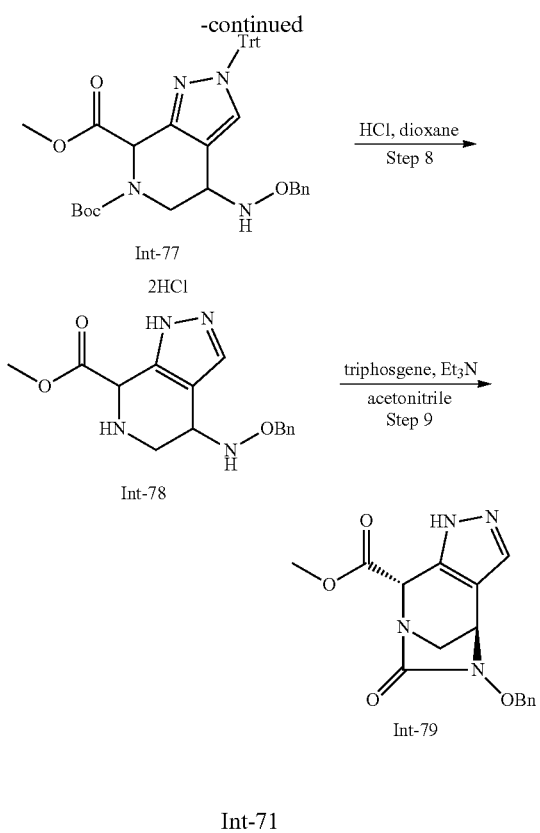

Int-71

A 1000-mL round-bottom flask was charged with tert-butyl 4-[(dimethylamino)methylidene]-3,5-dioxopiperidine-1-carboxylate (Int-1, 63 g, 234.80 mmol), ethanol (600 mL), NH$_2$NH$_2$·H$_2$O (62 g, 992 mmol). The resulting solution was stirred for overnight at 53° C. in an oil bath. The resulting mixture was concentrated under vacuum. MTBE (500 mL) was added, the solid formed was collected by filtration. The solid was dried in an oven under reduced pressure to afford tert-butyl (E)-4-hydrazinylidene-1,4,5,7-tetrahydro-6H-pyrazolo[3,4-c]pyridine-6-carboxylate (40 g, 68%) as a yellow solid. MS: 252 ES+ (C$_{11}$H$_{17}$N$_5$O$_2$).

Int-72

A 2000-mL round-bottom flask was charged with tert-butyl 4-hydrazinylidene-2H,4H,5H,6H,7H-pyrazolo[3,4-c]pyridine-6-carboxylate (Int-71, 80 g, 318.36 mmol), acetone (800 mL), and hydrogen chloride (1M) (800 mL). The resulting solution was stirred for 2 h at room temperature. Water (700 mL) was added, and the reaction mixture was extracted with ethyl acetate (3×500 mL). The organic layers were combined, washed with brine (3×2 L), dried over anhydrous sodium sulfate and concentrated under vacuum to afford tert-butyl 4-oxo-1,4,5,7-tetrahydro-6H-pyrazolo[3,4-c]pyridine-6-carboxylate (75 g, 99%) as yellow oil. It was used directly in the next step. MS: 182 ES+ (C$_{11}$H$_{15}$N$_3$O$_3$).

Int-73

A 2000-mL round-bottom flask was charged with tert-butyl 4-oxo-1,4,5,7-tetrahydro-6H-pyrazolo[3,4-c]pyridine-6-carboxylate (Int-72, 75 g, 316.12 mmol), dichloromethane (750 mL), (chlorodiphenylmethyl)benzene (97 g, 347.95 mmol), and triethylamine (38 g, 375.53 mmol). The resulting solution was stirred for overnight at room temperature. The reaction was then quenched by the addition water (6000 mL). The reaction mixture was extracted with dichloromethane (2×400 mL). The organic extracts were combined, washed with brine (3×100 mL), dried over anhydrous sodium sulfate and concentrated under vacuum. The residue was applied onto a silica gel column with ethyl acetate/petroleum ether (1:10). The collected fractions were combined and concentrated under vacuum to afford tert-butyl 4-oxo-2-trityl-2,4,5,7-tetrahydro-6H-pyrazolo[3,4-c]pyridine-6-carboxylate (50 g, 33%) as a white solid. $^1$H NMR (400 MHz, Chloroform-d) δ 7.96 (s, 1H); 7.41-7.30 (m, 9H); 7.20-7.12 (m, 6H); 4.76 (s, 2H); 4.22 (s, 2H); 1.50 (s, 9H).

Int-74

A 1000-mL 3-necked round-bottom flask was purged and maintained with an inert atmosphere of nitrogen. tert-butyl 4-oxo-2-trityl-2,4,5,7-tetrahydro-6H-pyrazolo[3,4-c]pyridine-6-carboxylate (Int-73, 46 g, 95.92 mmol), tetrahydrofuran (460 mL), and methanol (230 mL) were added, followed by the addition of NaBH$_4$ (3.65 g, 96.48 mmol) in several batches at 10° C. in 5 minutes. The resulting solution was stirred for 1 h at 10° C. in a water/ice bath and quenched by the addition of water (500 mL). The resulting solution was extracted with ethyl acetate (3×500 mL) and the organic layers combined. The organic extracts were washed with brine (3×1000 mL), dried over anhydrous sodium sulfate and concentrated under vacuum. The residue was applied onto a silica gel column with ethyl acetate/petroleum ether (1:10-1:0). The collected fractions were combined and concentrated under vacuum to afford tert-butyl 4-hydroxy-2-trityl-2,4,5,7-tetrahydro-6H-pyrazolo[3,4-c]pyridine-6-carboxylate (33 g, 71%) as a white solid. $^1$H NMR (300 MHz, Chloroform-d) δ 7.41 (s, 1H); 7.37-7.28 (m, 9H); 7.21-7.11 (m, 6H); 4.81 (d, J=28.0 Hz, 2H); 4.34 (d, J=16.5 Hz, 1H); 3.96 (dd, J=13.7, 4.3 Hz, 1H); 3.50 (dd, J=13.7, 3.4 Hz, 1H); 1.49 (s, 9H).

Int-75

A 1000-mL 3-necked round-bottom flask was purged and maintained with an inert atmosphere of nitrogen. tert-butyl 4-hydroxy-2-trityl-2,4,5,7-tetrahydro-6H-pyrazolo[3,4-c]pyridine-6-carboxylate (Int-74, 18 g, 37.38 mmol) and tetrahydrofuran (360 mL) were added, followed by the addition of n-BuLi (22.5 mL, 56.13 mmol) dropwise with stirring at −30° C. in 5 minutes. The solution was stirred at −20° C. for 20 minutes. Chlorotrimethylsilane (4.5 g, 41.42 mmol) was added dropwise with stirring at −30° C. in 5 minutes. The solution was stirred at −20° C. for 30 minutes. To the mixture was added n-BuLi (45 mL, 112.3 mmol) dropwise with stirring at −50° C. in 10 minutes. The solution was stirred at −50° C. for 2 hours. Then CO$_2$ was purged into the reaction at −50° C. in 20 minutes. The resulting solution was stirred for 20 minutes at room temperature. The reaction was then quenched by the addition of water (1000 mL). The pH value of the solution was adjusted to 3 with hydrogen chloride (1 mol/L). The resulting solution was extracted with ethyl acetate (3×1000 mL) and the organic layers combined. The organic extracts were washed with brine (2×2000 mL), dried over anhydrous sodium sulfate and concentrated under vacuum. The residue was triturated with petroleum ether (200 mL). The solid was filter out and dried to afford 6-(tert-butoxycarbonyl)-4-hydroxy-2-trityl-4,5,6,7-tetrahydro-2H-pyrazol[3,4-c]pyridine-7-carboxylic acid (19 g, 96.7%) as a yellow solid. It was directly used in the next step.

Int-76

A 500-mL round-bottom flask was charged with 6-(tert-butoxycarbonyl)-4-hydroxy-2-trityl-4,5,6,7-tetrahydro-2H-pyrazolo[3,4-c]pyridine-7-carboxylic acid (Int-75, 19 g, 36.15 mmol), acetone (190 mL), potassium carbonate (7.5 g, 54.27 mmol), dimethyl sulfate (4.9 g, 38.85 mmol). The resulting solution was stirred for overnight at room temperature. The solids were filtered out and washed with EtOAc (500 mL). The filtrate was concentrated under vacuum. The residue was applied onto a silica gel column with ethyl acetate/petroleum ether (1:10-1:3). The collected fractions were combined and concentrated under vacuum to afford 6-(tert-butyl) 7-methyl 4-hydroxy-2-trityl-2,4,5,7-tetrahydro-6H-pyrazolo[3,4-c]pyridine-6,7-dicarboxylate (13.24 g, 68%) as a white solid. MS: 562 ES+1+Na ($C_{32}H_{33}N_3O_5$).

Int-77

A 500-mL 3-necked round-bottom flask was purged and maintained with an inert atmosphere of nitrogen. 6-(tert-butyl) 7-methyl 4-hydroxy-2-trityl-2,4,5,7-tetrahydro-6H-pyrazolo[3,4-c]pyridine-6,7-dicarboxylate (Int-76, 8 g, 14.83 mmol) and dichloromethane (160 mL) were added, followed by triethylamine (3 g, 29.65 mmol) dropwise with stirring at −60° C. in 2 minutes. To this was added a solution of methanesulfonyl methanesulfonate (5.2 g, 29.85 mmol) in dichloromethane (35 mL) dropwise with stirring at −60° C. in 30 minutes. The solution was stirred at −60° C. for 2 hours. To the mixture was added a solution of O-benzylhydroxylamine (5.5 g, 44.66 mmol) in dichloromethane (35 mL) dropwise with stirring at −60° C. in 30 minutes. The solution was stirred at −60° C. for 30 minutes. The resulting solution was stirred for overnight at room temperature and then quenched by the addition water (500 mL). The resulting solution was extracted with dichloromethane (2×500 mL) and the organic layers combined. The organic extracts were washed with brine (3×1000 mL), dried over anhydrous sodium sulfate and concentrated under vacuum. The residue was applied onto a silica gel column with ethyl acetate/petroleum ether (1:30-1:10). The collected fractions were combined and concentrated under vacuum. To afford 6-(tert-butyl) 7-methyl 4-((benzyloxy)amino)-2-trityl-2,4,5,7-tetrahydro-6H-pyrazolo[3,4-c]pyridine-6,7-dicarboxylate (5.6 g, 58.6%) as a white solid. MS: 645 ES+ ($C_{39}H_{40}N_4O_5$).

Int-78

A 250-mL round-bottom flask was purged and maintained with an inert atmosphere of nitrogen. 6-(tert-butyl) 7-methyl 4-((benzyloxy)amino)-2-trityl-2,4,5,7-tetrahydro-6H-pyrazolo[3,4-c]pyridine-6,7-dicarboxylate (Int-77, 7 g, 10.86 mmol) and dioxane (28 mL) were added, followed by hydrogen chloride (4M in dioxane) (105 mL) dropwise with stirring at 0° C. in 20 minutes. The resulting solution was stirred for 2 hours at room temperature. Precipitation was collected by filtration. The solid was dried under reduced pressure to afford methyl 4-((benzyloxy)amino)-4,5,6,7-tetrahydro-1H-pyrazolo[3,4-c]pyridine-7-carboxylate (2.81 g, 85.8%) as a white solid. MS: 303 ES+ ($C_{15}H_{18}N_4O_3$).

Int-79

A 3000-mL 3-necked round-bottom flask purged and maintained with an inert atmosphere of nitrogen. Methyl 4-((benzyloxy)amino)-4,5,6,7-tetrahydro-1H-pyrazolo[3,4-c]pyridine-7-carboxylate (Int-78, 4.5 g, 12.03 mmol) and acetonitrile (1350 mL) were added. This was followed by the addition of a solution of triethylamine (7.3 g, 72.14 mmol) in acetonitrile (36 mL) dropwise with stirring at 0° C. in 5 minutes. The solution was stirred at 0° C. for 30 minutes. To this was added a solution of ditrichloromethyl carbonate (1.25 g, 4.21 mmol) in acetonitrile (125 mL) dropwise with stirring at 0° C. in 5 hours. The resulting solution was stirred for overnight at room temperature. The reaction mixture was concentrated under vacuum, and diluted with EtOAc (1000 mL). It was washed with brine (2×1000 mL), dried over anhydrous sodium sulfate and concentrated under vacuum to give the crude product. It was re-crystallized from EtOAc:MTBE in the ratio of 1:10 to afford methyl (4R,8S)-5-(benzyloxy)-6-oxo-4,5,6,8-tetrahydro-1H-4,7-methanopyrazolo[3,4-e][1,3]diazepine-8-carboxylate (1.3 g, 33%) as a white solid. MS: 329 ES+ ($C_{16}H_{16}N_4O_4$) $^1$H NMR (300 MHz, DMSO-d6) δ 7.80 (s, 1H); 7.49-7.34 (m, 5H); 5.02 (s, 1H); 4.94-7.88 (m, 2H); 4.57 (s, 1H); 3.75 (s, 3H); 3.44-3.35 (m, 2H).

Scheme 13

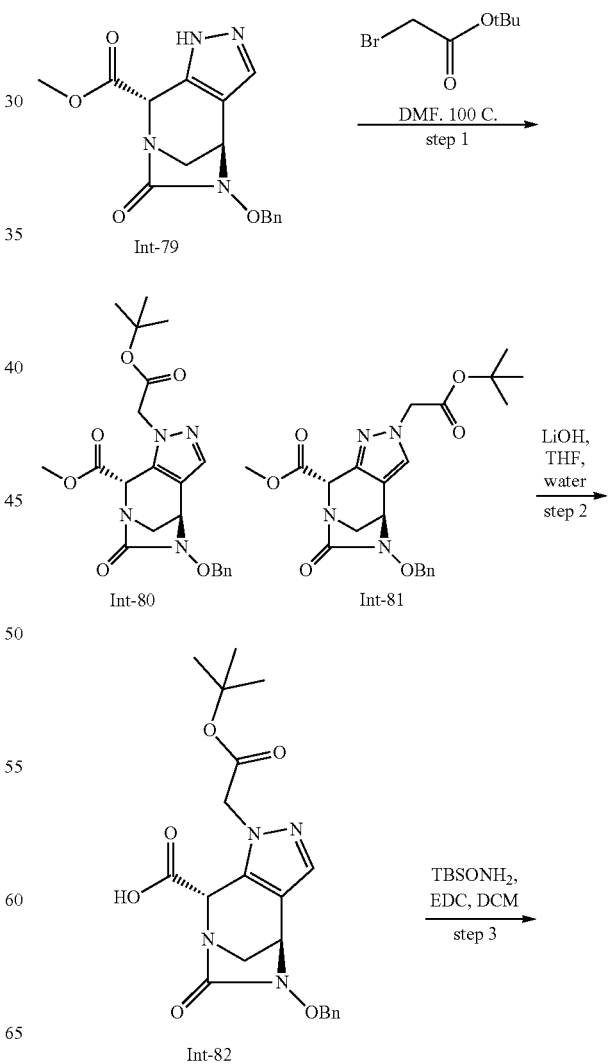

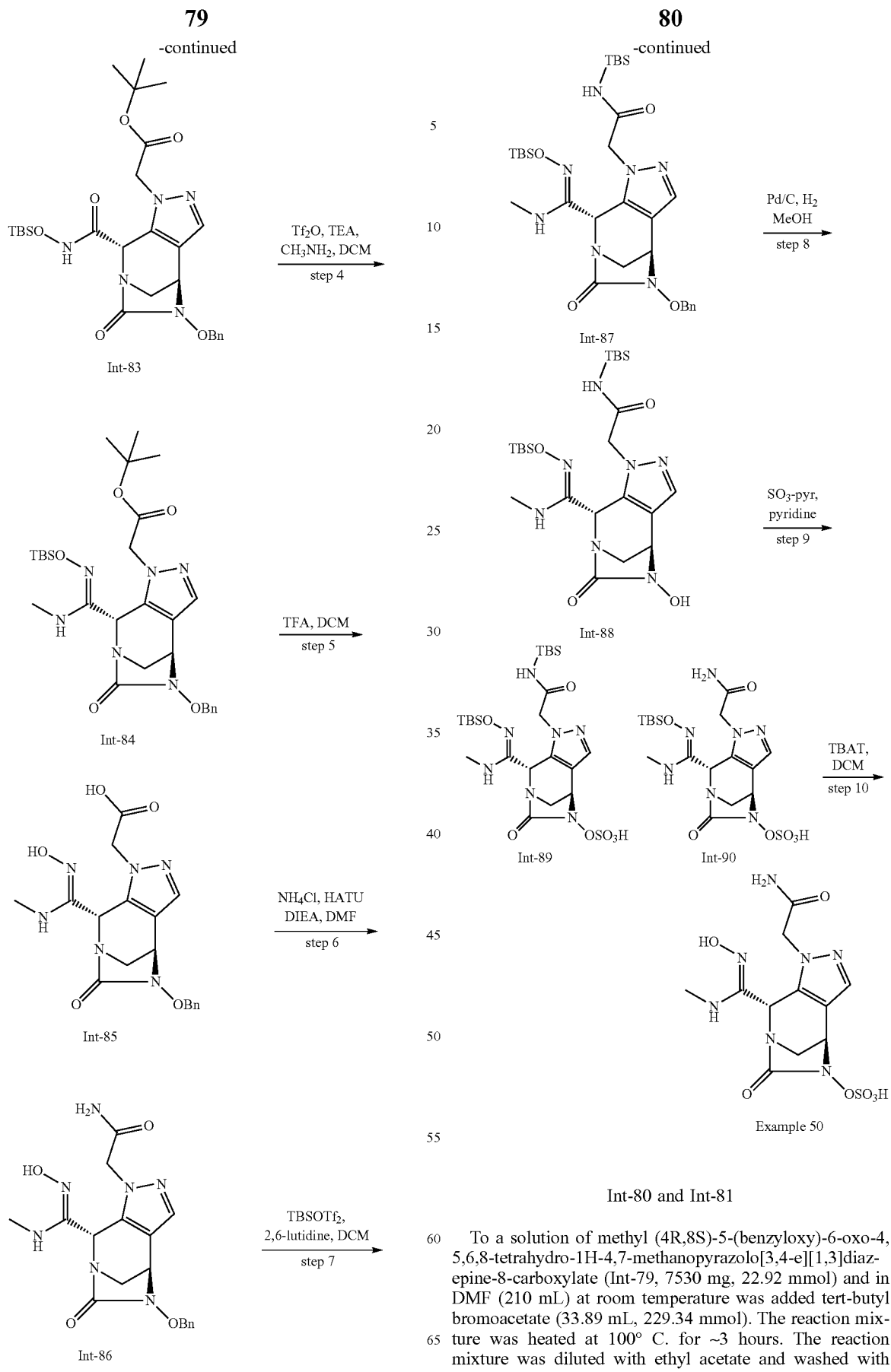

Int-80 and Int-81

To a solution of methyl (4R,8S)-5-(benzyloxy)-6-oxo-4,5,6,8-tetrahydro-1H-4,7-methanopyrazolo[3,4-e][1,3]diazepine-8-carboxylate (Int-79, 7530 mg, 22.92 mmol) and in DMF (210 mL) at room temperature was added tert-butyl bromoacetate (33.89 mL, 229.34 mmol). The reaction mixture was heated at 100° C. for ~3 hours. The reaction mixture was diluted with ethyl acetate and washed with water twice. The organics were dried over magnesium sulfate, filtered and concentrated. Silica gel chromatography (0%-5% acetone/DCM) afforded both regioisomers (Int-80 and Int-81) together. Repurified to separate (0%-5% acetone/DCM). First eluting: methyl (4R,8S)-5-(benzyloxy)-1-(2-(tert-butoxy)-2-oxoethyl)-6-oxo-4,5,6,8-tetrahydro-1H-4,7-methanopyrazolo[3,4-e][1,3]diazepine-8-carboxylate (Int-80, 2.928 g, 29%), MS: 443 ES+ ($C_{22}H_{26}N_4O_6$). Second eluting: methyl (4R,8S)-5-(benzyloxy)-2-(2-(tert-butoxy)-2-oxoethyl)-6-oxo-2,5,6,8-tetrahydro-4H-4,7-methanopyrazolo[3,4-e][1,3]diazepine-8-carboxylate (Int-81, 0.47 g, 5%), MS: 443 ES+ ($C_{22}H_{26}N_4O_6$).

Int-82

To a solution of methyl (4R,8S)-5-(benzyloxy)-1-(2-(tert-butoxy)-2-oxoethyl)-6-oxo-4,5,6,8-tetrahydro-1H-4,7-methanopyrazolo[3,4-e][1,3]diazepine-8-carboxylate (Int-80, 2928 mg, 6.62 mmol) in THF (40 mL) and water (20 mL) at 0° C. was added 1M lithium hydroxide (6.62 mL, 6.62 mmol). The reaction mixture was stirred at room temperature for 1 hour. Another 0.5 eq of lithium hydroxide added at 0° C. The reaction mixture was stirred at room temperature for 2 hours. Still only starting material. 0.2 eq lithium hydroxide added every hour until 1 eq more added. The reaction mixture was kept in freezer overnight. In the morning there is still only 50% product. Another 0.2 eq LiOH added and after 30 minutes the reaction is ~70-80% complete. Continue stirring at room temperature for 1 hour. The reaction mixture was cooled to 0° C., acidified to ~pH 4 with 0.5N HCl and extracted with ethyl acetate 4 times. The aqueous was further acidified to ~pH 2 and extracted four times with ethyl acetate. The organics were dried over sodium sulfate, filtered and concentrated to afford (4R,8S)-5-(benzyloxy)-1-(2-(tert-butoxy)-2-oxoethyl)-6-oxo-4,5,6,8-tetrahydro-1H-4,7-methanopyrazolo[3,4-e][1,3]diazepine-8-carboxylic acid (1.953 g, 69%) as a light yellow foam. MS: 429 ES+ ($C_{21}H_{24}N_4O_6$).

Int-83

To a suspension of (4R,8S)-5-(benzyloxy)-1-(2-(tert-butoxy)-2-oxoethyl)-6-oxo-4,5,6,8-tetrahydro-1H-4,7-methanopyrazolo[3,4-e][1,3]diazepine-8-carboxylic acid (Int-82, 1453 mg, 3.39 mmol) in DCM (30 mL) at room temperature was added O-(tert-butyldimethylsilyl) hydroxylamine (599.42 mg, 4.07 mmol) and EDC (780.15 mg, 4.07 mmol). The reaction mixture was stirred at room temperature for 1.5 hours. Another 0.4 eq of NH$_2$OTBS added and stirred for 3 hours. The reaction mixture was concentrated and purified by silica gel chromatography twice (0%-30% ethyl acetate/hexanes) to afford tert-butyl 2-((4R,8S)-5-(benzyloxy)-8-(((tert-butyldimethylsilyl)oxy)carbamoyl)-6-oxo-4,5,6,8-tetrahydro-1H-4,7-methanopyrazolo[3,4-e][1,3]diazepin-1-yl)acetate (369 mg, 20%) as a white foam. MS: 558 ES+ ($C_{27}H_{39}N_5O_6Si$).

Int-84

To a solution of tert-butyl 2-((4R,8S)-5-(benzyloxy)-8-(((tert-butyldimethylsilyl)oxy)carbamoyl)-6-oxo-4,5,6,8-tetrahydro-1H-4,7-methanopyrazolo[3,4-e][1,3]diazepin-1-yl)acetate (Int-83, 616.4 mg, 1.11 mmol) and triethylamine (0.15 mL, 1.11 mmol) in DCM (12 mL) at −78° C. was added triflic anhydride (0.19 mL, 1.11 mmol). The reaction mixture was stirred at −78° C. for 5 minutes. To the reaction mixture was added methylamine (6.63 mL, 13.26 mmol). The reaction mixture was warmed to room temperature and stirred for 6 hours. It was concentrated and purified by flash chromatography (20 g silica gel, 0%-30% ethyl acetate/hexanes) to afford tert-butyl 2-((4R,8S)-5-(benzyloxy)-8-((Z)—N'-((tert-butyldimethylsilyl)oxy)-N-methylcarbamimidoyl)-6-oxo-4,5,6,8-tetrahydro-1H-4,7-methanopyrazolo[3,4-e][1,3]diazepin-1-yl)acetate (138.5 mg, 22%). MS: 571 ES+ ($C_{28}H_{42}N_6O_5Si$).

Int-85

To a solution of tert-butyl 2-((4R,8S)-5-(benzyloxy)-8-((Z)—N'-((tert-butyldimethylsilyl)oxy)-N-methylcarbamimidoyl)-6-oxo-4,5,6,8-tetrahydro-1H-4,7-methanopyrazolo[3,4-e][1,3]diazepin-1-yl)acetate (Int-84, 138.5 mg, 0.24 mmol) in DCM (2 mL) at 0° C. was added TFA (1.02 mL, 13.35 mmol). The reaction mixture was warmed to room temperature and stirred for 3 hours. The reaction mixture was concentrated with DCM twice and the resulting yellow oil was dried under vacuum for 2 hours to afford a yellow solid. This was dissolved in ~2 mL 1:1 ACN/pH 7 phosphate buffer and purified by C18 ISCO (100% water, 3 min then to 50% ACN, 4 min) to afford 2-((4R,8S)-5-(benzyloxy)-8-((Z)—N'-hydroxy-N-methylcarbamimidoyl)-6-oxo-4,5,6,8-tetrahydro-1H-4,7-methanopyrazolo[3,4-e][1,3]diazepin-1-yl)acetic acid (67.9 mg, 70%) as a pale yellow solid. MS: 401 ES+ ($C_{18}H_{20}N_6O_5$).

Int-86

To a solution of 2-((4R,8S)-5-(benzyloxy)-8-((Z)—N'-hydroxy-N-methylcarbamimidoyl)-6-oxo-4,5,6,8-tetrahydro-1H-4,7-methanopyrazolo[3,4-e][1,3]diazepin-1-yl)acetic acid (Int-85, 67.9 mg, 0.17 mmol) in DMF (2 mL) at room temperature was added ammonium chloride (36.29 mg, 0.68 mmol), HATU (128.96 mg, 0.34 mmol) and DIEA (0.12 mL, 0.68 mmol). The reaction mixture was stirred for 15 minutes at room temperature then diluted with ethyl acetate and washed with saturated sodium bicarbonate solution and brine/water (1:1). Aqueous layer was extracted twice with ethyl acetate. The organics were pooled, dried over anhydrous magnesium sulfate, filtered and concentrated. Silica gel chromatography (0%-90% acetone/DCM) afforded 2-((4R,8S)-5-(benzyloxy)-8-((Z)—N'-hydroxy-N-methylcarbamimidoyl)-6-oxo-4,5,6,8-tetrahydro-1H-4,7-methanopyrazolo[3,4-e][1,3]diazepin-1-yl)acetamide (48.9 mg, 72%). MS: 400 ES+ ($C_{18}H_{21}N_7O_4$).

Int-87

To a solution of 2-((4R,8S)-5-(benzyloxy)-8-((Z)—N'-hydroxy-N-methylcarbamimidoyl)-6-oxo-4,5,6,8-tetrahydro-1H-4,7-methanopyrazolo[3,4-e][1,3]diazepin-1-yl)acetamide (Int-86, 48.9 mg, 0.12 mmol) (~50-60% pure) in DCM at 0° C. was added tert-butyldimethylsilyl trifluoromethanesulfonate (0.03 mL, 0.12 mmol) and 2,6-lutidine (0.01 mL, 0.12 mmol). The reaction mixture was stirred at room temperature for 30 minutes. See a mixture of starting material, mono and bis TBS protected. More tert-butyldimethylsilyl trifluoromethanesulfonate (0.03 mL, 0.12 mmol) and 2,6-lutidine (0.01 mL, 0.12 mmol) added. After 1 hour the major product is bis TBS protected. More tert-butyldimethylsilyl trifluoromethanesulfonate (0.03 mL, 0.12 mmol) and 2,6-lutidine (0.01 mL, 0.12 mmol) added again. After another hour the reaction mixture was diluted with dichloromethane and washed with saturated ammonium chloride solution. The organics were dried over sodium sulfate, filtered and concentrated. Silica gel chromatography (0%-

100% ethyl acetate/hexanes) afforded 2-((4R,8S)-5-(benzyloxy)-8-((Z)—N'-((tert-butyldimethylsilyl)oxy)-N-methylcarbamimidoyl)-6-oxo-4,5,6,8-tetrahydro-1H-4,7-methanopyrazolo[3,4-e][1,3]diazepin-1-yl)-N-(tert-butyldimethylsilyl)acetamide (23.9 mg, 31%). MS: 628 ES+ ($C_{30}H_{49}N_7O_4Si_2$).

Int-88

A solution of 2-((4R,8S)-5-(benzyloxy)-8-((Z)—N'-((tert-butyldimethylsilyl)oxy)-N-methylcarbamimidoyl)-6-oxo-4,5,6,8-tetrahydro-1H-4,7-methanopyrazolo[3,4-e][1,3]diazepin-1-yl)-N-(tert-butyldimethylsilyl)acetamide (Int-87, 31.1 mg, 0.05 mmol) in methanol (1 mL) and ethyl acetate (1 mL) was purged with nitrogen. Palladium on carbon (5.27 mg, 0.005 mmol) was added and the reaction mixture was purged again and placed under hydrogen balloon and stirred for 1 hour 45 minutes. The reaction mixture was filtered through a 0.45 am filter and concentrated to afford N-(tert-butyldimethylsilyl)-2-((4R,8S)-8-((Z)—N'-((tert-butyldimethylsilyl)oxy)-N-methylcarbamimidoyl)-5-hydroxy-6-oxo-4,5,6,8-tetrahydro-1H-4,7-methanopyrazolo[3,4-e][1,3]diazepin-1-yl)acetamide (24.5 mg, 92%). MS: 538 ES+ ($C_{23}H_{43}N_7O_4Si_2$).

Int-89 and Int-90

To a solution of N-(tert-butyldimethylsilyl)-2-((4R,8S)-8-((Z)—N'-((tert-butyldimethylsilyl)oxy)-N-methylcarbamimidoyl)-5-hydroxy-6-oxo-4,5,6,8-tetrahydro-1H-4,7-methanopyrazolo[3,4-e][1,3]diazepin-1-yl)acetamide (Int-88, 24.5 mg, 0.05 mmol) in pyridine (1 mL) at room temperature was added sulfur trioxide pyridine complex (43.5 mg, 0.27 mmol). The reaction mixture was stirred at room temperature for 3 hours then concentrated and dried under vacuum. Silica gel chromatography (0%-100% acetone/dichloromethane) afforded a 1:1 mixture of (4R,8S)-1-(2-((tert-butyldimethylsilyl)amino)-2-oxoethyl)-8-((Z)—N'-((tert-butyldimethylsilyl)oxy)-N-methylcarbamimidoyl)-6-oxo-4,8-dihydro-1H-4,7-methanopyrazolo[3,4-e][1,3]diazepin-5(6H)-yl hydrogen sulfate (Int-89). MS: 618 ES+ ($C_{23}H_{43}N_7O_7Si_2S$); and (4R)-1-(2-amino-2-oxoethyl)-8-((Z)—N'-((tert-butyldimethylsilyl)oxy)-N-methylcarbamimidoyl)-6-oxo-4,8-dihydro-1H-4,7-methanopyrazolo[3,4-e][1,3]diazepin-5(6H)-yl hydrogen sulfate (Int-90) (16.4 mg, 64%). MS: 504 ES+ ($C_{17}H_{29}N_7O_7SiS$).

Example 50

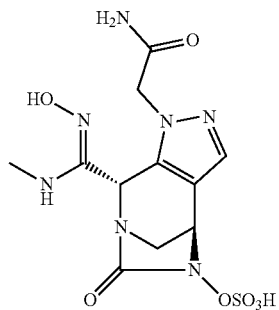

To a solution of (4R,8S)-1-(2-((tert-butyldimethylsilyl)amino)-2-oxoethyl)-8-((Z)—N'-((tert-butyldimethylsilyl)oxy)-N-methylcarbamimidoyl)-6-oxo-4,8-dihydro-1H-4,7-methanopyrazolo[3,4-e][1,3]diazepin-5(6H)-yl hydrogen sulfate (Int-89) and (4R)-1-(2-amino-2-oxoethyl)-8-((Z)—N'-((tert-butyldimethylsilyl)oxy)-N-methylcarbamimidoyl)-6-oxo-4,8-dihydro-1H-4,7-methanopyrazolo[3,4-e][1,3]diazepin-5(6H)-yl hydrogen sulfate (Int-90) (16.4 mg, 0.03 mmol) in DCM (1 mL) at room temperature was added tetrabutylammonium difluorotriphenylsilicate (21.49 mg, 0.04 mmol). The reaction mixture was stirred at room temperature for 35 minutes then loaded onto a 4 g silica gel column and purified (0%-100% acetone/DCM). The product eluted in 100% acetone. The fractions were combined and concentrated to afford a colorless film. The resulting film was dissolved in water/acetonitrile (1:1), frozen and lyophilized to afford TBA salt of (4R,8S)-1-(2-amino-2-oxoethyl)-8-((Z)—N'-hydroxy-N-methylcarbamimidoyl)-6-oxo-4,8-dihydro-1H-4,7-methanopyrazolo[3,4-e][1,3]diazepin-5(6H)-yl sulfate TBA salt as a white solid (11.9 mg, 70%). MS: 390 ES+ ($C_{11}H_{15}N_7O_7S$) $^1$H NMR (300 MHz, DMSO-$d_6$) δ: 0.85 (m, 9H); 1.23 (m, 6H); 1.47 (m, 6H); 2.82 (m, 3H); 3.09 (m, 6H); 3.30 (m, 2H); 4.41 (m, 2H); 4.61 (m, 1H); 5.47 (s, 1H); 7.17 (bs, 1H); 7.28 (s, 1H); 7.39 (bs, 1H); 9.50 (s, 1H). Compound:TBA=1:0.75.

Scheme 14

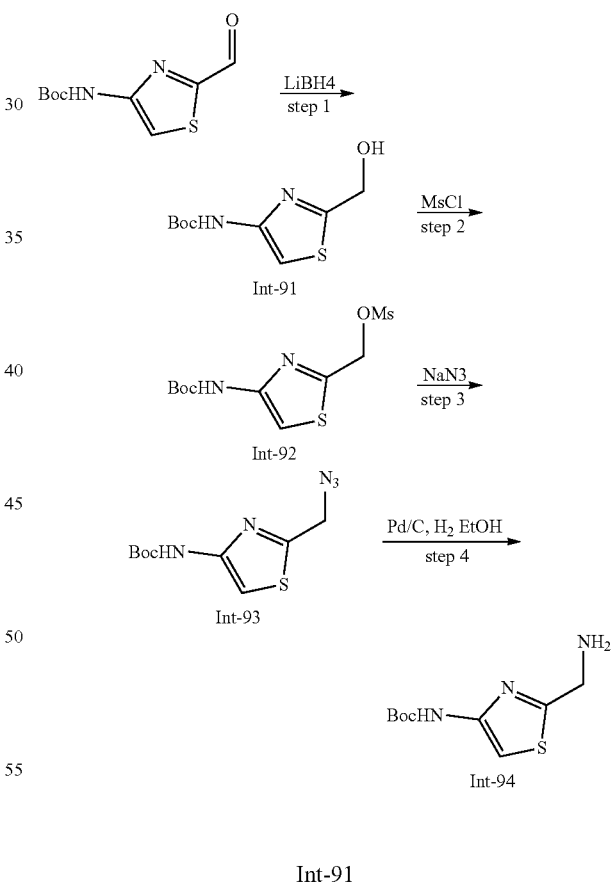

Int-91

To a suspension of tert-butyl (2-formylthiazol-4-yl)carbamate (500 mg, 2.19 mmol) in Methanol (100 mL) and THF (50 mL) at −16° C. was added a solution of LiBH$_4$ (5.48 mL, 10.95 mmol) in THF dropwise. After stirring at −16° C. for 2 hours, the reaction was quenched with saturated ammonium chloride solution (100 mL). The solvent was removed. The residue was partitioned between DCM (100 mL) and saturated ammonium chloride solution (100 mL). The organic layer was collected, washed with water (50 mL), brine (50 mL), dried over anhydrous sodium sulfate, filtered and concentrated. The residue was triturated with EtOAc to afford tert-butyl (2-(hydroxymethyl)thiazol-4-yl)carbamate (504 mg, 99%) as a white solid. MS: 231 ES+ ($C_9H_{14}N_2O_3S$).

Int-92

To a solution of tert-butyl (2-(hydroxymethyl)thiazol-4-yl)carbamate (Int-91, 500 mg, 2.18 mmol) in DCM (50 mL) at 0° C. was added DIEA (0.76 mL. 4.36 mmol), followed by methanesulfonyl chloride (0.19 mL, 2.4 mmol). The reaction mixture was stirred at 0° C. for 2 hours. DCM (50 mL) and saturated ammonium chloride solution (100 mL) were added. The organic layer was separated, washed with water (50 mL), brine (50 mL), dried over anhydrous sodium sulfate, filtered and concentrated to afford (4-((tert-butoxycarbonyl)amino)thiazol-2-yl)methyl methanesulfonate (673 mg, 99%) as a white solid. MS: 309 ES+ ($C_{10}H_{16}N_2O_5S_2$).

Int-93

To a solution of (4-((tert-butoxycarbonyl)amino)thiazol-2-yl)methyl methanesulfonate (Int-92, 606 mg, 1.96 mmol) in DMF (20 mL) at 0° C. was added sodium azide (255 mg, 3.93 mmol). The reaction mixture was stirred at room temperature for 16 hours. DCM (100 mL) and saturated ammonium chloride solution (100 mL) were added. The organic layer was separated, washed with water (50 mL), brine (50 mL), dried over anhydrous sodium sulfate, filtered and concentrated to give the crude product. It was triturated with EtOAc to afford tert-butyl (2-(azidomethyl)thiazol-4-yl)carbamate (501 mg, 99%) as a white solid. MS: 255 ES+ ($C_9H_{13}N_5O_2S$).

Int-94

Int-94 was synthesized by following similar reaction conditions as shown for Int-14 (Scheme 1, step 14), using tert-butyl (2-(azidomethyl)thiazol-4-yl)carbamate (Int-93, 501 mg, 01.96 mmo) as substrate, and EtOH as solvent, to afford tert-butyl (2-(aminomethyl)thiazol-4-yl)carbamate (380 mg, 84%) as a white solid. MS: 230 ES+ ($C_9H_{15}N_3O_2S$).

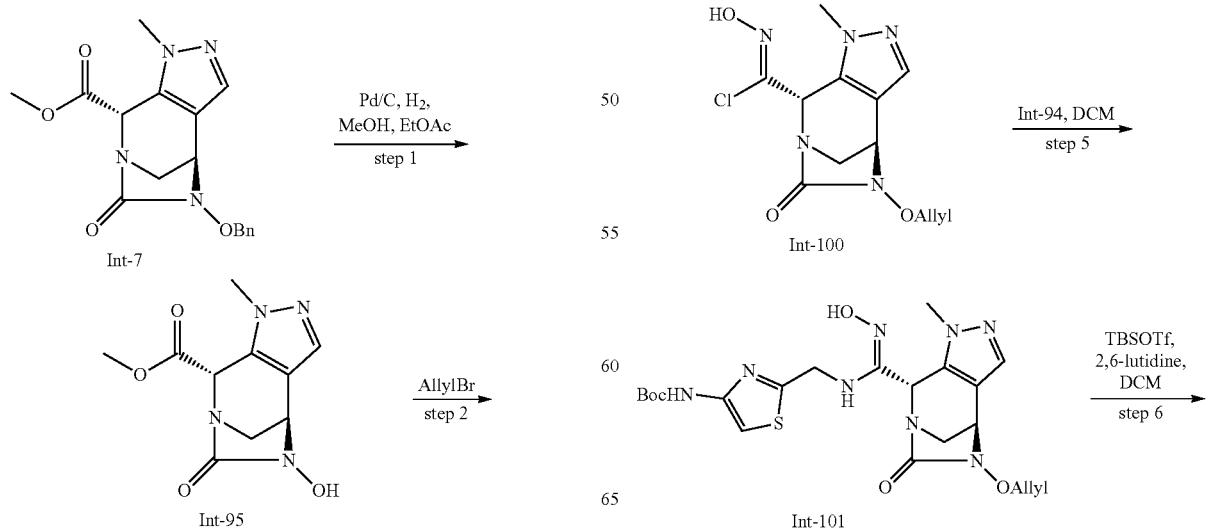

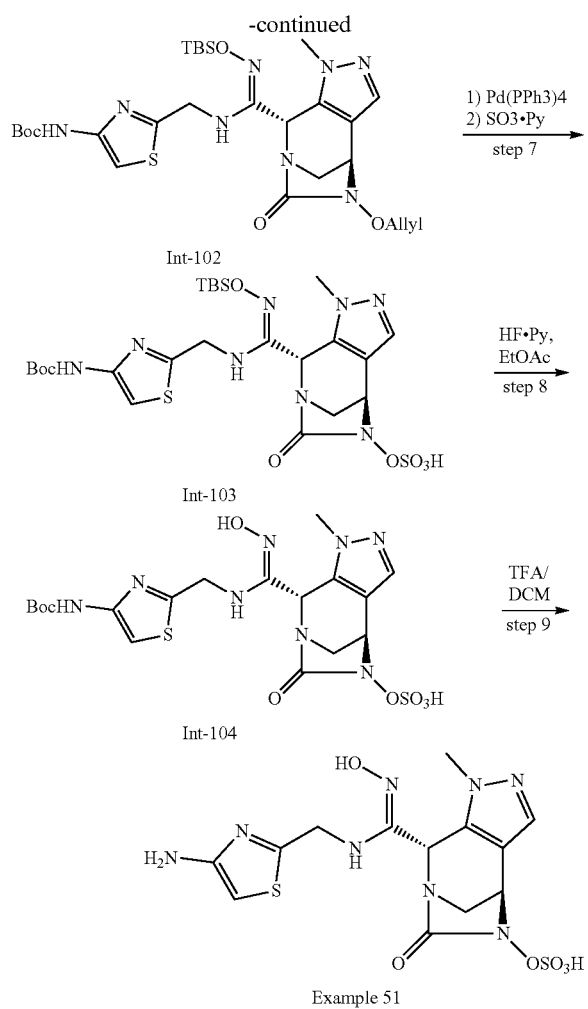

Int-102

Int-103

Int-104

Example 51

Int-95

Int-95 was synthesized by following similar reaction conditions as shown for Int-14 (Scheme 1, step 14), using methyl (4R,8S)-5-(benzyloxy)-1-methyl-6-oxo-4,5,6,8-tetrahydro-1H-4,7-methanopyrazolo[3,4-e][1,3]diazepine-8-carboxylate (Int-7, 2298 mg, 6.71 mmol) as the substrate, to afford methyl (4R,8S)-5-hydroxy-1-methyl-6-oxo-4,5,6,8-tetrahydro-1H-4,7-methanopyrazolo[3,4-e][1,3]diazepine-8-carboxylate (722 mg, 42%). MS: 253 ES+ ($C_{10}H_{12}N_4O_4$).

Int-96

To a suspension of methyl (4R,8S)-5-hydroxy-1-methyl-6-oxo-4,5,6,8-tetrahydro-1H-4,7-methanopyrazolo[3,4-e][1,3]diazepine-8-carboxylate (Int-95, 406 mg, 1.61 mmol) in DMF (5 mL) was added cesium carbonate (629.34 mg, 1.93 mmol) and Allyl bromide (0.14 mL, 1.61 mmol). The reaction mixture was stirred at room temperature for 3 hours. Water (20 mL) and EtOAc (50 mL) were added. The organic layer was separated, dried over anhydrous sodium sulfate, and concentrated to give the crude product. It was purified by flash chromatography (20 g silica gel, 0-100% EtOAc in Hexanes) to afford methyl (4R,8S)-5-(allyloxy)-1-methyl-6-oxo-4,5,6,8-tetrahydro-1H-4,7-methanopyrazolo[3,4-e][1,3]diazepine-8-carboxylate (350 mg, 74%) as a white solid. MS: 293 ES+ ($C_{13}H_{16}N_4O_4$).

Int-97

Int-97 was synthesized by following similar reaction conditions as shown for Int-8 (Scheme 1, step 8), using methyl (4R,8S)-5-(allyloxy)-1-methyl-6-oxo-4,5,6,8-tetrahydro-1H-4,7-methanopyrazolo[3,4-e][1,3]diazepine-8-carboxylate (Int-96, 350 mg, 1.19 mmol) as substrate, to afford (4R,8S)-5-(allyloxy)-8-(hydroxymethyl)-1-methyl-1,4,5,8-tetrahydro-6H-4,7-methanopyrazolo[3,4-e][1,3]diazepin-6-one (106 mg, 33%) as a white solid. MS: 265 ES+ ($C_{12}H_{16}N_4O_3$).

Int-98

Int-98 was synthesized by following similar reaction conditions as shown for Int-9 (Scheme 1, step 9), using (4R,8S)-5-(allyloxy)-8-(hydroxymethyl)-1-methyl-1,4,5,8-tetrahydro-6H-4,7-methanopyrazolo[3,4-e][1,3]diazepin-6-one (Int-97, 106 mg, 0.40 mmol) as substrate, to afford (4R,8S)-5-(allyloxy)-1-methyl-6-oxo-4,5,6,8-tetrahydro-1H-4,7-methanopyrazolo[3,4-e][1,3]diazepine-8-carbaldehyde (105 mg, 99%) as a white solid. MS: 263 ES+ ($C_{12}H_{14}N_4O_3$).

Int-99

Int-99 was synthesized by following similar reaction conditions as shown for Int-10 (Scheme 1, step 10), using (4R,8S)-5-(allyloxy)-1-methyl-6-oxo-4,5,6,8-tetrahydro-1H-4,7-methanopyrazolo[3,4-e][1,3]diazepine-8-carbaldehyde (Int-98, 647 mg, 2.467 mmol) as substrate, to afford (E)-5-(allyloxy)-1-methyl-6-oxo-4,5,6,8-tetrahydro-1H-4,7-methanopyrazolo[3,4-e][1,3]diazepine-8-carbaldehyde oxime (684 mg, 99%) as a white solid. MS: 278 ES+ ($C_{12}H_{15}N_5O_3$).

Int-100

Int-100 was synthesized by following similar reaction conditions as shown for Int-11 (Scheme 1, step 11), using (E)-5-(allyloxy)-1-methyl-6-oxo-4,5,6,8-tetrahydro-1H-4,7-methanopyrazolo[3,4-e][1,3]diazepine-8-carbaldehyde oxime (Int-99, 614 mg, 2.21 mmol) as substrate, to afford (4R,8S,Z)-5-(allyloxy)-N-hydroxy-1-methyl-6-oxo-4,5,6,8-tetrahydro-1H-4,7-methanopyrazolo[3,4-e][1,3]diazepine-8-carbimidoyl chloride (690 mg, 99%) as a white solid. MS: 312 ES+ ($C_{12}H_{14}C_1N_5O_3$).

Int-101

Int-101 was synthesized by following similar reaction conditions as shown for Int-12 (Scheme 1, step 12), using (4R,8S,Z)-5-(allyloxy)-N-hydroxy-1-methyl-6-oxo-4,5,6,8-tetrahydro-1H-4,7-methanopyrazolo[3,4-e][1,3]diazepine-8-carbimidoyl chloride (Int-100, 470 mg, 1.51 mmol), and tert-butyl (2-(aminomethyl)thiazol-4-yl)carbamate (Int-94, 380 mg, 1.66 mmol) as substrates, to afford tert-butyl (2-(((4R,8S,Z)-5-(allyloxy)-N'-hydroxy-1-methyl-6-oxo-4,5,6,8-tetrahydro-1H-4,7-methanopyrazolo[3,4-e][1,3]diazepine-8-carboximidamido)methyl)thiazol-4-yl)carbamate (115 mg, 15%) as a white solid. MS: 505 ES+ ($C_{21}H_{28}N_8O_5S$).

Int-102

Int-102 was synthesized by following similar reaction conditions as shown for Int-13 (Scheme 1, step 13), using tert-butyl (2-(((4R,8S,Z)-5-(allyloxy)-N'-hydroxy-1-methyl-6-oxo-4,5,6,8-tetrahydro-1H-4,7-methanopyrazolo[3,4-e][1,3]diazepine-8-carboximidamido)methyl)thiazol-4-yl)carbamate (Int-101, 58 mg, 0.11 mmol) as substrates, to afford tert-butyl (2-((Z)-3-((4R,8S)-5-(allyloxy)-1-methyl-6-oxo-4,5,6,8-tetrahydro-1H-4,7-methanopyrazolo[3,4-e][1,3]diazepin-8-yl)-6,6,7,7-tetramethyl-5-oxa-2,4-diaza-6-silaoct-3-en-1-yl)thiazol-4-yl)carbamate (65 mg, 92%) as a white solid. MS: 619 ES+ ($C_{27}H_{42}N_8O_5SiS$).

Int-103

To a solution of tert-butyl (2-((Z)-3-((4R,8S)-5-(allyloxy)-1-methyl-6-oxo-4,5,6,8-tetrahydro-1H-4,7-methanopyrazolo[3,4-e][1,3]diazepin-8-yl)-6,6,7,7-tetramethyl-5-oxa-2,4-diaza-6-silaoct-3-en-1-yl)thiazol-4-yl)carbamate (Int-102, 65 mg, 0.10 mmol) in MeOH (5 mL) at room temperature was added 1,3-dimethylbarbituric acid (32.8 mg, 0.21 mmol) and tetrakis(triphenylphosphine)palladium (0) (121.38 mg, 0.11 mmol). The reaction mixture was stirred for 1 hour at room temperature and concentrated.

To the crude material describe above at ambient temperature was added pyridine (5 mL) and sulfur trioxide pyridine complex (132 mg, 0.83 mmol). The reaction mixture was stirred overnight, then concentrated under reduced pressure to give the crude product. It was purified on a short silica pad, eluting with hexanes (100 mL), followed by ethyl acetate/hexanes (1:1, 100 mL), ethyl acetate (100 mL) and acetone (200 mL) to afford (4R,8S)-8-((Z)—N-((4-((tert-butoxycarbonyl)amino)thiazol-2-yl)methyl)-N'-hydroxycarbamimidoyl)-1-methyl-6-oxo-4,8-dihydro-1H-4,7-methanopyrazolo[3,4-e][1,3]diazepin-5(6H)-yl hydrogen sulfate (54 mg, 79%) as a white solid. MS: 659 ES+ ($C_{24}H_{38}N_8O_8SiS_2$).

Int-104

Int-104 was synthesized by following similar reaction conditions as shown for Int-16 (Scheme 1, step 16), using (4R,8S)-8-((Z)—N-((4-((tert-butoxycarbonyl)amino)thiazol-2-yl)methyl)-N'-hydroxycarbamimidoyl)-1-methyl-6-oxo-4,8-dihydro-1H-4,7-methanopyrazolo[3,4-e][1,3]diazepin-5(6H)-yl hydrogen sulfate (Int-103, 54 mg, 0.082 mmol) as substrates, to afford (4R,8S)-8-((Z)—N-((4-((tert-butoxycarbonyl)amino)thiazol-2-yl)methyl)-N'-hydroxycarbamimidoyl)-1-methyl-6-oxo-4,8-dihydro-1H-4,7-methanopyrazolo[3,4-e][1,3]diazepin-5(6H)-yl hydrogen sulfate (38 mg, 85%) as a white solid. MS: 545 ES+ ($C_{18}H_{24}N_8O_8S_2$).

Example 51

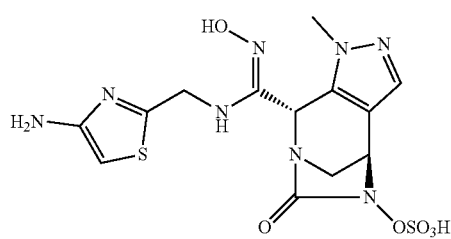

To a solution of (4R,8S)-8-((Z)—N-((4-((tert-butoxycarbonyl)amino)thiazol-2-yl)methyl)-N'-hydroxycarbamimidoyl)-1-methyl-6-oxo-4,8-dihydro-1H-4,7-methanopyrazolo[3,4-e][1,3]diazepin-5(6H)-yl hydrogen sulfate (Int-104, 25 mg, 0.046 mmol) in DCM (2 mL) at 0° C. was added TFA (1.2 mL, 15.6 mmol). The reaction mixture was stirred at 0° C. for 2 hours. Solvent was removed. The residue was dissolved in water and purified by reversed phase chromatography (12 g sepabeads, 100% water) to afford (4R,8S)-8-((Z)—N-((4-aminothiazol-2-yl)methyl)-N'-hydroxycarbamimidoyl)-1-methyl-6-oxo-4,8-dihydro-1H-4,7-methanopyrazolo[3,4-e][1,3]diazepin-5(6H)-yl hydrogen sulfate TBA salt (4 mg, 15.6%) as a white solid. MS: 445 ES+ ($C_{13}H_{16}N_8O_6S_2$) $^1$HNMR (300 MHz, $D_2O$) δ: 3.39-3.49 (m, 5H); 4.35 (m, 1H); 4.56 (m, 1H); 4.86 (m, 1H); 5.51 (m, 1H); 6.56 (s, 1H); 7.54 (s, 1H). Compound/TBA=1:1.

Scheme 16

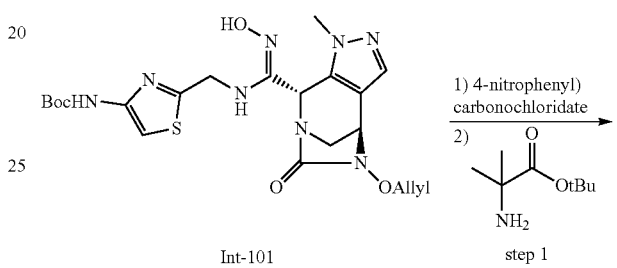

Int-101 step 1

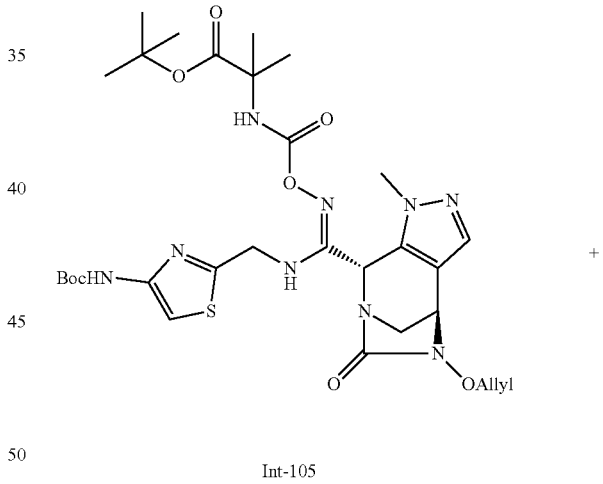

Int-105

+

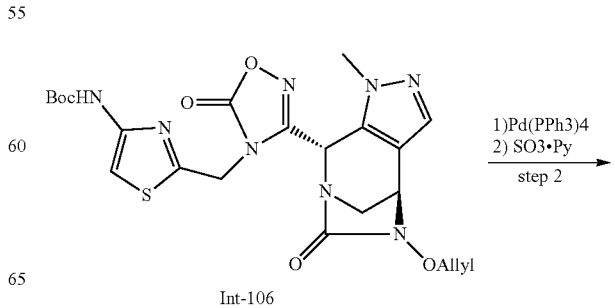

Int-106

1) Pd(PPh3)4
2) SO3·Py step 2

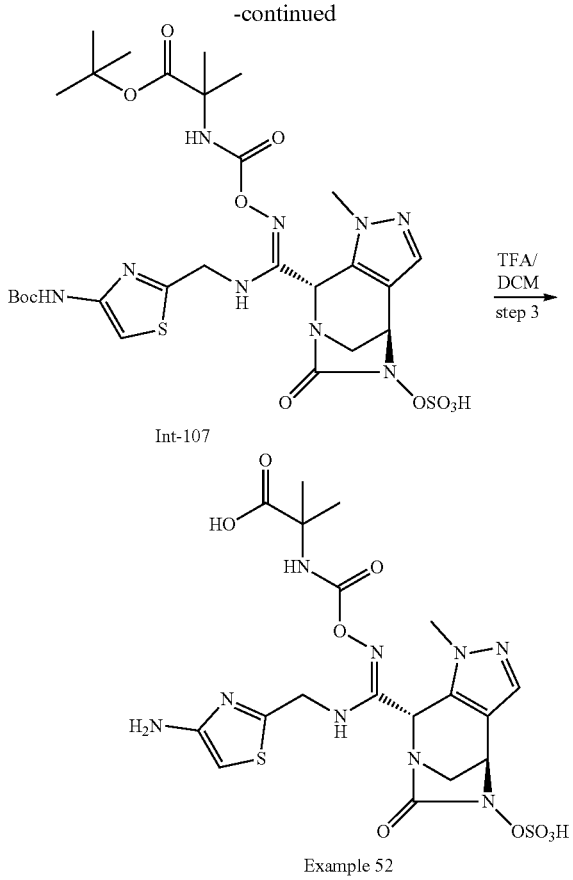

Int-107

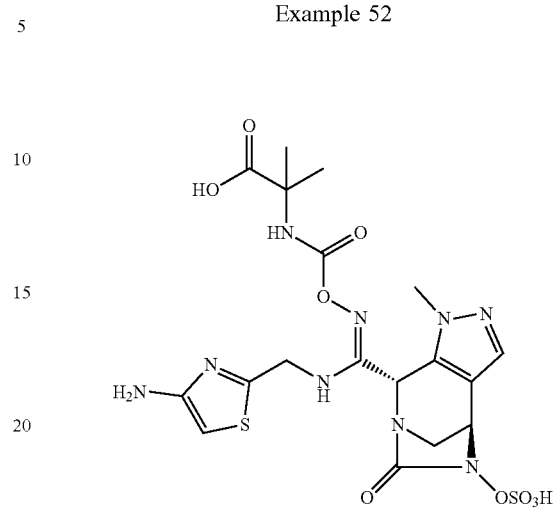

Example 52 yl)-6-oxo-5-oxa-2,4,7-triazanon-3-en-9-oate (15 mg, 95%) as a white solid. MS: 730 ES+ ($C_{27}H_{39}N_9O_{11}S_2$).

Example 52

Example 52 was synthesized by following similar reaction conditions as shown for Example 51 (Scheme 15, step 9), using tert-butyl (Z)-1-(4-((tert-butoxycarbonyl)amino) thiazol-2-yl)-8,8-dimethyl-3-((4R,8S)-1-methyl-6-oxo-5-(sulfooxy)-4,5,6,8-tetrahydro-1H-4,7-methanopyrazolo[3,4-e][1,3]diazepin-8-yl)-6-oxo-5-oxa-2,4,7-triazanon-3-en-9-oate (Int-107, 15 mg, 0.02 mmol) as the substrate, to afford (Z)-1-(4-aminothiazol-2-yl)-8,8-dimethyl-3-((4R,8S)-1-methyl-6-oxo-5-(sulfooxy)-4,5,6,8-tetrahydro-1H-4,7-methanopyrazolo[3,4-e][1,3]diazepin-8-yl)-6-oxo-5-oxa-2,4,7-triazanon-3-en-9-oic acid (1.5 mg, 10%) as a white solid. MS: 574 ES+ ($C_{18}H_{23}N_9O_9S_2$) $^1$HNMR (300 MHz, $D_2O$) δ: 1.48 (s, 3H); 1.54 (s, 3H); 3.56 (m, 2H); 3.63 (s, 3H); 4.67 (m, 2H); 4.92 (m, 1H); 5.66 (m, 1H); 6.65 (s, 1H); 7.60 (s, 1H).

Int-105 and Int-106

Int-105 and Int-106 was synthesized by following similar reaction conditions as shown for Int-20 (Scheme 3, step 1 and 2), using tert-butyl (2-(((4R,8S,Z)-5-(allyloxy)-N'-hydroxy-1-methyl-6-oxo-4,5,6,8-tetrahydro-1H-4,7-methanopyrazolo[3,4-e][1,3]diazepine-8-carboximidamido)methyl) thiazol-4-yl)carbamate (Int-101, 52.3 mg, 0.10 mmol) as substrate, to afford tert-butyl (Z)-3-((4R,8S)-5-(allyloxy)-1-methyl-6-oxo-4,5,6,8-tetrahydro-1H-4,7-methanopyrazolo [3,4-e][1,3]diazepin-8-yl)-1-(4-((tert-butoxycarbonyl) amino)thiazol-2-yl)-8,8-dimethyl-6-oxo-5-oxa-2,4,7-triazanon-3-en-9-oate (Int-105, 18 mg, 25%) MS: 690 ES+ ($C_{30}H_{43}N_9O_8S$); and tert-butyl (2-((3-((4R,8S)-5-(allyloxy)-1-methyl-6-oxo-4,5,6,8-tetrahydro-1H-4,7-methanopyrazolo[3,4-e][1,3]diazepin-8-yl)-5-oxo-1,2,4-oxadiazol-4 (5H)-yl)methyl)thiazol-4-yl)carbamate (Int-106, 27 mg, 49%). MS: 531 ES+ ($C_{22}H_{26}N_8O_6S$).

Int-107

Int-107 was synthesized by following similar reaction conditions as shown for Int-103 (Scheme 15, step 7), using tert-butyl (Z)-3-((4R,8S)-5-(allyloxy)-1-methyl-6-oxo-4,5, 6,8-tetrahydro-1H-4,7-methanopyrazolo[3,4-e][1,3]diazepin-8-yl)-1-(4-((tert-butoxycarbonyl)amino)thiazol-2-yl)-8,8-dimethyl-6-oxo-5-oxa-2,4,7-triazanon-3-en-9-oate (Int-105, 18 mg, 0.03 mmol) as the substrate, to afford tert-butyl (Z)-1-(4-((tert-butoxycarbonyl)amino)thiazol-2-yl)-8,8-dimethyl-3-((4R,8S)-1-methyl-6-oxo-5-(sulfooxy)-4,5,6,8-tetrahydro-1H-4,7-methanopyrazolo[3,4-e][1,3]diazepin-8-

Scheme 17

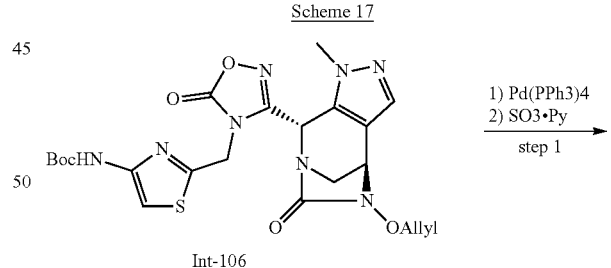

Int-106

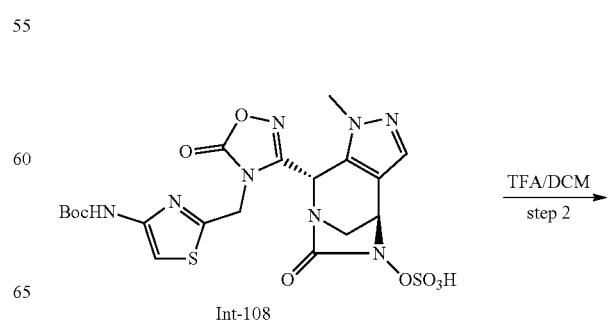

Int-108

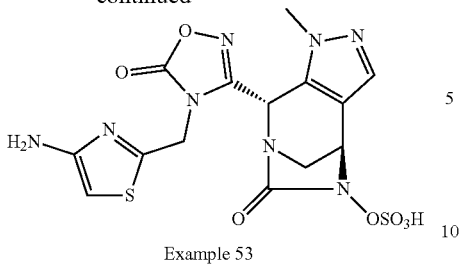

Int-108

Int-108 was synthesized by following similar reaction conditions as shown for Int-107 (Scheme 16, step 2), using tert-butyl (2-((3-(((4R,8S)-5-(allyloxy)-1-methyl-6-oxo-4,5,6,8-tetrahydro-1H-4,7-methanopyrazolo[3,4-e][1,3]diazepin-8-yl)-5-oxo-1,2,4-oxadiazol-4(5H)-yl)methyl)thiazol-4-yl)carbamate (Int-106, 27 mg, 0.05 mmol) as the substrate, to afford (4R,8S)-8-(4-((4-((tert-butoxycarbonyl)amino)thiazol-2-yl)methyl)-5-oxo-4,5-dihydro-1,2,4-oxadiazol-3-yl)-1-methyl-6-oxo-4,8-dihydro-1H-4,7-methanopyrazolo[3,4-e][1,3]diazepin-5(6H)-yl hydrogen sulfate (13 mg, 99%) as a white solid. MS: 571 ES+ ($C_{19}H_{22}N_8O_9S_2$).

Example 53

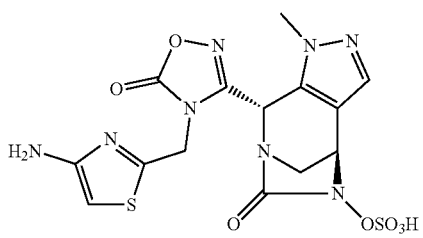

Example 53 was synthesized by following similar reaction conditions as shown for Example 52 (Scheme 16, step 3), using (4R,8S)-8-(4-((4-((tert-butoxycarbonyl)amino)thiazol-2-yl)methyl)-5-oxo-4,5-dihydro-1,2,4-oxadiazol-3-yl)-1-methyl-6-oxo-4,8-dihydro-1H-4,7-methanopyrazolo[3,4-e][1,3]diazepin-5(6H)-yl hydrogen sulfate (Int-108, 13 mg, 0.02 mmol) as the substrate, to afford (4R,8S)-8-(4-((4-aminothiazol-2-yl)methyl)-5-oxo-4,5-dihydro-1,2,4-oxadiazol-3-yl)-1-methyl-6-oxo-4,8-dihydro-1H-4,7-methanopyrazolo[3,4-e][1,3]diazepin-5(6H)-yl hydrogen sulfate (1 mg, 8.2%) as a white solid. MS: 471 ES+ ($C_{14}H_{14}N_8O_7S_2$) $^1$HNMR (300 MHz, $D_2O$) δ: 3.31 (m, 1H); 3.52 (m, 1H); 3.59 (s, 3H); 4.95 (m, 3H); 5.92 (m, 1H); 6.78 (s, 1H); 7.64 (s, 1H).

Example 54

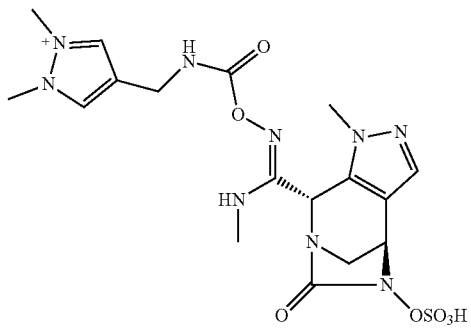

A solution (4R,8S)-1-methyl-8-((Z)—N-methyl-N'-((((1-methyl-1H-pyrazol-4-yl)methyl)carbamoyl)oxy)carbamimidoyl)-6-oxo-4,8-dihydro-1H-4,7-methanopyrazolo[3,4-e][1,3]diazepin-5(6H)-yl hydrogen sulfate (Example 15, 18 mg, 0.04 mmol) in DMF (0.3 mL) at 0° C. was added Trimethyloxonium tetrafluoroborate (27 mg, 0.19 mmol) in portions. The reaction mixture was warmed to room temperature and stirred for 15 minutes. Most of DMF was removed to give the crude product. It was purified via reversed phase chromatography (12 g Sepabeads, eluting with 0-15% Acetonitrile/water) to afford 1,2-dimethyl-4-((Z)-3-((4R,8S)-1-methyl-6-oxo-5-(sulfooxy)-4,5,6,8-tetrahydro-1H-4,7-methanopyrazolo[3,4-e][1,3]diazepin-8-yl)-6-oxo-5-oxa-2,4,7-triazaoct-3-en-8-yl)-1H-pyrazol-2-ium (5 mg, 27%) as a white solid. MS: 498 ES+ ($C_{17}H_{23}N_9O_7S$) $^1$HNMR 300 MHz, DMSO-d6) δ: 2.99 (d, 3H); 3.36 (m, 2H); 3.63 (s, 3H); 4.05 (s, 6H); 4.08 (m, 2H); 4.70 (s, 1H); 5.64 (s, 1H); 4.80 (d, 1H); 7.20 (t, 1H); 7.36 (s, 1H); 8.31 (s, 2H).

Scheme 18

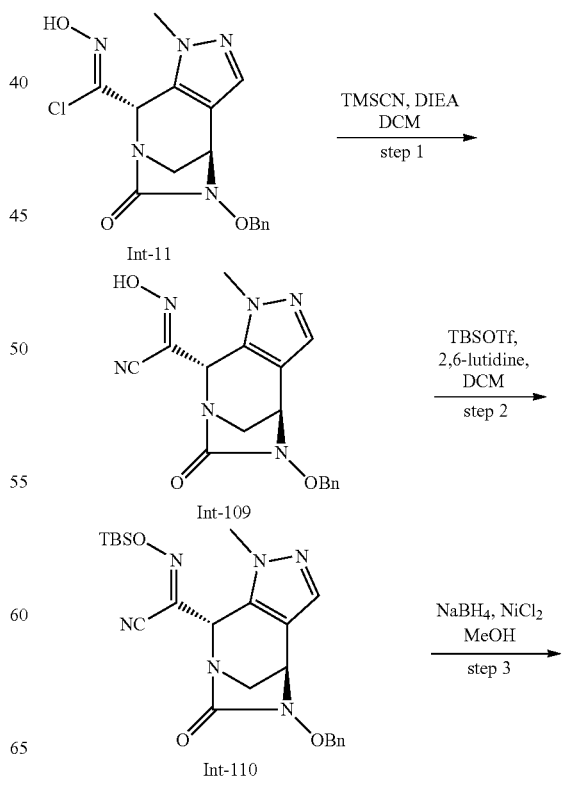

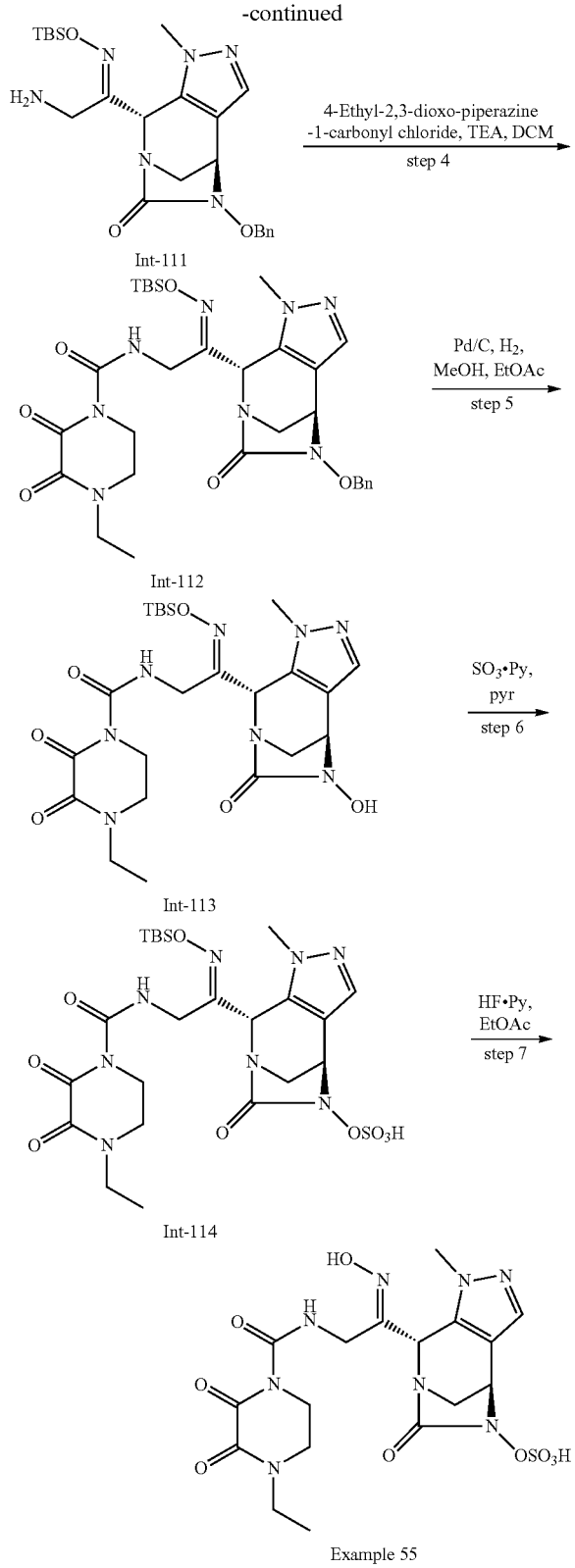

Int-109

To a solution of ((4R,8S,Z)-5-(benzyloxy)-N-hydroxy-1-methyl-6-oxo-4,5,6,8-tetrahydro-1H-4,7-methanopyrazolo [3,4-e][1,3]diazepine-8-carbimidoyl chloride (Int-11, 500 mg, 1.38 mmol) in DCM (8 mL) at room temperature was added trimethylsilyl cyanide (0.21 mL, 1.66 mmol) and DIEA (0.36 mL, 2.07 mmol). The reaction mixture was stirred at ambient temperature for 30 minutes. Saturated ammonium chloride solution and DCM were added. The organic layer was separated, washed with water, brine and dried over anhydrous sodium sulfate and concentrated to give the crude product. Silica gel chromatography (0%-50% ethyl acetate/hexanes) afforded ((4R,8S,Z)-5-(benzyloxy)-N-hydroxy-1-methyl-6-oxo-4,5,6,8-tetrahydro-1H-4,7-methanopyrazolo[3,4-e][1,3]diazepine-8-carbimidoyl cyanide (150 mg, 30.8% yield) as a white solid. MS: 353 ES+ ($C_{17}H_{16}N_6O_3$).

Int-110

To a solution of ((4R,8S,Z)-5-(benzyloxy)-N-hydroxy-1-methyl-6-oxo-4,5,6,8-tetrahydro-1H-4,7-methanopyrazolo [3,4-e][1,3]diazepine-8-carbimidoyl cyanide (Int-109, 150 mg, 0.43 mmol) in DCM (50 mL) at room temperature was added tert-butyldimethylsilyl trifluoromethanesulfonate (0.21 mL, 0.64 mmol) and 2,6-lutidine (0.074 mL, 0.64 mmol). The reaction mixture was stirred at room temperature for 30 minutes. DCM and saturated ammonium chloride solution were added. The organic layer was separated, washed with water, brine and dried over anhydrous sodium sulfate and concentrated. Silica gel chromatography (0%-50% ethyl acetate/hexanes) afforded ((4R,8S,Z)-5-(benzyloxy)-N-((tert-butyldimethylsilyl)oxy)-1-methyl-6-oxo-4,5,6,8-tetrahydro-1H-4,7-methanopyrazolo[3,4-e][1,3] diazepine-8-carbimidoyl cyanide (120 mg, 60.4% yield) as a white solid. MS: 467 ES+ ($C_{23}H_{30}N_6O_3Si$).

Int-111

To the mixture of ((4R,8S,Z)-5-(benzyloxy)-N-((tert-butyldimethylsilyl)oxy)-1-methyl-6-oxo-4,5,6,8-tetrahydro-1H-4,7-methanopyrazolo[3,4-e][1,3]diazepine-8-carbimidoyl cyanide (Int-10, 120 mg, 0.26 mmol) and nickel (II) chloride hexahydrate (50.0 mg, 0.39 mmol) in MeOH (10 mL) at 0° C. was added $NaBH_4$ (77.8 mg, 2.06 mmol). The reaction mixture was stirred at 0° C. for 30 minutes. Saturated ammonium chloride solution was added. The mixture was then extracted with ethyl acetate. The organic layer was separated, washed with water, brine and dried over anhydrous sodium sulfate and concentrated to afford the crude (4R,8S)-8-((E)-2-amino-1-(((tert-butyldimethylsilyl)oxy) imino)ethyl-5-(benzyloxy)-1-methyl-1,4,5,8-tetrahydro-6H-4,7-methanopyrazolo[3,4-e][1,3]diazepin-6-one (80 mg, 66.1% yield) as a white solid. It was used directly in the next step. MS: 471 ES+ ($C_{23}H_{34}N_6O_3Si$).

Int-112

To a solution of (4R,8S)-8-((E)-2-amino-1-(((tert-butyldimethylsilyl)oxy)imino)ethyl-5-(benzyloxy)-1-methyl-1,4,5,8-tetrahydro-6H-4,7-methanopyrazolo[3,4-e][1,3]diazepin-6-one (Int-111, 80 mg, 0.17 mmol) in pyridine (3 mL) was added 4-ethyl-2,3-dioxo-piperazine-1-carbonyl chloride (41.7 mg, 0.20 mmol) and TEA (34.4 mg, 0.34 mmol). The reaction mixture was stirred at room temperature for 20 minutes. Saturated ammonium chloride solution was added. The mixture was then extracted with ethyl acetate. The organic layer was separated, washed with water, brine and dried over anhydrous sodium sulfate and concentrated. Silica gel chromatography (0%-100% ethyl acetate/hexanes)

afforded N—((E)-2-((4R,8S)-5-(benzyloxy)-1-methyl-6-oxo-4,5,6,8-tetrahydro-1H-4,7-methanopyrazolo[3,4-e][1,3]diazepin-8-yl)-2-(((tert-butyldimethylsilyl)oxy)imino)ethyl)-4-ethyl-2,3-dioxopiperazine-1-carboxamide (20 mg, 18.4% yield) as a white solid. MS: 639 ES+ ($C_{30}H_{42}N_8O_6Si$).

Int-113

A solution of N—((E)-2-((4R,8S)-5-(benzyloxy)-1-methyl-6-oxo-4,5,6,8-tetrahydro-1H-4,7-methanopyrazolo[3,4-e][1,3]diazepin-8-yl)-2-(((tert-butyldimethylsilyl)oxy)imino)ethyl)-4-ethyl-2,3-dioxopiperazine-1-carboxamide (Int-112, 20 mg, 0.031 mmol) in MeOH (2 mL) and ethyl acetate (4 mL) was purged with nitrogen 3 times, and 10% Pd/C (9.02 mg, 0.0094 mmol) was added. The reaction mixture was purged with nitrogen 3 times and then stirred under hydrogen atmosphere at ambient temperature for 2 hours. The reaction mixture was filtered through the celite. The filtrate was concentrated to give N—((E)-2-(((tert-butyldimethylsilyl)oxy)imino)-2-((4R,8S)-5-hydroxy-1-methyl-6-oxo-4,5,6,8-tetrahydro-1H-4,7-methanopyrazolo[3,4-e][1,3]diazepin-8-yl)ethyl)-4-ethyl-2,3-dioxopiperazine-1-carboxamide (15 mg, yield 87.3%) as a white solid. MS: 549 ES+ ($C_{23}H_{36}N_8O_6Si$).

Int-114

To a solution N—((E)-2-(((tert-butyldimethylsilyl)oxy)imino)-2-((4R,8S)-5-hydroxy-1-methyl-6-oxo-4,5,6,8-tetrahydro-1H-4,7-methanopyrazolo[3,4-e][1,3]diazepin-8-yl)ethyl)-4-ethyl-2,3-dioxopiperazine-1-carboxamide (Int-113, 15 mg, 0.0273 mmol) in pyridine (2 mL) at ambient temperature was added sulfur trioxide pyridine complex (13.0 mg, 0.082 mmol). The reaction mixture was stirred for 3 hours, then concentrated under reduced pressure. The material was triturated with DCM and the solids were removed by filtration. The filtrate was concentrated to give the crude product. It was dissolved in pH ~7 buffer and purified by reversed phase chromatography (Sepabeads, 12 g, ACN/water 0-50%) to afford (4R,8S)-8-((E)-1-(4-ethyl-2,3-dioxopiperazin-1-yl)-7,7,8,8-tetramethyl-1-oxo-6-oxa-2,5-diaza-7-silanon-4-en-4-yl)-1-methyl-6-oxo-4,8-dihydro-1H-4,7-methanopyrazolo[3,4-e][1,3]diazepin-5(6H)-yl hydrogen sulfate (10 mg, yield 58.2%) as a white solid. MS: 627 ES– ($C_{23}H_{36}N_8O_9SiS$).

Example 55

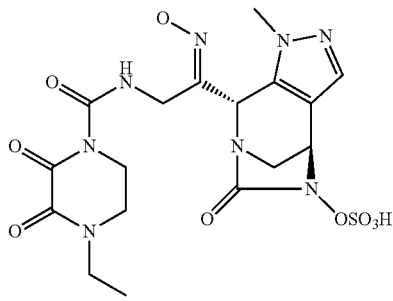

To a solution of (4R,8S)-8-((E)-1-(4-ethyl-2,3-dioxopiperazin-1-yl)-7,7,8,8-tetramethyl-1-oxo-6-oxa-2,5-diaza-7-silanon-4-en-4-yl)-1-methyl-6-oxo-4,8-dihydro-1H-4,7-methanopyrazolo[3,4-e][1,3]diazepin-5(6H)-yl hydrogen sulfate (Int-114, 8 mg, 0.0127 mmol) in ethyl acetate (1 mL) and THF (0.5 mL) at ambient temperature was added HF.Pyridine (1.27 mg, 0.0383 mmol). The reaction mixture was stirred for 3 hours, then concentrated. The resulting solid was purified by reversed phase chromatography (Sepabeads, ACN/water 0-50%) to afford the pyridinium salt of (4R,8S)-8-((E)-2-(4-ethyl-2,3-dioxopiperazine-1-carboxamido)-1-(hydroxyimino)ethyl)-1-methyl-6-oxo-4,8-dihydro-1H-4,7-methanopyrazolo[3,4-e][1,3]diazepin-5(6H)-yl hydrogen sulfate (4.5 mg, 61.9%) as a white solid. MS: 513 ES– ($C_{17}H_{22}N_8O_9S$) $^1$H NMR (300 MHz, D2O) δ: 1.20 (m, 3H); 3.26-3.85 (m, 9H); 4.12 (m, 2H); 4.53 (m, 2H); 4.97 (m, 1H); 5.51 (s, 1H); 7.65 (s, 1H); 7.90 (m, 0.8H); 0.41 (m, 0.4H); 8.74 (m, 0.8H). compound/pyridine ratio (1:0.4).

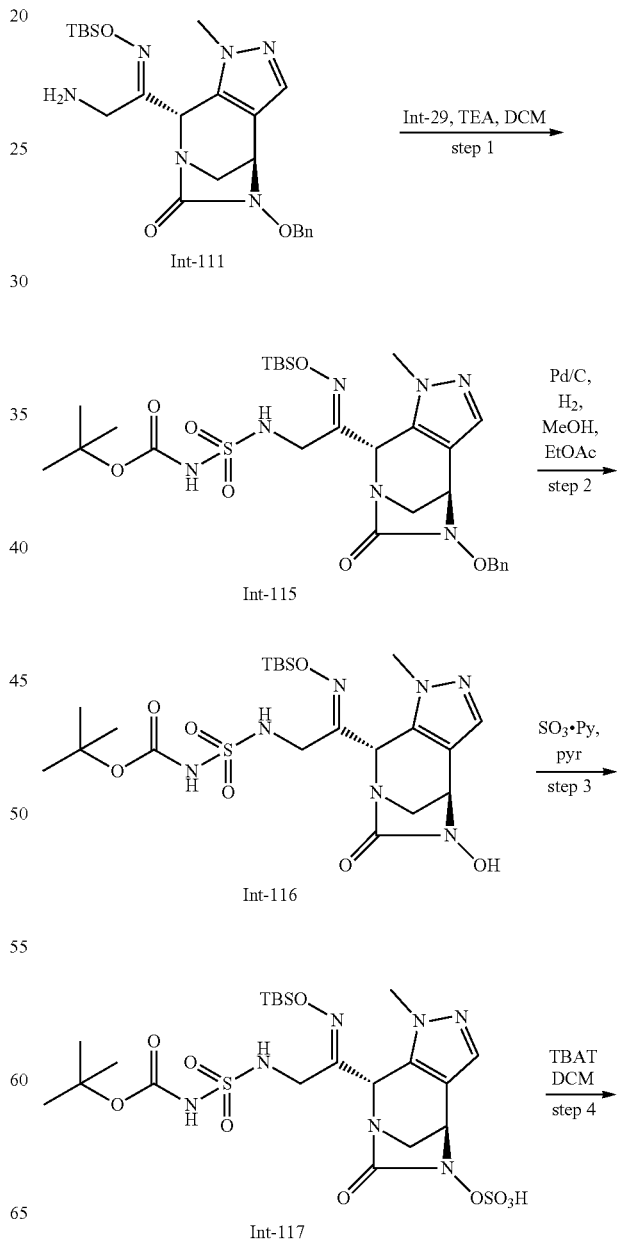

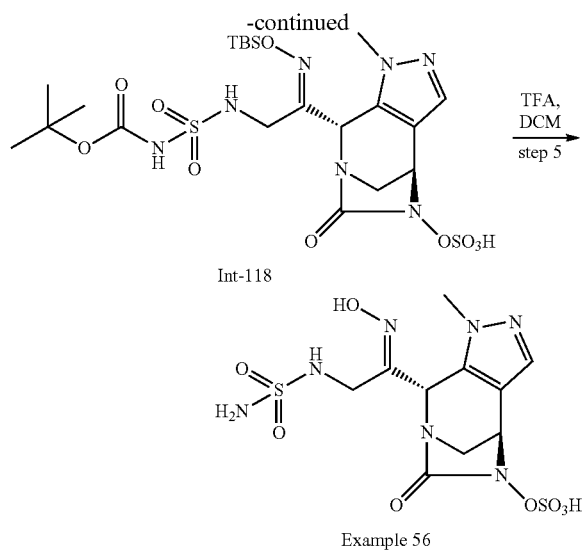

Int-115

To a stirred solution of (4R,8S)-8-((E)-2-amino-1-(((tert-butyldimethylsilyl)oxy)imino)ethyl-5-(benzyloxy)-1-methyl-1,4,5,8-tetrahydro-6H-4,7-methanopyrazolo[3,4-e][1,3]diazepin-6-one (Int-111, 200 mg, 0.42 mmol) in DCM (10 mL) at 0° C. was added TEA (86.2 mg, 0.849 mmol) and tert-butyl (chlorosulfonyl)carbamate (Int-29, 109.9 mg, 0.509 mmol). The reaction mixture was stirred at room temperature for 20 minutes. Saturated ammonium chloride solution and DCM were added to the reaction mixture. The organic layer was separated, washed with water, brine and dried over anhydrous sodium sulfate, and concentrated to give the crude product. It was purified by flash chromatography (0-100% EtOAc in Hexanes) to afford tert-butyl (N—((E)-2-((4R,8S)-5-(benzyloxy)-1-methyl-6-oxo-4,5,6,8-tetrahydro-1H-4,7-methanopyrazolo[3,4-e][1,3]diazepin-8-yl)-2-(((tert-butyldimethylsilyl)oxy)imino)ethyl)sulfamoyl)carbamate (50 mg, yield, 18.1%) as a white solid. MS: 648 ES– ($C_{28}H_{43}N_7O_7SiS$).

Int-116

A solution of tert-butyl (N—((E)-2-((4R,8S)-5-(benzyloxy)-1-methyl-6-oxo-4,5,6,8-tetrahydro-1H-4,7-methanopyrazolo[3,4-e][1,3]diazepin-8-yl)-2-(((tert-butyldimethylsilyl)oxy)imino)ethyl)sulfamoyl)carbamate (Int-115, 50 mg, 0.0769 mmol) in Ethyl acetate (8 mL) and Methanol (4 mL) was purged with nitrogen 3 times, and 10% Pd/C (22.2 mg, 0.023 mmol) was added. The reaction mixture was purged with nitrogen 3 times and then stirred under hydrogen atmosphere at ambient temperature for 2 hours. The reaction mixture was filtered through the celite. The filtrate was concentrated to give tert-butyl (N—((E)-2-(((tert-butyldimethylsilyl)oxy)imino-2-(4R,8S)-5-hydroxy-1-methyl-6-oxo-4,5,6,8-tetrahydro-1H-4,7-methanopyrazolo[3,4-e][1,3]diazepin-8-yl)-)ethyl)sulfamoyl)carbamate (38 mg, 88.2%) as a white solid. MS: 560 ES+ ($C_{21}H_{37}N_7O_7SiS$).

Int-117

To a solution of tert-butyl (N—((E)-2-(((tert-butyldimethylsilyl)oxy)imino-2-(4R,8S)-5-hydroxy-1-methyl-6-oxo-4,5,6,8-tetrahydro-1H-4,7-methanopyrazolo[3,4-e][1,3]diazepin-8-yl)-)ethyl)sulfamoyl)carbamate (Int-116, 38 mg, 0.0679 mmol) in pyridine (2 mL) at ambient temperature was added sulfur trioxide pyridine complex (32.4 mg, 0.204 mmol). The reaction mixture was stirred at room temperature for 3 hours, then concentrated under reduced pressure. The material was triturated with DCM and the solids were removed by filtration. The filtrate was concentrated. The resulting solid was purified by reversed phase chromatography (Sepabeads, ACN/water 0-50%) to (4R,8S)-8-((E)-2-((N-(tert-butoxycarbonyl) sulfamoyl)amino)-1-(((tert-butyldimethylsilyl)oxy)imino)ethyl-1-methyl-6-oxo-4,8-dihydro-1H-4,7-methanopyrazolo[3,4-e][1,3]diazepin-5(6H)-yl hydrogen sulfate (30 mg, 69.1%) as a white solid. MS: 638 ES– ($C_{21}H_{37}N_7O_{10}SiS_2$).

INT-118

To a stirred solution of (4R,8S)-8-((E)-2-((N-(tert-butoxycarbonyl) sulfamoyl)amino)-1-(((tert-butyldimethylsilyl)oxy)imino)ethyl-1-methyl-6-oxo-4,8-dihydro-1H-4,7-methanopyrazolo[3,4-e][1,3]diazepin-5(6H)-yl hydrogen sulfate (Int-117, 20 mg, 0.0313 mmol) in DCM (2 mL) was added TBAT (20.2 mg, 0.0375 mmol). The reaction mixture was stirred at room temperature for 3 hours. Solvent was removed. The resulting solid was purified by reversed phase chromatography (Sepabeads, ACN/water 0-50%) to afford (4R,8S)-8-((E)-2-((N-(tert-butoxycarbonyl)sulfamoyl) amino)-1-(hydroxyimino)ethyl)-1-methyl-6-oxo-4,8-dihydro-1H-4,7-methanopyrazolo[3,4-e][1,3]diazepin-5(6H)-yl hydrogen sulfate as a tetrabutylammonium salt (20 mg, 83.3%) MS: 524 ES– ($C_{15}H_{23}N_7O_{10}S_2$).

Example 56

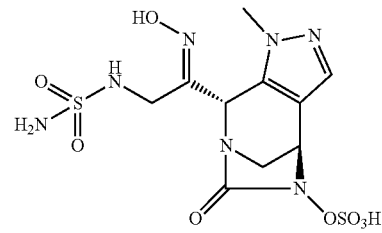

To a stirred solution of (4R,8S)-8-((E)-2-((N-(tert-butoxycarbonyl) sulfamoyl)amino)-1-(hydroxyimino)ethyl)-1-methyl-6-oxo-4,8-dihydro-1H-4,7-methanopyrazolo[3,4-e][1,3]diazepin-5(6H)-yl hydrogen sulfate tetrabutylammonium (Int-118, 20 mg, 0.026 mmol) in DCM (2 mL) was added TFA (297 mg, 2.60 mmol). The reaction mixture was stirred at room temperature for 2 hours. Solvent was removed to give the crude product. It was dissolved in pH ~7 buffer and purified by reversed phase chromatography (Sepabeads, 12 g, ACN/water 0-50%) to afford (4R,8S)-8-((E)-1-(hydroxyamino)-2-(sulfamoyl)amino)ethyl)-1-methyl-6-oxo-4,8-dihydro-1H-4,7-methanopyrazolo[3,4-e][1,3]diazepin-5(6H)-yl hydrogen sulfate (4.0 mg, 28.9%) as a white solid. MS: 424 ES– ($C_{10}H_{15}N_7O_8S_2$) $^1$H NMR (300 MHz, $D_2O$) δ: (300 MHz, $D_2O$) δ: 3.37 (m, 1H); 3.51-3.72 (m, 4H); 4.03 (m, 1H); 4.53 (m, 1H); 4.96 (m, 1H); 5.70 (s, 1H); 7.65 (s, 1H).

Scheme 20

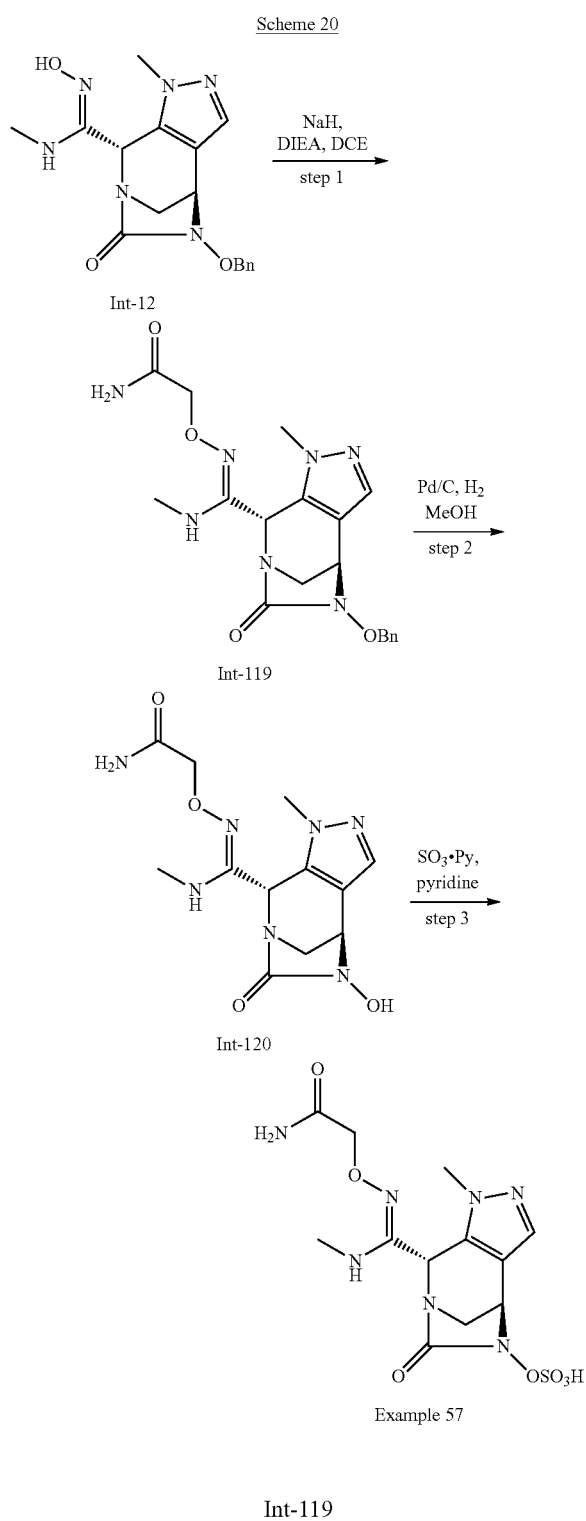

Int-119

To a solution of (4R,8S,Z)-5-(benzyloxy)-N-hydroxy-N,1-dimethyl-6-oxo-4,5,6,8-tetrahydro-1H-4,7-methanopyrazolo[3,4-e][1,3]diazepine-8-carboximidamide (Int-12, 70 mg, 0.2 mmol) in DMF (1 mL) at 0° C. was added NaH (11.8 mg, 0.29 mmol, 60%) and stirred for 10 minutes, 2-bromoacetamide (32.5 mg, 0.24 mmol) was added. It was then warmed up to room temperature and stirred for 10 minutes. Ethyl acetate and saturated ammonium chloride solution were added. Organic layer was separated, dried over anhydrous sodium sulfate, and concentrated to give the crude product. It was purified by flash chromatography (0-100% Acetone in DCM) to afford 2-((((Z)-((4R,8S)-5-(benzyloxy)-1-methyl-6-oxo-4,5,6,8-tetrahydro-1H-4,7-methanopyrazolo[3,4-e][1,3]diazepin-8-yl)(methylamino)methylene)amino)oxy)acetamide (58 mg, yield, 71%) as a white solid. MS: 414 ES+ ($C_{19}H_{23}N_7O_4$).

Int-120

To a solution of 2-((((Z)-((4R,8S)-5-(benzyloxy)-1-methyl-6-oxo-4,5,6,8-tetrahydro-1H-4,7-methanopyrazolo[3,4-e][1,3]diazepin-8-yl)(methylamino)methylene)amino)oxy)acetamide (Int-119, 58 mg, 0.14 mmol) in MeOH (5 mL) was purged with nitrogen 3 times, and 10% Pd/C (29.9 mg, 0.03 mmol) was added. The reaction mixture was purged with nitrogen 3 times and then stirred under hydrogen atmosphere at room temperature for 2 hours. The reaction mixture was filtered through Celite. The filtrate was concentrated to give 2-((((Z)-((4R,8S)-5-hydroxy-1-methyl-6-oxo-4,5,6,8-tetrahydro-1H-4,7-methanopyrazolo[3,4-e][1,3]diazepin-8-yl)(methylamino)methylene)amino)oxy)acetamide (40 mg, 88.1%) as a white solid. MS: 324 ES+ ($C_{12}H_{17}N_7O_4$).

Example 57

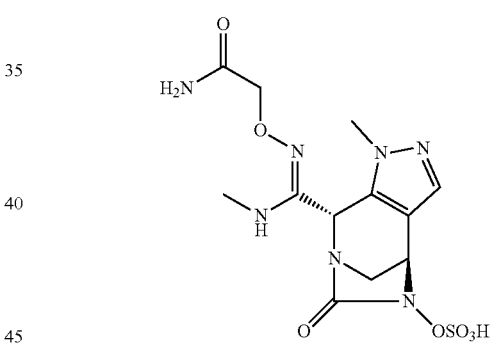

To a solution of 2-((((Z)-((4R,8S)-5-hydroxy-1-methyl-6-oxo-4,5,6,8-tetrahydro-1H-4,7-methanopyrazolo[3,4-e][1,3]diazepin-8-yl)(methylamino)methylene)amino)oxy)acetamide (Int-120, 40 mg, 0.12 mmol) in pyridine (1 mL) at room temperature was added sulfur trioxide pyridine complex (59.1 mg, 0.38 mmol). The reaction mixture was stirred 6 hours, then concentrated under reduced pressure to give the crude product. The material was purified by reversed phase chromatography (Sepabeads, 12 g, ACN/water 0-50%) to afford pyridium (4R,8S)-8-((Z)—N'-(2-amino-2-oxoethoxy)-N-methylcarbamimidoyl)-1-methyl-6-oxo-4,8-dihydro-1H-4,7-methanopyrazolo[3,4-e][1,3]diazepin-5(6H)-yl hydrogen sulfate (15 mg, 27%) as a white solid. MS: 402 ES− ($C_{12}H_{17}N_7O_7S$) $^1$H NMR (300 MHz, $D_2O$) δ: 3.00 (s, 3H); 3.31 (m, 2H); 3.57 (s, 3H); 4.07 (m 2H); 4.67 (m, 1H); 5.50 (s, 1H); 6.48 (b, 1H); 7.25 (m, 2H); 7.31 (s, 1H); 7.90 (m, 1.4H); 8.39 (m, 0.7H); 8.86 (m, 1.4H) compound/pyridine ratio (1:0.7).

Scheme 21

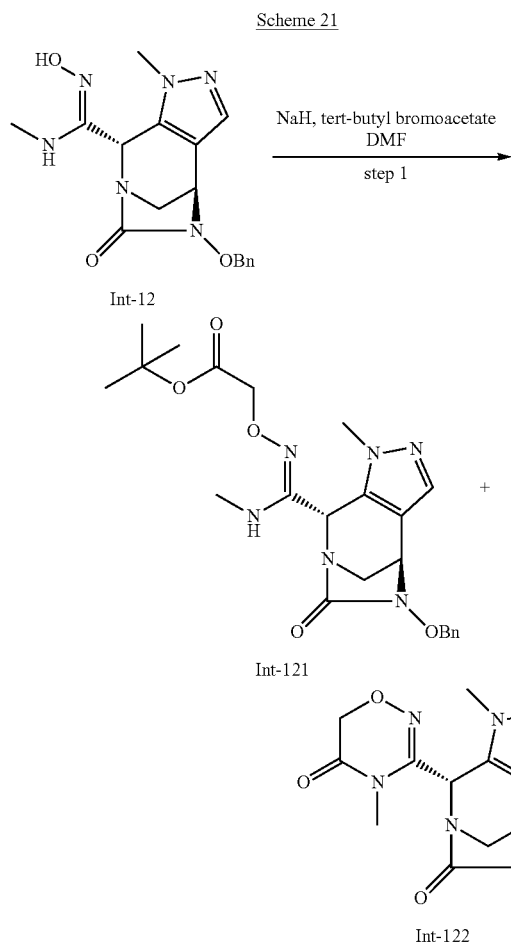

Scheme 22

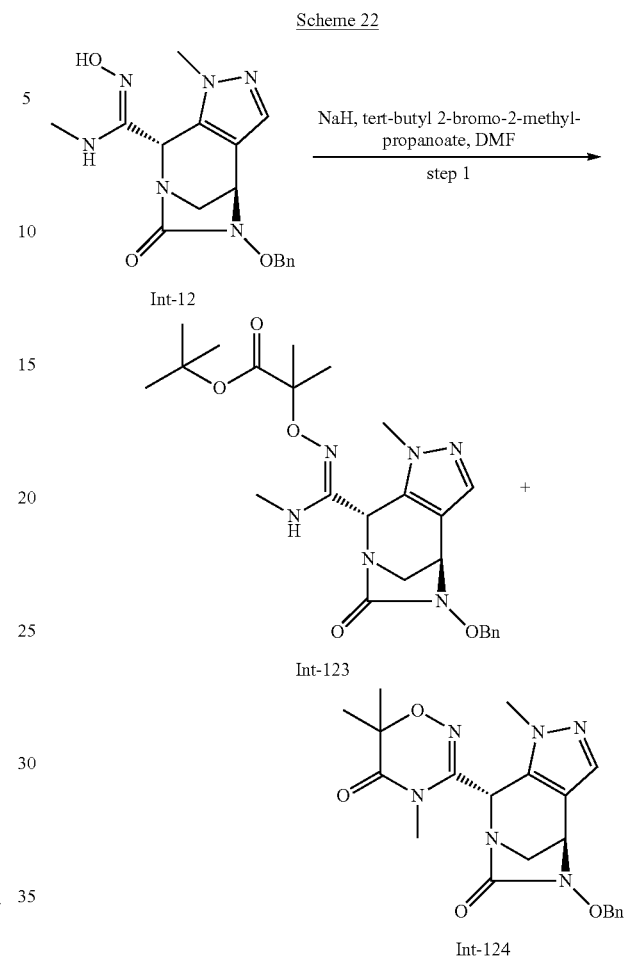

Int-121 and Int-122

To a solution of (4R,8S,Z)-5-(benzyloxy)-N'-hydroxy-N,1-dimethyl-6-oxo-4,5,6,8-tetrahydro-1H-4,7-methanopyrazolo[3,4-e][1,3]diazepine-8-carboximidamide (Int-12, 150 mg, 0.42 mmol) in DMF (2 mL) at 0° C. was added NaH (25.2 mg, 0.63 mmol, 60%). After stirring at 0° C. for 10 minutes, tert-butyl bromoacetate (0.014 mL, 0.51 mmol) was added. It was then warmed up to room temperature and stirred for 10 minutes. Ethyl acetate and saturated ammonium chloride solution were added. Organic layer was separated, dried over anhydrous magnesium sulfate, and concentrated to give the crude product. It was purified by flash chromatography (0-100% Acetone in DCM) to afford two products.

Int-121: tert-butyl 2-((((Z)-((4R,8S)-5-(benzyloxy)-1-methyl-6-oxo-4,5,6,8-tetrahydro-1H-4,7-methanopyrazolo[3,4-e][1,3]diazepin-8-yl)(methylamino)methylene)amino)oxy)acetate (120 mg, yield, 60%) as a white solid. MS: 471 ES+ ($C_{23}H_{30}N_6O_5$).

Int-122: 3-((4R,8S)-5-(benzyloxy)-1-methyl-6-oxo-4,5,6,8-tetrahydro-1H-4,7-methanopyrazolo[3,4-e][1,3]diazepin-8-yl)-4-methyl-4H-1,2,4-oxadiazin-5(6H)-one (30 mg, yield, 17.9%) as a white solid. MS: 397 ES+ ($C_{19}H_{20}N_6O_4$).

Int-123 and Int-124

Tert-butyl 2-((((Z)-((4R,8S)-5-(benzyloxy)-1-methyl-6-oxo-4,5,6,8-tetrahydro-1H-4,7-methanopyrazolo[3,4-e][1,3]diazepin-8-yl)(methylamino)methylene)amino)oxy)-2-methylpropanoate (Int-123) and 3-((4R,8S)-5-(benzyloxy)-1-methyl-6-oxo-4,5,6,8-tetrahydro-1H-4,7-methanopyrazolo[3,4-e][1,3]diazepin-8-yl)-4,6,6-trimethyl-4H-1,2,4-oxadiazin-5(6H)-one (Int-124) were synthesized by following similar reactions as shown for Int-121 and Int-122 in Scheme 21, step 1, using tert-butyl 2-bromo-2-methyl-propanoate.

Scheme 23

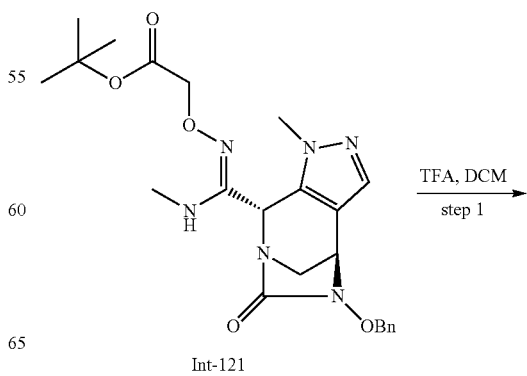

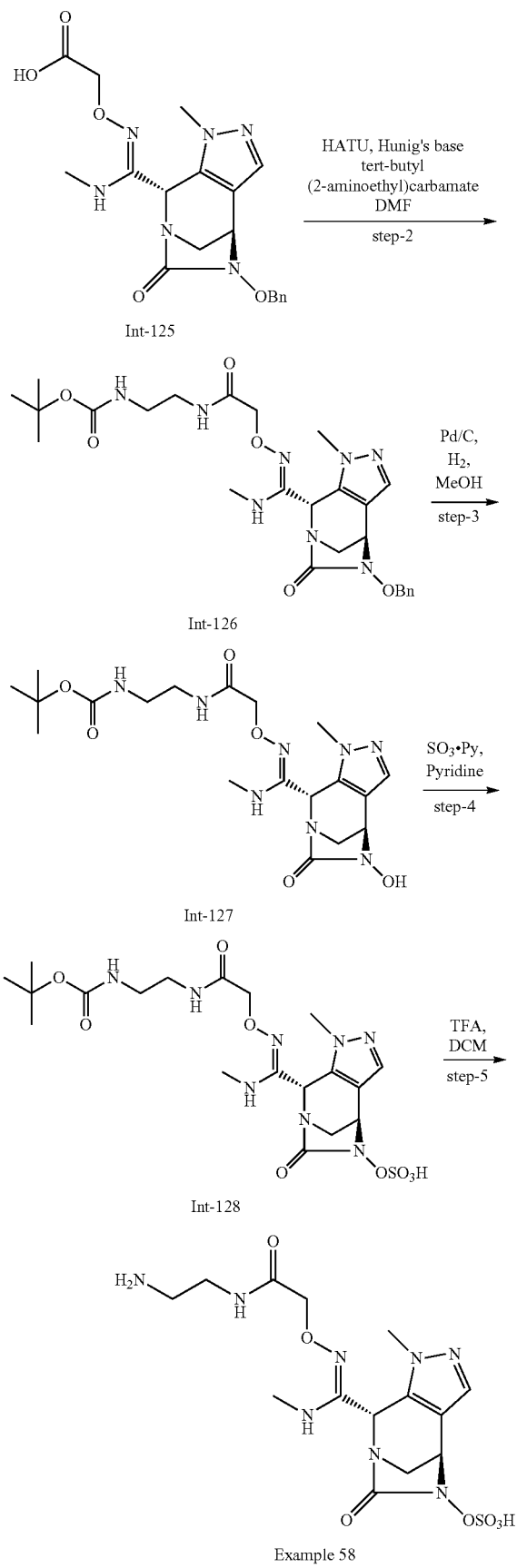

Int-125

To a solution of tert-butyl 2-((((Z)-((4R,8S)-5-(benzyloxy)-1-methyl-6-oxo-4,5,6,8-tetrahydro-1H-4,7-methanopyrazolo[3,4-e][1,3]diazepin-8-yl)(methylamino)methylene)amino)oxy)acetate (Int-121, 100 mg, 0.21 mmol) in DCM (3 mL) was added TFA (0.81 mL, 10.63 mmol). The reaction mixture was stirred at room temperature for 2 hours. TFA was removed to afford 2-((((Z)-((4R,8S)-5-(benzyloxy)-1-methyl-6-oxo-4,5,6,8-tetrahydro-1H-4,7-methanopyrazolo[3,4-e][1,3]diazepin-8-yl)(methylamino)methylene)amino)oxy)acetic acid (88 mg, yield, 99%) as a white solid. MS: 415 ES+ ($C_{19}H_{22}N_6O_5$).

Int-126

To a solution of afford 2-((((Z)-((4R,8S)-5-(benzyloxy)-1-methyl-6-oxo-4,5,6,8-tetrahydro-1H-4,7-methanopyrazolo[3,4-e][1,3]diazepin-8-yl)(methylamino)methylene)amino)oxy)acetic acid (Int-125, 30 mg, 0.07 mmol) in DMF (1.5 mL) was added HATU (55.1 mg, 0.14 mmol), tert-butyl (2-aminoethyl)carbamate (17.4 mg, 0.11 mmol) and Hunig's base (0.03 mL, 0.14 mmol). The reaction mixture was stirred at room temperature for 30 minutes. Ethyl acetate and saturated ammonium chloride solution were added. Organic layer was separated, dried over anhydrous magnesium sulfate, and concentrated to give the crude product. It was purified by flash chromatography (0-100% EtOAc/Hexanes) to afford tert-butyl ((Z)-3-((4R,8S)-5-(benzyloxy)-1-methyl-6-oxo-4,5,6,8-tetrahydro-1H-4,7-methanopyrazolo[3,4-e][1,3]diazepin-8-yl)-7-oxo-5-oxa-2,4,8-triazadec-3-en-10-yl)carbamate (35 mg, 86.7%) as a white solid. MS: 557 ES+ ($C_{26}H_{36}N_8O_6$).

Int-127

A solution tert-butyl ((Z)-3-((4R,8S)-5-(benzyloxy)-1-methyl-6-oxo-4,5,6,8-tetrahydro-1H-4,7-methanopyrazolo[3,4-e][1,3]diazepin-8-yl)-7-oxo-5-oxa-2,4,8-triazadec-3-en-10-yl)carbamate (Int-126, 35 mg, 0.06 mmol) in MeOH (3 mL) was purged with nitrogen 3 times, and 10% Pd/C (13.1 mg, 0.126 mmol) was added. The reaction mixture was purged with nitrogen 3 times and then stirred under hydrogen atmosphere at room temperature for 2 hours. The reaction mixture was filtered through Celite. The filtrate was concentrated to give tert-butyl ((Z)-3-((4R,8S)-5-hydroxy-1-methyl-6-oxo-4,5,6,8-tetrahydro-1H-4,7-methanopyrazolo[3,4-e][1,3]diazepin-8-yl)-7-oxo-5-oxa-2,4,8-triazadec-3-en-10-yl)carbamate (25 mg, 85%) as a white solid. MS: 467 ES+ ($C_{19}H_{30}N_8O_6$).

Int-128

To a solution of tert-butyl ((Z)-3-((4R,8S)-5-hydroxy-1-methyl-6-oxo-4,5,6,8-tetrahydro-1H-4,7-methanopyrazolo[3,4-e][1,3]diazepin-8-yl)-7-oxo-5-oxa-2,4,8-triazadec-3-en-10-yl)carbamate (Int-127, 25 mg, 0.05 mmol) in pyridine (2 mL) at room temperature was added sulfur trioxide pyridine complex (25.6 mg, 0.16 mmol). The reaction mixture was stirred 6 hours, then concentrated under reduced pressure to give the crude product. The material was purified by reversed phase chromatography (Sepabeads, ACN/water 0-50%) to afford (4R,8S)-8-((Z)—N'-(2-((2-((tert-butoxycarbonyl)amino)ethyl)amino)-2-oxoethoxy)-N-methylcarbamimidoyl)-1-methyl-6-oxo-4,8-dihydro-1H-4,7-methanopyrazolo[3,4-e][1,3]diazepin-5(6H)-yl hydrogen sulfate (20 mg, 68.2%) as a white solid. MS: 545 ES− ($C_{19}H_{30}N_8O_9S$)

Example 58

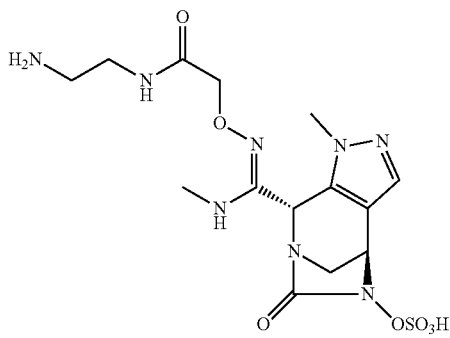

To a stirred solution of (4R,8S)-8-((Z)—N'-(2-((2-((tert-butoxycarbonyl)amino)ethyl)amino)-2-oxoethoxy)-N-methylcarbamimidoyl)-1-methyl-6-oxo-4,8-dihydro-1H-4,7-methanopyrazolo[3,4-e][1,3]diazepin-5(6H)-yl hydrogen sulfate (Int-128, 20 mg, 0.04 mmol) in DCM (2 mL) at room temperature was added TFA (0.14 mL, 1.83 mmol). The reaction mixture was stirred at room temperature for 30 minutes. Solvent was removed to give the crude product. It was purified by reversed phase chromatography (Sepabeads, ACN/water 0-50%) to afford (4R,8S)-8-((Z)—N'-(2-((2-aminoethyl)amino)-2-oxoethoxy)-N-methylcarbamimidoyl)-1-methyl-6-oxo-4,8-dihydro-1H-4,7-methanopyrazolo[3,4-e][1,3]diazepin-5(6H)-yl hydrogen sulfate (10 mg, 55.1%) as a white solid. MS: 447 ES+ ($C_{14}H_{22}N_8O_7S$) $^1$H NMR (300 MHz, DMSO-$d_6$) δ: 2.82 (m, 2H); 3.01 (m, 3H); 3.31 (m, 2H); 3.58 (s, 3H); 4.14 (m 2H); 4.70 (m, 1H); 5.52 (s, 1H); 6.37 (m, 1H); 7.25 (m, 2H); 7.31 (s, 1H); 7.60 (m, 2H); 7.92 (m, 1H).

Analytical Data for Additional Examples

All compounds in Table 4 were synthesized according to the above or using similar reactions easily known to a person skilled in the art. All compounds were isolated as trans racemic.

TABLE 4

| Example # | Structure | Calc. MW | MS | 1H NMR |
|---|---|---|---|---|
| 59 | ![structure] | 474.49 ($C_{16}H_{26}N_8O_7S$) | ES − 473 | (300 MHz, $D_2O$) δ: 1.61 (m, 4H); 3.03 (m, 2H); 3.11 (s, 3H); 3.27 (m, 2H); 3.47-3.71 (m, 5H); 4.38 (s, 2H); 4.95 (m, 1H); 5.74 (s, 1H); 7.63 (s, 1H) |
| 60 | ![structure] | 532.53 ($C_{18}H_{28}N_8O_9S$) | ES − 531 | (300 MHz, $D_2O$) δ: 1.32-1.63 (m, 4H); 1.93(m, 2H); 3.13 (s, 3H); 3.23 (m, 2H); 3.50-3.65 (m, 5H); 3.84 (m, 1H); 4.38 (m, 2H); 4.98 (m, 1H); 5.74 (s, 1H); 7.65 (s, 1H) |

TABLE 4-continued

| Example # | Structure | Calc. MW | MS | 1H NMR |
|---|---|---|---|---|
| 61 | 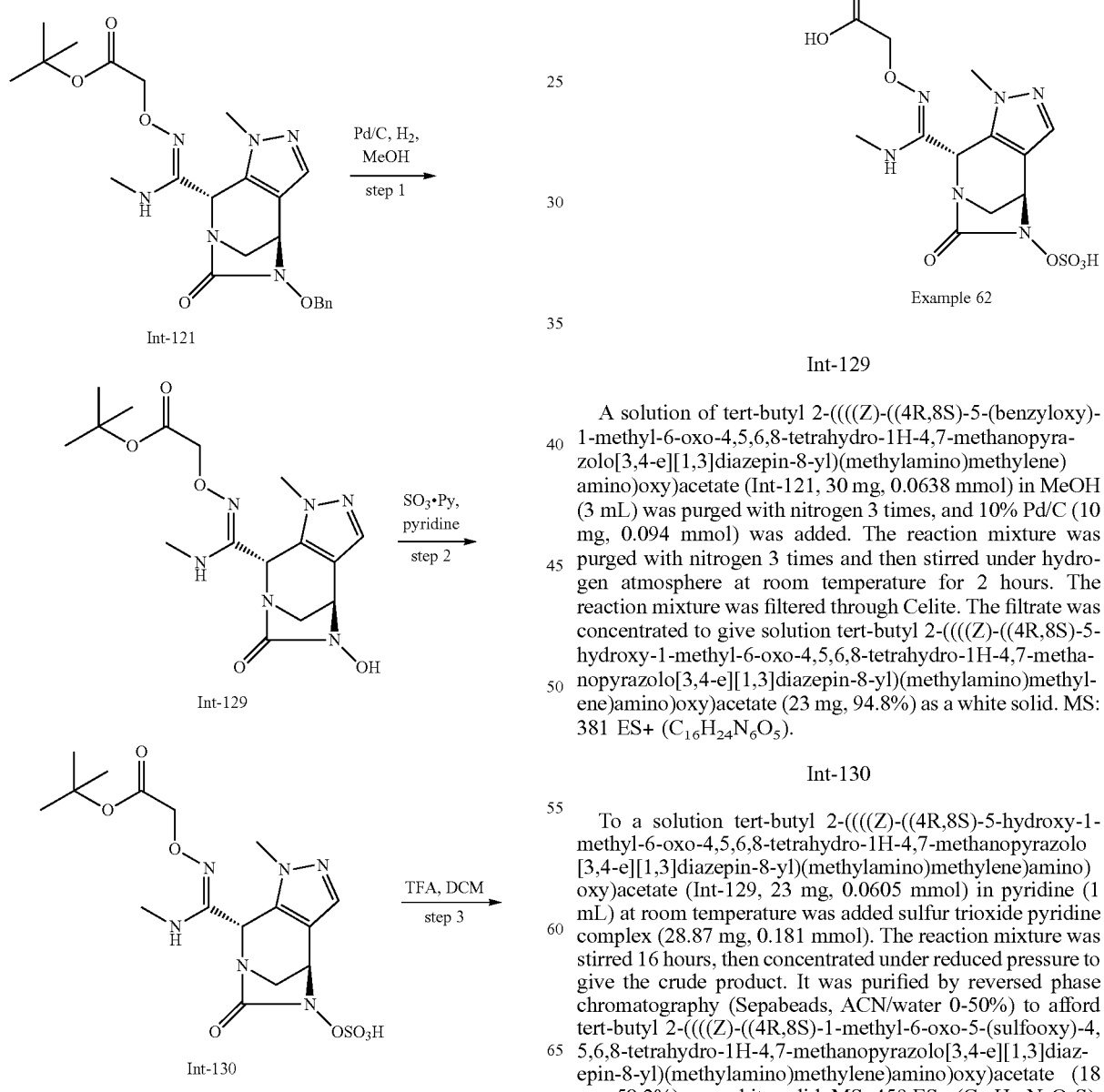 | 458.45 (C₁₅H₂₂N₈O₇S) | ES + 457 | (300 MHz, D₂O) δ: 3.13 (s, 3H); 3.45-3.84 (m, 5H); 3.91-4.34 (m, 5H); 4.40 (m, 2H); 4.95 (m, 1H); 5.76 (s, 1H); 7.66 (s, 1H) |

Scheme 24

Example 62

Int-129

A solution of tert-butyl 2-((((Z)-((4R,8S)-5-(benzyloxy)-1-methyl-6-oxo-4,5,6,8-tetrahydro-1H-4,7-methanopyrazolo[3,4-e][1,3]diazepin-8-yl)(methylamino)methylene)amino)oxy)acetate (Int-121, 30 mg, 0.0638 mmol) in MeOH (3 mL) was purged with nitrogen 3 times, and 10% Pd/C (10 mg, 0.094 mmol) was added. The reaction mixture was purged with nitrogen 3 times and then stirred under hydrogen atmosphere at room temperature for 2 hours. The reaction mixture was filtered through Celite. The filtrate was concentrated to give solution tert-butyl 2-((((Z)-((4R,8S)-5-hydroxy-1-methyl-6-oxo-4,5,6,8-tetrahydro-1H-4,7-methanopyrazolo[3,4-e][1,3]diazepin-8-yl)(methylamino)methylene)amino)oxy)acetate (23 mg, 94.8%) as a white solid. MS: 381 ES+ (C₁₆H₂₄N₆O₅).

Int-130

To a solution tert-butyl 2-((((Z)-((4R,8S)-5-hydroxy-1-methyl-6-oxo-4,5,6,8-tetrahydro-1H-4,7-methanopyrazolo[3,4-e][1,3]diazepin-8-yl)(methylamino)methylene)amino)oxy)acetate (Int-129, 23 mg, 0.0605 mmol) in pyridine (1 mL) at room temperature was added sulfur trioxide pyridine complex (28.87 mg, 0.181 mmol). The reaction mixture was stirred 16 hours, then concentrated under reduced pressure to give the crude product. It was purified by reversed phase chromatography (Sepabeads, ACN/water 0-50%) to afford tert-butyl 2-((((Z)-((4R,8S)-1-methyl-6-oxo-5-(sulfooxy)-4,5,6,8-tetrahydro-1H-4,7-methanopyrazolo[3,4-e][1,3]diazepin-8-yl)(methylamino)methylene)amino)oxy)acetate (18 mg, 58.2%) as a white solid. MS: 459 ES− (C₁₆H₂₄N₆O₈S).

Example 62

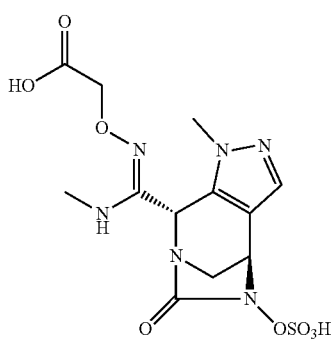

To a stirred solution of tert-butyl 2-((((Z)-((4R,8S)-1-methyl-6-oxo-5-(sulfooxy)-4,5,6,8-tetrahydro-1H-4,7-methanopyrazolo[3,4-e][1,3]diazepin-8-yl)(methylamino)methylene)amino)oxy)acetate (Int-130, 14 mg, 0.030 mmol) in DCM (3 mL) at room temperature was added TFA (0.12 mL, 1.52 mmol). The reaction mixture was stirred at room temperature for 2 hours. Solvent was removed to give the crude product. It was then dissolved in water (2 mL) and eluted through a Dowex® 50WX8 Na$^r$-form ion exchange resin cartridge with water as the eluent. Fractions containing the product were pooled and lyophilized to afford an off-white solid. The solid was purified by reversed phase chromatography (Sepabeads, ACN/water 0-50%) to afford sodium salt of 2-((((Z)-((4R,8S)-1-methyl-6-oxo-5-(sulfooxy)-4,5,6,8-tetrahydro-1H-4,7-methanopyrazolo[3,4-e][1,3]diazepin-8-yl)(methylamino)methylene)amino)oxy)acetic acid (2.0 mg, 13.8%) as a white solid. MS: 405 ES+ ($C_{12}H_{16}N_6O_8S$) $^1$H NMR (300 MHz, $D_2O$) δ: 3.13 (s, 3H); 3.60 (m, 2H); 3.67 (s, 3H); 4.27 (m, 2H); 4.98 (m, 1H); 5.73 (s, 1H); 7.63 (s, 1H).

Example 63

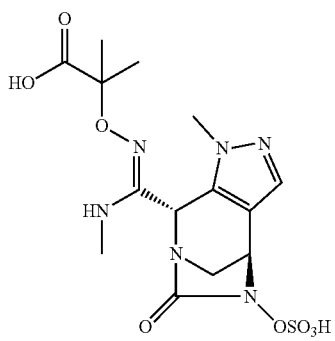

Example 63 was synthesized by following similar reaction conditions as shown for Example 62. Using Tert-butyl 2-((((Z)-((4R,8S)-5-(benzyloxy)-1-methyl-6-oxo-4,5,6,8-tetrahydro-1H-4,7-methanopyrazolo[3,4-e][1,3]diazepin-8-yl)(methylamino)methylene)amino)oxy)-2-methylpropanoate (Int-123) as substrate in Scheme 24, step 1. MS 433 ($C_{14}H_{20}N_6O_8S$) $^1$H NMR (300 MHz, $D_2O$) δ: 1.38 (m, 6H); 3.05 (s, 3H); 3.10 (m, 5H); 4.93 (m, 1H); 5.68 (s, 1H); 7.59 (s, 1H); 8.10 (m, 0.6H); 8.61 (m, 0.3H); 8.80 (m, 0.6H) Compound/pyridine ratio (1:0.3).

Scheme 25

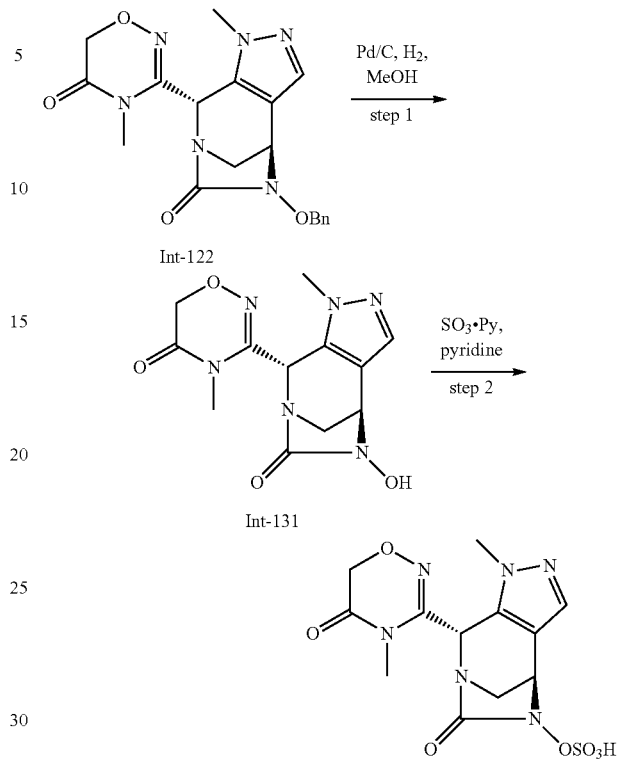

Int-131

A solution 3-((4R,8S)-5-(benzyloxy)-1-methyl-6-oxo-4,5,6,8-tetrahydro-1H-4,7-methanopyrazolo[3,4-e][1,3]diazepin-8-yl)-4-methyl-4H-1,2,4-oxadiazin-5(6H)-one (Int-122, 30 mg, 0.0757 mmol) in MeOH (3 mL) was purged with nitrogen 3 times, and 10% Pd/C (8.05 mg, 0.0076 mmol) was added. The reaction mixture was purged with nitrogen 3 times and then stirred under hydrogen atmosphere at room temperature for 2 hours. The reaction mixture was filtered through Celite. The filtrate was concentrated to give 3-((4R,8S)-5-hydroxy-1-methyl-6-oxo-4,5,6,8-tetrahydro-1H-4,7-methanopyrazolo[3,4-e][1,3]diazepin-8-yl)-4-methyl-4H-1,2,4-oxadiazin-5(6H)-one (20 mg, 86.3%) as a white solid. MS: 307 ES+ ($C_{12}H_{14}N_6O_4$).

Example 64

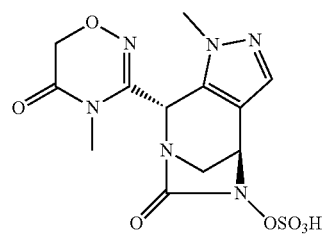

To a solution of 3-((4R,8S)-5-hydroxy-1-methyl-6-oxo-4,5,6,8-tetrahydro-1H-4,7-methanopyrazolo[3,4-e][1,3]diazepin-8-yl)-4-methyl-4H-1,2,4-oxadiazin-5(6H)-one (Int-131, 20 mg, 0.0653 mmol) in pyridine (2 mL) at room temperature was added sulfur trioxide pyridine complex (31.18 mg, 0.196 mmol). The reaction mixture was stirred for 3 hours, then concentrated under reduced pressure to give the crude product. The material was purified by reversed phase chromatography (Sepabeads, ACN/water 0-50%) to afford ((4R,8S)-1-methyl-8-(4-methyl-5-oxo-5,6-dihydro-4H-1,2,4-oxadiazin-3-yl)-6-oxo-4,8-dihydro-1H-4,7-methanopyrazolo[3,4-e][1,3]diazepin-5(6H)-yl) hydrogen sulfate (15 mg, 56.5%) as a white solid. MS: 387 ES+ ($C_{12}H_{14}N_6O_7S$) $^1$H NMR (300 MHz, $D_2O$) δ: 3.45-3.57 (m, 4H); 3.61-3.78 (m, 4H); 4.41-4.69 (m, 2H); 4.99 (m, 1H); 6.02 (s, 1H); 7.69 (s, 1H); 8.08 (m, 1.4H); 8.64 (m, 0.7H); 8.79 (m, 1.4H) Compound/pyridine ratio (1:0.7).

Example 65

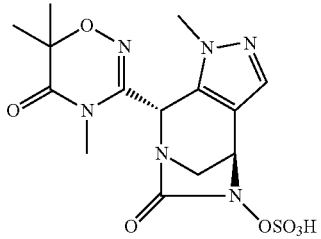

Example 65 was synthesized by following similar reaction conditions as shown for Example 64 using 3-((4R,8S)-5-(benzyloxy)-1-methyl-6-oxo-4,5,6,8-tetrahydro-1H-4,7-methanopyrazolo[3,4-e][1,3]diazepin-8-yl)-4,6,6-trimethyl-4H-1,2,4-oxadiazin-5(6H)-one (Int-124) as substrate in Scheme 25, step 1. MS: 415 ($C_{14}H_{18}N_6O_7S$) $^1$H NMR (300 MHz, $D_2O$) δ: δ: 1.41 (s, 3H); 1.52 (s, 3H); 3.53 (m, 4H); 3.73 (m, 4H); 5.02 (m, 1H); 6.02 (s, 1H); 7.69 (s, 1H); 8.10 (m, 2H); 8.67 (m, 1H); 8.80 (m, 2H) Compound/pyridine ratio (1:1).

Scheme 26

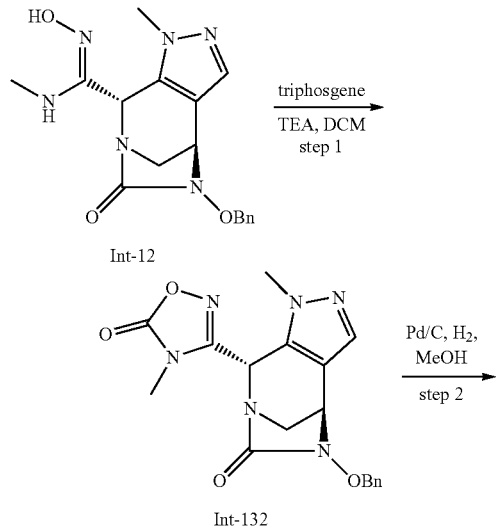

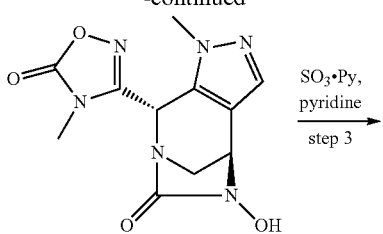

Int-133

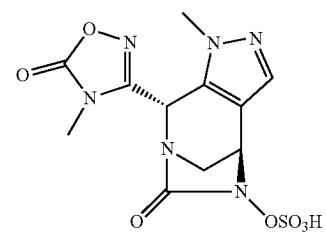

Example 66

Int-132

To a stirred solution of (4R,8S,Z)-5-(benzyloxy)-N-hydroxy-N,1-dimethyl-6-oxo-4,5,6,8-tetrahydro-1H-4,7-methanopyrazolo[3,4-e][1,3]diazepine-8-carboximidamide (Int-12, 50 mg, 0.143 mmol) in DCM (25 mL) at 0° C. was added Hunig's base (0.029 mL, 0.168 mmol). A solution of triphosgene (20.8 mg, 0.701 mmol) in DCM (15 mL) was added dropwise. After the addition, the reaction was warmed up to room temperature and stirred at room temperature for 30 minutes. The reaction was diluted with DCM. Organic layer was separated, washed with water, brine, dried over anhydrous magnesium sulfate, and concentrated to give the crude product. It was purified by flash chromatography (0-100% EtOAc/Hexanes) to afford 3-((4R,8S)-5-(benzyloxy)-1-methyl-6-oxo-4,5,6,8-tetrahydro-1H-4,7-methanopyrazolo[3,4-e][1,3]diazepin-8-yl)-4-methyl-1,2,4-oxadiazol-5(4H)-one (30 mg, 55.9%) as a white solid. MS: 383 ES+ ($C_{18}H_{18}N_6O_4$).

Int-133

A solution of 3-((4R,8S)-5-(benzyloxy)-1-methyl-6-oxo-4,5,6,8-tetrahydro-1H-4,7-methanopyrazolo[3,4-e][1,3]diazepin-8-yl)-4-methyl-1,2,4-oxadiazol-5(4H)-one (Int-132, 15 mg, 0.0392 mmol) in Methanol (3 mL) was purged with nitrogen 3 times, and 10% Pd/C (4.17 mg, 0.0039 mmol) was added. The reaction mixture was purged with nitrogen 3 times and then stirred under hydrogen atmosphere at ambient temperature for 2 hours. The reaction mixture was filtered through the Celite. The filtrate was concentrated to give 3-((4R,8S)-5-hydroxy-1-methyl-6-oxo-4,5,6,8-tetrahydro-1H-4,7-methanopyrazolo[3,4-e][1,3]diazepin-8-yl)-4-methyl-1,2,4-oxadiazol-5(4H)-one (8 mg, 69.8%) as a white solid. MS: 293 ES+ ($C_{11}H_{12}N_6O_4$).

Example 66

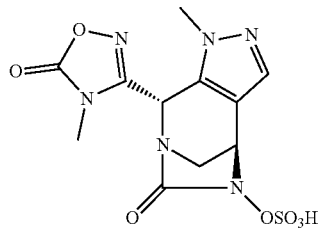

To a solution of 3-((4R,8S)-5-hydroxy-1-methyl-6-oxo-4,5,6,8-tetrahydro-1H-4,7-methanopyrazolo[3,4-e][1,3]diazepin-8-yl)-4-methyl-1,2,4-oxadiazol-5(4H)-one (8 mg, 0.027 mmol) in pyridine (2 mL) was added sulfur trioxide pyridine complex (43.57 mg, 0.27 mmol). The reaction mixture was stirred at room temperature for 16 hours, then concentrated under reduced pressure. The material was triturated with DCM and the solids were removed by filtration. The filtrate was concentrated to give crude product. It was purified by reversed phase chromatography (Sepabeads, ACN/water 0-50%) to afford ((4R,8S)-1-methyl-8-(4-methyl-5-oxo-4,5-dihydro-1,2,4-oxadiazol-3-yl)-6-oxo-4,8-dihydro-1H-4,7-methanopyrazolo[3,4-e][1,3]diazepin-5 (6H)-yl) hydrogen sulfate (5 mg, 41.7%) as a white solid. MS: 371 ES– ($C_{11}H_{12}N_6O_7S$) $^1$H NMR (300 MHz, $D_2O$) δ: 3.41 (m, 1H); 3.51 (s, 3H); 3.67 (m, 1H); 3.72 (s, 3H); 5.01 (m, 1H); 6.15 (s, 1H); 7.71 (s, 1H); 8.09 (m, 4H); 8.66 (m, 2H); 8.79 (m, 4H) Compound/pyridine ratio (1:2)

Scheme 27

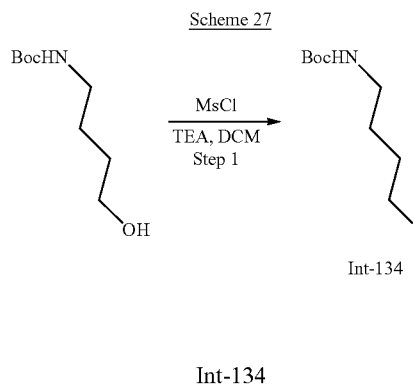

Int-134

To a stirred solution of tert-butyl (4-hydroxybutyl)carbamate (1.4 g, 7.4 mmol) in DCM (50 mL) at 0° C. was added TEA (2.04 mL, 14.6 mmol). Methanesulfonyl chloride (0.69 mL, 8.88 mmol) was added dropwise. After the addition, the reaction mixture was warmed to room temperature and stirred at room temperature for 3 hours. DCM was added. Organic layer was washed with dilute HCl solution, water, brine, dried over anhydrous sodium sulfate, and concentrated to give Int-134 4-((tert-butoxycarbonyl)amino)butyl methanesulfonate (1.8 g, yield, 91%) as yellow oil. $^1$H NMR (300 MHz, DMSO-$d_6$) δ: 1.30 (s, 9H); 1.40-1.50 (m, 2H); 1.60-1.70 (m, 2H); 2.92 (m, 2H), 3.15 (s, 3H); 4.25 (m, 2H); 6.79 (m, 1H).

Scheme 28

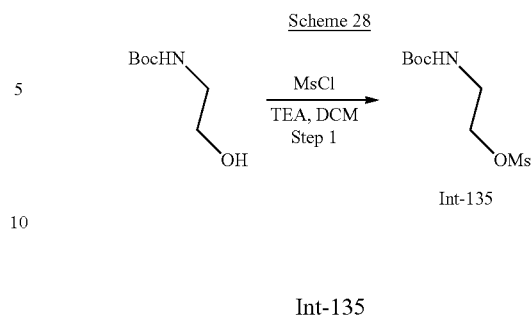

Int-135

2-((tert-butoxycarbonyl)amino)ethyl methanesulfonate was synthesized by following a similar reaction as shown for Int-134, using tert-butyl (2-hydroxyethyl)carbamate as the substrate. $^1$H NMR (300 MHz, DMSO-$d_6$) δ: 1.39 (s, 9H); 3.15 (s, 3H); 3.35 (m, 2H); 4.25 (m, 2H); 7.12 (m, 1H).

Scheme 29

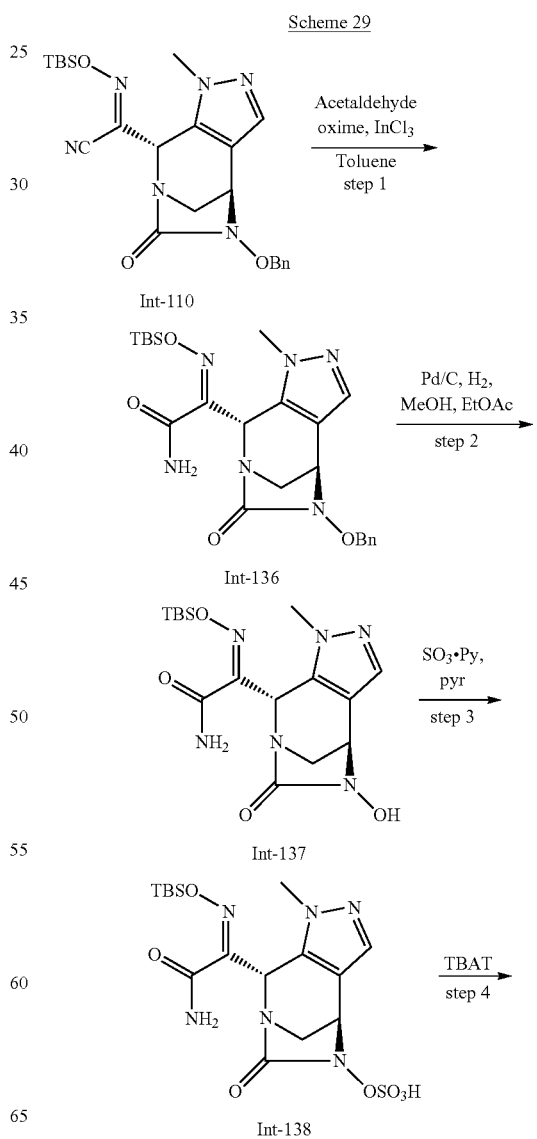

117

-continued

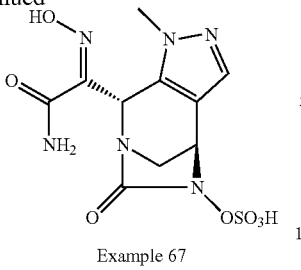

Example 67

Int-136

To a stirred solution of ((4R,8S,Z)-5-(benzyloxy)-N-(((tert-butyldimethylsilyl)oxy)-1-methyl-6-oxo-4,5,6,8-tetrahydro-1H-4,7-methanopyrazolo[3,4-e][1,3]diazepine-8-carbimidoyl cyanide (Int-10, 100 mg, 0.214 mmol) in Toluene (5 mL) was added Acetaldehyde oxime (101.3 mg, 1.71 mmol) and InCl$_3$ (47.4 mg, 0.214 mmol). The reaction was heated at 60° C. for 8 hours. The reaction mixture was cooled to room temperature. Saturated ammonium chloride solution and Ethyl acetate were added to the reaction mixture. The organic layer was separated, washed with water, brine, dried over anhydrous magnesium sulfate, and concentrated to give the crude product. It was purified by flash chromatography (0-100% EtOAc in Hexanes) to afford (Z)-2-((4R,8S)-5-(benzyloxy)-1-methyl-6-oxo-4,5,6,8-tetrahydro-1H-4,7-methanopyrazolo[3,4-e][1,3]diazepin-8-yl)-2-(((tert-butyldimethylsilyl)oxy)imino)acetamide (32 mg, yield, 30.8%) as a white solid. MS: 485 ES+ ($C_{23}H_{32}N_6O_4Si$).

Int-137

A solution of (Z)-2-((4R,8S)-5-(benzyloxy)-1-methyl-6-oxo-4,5,6,8-tetrahydro-1H-4,7-methanopyrazolo[3,4-e][1,3]diazepin-8-yl)-2-(((tert-butyldimethylsilyl)oxy)imino)acetamide (Int-136, 32 mg, 0.066 mmol) in Ethyl acetate (5 mL) and Methanol (2.5 mL) was purged with nitrogen 3 times, and 10% Pd/C (19.02 mg, 0.0198 mmol) was added. The reaction mixture was purged with nitrogen 3 times and then stirred under hydrogen atmosphere at ambient temperature for 30 minutes. The reaction mixture was filtered through the Celite. The filtrate was concentrated to give (Z)-2-(((tert-butyldimethylsilyl)oxy)imino)-2-((4R,8S)-5-hydroxy-1-methyl-6-oxo-4,5,6,8-tetrahydro-1H-4,7-methanopyrazolo[3,4-e][1,3]diazepin-8-yl)acetamide (25 mg, 95.9%) as a white solid. MS: 395 ES+ ($C_{16}H_{26}N_6O_4Si$).

Int-138

To a solution of (Z)-2-(((tert-butyldimethylsilyl)oxy)imino)-2-((4R,8S)-5-hydroxy-1-methyl-6-oxo-4,5,6,8-tetrahydro-1H-4,7-methanopyrazolo[3,4-e][1,3]diazepin-8-yl)acetamide (Int-137, 25 mg, 0.063 mmol) in pyridine (2 mL) was added sulfur trioxide pyridine complex (30.3 mg, 0.19 mmol). The reaction mixture was stirred at room temperature for 3 hours, then concentrated under reduced pressure. The material was triturated with DCM and the solids were removed by filtration. The filtrate was concentrated to give crude product. It was purified by flash chromatography (0-100% Acetone in DCM) to afford (4R,8S)-8-((Z)-2-amino-1-(((tert-butyldimethylsilyl)oxyimino)-2-oxoethyl-1-methyl-6-oxo-4,8-dihydro-1H-4,7-methanopyrazolo[3,4-e]

118

[1,3]diazepin-5(6H)-yl hydrogen sulfate (20 mg, 66.5%) as a white solid. MS: 473 ES− ($C_{16}H_{26}N_6O_7SiS$).

Example 67

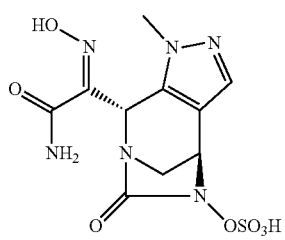

To a stirred solution of (4R,8S)-8-((Z)-2-amino-1-(((tert-butyldimethylsilyl)oxyimino)-2-oxoethyl-1-methyl-6-oxo-4,8-dihydro-1H-4,7-methanopyrazolo[3,4-e][1,3]diazepin-5(6H)-yl hydrogen sulfate (Int-138, 20 mg, 0.042 mmol) in DCM (5 mL) was added TBAT (27.3 mg, 0.051 mmol). The reaction mixture was stirred at room temperature for 30 minutes. The solvent was removed. The resulting solid was purified by flash chromatography (0-100% Acetone in DCM) to afford (4R,8S)-8-((Z)-2-amino-1-(hydroxyimino)-2-oxoethyl-1-methyl-6-oxo-4,8-dihydro-1H-4,7-methanopyrazolo[3,4-e][1,3]diazepin-5(6H)-yl hydrogen sulfate as a tetrabutylammonium salt (14 mg, 71.1%) MS: 359 ES− ($C_{10}H_{12}N_6O_7S$) $^1$H NMR (300 MHz, DMSO-$d_6$) δ: 0.94 (m, 10H); 1.30 (m, 7H); 1.58 (m, 7H); 3.04-3.40 (m, 9H); 3.56 (s, 3H); 4.70 (m, 1H); 5.47 (s, 1H); 7.36 (s, 1H); 7.79 (m, 2H); 11.86 (s, 1H) compound/tetrabutylammonium ratio (1:0.9).

Scheme 30

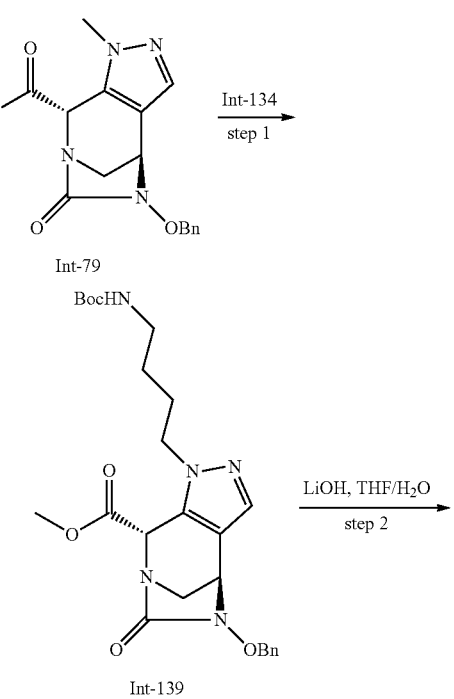

119
-continued

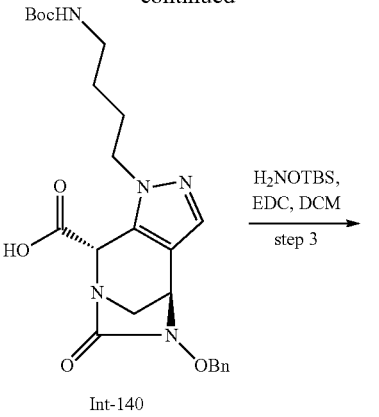
Int-140

H₂NOTBS,
EDC, DCM
step 3
→

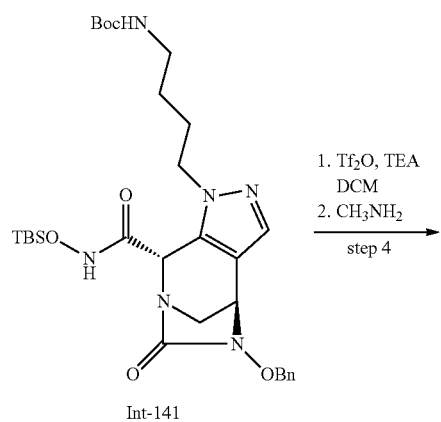
Int-141

1. Tf₂O, TEA DCM
2. CH₃NH₂
step 4
→

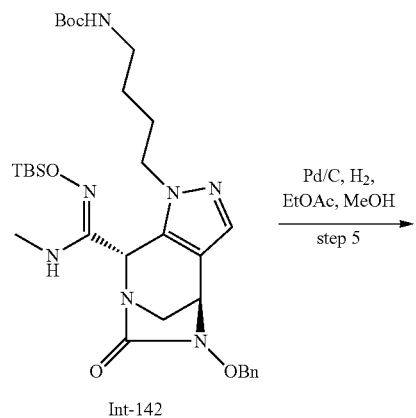
Int-142

Pd/C, H₂,
EtOAc, MeOH
step 5
→

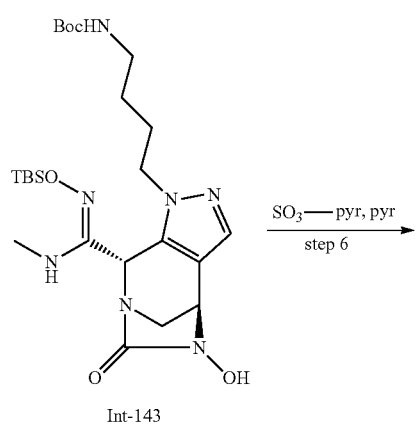
Int-143

SO₃—pyr, pyr
step 6
→

120
-continued

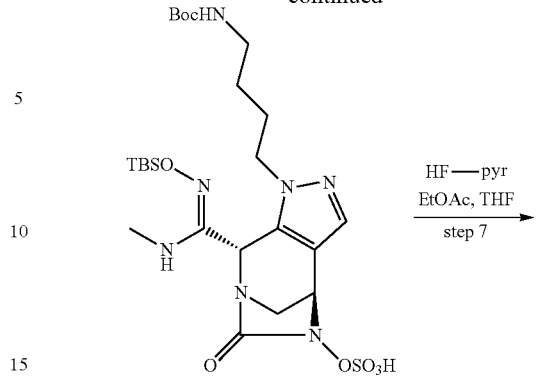
Int-144

HF—pyr
EtOAc, THF
step 7
→

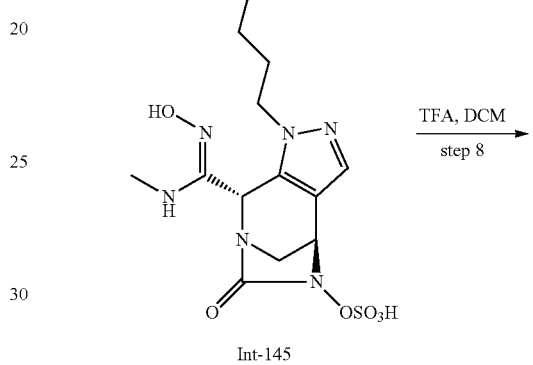
Int-145

TFA, DCM
step 8
→

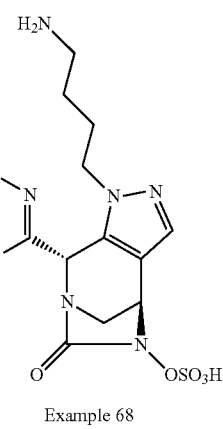
Example 68

Int-139

To a stirred solution of Methyl ((4R,8S)-5-(benzyloxy)-6-oxo-4,5,6,8-tetrahydro-1H-4,7-methanopyrazolo[3,4-e][1,3]diazepine-8-carboxylate (Int-79, 700 mg, 2.13 mmol) in DMF (8 mL) was added 4-((tert-butoxycarbonyl)amino)butyl methanesulfonate (Int-134, 1424 mg, 2.13 mmol) and Cs₂CO₃ (4.17 g, 12.8 mmol). The reaction was heated at 80° C. for 20 minutes and cooled to room temperature. Ethyl acetate and water were added to the reaction mixture. The organic layer was separated, washed with water, brine, dried over anhydrous sodium sulfate, and concentrated to give the crude product. It was purified by flash chromatography (0-100% EtOAc in Hexanes) to afford methyl ((4R,8S)-5-(benzyloxy)-1-(4-((tert-butoxycarbonyl)amino)butyl-6-oxo-4,5,6,8-tetrahydro-1H-4,7-methanopyrazolo[3,4-e][1,3]diazepine-8-carboxylate (230 mg, yield, 21.6%) as a white solid. MS: 500 ES+ ($C_{25}H_{33}N_5O_6$).

Int-140

To a solution of methyl ((4R,8S)-5-(benzyloxy)-1-(4-(((tert-butoxycarbonyl)amino)butyl-6-oxo-4,5,6,8-tetrahydro-1H-4,7-methanopyrazolo[3,4-e][1,3]diazepine-8-carboxylate (Int-139, 230 mg, 0.46 mmol) in THF (5 mL) and water (1 mL) at 0° C. was added lithium hydroxide (0.48 mL, 0.48 mmol). The reaction mixture was warmed up to room temperature and stirred at room temperature for 1 hour. THF was removed. 1N HCl was added to the aqueous to adjust pH ~3-4 and the product was extracted with ethyl acetate. The organics were dried over anhydrous sodium sulfate, filtered and concentrated to afford (4R,8S)-5-(benzyloxy)-1-(4-((tert-butoxycarbonyl)amino)butyl-6-oxo-4,5,6,8-tetrahydro-1H-4,7-methanopyrazolo[3,4-e][1,3]diazepine-8-carboxylic acid (200 mg, 89.5%) as a white solid. MS: 486 ES+ ($C_{24}H_{31}N_5O_6$).

Int-141

To a solution of (4R,8S)-5-(benzyloxy)-1-(4-((tert-butoxycarbonyl)amino)butyl-6-oxo-4,5,6,8-tetrahydro-1H-4,7-methanopyrazolo[3,4-e][1,3]diazepine-8-carboxylic acid (Int-140, 200 mg, 0.41 mmol) in DCM (5 mL) at room temperature was added O-(tert-butyldimethylsilyl) hydroxylamine (78.9 mg, 0.54 mmol) and EDC (94.8 mg, 0.49 mmol). The reaction mixture was stirred at room temperature for 40 minutes. The reaction mixture was directly loaded on silica gel and purified by flash chromatography (20 g silica gel, 0%-50% ethyl acetate/hexanes) to afford tert-butyl (4-((4R,8S)-5-(benzyloxy)-8-((((tert-butyldimethylsilyl)oxy)carbamoyl)-6-oxo-4,5,6,8-tetrahydro-1H-4,7-methanopyrazolo[3,4-e][1,3]diazepin-1-yl)butyl)carbamate (103 mg, 40.6%) as a white foam. MS: 615 ES+ ($C_{30}H_{46}N_6O_6Si$).

Int-142

To a solution of tert-butyl (4-((4R,8S)-5-(benzyloxy)-8-(((tert-butyldimethylsilyl)oxy)carbamoyl)-6-oxo-4,5,6,8-tetrahydro-1H-4,7-methanopyrazolo[3,4-e][1,3]diazepin-1-yl)butyl)carbamate (Int-141, 100 mg, 0.16 mmol) and triethylamine (0.090 mL, 0.65 mmol) in DCM (2 mL) at −78° C. was added triflic anhydride (0.055 mL, 0.33 mmol). The reaction mixture was stirred for 5 minutes. To the solution was added methylamine (0.36 mL, 0.72 mmol, 2N in THF) dropwise. The reaction mixture was then allowed to warm to room temperature and stir for 2 hours. The reaction mixture was diluted with DCM and washed once with saturated ammonium chloride solution. The organics were dried over magnesium sulfate, filtered and concentrated. Silica gel chromatography (0%-50% ethyl acetate/hexanes) afforded tert-butyl (4-((4R,8S)-5-(benzyloxy)-8-((Z)—N'-((tert-butyldimethylsilyl)oxy)-N-methylcarbamimidoyl)-6-oxo-4,5,6,8-tetrahydro-1H-4,7-methanopyrazolo[3,4-e][1,3]diazepin-1-yl)butyl)carbamate as white foam (18 mg, 17.7%). MS: 628 ES+ ($C_{31}H_{49}N_7O_5Si$).

Int-143

To a solution of tert-butyl (4-((4R,8S)-5-(benzyloxy)-8-((Z)—N'-((tert-butyldimethylsilyl)oxy)-N-methylcarbamimidoyl)-6-oxo-4,5,6,8-tetrahydro-1H-4,7-methanopyrazolo[3,4-e][1,3]diazepin-1-yl)butyl)carbamate (Int-142, 18 mg, 0.0287 mmol) in ethyl acetate (3 mL) was degassed with nitrogen and Pd/C (3.6 mg, 0.0057 mmol) was added. The mixture was degassed again and placed under hydrogen balloon. The reaction mixture was stirred for 2 hours. The reaction mixture was filtered through the celite. The filtrate was concentrated to afford tert-butyl (4-((4R,8S)-8-((Z)—N-((tert-butyldimethylsilyl)oxy)-N-methylcarbamimidoyl)-5-hydroxy-6-oxo-4,5,6,8-tetrahydro-1H-4,7-methanopyrazolo[3,4-e][1,3]diazepin-1-yl)butyl)carbamate (14 mg, 90.8% yield) as a colorless oil. MS: 538 ES+ ($C_{24}H_{43}N_7O_5Si$).

Int-144

To a solution of tert-butyl (4-((4R,8S)-8-((Z)—N-((tert-butyldimethylsilyl)oxy)-N-methylcarbamimidoyl)-5-hydroxy-6-oxo-4,5,6,8-tetrahydro-1H-4,7-methanopyrazolo[3,4-e][1,3]diazepin-1-yl)butyl)carbamate (Int-143, 14 mg, 0.03 mmol) in pyridine (2 mL) at room temperature was added sulfur trioxide pyridine complex (33.15 mg, 0.21 mmol). The reaction mixture was stirred at room temperature for 3 hours, then diluted with DCM and filtered to remove solids. The filtrate was concentrated. The residue was purified by flash chromatography (0-100% Acetone in DCM) to afford (4R,8S)-1-(4-((tert-butoxycarbonyl)amino)butyl)-8-((Z)—N-((tert-butyldimethylsilyl)oxy)-N-methylcarbamimidoyl)-6-oxo-4,8-dihydro-1H-4,7-methanopyrazolo[3,4-e][1,3]diazepin-5(6H)-yl hydrogen sulfate (13 mg, 80.8%) as a colorless oil. MS: 616 ES− ($C_{24}H_{43}N_7O_8SiS$).

Int-145

To a solution of (4R,8S)-1-(4-((tert-butoxycarbonyl)amino)butyl)-8-((Z)—N-((tert-butyldimethylsilyl)oxy)-N-methylcarbamimidoyl)-6-oxo-4,8-dihydro-1H-4,7-methanopyrazolo[3,4-e][1,3]diazepin-5(6H)-yl hydrogen sulfate (Int-144, 13 mg, 0.021 mmol) in ethyl acetate (1 mL) and THF (0.5 mL) at room temperature was added HF.pyridine (0.0006 mL, 0.023 mmol). The reaction mixture was stirred for 30 minutes. After 30 minutes the reaction mixture was concentrated to afford (4R,8S)-1-(4-((tert-butoxycarbonyl)amino)butyl)-8-((Z)—N-hydroxy-N-methylcarbamimidoyl)-6-oxo-4,8-dihydro-1H-4,7-methanopyrazolo[3,4-e][1,3]diazepin-5(6H)-yl hydrogen sulfate (11 mg, 100%) as a white solid. MS: 504 ES+ ($C_{18}H_{29}N_7O_8S$).

Example 68

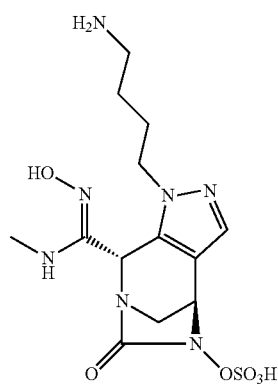

To a solution of (4R,8S)-1-(4-((tert-butoxycarbonyl)amino)butyl)-8-((Z)—N-hydroxy-N-methylcarbamimidoyl)-6-oxo-4,8-dihydro-1H-4,7-methanopyrazolo[3,4-e][1,3]diazepin-5(6H)-yl hydrogen sulfate (Int-145, 10 mg, 0.0199 mmol) in DCM (1 mL) at 0° C. was added trifluoroacetic acid (0.076 mL, 0.99 mmol). The reaction mixture was stirred at room temperature for 30 minutes. The reaction mixture was concentrated with DCM several times to remove excess TFA. The residue was dissolved in pH ~7 buffer and purified by reversed phase chromatography (Sepabeads, ACN/water 0-50%) to afford (4R,8S)-1-(4-aminobutyl)-8-((Z)—N'-hydroxy-N-methylcarbamimidoyl)-6-oxo-4,8-dihydro-1H-4,7-methanopyrazolo[3,4-e][1,3]diazepin-5(6H)-yl hydrogen sulfate (3.5 mg, 37.1%) as a white solid. MS: 404 ES+ ($C_{13}H_{21}N_7O_6S$) $^1$H NMR (300 MHz, $D_2O$) δ: 1.42-1.75 (m, 2H); 1.79-2.04 (m, 2H); 2.94 (m, 2H); 3.10 (s, 3H); 3.51-3.72 (m, 2H); 3.88-4.14 (m, 2H); 4.99 (m, 1H); 5.62 (s, 1H); 7.69 (s, 1H).

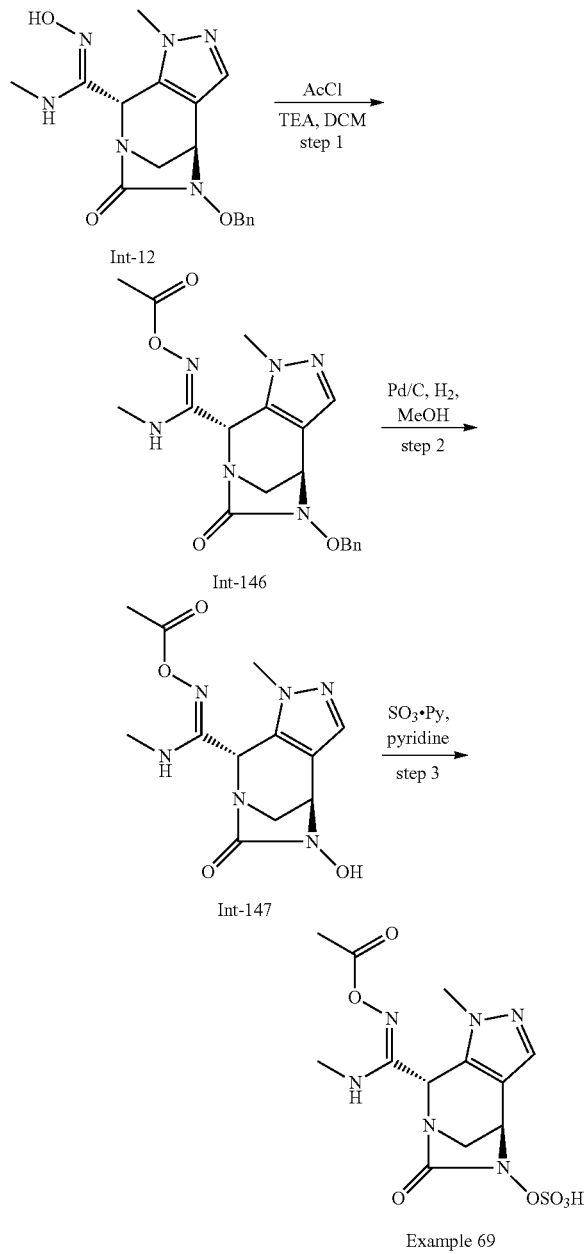

Scheme 31

Int-146

To a stirred solution of (4R,8S,Z)-5-(benzyloxy)-N'-hydroxy-N,1-dimethyl-6-oxo-4,5,6,8-tetrahydro-1H-4,7-methanopyrazolo[3,4-e][1,3]diazepine-8-carboximidamide (Int-12, 110 mg, 0.31 mmol) in DCM (10 mL) was added TEA (0.064 mL, 0.46 mmol) and Acetyl chloride (0.029 mL, 0.37 mmol). The reaction was stirred at room temperature for 30 minutes. Saturated ammonium chloride solution was added to quench the reaction. Organic layer was separated, washed with water, brine, dried over anhydrous magnesium sulfate, and concentrated to give the crude product. It was purified by flash chromatography (0-100% Acetone in DCM) to afford (4R,8S,Z)—N'-acetoxy-5-(benzyloxy)-N,1-dimethyl-6-oxo-4,5,6,8-tetrahydro-1H-4,7-methanopyrazolo[3,4-e][1,3]diazepine-8-carboximidamide (70 mg, yield, 56.9%) as a white solid. MS: 399 ES+ ($C_{19}H_{22}N_6O_4$).

Int-147

A solution of (4R,8S,Z)—N'-acetoxy-5-(benzyloxy)-N,1-dimethyl-6-oxo-4,5,6,8-tetrahydro-1H-4,7-methanopyrazolo[3,4-e][1,3]diazepine-8-carboximidamide (Int-146, 70 mg, 0.175 mmol) in Methanol (5 mL) was purged with nitrogen 3 times, and 10% Pd/C (12.9 mg, 0.012 mmol) was added. The reaction mixture was purged with nitrogen 3 times and then stirred under hydrogen atmosphere at ambient temperature for 30 minutes. The reaction mixture was filtered through the Celite. The filtrate was concentrated to give (4R,8S,Z)—N'-acetoxy-5-hydroxy-N,1-dimethyl-6-oxo-4,5,6,8-tetrahydro-1H-4,7-methanopyrazolo[3,4-e][1,3]diazepine-8-carboximidamide (50 mg, 92.3%) as a white solid. MS: 309 ES+ ($C_{12}H_{16}N_6O_4$).

Example 69

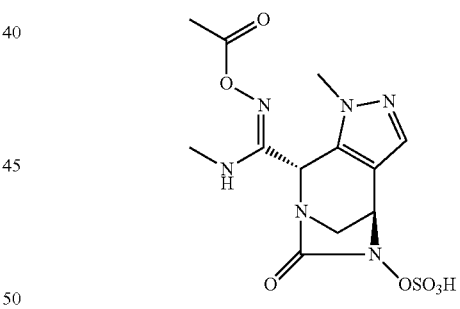

To a solution of (4R,8S,Z)—N'-acetoxy-5-hydroxy-N,1-dimethyl-6-oxo-4,5,6,8-tetrahydro-1H-4,7-methanopyrazolo[3,4-e][1,3]diazepine-8-carboximidamide (Int-147, 50 mg, 0.16 mmol) in pyridine (1 mL) was added sulfur trioxide pyridine complex (77.4 mg, 0.49 mmol). The reaction mixture was stirred at room temperature for 6 hours, then concentrated under reduced pressure. The material was triturated with DCM and the solids were removed by filtration. The filtrate was concentrated to give crude product. It was purified by reversed phase chromatography (Sepabeads, ACN/water 0-50%) to afford pyridium (4R,8S)-8-((Z)—N'-acetoxy-N-methylcarbamimidoyl)-1-methyl-6-oxo-4,8-dihydro-1H-4,7-methanopyrazolo[3,4-e][1,3]diazepin-5(6H)-hydrogen sulfate (35 mg, 55.6%) as a white solid. MS: 387 ES− ($C_{12}H_{16}N_6O_7S$) $^1$H NMR (300 MHz, DMSO-$d_6$) δ: 2.03 (s, 3H); 3.00 (m, 2H); 3.36 (m, 2H); 3.65 (s, 3H); 4.71

(m, 1H); 5.62 (s, 1H); 6.84 (b, 2H); 7.31 (s, 1H); 7.90 (m, 2H); 8.39 (m, 1H); 8.86 (m, 2H) Compound/pyridine ratio (1:1).

Example 70

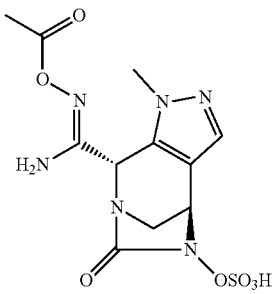

Pyridium (4R,8S)-8-((Z)—N'-acetoxycarbamimidoyl)-1-methyl-6-oxo-4,8-dihydro-1H-4,7-methanopyrazolo[3,4-e][1,3]diazepin-5(6H)-yl hydrogen sulfate was synthesized by following similar reactions as shown for Example 69, using a solution of ammonia in THF in step 12 in Scheme 1, Step 12. MS 373 ES– ($C_{11}H_{14}N_6O_7S$) $^1$H NMR 300 MHz, DMSO-$d_6$) δ: 2.03 (s, 3H); 3.34 (m, 2H); 3.68 (s, 3H); 4.67 (m, 1H); 5.22 (s, 1H); 6.84 (bs, 2H); 7.31 (s, 1H); 7.90 (m, 3H); 8.39 (m, 1.5H); 8.86 (m, 3H) Compound/pyridine ratio (1:1.5).

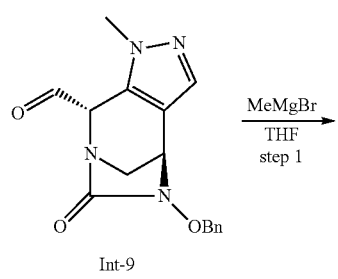

Int-9 → MeMgBr / THF / step 1

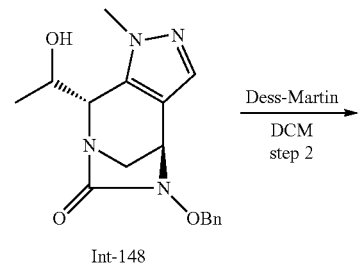

Int-148 → Dess-Martin / DCM / step 2

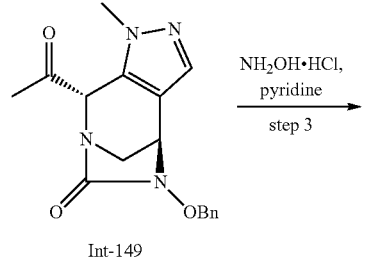

Int-149 → NH$_2$OH·HCl, pyridine / step 3

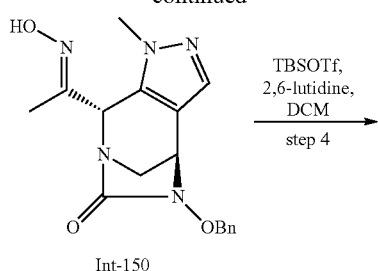

Int-150 → TBSOTf, 2,6-lutidine, DCM / step 4

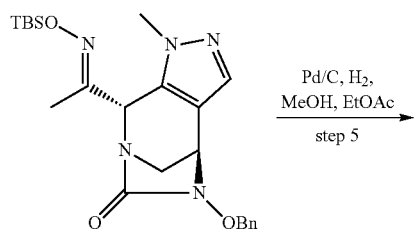

Int-151 → Pd/C, H$_2$, MeOH, EtOAc / step 5

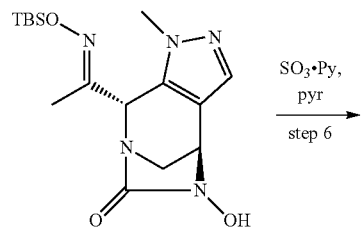

Int-152 → SO$_3$·Py, pyr / step 6

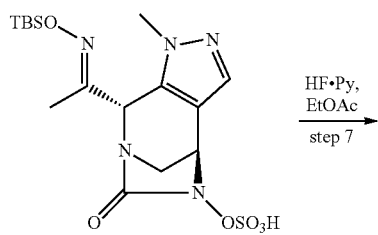

Int-153 → HF·Py, EtOAc / step 7

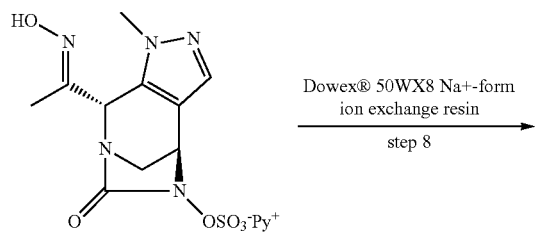

Int-154 → Dowex® 50WX8 Na+-form ion exchange resin / step 8

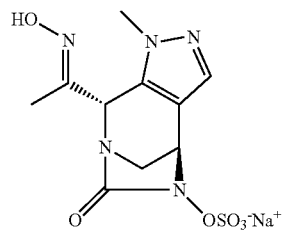

Example 71

Int-148

To a stirred solution of (4R,8S)-5-(benzyloxy)-1-methyl-6-oxo-4,5,6,8-tetrahydro-1H-4,7-methanopyrazolo[3,4-e][1,3]diazepine-8-carbaldehyde (Int-9, 200 mg, 0.64 mmol) in THF (10 mL) at 0° C. was added MeMgBr (0.38 mL, 1.15 mmol, 3N in Et$_2$O) dropwise. The reaction was stirred at 0° C. for 4 hours. Saturated ammonium chloride solution was added to quench the reaction. Ethyl acetate was added. The organic layer was separated, washed with water, brine, dried over anhydrous magnesium sulfate, and concentrated to afford (4R,8S)-5-(benzyloxy)-8-((R)-1-hydroxyethyl)-1-methyl-1,4,5,8-tetrahydro-6H-4,7-methanopyrazolo[3,4-e][1,3]diazepin-6-one (100 mg, 47.6%) as a white solid. It was used directly in the next step MS: 329 ES+ (C$_{17}$H$_{20}$N$_4$O$_3$).

Int-149

To a solution of (4R,8S)-5-(benzyloxy)-8-((R)-1-hydroxyethyl)-1-methyl-1,4,5,8-tetrahydro-6H-4,7-methanopyrazolo[3,4-e][1,3]diazepin-6-one (Int-148, 100 mg, 0.30 mmol) in dichloromethane (10 mL) at ambient temperature was added Dess-Martin periodinane (155 mg, 0.37 mmol). The reaction mixture was stirred for 30 minutes. Aqueous sodium thiosulfate solution (1N) and aqueous saturated sodium bicarbonate solution were added to the reaction mixture and stirred for 15 minutes. The biphasic mixture was separated and the aqueous extracted with dichloromethane. The combined organics were dried over anhydrous magnesium sulfate, filtered and concentrated to give the crude product. Flash chromatography (0%-100% ethyl acetate/hexanes) afforded (4R,8S)-8-acetyl-5-(benzyloxy)-1-methyl-1,4,5,8-tetrahydro-6H-4,7-methanopyrazolo[3,4-e][1,3]diazepin-6-one (40 mg, 40.2%) as a white solid. MS: 327 ES+ (C$_{17}$H$_{18}$N$_4$O$_3$)

Int-150

To a solution of (4R,8S)-8-acetyl-5-(benzyloxy)-1-methyl-1,4,5,8-tetrahydro-6H-4,7-methanopyrazolo[3,4-e][1,3]diazepin-6-one (Int-149, 40 mg, 0.12 mmol) in pyridine (2 mL) at ambient temperature was added hydroxylamine hydrochloride (10.2 mg, 0.15 mmol). The reaction mixture was stirred for 30 minutes. Aqueous ammonium chloride solution and ethyl acetate were added. The organic layer was separated, washed with water, brine, dried over anhydrous sodium sulfate and concentrated to give (4R,8S)-5-(benzyloxy)-8-(E)-1-(hydroxyimino)ethyl)-1-methyl-1,4,5,8-tetrahydro-6H-4,7-methanopyrazolo[3,4-e][1,3]diazepin-6-one (30 mg, 71.7%) as a white solid. It was used directly in the next step. MS: 342 ES+ (C$_{17}$H$_{19}$N$_5$O$_3$).

Int-151

To a solution of (4R,8S)-5-(benzyloxy)-8-(E)-1-(hydroxyimino)ethyl)-1-methyl-1,4,5,8-tetrahydro-6H-4,7-methanopyrazolo[3,4-e][1,3]diazepin-6-one (Int-150, 30 mg, 0.088 mmol) in DCM (5 mL) at 0° C. was added tert-butyldimethylsilyl trifluoromethanesulfonate (0.022 mL, 0.097 mmol) and 2,6-lutidine (0.012 mL, 0.11 mmol). The reaction mixture was warmed up to room temperature and stirred for 2 hours. DCM and saturated ammonium chloride solution were added. The organic layer was separated, dried over anhydrous sodium sulfate and concentrated. The residue was purified by flash chromatography (0-100% EtOAc/Hexanes) to afford (4R,8S)-5-(benzyloxy)-8-(E)-1-(((tert-butyldimethylsilyl)oxy)imino)ethyl)-1-methyl-1,4,5,8-tetrahydro-6H-4,7-methanopyrazolo[3,4-e][1,3]diazepin-6-one (25 mg, 62.4%) as a white solid. MS: 456 ES+ (C$_{23}$H$_{33}$N$_5$O$_3$Si).

Int-152

A solution of (4R,8S)-5-(benzyloxy)-8-(E)-1-(((tert-butyldimethylsilyl)oxy)imino)ethyl)-1-methyl-1,4,5,8-tetrahydro-6H-4,7-methanopyrazolo[3,4-e][1,3]diazepin-6-one (Int-151, 25 mg, 0.055 mmol) in MeOH (10 mL) was purged with nitrogen 3 times, and 10% Pd/C (5.84 mg, 0.0055 mmol) was added. The reaction mixture was purged with nitrogen 3 times and then stirred under hydrogen atmosphere at ambient temperature for 1 hour. The reaction mixture was filtered through the celite. The filtrate was concentrated to give (4R,8S)-8-((E)-1-(((tert-butyldimethylsilyl)oxy)imino)ethyl)-5-hydroxy-1-methyl-1,4,5,8-tetrahydro-6H-4,7-methanopyrazolo[3,4-e][1,3]diazepin-6-one (17 mg, 84.7%) as a white solid. MS: 366 ES+ (C$_{16}$H$_{27}$N$_5$O$_3$Si).

Int-153

To a solution (4R,8S)-8-((E)-1-(((tert-butyldimethylsilyl)oxy)imino)ethyl)-5-hydroxy-1-methyl-1,4,5,8-tetrahydro-6H-4,7-methanopyrazolo[3,4-e][1,3]diazepin-6-one (Int-152, 17 mg, 0.047 mmol) in pyridine (2 mL) at ambient temperature was added sulfur trioxide pyridine complex (1338 mg, 8.41 mmol). The reaction mixture was stirred overnight, then concentrated under reduced pressure to give the crude product. The material was triturated with DCM and more solids were removed by filtration. The filtrate was concentrated. The residue was purified with flash chromatography (0%-100% Acetone/DCM) to afford (4R,8S)-8-((E)-1-(((tert-butyldimethylsilyl)oxy)imino)ethyl)-1-methyl-6-oxo-4,8-dihydro-1H-4,7-methanopyrazolo[3,4-e][1,3]diazepin-5(6H)-yl hydrogen sulfate (18 mg, 86.9%) as a white solid. MS: 446 ES+ (C$_{16}$H$_{27}$N$_5$O$_6$SSi).

Int-154 and Example 71

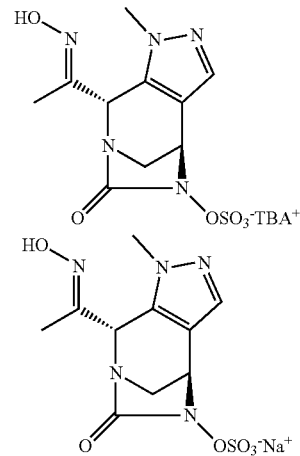

To a solution of afford (4R,8S)-8-((E)-1-(((tert-butyldimethylsilyl)oxy)imino)ethyl)-1-methyl-6-oxo-4,8-dihydro-1H-4,7-methanopyrazolo[3,4-e][1,3]diazepin-5(6H)-yl hydrogen sulfate (Int-153, 18 mg, 0.040 mmol) in THF (2 mL) at ambient temperature was added TBAF (0.014 mL, 0.049 mmol, 1N in THF). The reaction mixture was stirred for 2 hours, then concentrated. The residue was purified by reversed phase chromatography (Sepabeads, ACN/water 0-50%) to afford the tetrabutylammonium salt of (4R,8S)-8-((E)-1-(hydroxyimino)ethyl)-1-methyl-6-oxo-4,8-dihydro-1H-4,7-methanopyrazolo[3,4-e][1,3]diazepin-5(6H)-yl hydrogen sulfate Int-154 as a white solid. It was then dissolved in water (2 mL) and eluted through a Dowex® 50WX8 Na+-form ion exchange resin cartridge with water as the eluent. Fractions containing the product were pooled and lyophilized to afford a sodium salt of (4R,8S)-8-((E)-1-(hydroxyimino)ethyl)-1-methyl-6-oxo-4,8-dihydro-1H-4,7-methanopyrazolo[3,4-e][1,3]diazepin-5(6H)-yl hydrogen sulfate (10 mg, 67.2%) as a white solid. MS: 332 ES+ ($C_{10}H_{13}N_5O_6S$) $^1$H NMR (300 MHz, DMSO-d$_6$) δ: 3.04 (m, 1H); 3.25 (m, 1H); 3.30 (s, 3H); 3.54 (s, 3H); 4.62 (m, 1H); 5.23 (s, 1H); 7.30 (s, 1H); 11.16 (s, 1H).

Scheme 33

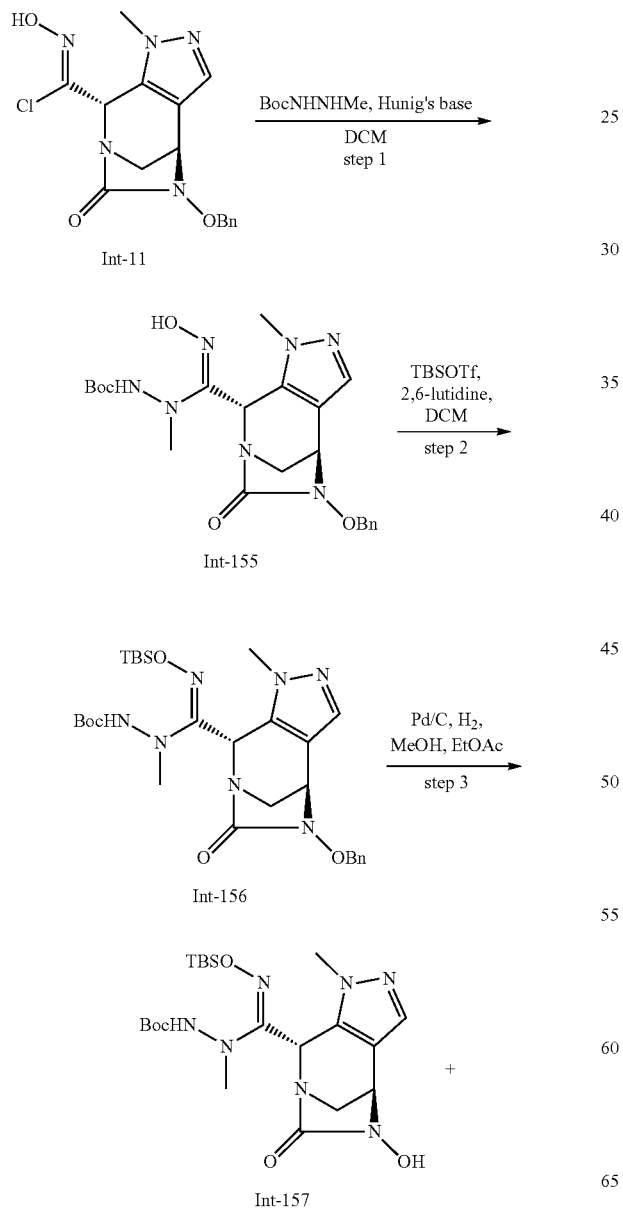

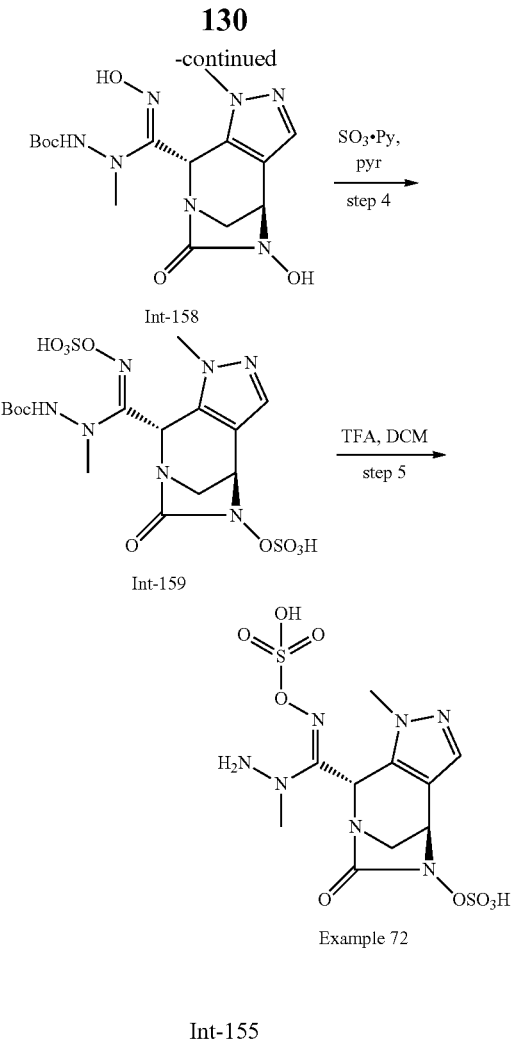

Int-155

To a solution of ((4R,8S,Z)-5-(benzyloxy)-N-hydroxy-1-methyl-6-oxo-4,5,6,8-tetrahydro-1H-4,7-methanopyrazolo[3,4-e][1,3]diazepine-8-carbimidoyl chloride (Int-11, 80 mg, 0.221 mmol) in DCM (10 mL) at room temperature was added tert-butyl N-(methylamino)carbamate (48.5 mg, 0.332 mmol) and Hunig's base (85.7 mg, 0.66 mmo). The reaction mixture was stirred at ambient temperature for 30 minutes. Saturated ammonium chloride solution and DCM were added. The organic layer was separated, washed with water, brine and dried over anhydrous sodium sulfate and concentrated to afford tert-butyl 2-((Z)-((4R,8S)-5-(benzyloxy)-1-methyl-6-oxo-4,5,6,8-tetrahydro-1H-4,7-methanopyrazolo[3,4-e][1,3]diazepin-8-yl)(hydroxyimino)methyl)-2-methylhydrazine-1-carboxylate (60 mg, 57.5%) as a white solid. It was used directly in the next step. MS: 357 ES+ ($C_{22}H_{29}N_7O_5$).

Int-156

To a solution of tert-butyl 2-((Z)-((4R,8S)-5-(benzyloxy)-1-methyl-6-oxo-4,5,6,8-tetrahydro-1H-4,7-methanopyrazolo[3,4-e][1,3]diazepin-8-yl)(hydroxyimino)methyl)-2-methylhydrazine-1-carboxylate (Int-155, 60 mg, 0.127 mmol) in DCM (8 mL) at 0° C. was added tert-butyldimethylsilyl trifluoromethanesulfonate (0.064 mL, 0.28 mmol) and 2,6-lutidine (0.037 mL, 0.32 mmol). The reaction mixture was warmed up to room temperature and stirred at room temperature for 1 hour. DCM and saturated ammonium chloride solution were added. The organic layer was separated, washed with water, brine and dried over anhydrous sodium sulfate and concentrated. Silica gel chromatography (0%-100% ethyl acetate/hexanes) afforded tert-butyl (Z)-4-((4R,8S)-5-(benzyloxy)-1-methyl-6-oxo-4,5,6,8-tetrahydro-1H-4,7-methanopyrazolo[3,4-e][1,3]diazepin-8-yl)-3,7,7,8,8-pentamethyl-6-oxa-2,3,5-triaza-7-silanon-4-enoate (30 mg, 40.2% yield) as a white solid. MS: 586 ES+ ($C_{28}H_{43}N_7O_5Si$).

Int-157 and Int-158

A solution of tert-butyl (Z)-4-((4R,8S)-5-(benzyloxy)-1-methyl-6-oxo-4,5,6,8-tetrahydro-1H-4,7-methanopyrazolo[3,4-e][1,3]diazepin-8-yl)-3,7,7,8,8-pentamethyl-6-oxa-2,3,5-triaza-7-silanon-4-enoate (Int-156, 28 mg, 0.0478 mmol) in MeOH (2 mL) and ethyl acetate (4 mL) was purged with nitrogen 3 times, and 10% Pd/C (10.1 mg, 0.0096 mmol) was added. The reaction mixture was purged with nitrogen 3 times and then stirred under hydrogen atmosphere at ambient temperature for 1 hour. The reaction mixture was filtered through the celite. The filtrate was concentrated to give the mixture of tert-butyl (Z)-4-((4R,8S)-5-hydroxy-1-methyl-6-oxo-4,5,6,8-tetrahydro-1H-4,7-methanopyrazolo[3,4-e][1,3]diazepin-8-yl)-3,7,7,8,8-pentamethyl-6-oxa-2,3,5-triaza-7-silanon-4-enoate (Int-157) MS: 496 ES+ ($C_{21}H_{37}N_7O_5Si$) and tert-butyl 2-((Z)-((4R,8S)-5-hydroxy-1-methyl-6-oxo-4,5,6,8-tetrahydro-1H-4,7-methanopyrazolo[3,4-e][1,3]diazepin-8-yl)(hydroxyimino)methyl)-2-methylhydrazine-1-carboxylate (Int-158) as a white solid (18 mg). MS: 382 ES+ ($C_{15}H_{23}N_7O_5$).

Int-159

To a mixture of tert-butyl (Z)-4-((4R,8S)-5-hydroxy-1-methyl-6-oxo-4,5,6,8-tetrahydro-1H-4,7-methanopyrazolo[3,4-e][1,3]diazepin-8-yl)-3,7,7,8,8-pentamethyl-6-oxa-2,3,5-triaza-7-silanon-4-enoate (Int-157) and tert-butyl 2-((Z)-((4R,8S)-5-hydroxy-1-methyl-6-oxo-4,5,6,8-tetrahydro-1H-4,7-methanopyrazolo[3,4-e][1,3]diazepin-8-yl)(hydroxyimino)methyl)-2-methylhydrazine-1-carboxylate (Int-158) (18 mg) in pyridine (2 mL) at ambient temperature was added sulfur trioxide pyridine complex (17.3 mg, 0.11 mmol). The reaction mixture was stirred overnight, then concentrated under reduced pressure to give the crude product. It was triturated with DCM and solid was removed by filtration. The filtrate was concentrated. The residue was purified with reversed phase chromatography (Sepabeads, ACN/water 0-50%) to afford ((((Z)-(2-(tert-butoxycarbonyl)-1-methylhydrazineyl)((4R,8S)-1-methyl-6-oxo-5-(sulfooxy)-4,5,6,8-tetrahydro-1H-4,7-methanopyrazolo[3,4-e][1,3]diazepin-8-yl)methylene)amino)oxy)sulfonic acid (18 mg, 86.9%) as a white solid. MS: 539 ES− ($C_{15}H_{23}N_7O_{11}S_2$)

Example 72

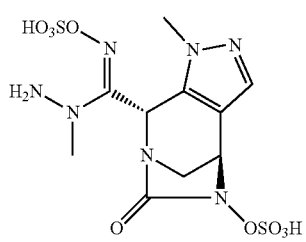

To a solution of ((((Z)-(2-(tert-butoxycarbonyl)-1-methylhydrazineyl)((4R,8S)-1-methyl-6-oxo-5-(sulfooxy)-4,5,6,8-tetrahydro-1H-4,7-methanopyrazolo[3,4-e][1,3]diazepin-8-yl)methylene)amino)oxy)sulfonic acid (Int-159, 2 mg, 0.037 mmol) in DCM (2 mL) at room temperature was added trifluoroacetic acid (0.0283 mL, 0.369 mmol). The reaction mixture was stirred at room temperature for 30 minutes. The reaction mixture was concentrated with DCM several times to remove excess TFA. The residue was dissolved in ACN/water and dried under lyophilizer to afford TFA salt of ((((Z)-((4R,8S)-1-methyl-6-oxo-5-(sulfooxy)-4,5,6,8-tetrahydro-1H-4,7-methanopyrazolo[3,4-e][1,3]diazepin-8-yl)(1-methylhydrazineyl)methylene)amino)oxy)sulfonic acid (2.2 mg, 100%) as a white solid. MS: 442 ES+ ($C_{10}H_{15}N_7O_9S_2$) $^1$H NMR (300 MHz, $D_2O$) δ: 3.23-4.95 (m, 8H); 5.02 (m, 1H); 5.99 (m, 1H); 7.67 (s, 1H); 8.09 (m, 1.36H); 8.66 (m, 0.68H); 8.80 (m, 1.36H) Compound/pyridine ratio (1:0.68).

Example 34

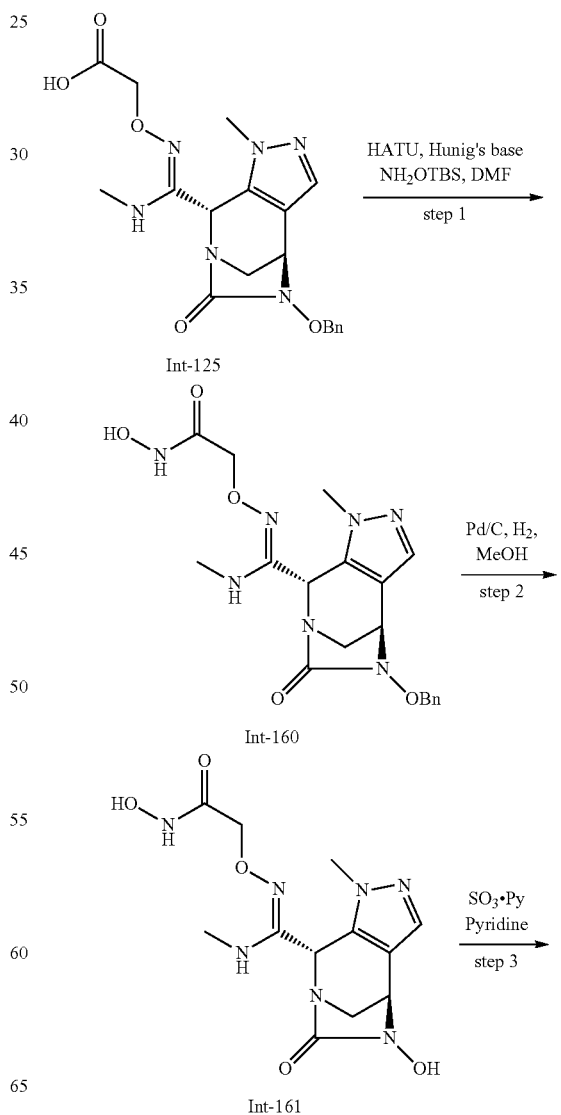

133

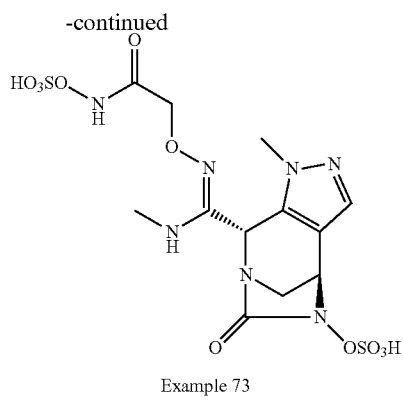

Example 73

Int-160

To a solution of afford 2-((((Z)-((4R,8S)-5-(benzyloxy)-1-methyl-6-oxo-4,5,6,8-tetrahydro-1H-4,7-methanopyrazolo[3,4-e][1,3]diazepin-8-yl)(methylamino)methylene)amino)oxy)acetic acid (Int-125, 60 mg, 0.14 mmol) in DMF (3 mL) at 0° C. was added HATU (110 mg, 0.29 mmol), O-(tert-butyldimethylsilyl)hydroxyamine (31.9 mg, 0.22 mmol) and Hunig's base (0.050 mL, 0.299 mmol). The reaction mixture was warmed up to room temperature and stirred at room temperature for 30 minutes. Ethyl acetate and saturated ammonium chloride solution were added. Organic layer was separated, washed with water, brine, dried over anhydrous magnesium sulfate, and concentrated to give the crude product. It was purified by flash chromatography (0-100% Acetone/DCM) to afford 2-((((Z)-((4R,8S)-5-(benzyloxy)-1-methyl-6-oxo-4,5,6,8-tetrahydro-1H-4,7-methanopyrazolo[3,4-e][1,3]diazepin-8-yl)(methylamino)methylene)amino)oxy)-N-hydroxyacetamide (30 mg, yield, 48.3%) as a white solid. MS: 430 ES+ ($C_{19}H_{27}N_3O_5$).

Int-161

To the solution of 2-((((Z)-((4R,8S)-5-(benzyloxy)-1-methyl-6-oxo-4,5,6,8-tetrahydro-1H-4,7-methanopyrazolo[3,4-e][1,3]diazepin-8-yl)(methylamino)methylene)amino)oxy)-N-hydroxyacetamide (Int-160, 25 mg, 0.058 mmol) in MeOH (3 mL) was purged with nitrogen 3 times, and 10% Pd/C (6.19 mg, 0.0058 mmol) was added. The reaction mixture was purged with nitrogen 3 times and then stirred under hydrogen atmosphere at room temperature for 2 hours. The reaction mixture was filtered through the celite. The filtrate was concentrated to afford N-hydroxy-2-((((Z)-((4R,8S)-5-hydroxy-1-methyl-6-oxo-4,5,6,8-tetrahydro-1H-4,7-methanopyrazolo[3,4-e][1,3]diazepin-8-yl)(methylamino)methylene)amino)oxy)acetamide (16 mg, 80.9%) as a white solid. MS: 338 ES- ($C_{12}H_{17}N_7O_5$).

134

Example 73

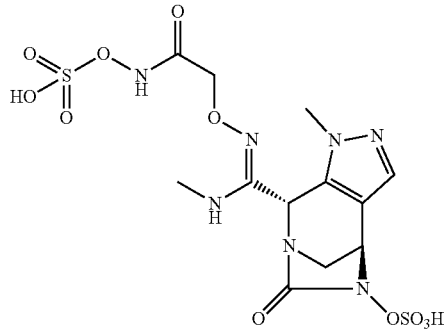

To a solution of N-hydroxy-2-((((Z)-((4R,8S)-5-hydroxy-1-methyl-6-oxo-4,5,6,8-tetrahydro-1H-4,7-methanopyrazolo[3,4-e][1,3]diazepin-8-yl)(methylamino)methylene)amino)oxy)acetamide (Int-161, 16 mg, 0.047 mmol) in pyridine (2 mL) at room temperature was added sulfur trioxide pyridine complex (22.5 mg, 0.14 mmol). The reaction mixture was stirred at room temperature for 6 hours, then concentrated under reduced pressure to give the crude product. The material was triturated with DCM and the solids were removed by filtration. The filtrate was concentrated to give crude product. It was purified by reversed phase chromatography (Sepabeads, ACN/water 0-50%) twice to afford pyridium ((2-((((Z)-((4R,8S)-1-methyl-6-oxo-5-(sulfooxy)-4,5,6,8-tetrahydro-1H-4,7-methanopyrazolo[3,4-e][1,3]diazepin-8-yl)(methylamino)methylene)amino)acetamido)oxy)sulfonic acid (6 mg, 21.6%) as a white solid. MS: 498 ES- ($C_{12}H_{17}N_7O_{11}S_2$) $^1$H NMR (300 MHz, $D_2O$) δ: 3.13 (s, 3H); 3.58 (m, 2H); 3.64 (s, 3H); 4.50 (m, 2H); 4.98 (m, 1H); 5.72 (s, 1H); 7.67 (s, 1H); 8.11 (m, 2H); 8.67 (m, 1H); 8.82 (m, 2H) Compound/pyridine ratio (1:1).

The following additional compounds can be made according to procedures similar to the ones described herein or procedures found in the literature.

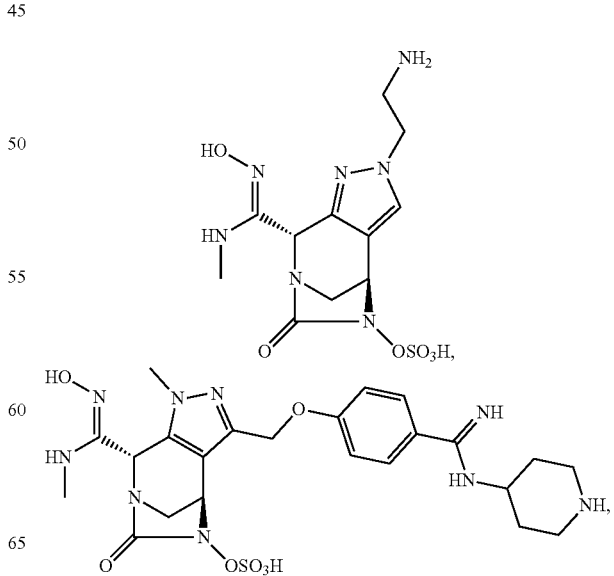

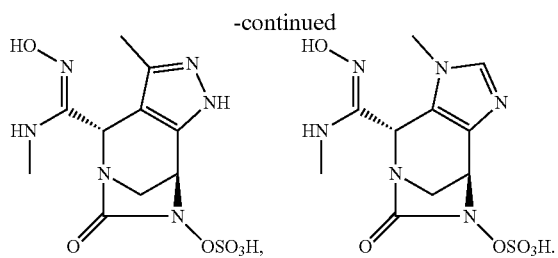

Measurement of Acylation Rate Constants for *P. aeruginosa* PBP1a, PBP2 and PBP3

Second-order acylation rate constants with PBP1a, PBP2 and PBP3 from *P. aeruginosa* were measured using the BOCILLIN FL penicillin fluorescence anisotropy assay method (Anal. Biochem. 463, 15-22 (2014)). The BOCILLIN FL (Thermo-Fisher Scientific, Waltham, Mass.) concentration was 30 nM in each case. The PBP concentrations were 60 nM for *P. aeruginosa* PBP1a and PBP3, and 300 nM for *P. aeruginosa* PBP2. The assay buffer was 0.1 M sodium phosphate with 0.01% Triton X-100. The pH was 7.0 for all the PBPs with the exception of *P. aeruginosa* PBP2, for which the pH was 6.2. Serial 2-fold dilutions of compounds were employed, with concentrations ranging from 328 to 0.02 µM for the *P. aeruginosa* PBPs. Results are shown below in Table 5.

TABLE 5

| Example # | PBP1a acylation rate, $k_{(on)}$ ($M^{-1} \cdot s^{-1}$) | PBP2 acylation rate, $k_{(on)}$ ($M^{-1} \cdot s^{-1}$) | PBP3 acylation rate, $k_{(on)}$ ($M^{-1} \cdot s^{-1}$) |
|---|---|---|---|
| Comparator 1 (chiral) | * | *** | * |
| Comparator 2 (racemic trans) | * | * | ** |
| 1 | ** | * | *** |
| 2 | ** | * | *** |
| 3 | * | * | ** |
| 4 | ** | * | *** |
| 5 | ** | * | ** |
| 6 | * | * | ** |
| 7 | * | * | ** |
| 8 | * | * | * |
| 9 | ** | * | ** |
| 10 | * | * | ** |
| 11 | ** | * | *** |
| 12 | ** | * | ** |
| 13 | * | * | ** |
| 14 | ** | * | *** |
| 15 | ** | NT | *** |
| 16 | ** | NT | *** |
| 17 | ** | NT | *** |
| 18 | ** | NT | *** |
| 19 | ** | NT | *** |
| 20 | ** | NT | *** |
| 21 | ** | NT | *** |
| 22 | ** | NT | *** |
| 23 | ** | NT | *** |
| 24 | ** | NT | *** |
| 25 | ** | NT | *** |

TABLE 5-continued

| Example # | PBP1a acylation rate, $k_{(on)}$ ($M^{-1} \cdot s^{-1}$) | PBP2 acylation rate, $k_{(on)}$ ($M^{-1} \cdot s^{-1}$) | PBP3 acylation rate, $k_{(on)}$ ($M^{-1} \cdot s^{-1}$) |
|---|---|---|---|
| 26 | ** | NT | *** |
| 27 | ** | NT | *** |
| 28 | ** | NT | *** |
| 29 | ** | NT | *** |
| 30 | ** | NT | *** |
| 31 | ** | NT | *** |
| 32 | ** | NT | *** |
| 33 | ** | NT | *** |
| 34 | ** | NT | *** |
| 35 | * | * | ** |
| 36 | ** | * | ** |
| 37 | * | * | ** |
| 38 | * | * | * |
| 39 | * | * | ** |
| 40 | ** | * | *** |
| 41 | * | * | ** |
| 42 | ** | NT | *** |
| 43 | ** | NT | *** |
| 44 | ** | NT | *** |
| 45 | ** | NT | *** |
| 46 | ** | NT | *** |
| 47 | ** | * | *** |
| 48 | * | NT | *** |
| 49 | * | NT | *** |
| 50 | ** | NT | *** |
| 51 | ** | * | ** |
| 52 | ** | * | ** |
| 53 | ** | * | ** |
| 54 | * | NT | *** |
| 55 | * | * | * |
| 56 | ** | * | ** |
| 57 | ** | NT | *** |
| 58 | * | NT | *** |
| 59 | ** | NT | *** |
| 60 | * | NT | *** |
| 61 | * | NT | ** |
| 62 | ** | NT | *** |
| 63 | ** | NT | *** |
| 64 | ** | NT | ** |
| 65 | ** | NT | ** |
| 66 | ** | * | ** |
| 67 | * | * | ** |
| 68 | * | * | ** |
| 69 | ** | NT | *** |

TABLE 5-continued

| Example # | PBP1a acylation rate, $k_{(on)}$ (M$^{-1}$·s$^{-1}$) | PBP2 acylation rate, $k_{(on)}$ (M$^{-1}$·s$^{-1}$) | PBP3 acylation rate, $k_{(on)}$ (M$^{-1}$·s$^{-1}$) |
|---|---|---|---|
| 70 | * | * | ** |
| 71 | * | * | ** |
| 72 | ** | * | *** |
| 73 | ** | NT | *** |

For PBP1a acylation rates, * represents a $k_{(on)}$ < 100 M$^{-1}$·s$^{-1}$,  represents a $k_{(on)}$ of 100 to 10,000 M$^{-1}$·s$^{-1}$, and * represents a $k_{(on)}$ > 10,000 M$^{-1}$·s$^{-1}$;
for PBP2 acylation rates, * represents a $k_{(on)}$ < 100 M$^{-1}$·s$^{-1}$,  represents a $k_{(on)}$ of 100 to 5,000 M$^{-1}$·s$^{-1}$, and * represents a $k_{(on)}$ > 5,000 M$^{-1}$·s$^{-1}$;
for PBP3 acylation rates, * represents a $k_{(on)}$ < 100 M$^{-1}$·s$^{-1}$,  represents a $k_{(on)}$ of 100 to 10,000 M$^{-1}$·s$^{-1}$, and * represents a $k_{(on)}$ > 10,000 M$^{-1}$·s$^{-1}$.
NT: not tested MIC Against Gram-Negative Clinical Isolates The minimal inhibitory concentration (MIC) values against *P. aeruginosa* and compounds were determined using the Clinical and Laboratory Standards Institute guidelines (CLSI) broth microdilution methodology (CLSI M07-A10). Results are shown below in Table 6.

TABLE 6

| Example # | *P. aeruginosa* WT (PAO1) MIC (mg/L) |
|---|---|
| Comparator 1 (chiral) | *** |
| Comparator 2 (racemic trans) | * |
| 1 | *** |
| 2 | * |
| 3 | * |
| 4 | * |
| 5 | * |
| 6 | ** |
| 7 | ** |
| 8 | * |
| 9 | *** |
| 10 | * |
| 11 | ** |
| 12 | * |
| 13 | * |
| 14 | *** |
| 15 | * |
| 16 | ** |
| 17 | ** |
| 18 | *** |
| 19 | *** |
| 20 | ** |
| 21 | * |
| 22 | ** |
| 23 | ** |
| 24 | *** |
| 25 | *** |
| 26 | *** |
| 27 | ** |
| 28 | *** |
| 29 | *** |
| 30 | *** |
| 31 | ** |
| 32 | * |
| 33 | ** |
| 34 | ** |
| 35 | * |
| 36 | * |
| 37 | * |
| 38 | * |
| 39 | * |
| 40 | *** |
| 41 | * |
| 42 | ** |
| 43 | * |
| 44 | * |
| 45 | * |
| 46 | ** |
| 47 | *** |
| 48 | ** |
| 49 | *** |
| 50 | *** |
| 51 | * |
| 52 | * |
| 53 | * |
| 54 | ** |
| 55 | * |
| 56 | * |
| 57 | *** |
| 58 | *** |
| 59 | *** |
| 60 | ** |
| 61 | ** |
| 62 | *** |
| 63 | ** |
| 64 | * |
| 65 | * |
| 66 | * |
| 67 | * |
| 68 | *** |
| 69 | * |
| 70 | * |
| 71 | ** |
| 72 | * |
| 73 | ** |

* represents an MIC > 16 mg/L,
** represents an MIC of 8 to 16 mg/L and
*** represents an MIC < 8 mg/L.

The minimal inhibitory concentration (MIC) values against *E. coli*, *K. pneumoniae*, and *A. baumannii* are shown below in Table 7.

TABLE 7

| Example # | E. coli MIC (ATCC25922) (mg/L) | K. pneumoniae MIC (ATCC700603) | A. baumannii MIC (ARC3495) (mg/L) |
|---|---|---|---|
| Comparator 1 (chiral) | *** | *** | * |
| Comparator 2 (racemic trans) | *** | * | * |
| 1 | *** | *** | *** |
| 2 | ** | ** | ** |
| 3 | *** | *** | * |
| 4 | *** | * | * |
| 5 | *** | * | * |
| 6 | ** | * | * |
| 7 | ** | ** | * |
| 8 | *** | * | * |
| 9 | *** | ** | ** |
| 10 | ** | ** | * |
| 11 | *** | *** | ** |
| 12 | *** | * | * |
| 13 | *** | * | * |
| 14 | *** | *** | ** |
| 15 | *** | * | * |
| 16 | ** | * | * |
| 17 | ** | ** | * |
| 18 | *** | ** | ** |
| 19 | ** | * | ** |
| 20 | ** | * | ** |
| 21 | *** | * | * |
| 22 | *** | ** | * |
| 23 | ** | ** | * |
| 24 | ** | ** | ** |
| 25 | ** | * | ** |
| 26 | *** | *** | *** |
| 27 | *** | * | * |
| 28 | *** | * | ** |
| 29 | ** | * | ** |
| 30 | ** | * | ** |
| 31 | *** | * | * |
| 32 | *** | * | * |
| 33 | ** | * | ** |
| 34 | ** | * | * |
| 35 | *** | * | * |
| 36 | *** | * | * |
| 37 | *** | * | * |
| 38 | ** | * | * |
| 39 | *** | * | * |
| 40 | *** | *** | *** |
| 41 | *** | * | * |
| 42 | ** | * | ** |
| 43 | *** | * | * |
| 44 | ** | * | * |
| 45 | *** | * | * |
| 46 | ** | ** | * |
| 47 | *** | *** | *** |

TABLE 7-continued

| Example # | E. coli MIC (ATCC25922) (mg/L) | K. pneumoniae MIC (ATCC700603) | A. baumannii MIC (ARC3495) (mg/L) |
|---|---|---|---|
| 48 | *** | * | * |
| 49 | ** | ** | ** |
| 50 | *** | *** | ** |
| 51 | *** | * | * |
| 52 | *** | * | * |
| 53 | *** | * | * |
| 54 | *** | * | * |
| 55 | *** | * | * |
| 56 | *** | * | * |
| 57 | ** | ** | ** |
| 58 | ** | ** | ** |
| 59 | ** | * | ** |
| 60 | *** | * | * |
| 61 | *** | * | * |
| 62 | ** | ** | * |
| 63 | *** | * | * |
| 64 | *** | * | * |
| 65 | *** | * | * |
| 66 | *** | * | * |
| 67 | *** | * | * |
| 68 | ** | * | ** |
| 69 | ** | ** | * |
| 70 | ** | * | * |
| 71 | ** | * | * |
| 72 | *** | * | * |
| 73 | ** | ** | * |

\* represents an MIC > 16 mg/L,
\*\* represents an MIC of 8 to 16 mg/L and
\*\*\* represents an MIC < 8 mg/L.

MIC Against *B. pseudomallei*, *B. mallei*, *F. tularensis*, *Y. pestis* and *B. anthracis*

Example 40 was shown to exhibit inhibitory activity (MIC <4 mg/L) against *B. pseudomallei*, *B. mallei*, *F. tularensis*, *Y. pestis* and *B. anthracis*.

In Vivo Profiling for *P. aeruginosa* PBP Inhibitors

Figure 2:
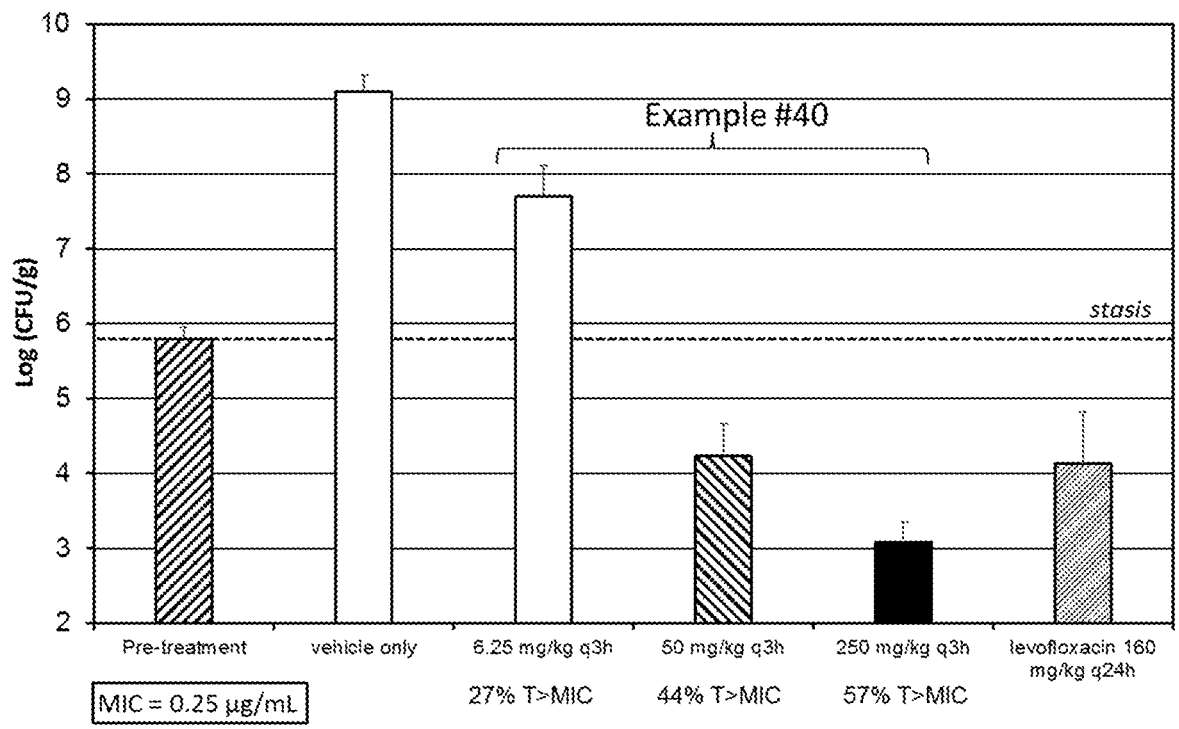
FIG. 2 shows the in vivo efficacy of a PBP3 compound of the subject application (Example 40) against a *P. aeruginosa* clinical isolate (ARC6347, AmpC+, PoxB+) in a neutropenic murine thigh model.

In vivo efficacy of Comparator 1 (a PBP2 targeting compound) and Example 40 of the subject disclosure was evaluated against a *P. aeruginosa* clinical isolate (ARC6347, AmpC+, PoxB+) in a neutropenic murine thigh model. See FIGS. 1 and 2. The only structural difference between Example 40 and Comparator 1 is the replacement of an amino methyl group by an N-methyl-amidoxime group. However, the PBP2 targeting compound (Comparator 1) was not active (did not achieve stasis in this study even with exposures of 100% Time above the MIC) while the PBP3 inhibiting compound (Example 40) showed robust efficacy (more than 2 Log(CFU/g) reduction with an exposure of 57% Time above the MIC).

Female CD-1 mice from Charles River Laboratories and were allowed to acclimate for 5 days prior to start of study. Animals were housed 5 per cage with free access to food and water. To induce a transient state of neutropenia mice received two doses of cyclophosphamide on days −4 and −1 with 150 mg/kg and 100 mg/kg delivered intraperitoneally, respectively. All procedures were performed to corporate animal welfare policy with IACUC procedures and guidelines as well as OLAW standards. *P. aeruginosa* strain ARC 6347 (AmpC+, PoxB+) was prepared for infection from an overnight plate culture. A portion of the plate was resuspended in sterile saline and adjusted to an OD of 0.1 at 625 nm. The adjusted bacterial suspension was further diluted to target an infecting inoculum of approx. 5.0×10⁵ CFU/mouse. Plate counts of the inoculum was performed to confirm inoculum concentration. Mice were infected with 100 uL of the prepared bacterial inoculum into both the left and right thigh muscles. Beginning at two hours post infection mice were dosed with either test article, positive control antibiotic (levofloxacin), or vehicle. Mice receiving Example 40 or Comparator 1 or vehicle were dosed subcutaneous at 10 mL/kg for 8 doses spaced 3 hours apart. Animals receiving levofloxacin were dosed with a single oral dose of 160 mg/kg at two hours post infection.

Three animals were dosed per group/concentration. One group of three mice were euthanized at initiation of therapy (T-Rx) and CFUs determined. All remaining mice were euthanized at 26 hours post infection. Both thighs were aseptically removed, weighed, homogenized to a uniform consistency, serially diluted and plated on bacterial growth media. The CFUs were enumerated after overnight incubation.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:
1. A compound of the Formula:

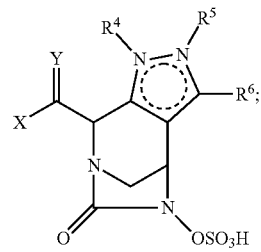

or a pharmaceutically acceptable salt thereof, wherein
X is H, CN, C(O)NR¹R², NR¹R² or (C₁-C₆)alkyl optionally substituted with NHC(O)R$^g$ or S(O)NH₂;

Y is NOR³; or R³ and X taken together with the atoms to which they are attached form a 4- to 6-membered heterocyclyl or 5- to 6-membered heteroaryl, each of which is optionally substituted with one or more groups selected from $(C_1-C_6)$alkyl, C=O, C(O)OH, and C(O)O$(C_1-C_6)$alkyl, wherein said $(C_1-C_6)$alkyl is optionally substituted with one or more groups selected from OH, $(C_1-C_6)$alkoxy, phenyl, and 5- to 6-membered heteroaryl, wherein said 5- to 6-membered heteroaryl is optionally substituted with NH₂, NH$(C_1-C_6)$alkyl, and N$((C_1-C_6)$alkyl$)_2$;

R¹ and R² are each independently hydrogen, cyano, C(O)NH₂, NH₂, OH, $(C_1-C_6)$alkoxy, or $(C_1-C_6)$alkyl optionally substituted with one or more R⁷;

R³ is hydrogen, C(O)$(C_1-C_6)$alkyl, C(O)NR$^d$R$^e$, SO₂NH₂, SO₂OH, or $(C_1-C_6)$alkyl optionally substituted with one or more R⁷;

R⁴, R⁵, and R⁶ are each independently hydrogen, $(C_1-C_6)$alkyl, or C(O)NR$^a$R$^b$, wherein said $(C_1-C_6)$alkyl for R⁴, R⁵, and R⁶ is optionally substituted with one or more R⁷, provided that at least one of R⁴ and R⁵ is not hydrogen and provided that R⁴ and R⁵ are not present when the corresponding nitrogen atom to which R⁴ and R⁵ are bound is connected to an adjacent ring atom via a double bond;

each R⁷ is independently selected from halo, OH, OR$^c$, $(C_1-C_6)$alkoxy, CN, 4- to 6-membered heterocyclyl, 5- to 6-membered heteroaryl, phenyl, C(=NH)NH₂, NHC(=NH)NH₂, NR$^d$R$^e$, C(O)OH, C=NO$(C_1-C_6)$alkylNH₂, NHC(O)$(C_1-C_6)$alkyl, C(O)NR$^d$R$^e$, SO₂R$^f$, and S(O)R$^f$, wherein said 5- to 6-membered heteroaryl is optionally substituted with NH₂ and said phenyl is optionally substituted with NH₂;

R$^a$, R$^b$, R$^d$, and R$^e$ are each independently hydrogen, OH, $(C_1-C_6)$alkyl, $(C_1-C_6)$alkoxy, phenyl, OSO₂OH, 4- to 6-membered cycloalkyl, 4- to 6-membered heterocyclyl or 5- to 6-membered heteroaryl, wherein each of said $(C_1-C_6)$alkyl and $(C_1-C_6)$alkoxy for R$^a$, R$^b$, R$^d$, and R$^e$ are optionally and independently substituted with one or more groups selected from OH, NH₂, C(O)OH, C(O)O$(C_1-C_6)$alkyl, NHC(O)NH₂, NHC(O)NH$(C_1-C_6)$alkyl, C(O)NH₂, NHC(O)N$((C_1-C_6)$alkyl$)_2$, NHC(O)$(C_1-C_6)$alkyl, NHC(O)halo$(C_1-C_6)$alkyl, 4- to 6-membered heterocyclyl, 5- to 6-membered heteroaryl, NH$(C_1-C_6)$alkyl, and N$((C_1-C_6)$alkyl$)_2$, wherein each of said phenyl, 4- to 6-membered heterocyclyl, 4- to 6-membered cycloalkyl, and 5- to 6-membered heteroaryl for R$^a$, R$^b$, R$^d$, and R$^e$, and said 5- to 6-membered optional heteroaryl group substituted on the $(C_1-C_6)$alkyl and $(C_1-C_6)$alkoxy for R$^a$, R$^b$, R$^d$, and R$^e$ are optionally and independently substituted with one or more groups selected from $(C_1-C_6)$alkyl, NH₂, NH$(C_1-C_6)$alkyl, and —N$((C_1-C_6)$alkyl$)_2$;

R$^c$ is phenyl optionally substituted with one or more groups selected from C(=NH)NH₂, C(=NH)NH(5- to 6-membered heterocyclyl), C(=NH)NH$(C_1-C_6)$alkyl, NHC(=NH)NH₂, —NR$^d$R$^e$, C(O)NR$^d$R$^e$, SO₂R$^f$, and SOR$^f$, wherein said $(C_1-C_6)$alkyl in the group C(=NH)NH$(C_1-C_6)$alkyl is optionally substituted with one or more groups selected from NH₂, NH$(C_1-C_6)$alkyl, and N$((C_1-C_6)$alkyl$)_2$;

R$^f$ is hydrogen or $(C_1-C_6)$alkyl; and

R$^g$ is 4- to 6-membered heterocyclyl optionally substituted with one or more groups selected from C=O and $(C_1-C_6)$alkyl.

2. The compound of claim 1, wherein the compound is of the Formula:

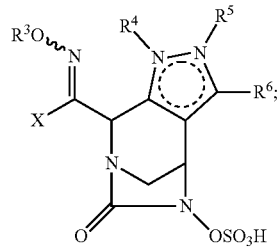

or a pharmaceutically acceptable salt thereof, wherein
X is H, CN, C(O)NR¹R², NR¹R² or $(C_1-C_6)$alkyl;

R¹ and R² are each independently hydrogen, cyano, or $(C_1-C_6)$alkyl optionally substituted with one or more R⁷;

R³ is hydrogen or $(C_1-C_6)$alkyl optionally substituted with one or more R⁷;

R⁴, R⁵, and R⁶ are each independently hydrogen, $(C_1-C_6)$alkyl, or C(O)NR$^a$R$^b$, wherein said $(C_1-C_6)$alkyl for R⁴, R⁵, and R⁶ is optionally substituted with one or more R⁷, provided that at least one of R⁴ and R⁵ is not hydrogen and provided that R⁴ and R⁵ are not present when the corresponding nitrogen atom to which R⁴ and R⁵ are bound is connected to an adjacent ring atom via a double bond;

each R⁷ is independently selected from halo, OH, OR$^c$, $(C_1-C_6)$alkoxy, CN, 4- to 6-membered heterocyclyl, 5- to 6-membered heteroaryl, phenyl, C(=NH)NH₂, NHC(=NH)NH₂, NR$^d$R$^e$, C(O)NR$^d$R$^e$, SO₂R$^f$, and S(O)R$^f$;

R$^a$, R$^b$, R$^d$, and R$^e$ are each independently hydrogen, $(C_1-C_6)$alkyl, $(C_1-C_6)$alkoxy, phenyl, 4- to 6-membered heterocyclyl or 5- to 6-membered heteroaryl, wherein each of said $(C_1-C_6)$alkyl and $(C_1-C_6)$alkoxy for R$^a$, R$^b$, R$^d$, and R$^e$ are optionally and independently substituted with one or more groups selected from NH₂, NH$(C_1-C_6)$alkyl, and N$((C_1-C_6)$alkyl$)_2$, and wherein each of said phenyl, 4- to 6-membered heterocyclyl, and 5- to 6-membered heteroaryl for R$^a$, R$^b$, R$^d$, and R$^e$ are optionally and independently substituted with one or more groups selected from $(C_1-C_6)$alkyl, NH₂, NH$(C_1-C_6)$alkyl, and N$((C_1-C_6)$alkyl$)_2$;

R$^c$ is phenyl optionally substituted with one or more groups selected from C(=NH)NH₂, C(=NH)NH$(C_1-C_6)$alkyl, NHC(=NH)NH₂, NR$^d$R$^e$, C(O)NR$^d$R$^e$, SO₂R$^f$, and SOR$^f$, wherein said $(C_1-C_6)$alkyl in the group C(=NH)NH$(C_1-C_6)$alkyl is optionally substituted with one or more groups selected from NH₂, NH$(C_1-C_6)$alkyl, and N$((C_1-C_6)$alkyl$)_2$; and R$^f$ is hydrogen or $(C_1-C_6)$alkyl.

3. The compound of claim 1, wherein the compound is of the Formula:

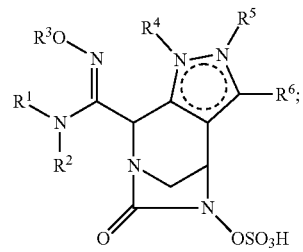

or a pharmaceutically acceptable salt thereof.

4. The compound of claim 1, wherein the compound is of the Formula:

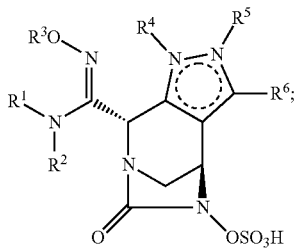

or a pharmaceutically acceptable salt thereof.

5. The compound of claim 4, or a pharmaceutically acceptable salt thereof, wherein $R^3$ is hydrogen or $(C_1-C_6)$ alkyl optionally substituted with amino.

6. The compound of claim 5, or a pharmaceutically acceptable salt thereof, wherein $R^1$ is hydrogen and $R^2$ is $(C_1-C_6)$alkyl.

7. The compound of claim 6, wherein the compound is of the Formula:

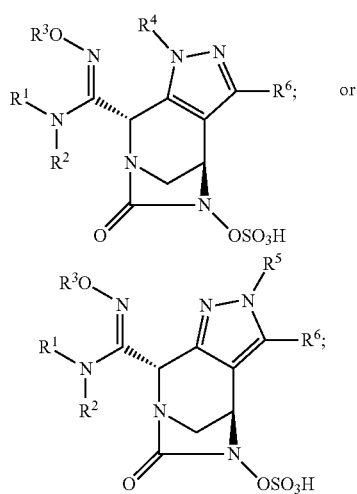

or a pharmaceutically acceptable salt thereof.

8. The compound of claim 7, or a pharmaceutically acceptable salt thereof, wherein $R^6$ is hydrogen, C(O)N-$R^aR^b$, or $(C_1-C_6)$alkyl optionally substituted with $OR^c$.

9. The compound of claim 8, or a pharmaceutically acceptable salt thereof, wherein $R^a$ is hydrogen; $R^b$ is 5- to 6-membered heteroaryl optionally substituted with one or more $(C_1-C_6)$alkyl; or $R^6$ is $(C_1-C_6)$alkyl optionally substituted with $OR^c$; and $R^c$ is phenyl optionally substituted with C(=NH)NH$(C_1-C_6)$alkylNH$_2$.

10. The compound of claim 7, wherein the compound is of the Formula:

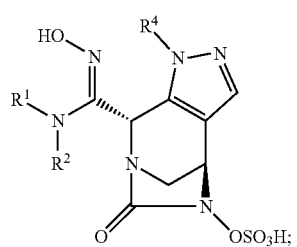

or a pharmaceutically acceptable salt thereof.

11. The compound of claim 10, or a pharmaceutically acceptable salt thereof, wherein $R^4$ is C(O)NR$^a$R$^b$ or $(C_1-C_6)$alkyl optionally substituted with NH$_2$; $R^a$ is hydrogen; and $R^b$ is $(C_1-C_6)$alkyl optionally substituted with NH$_2$.

12. The compound of claim 11, or a pharmaceutically acceptable salt thereof, wherein $R^4$ is $(C_1-C_6)$alkyl.

13. The compound of claim 7, wherein the compound is of the Formula:

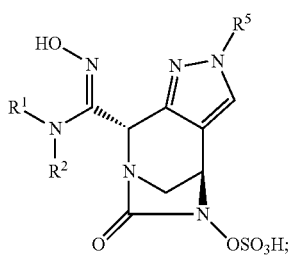

or a pharmaceutically acceptable salt thereof.

14. The compound of claim 1, wherein the compound is selected from the Formula:

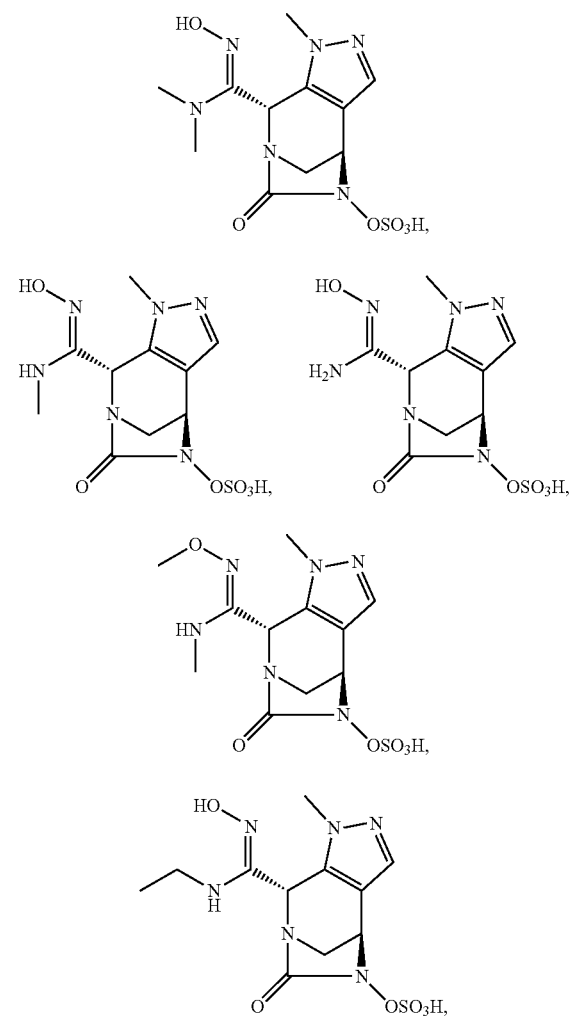

149
-continued
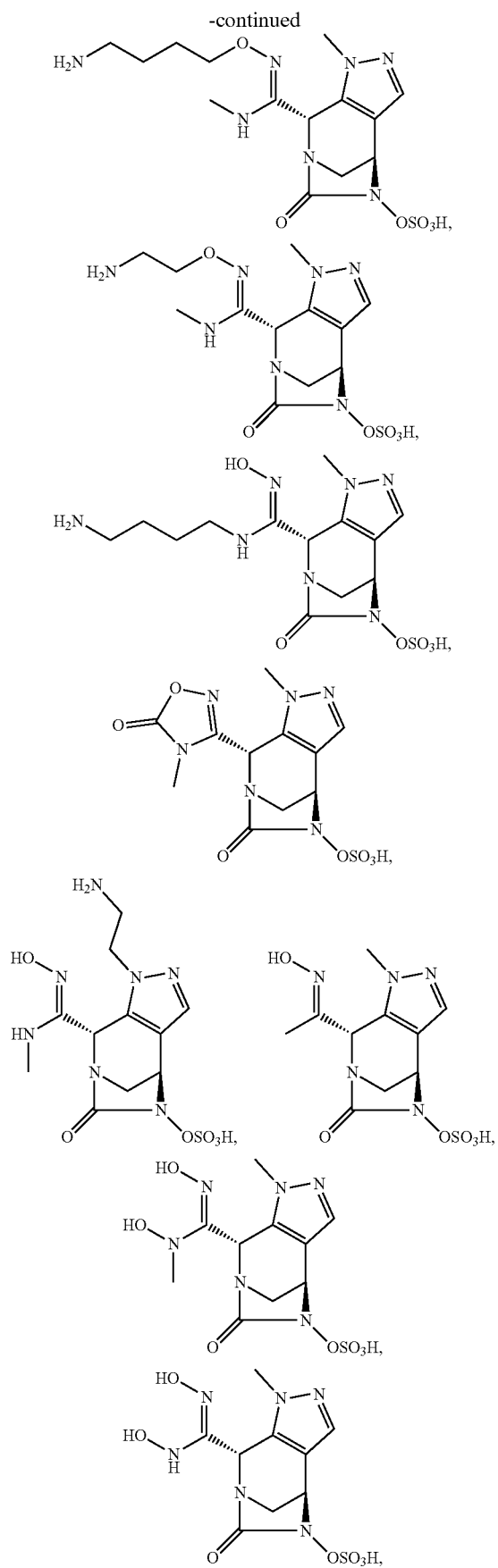
150
-continued
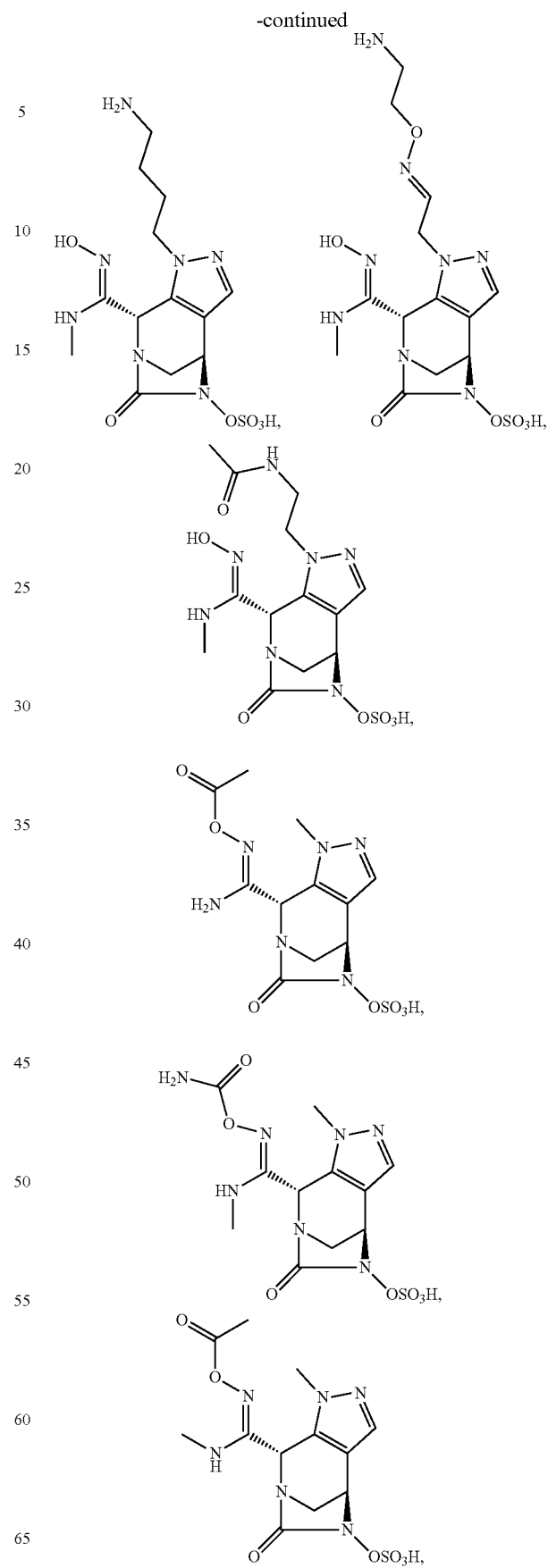

151
-continued
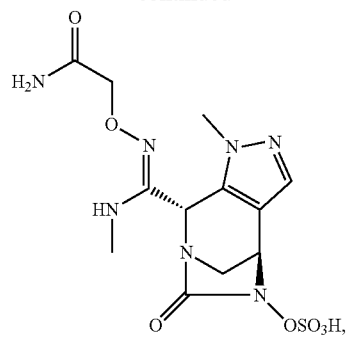
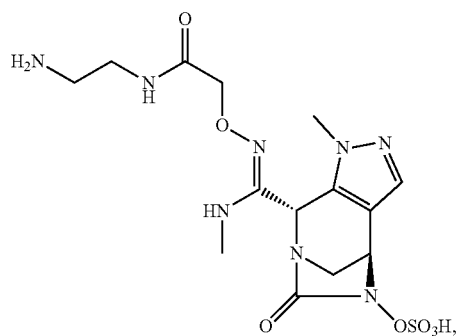
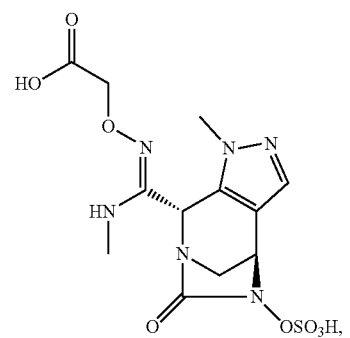
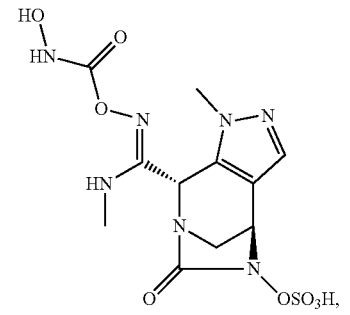
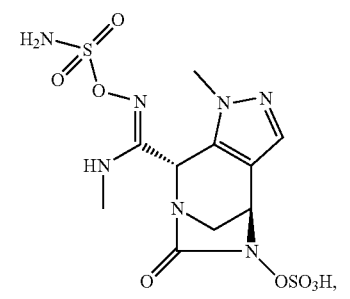
152
-continued
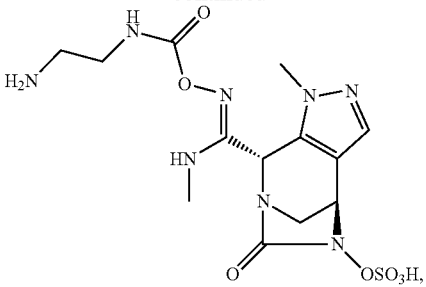
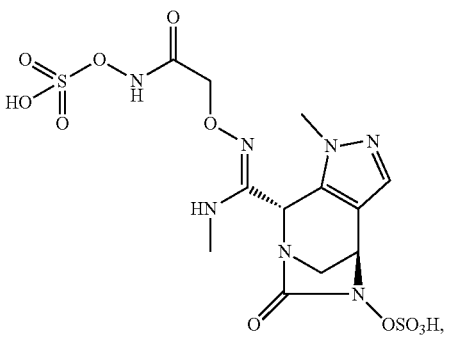
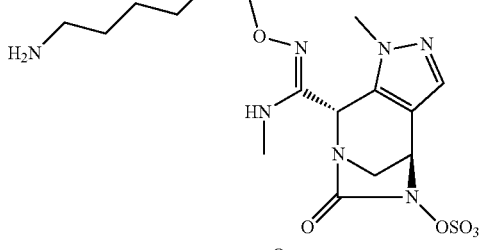
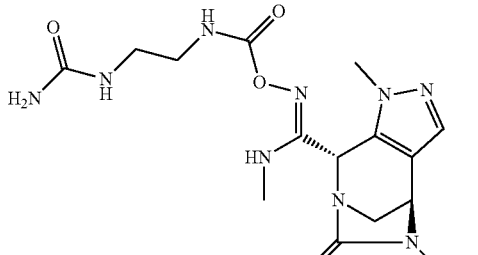
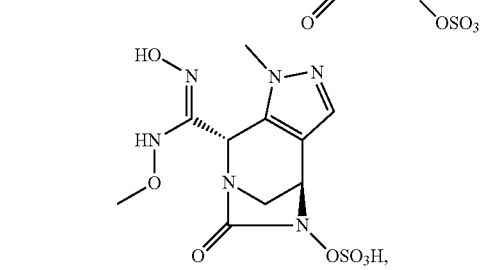
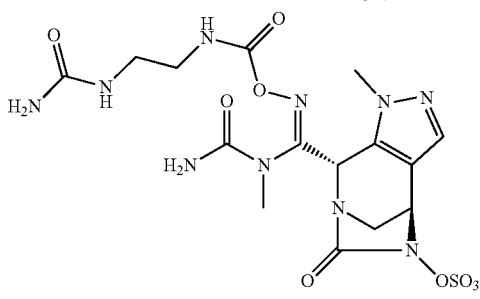

153
-continued
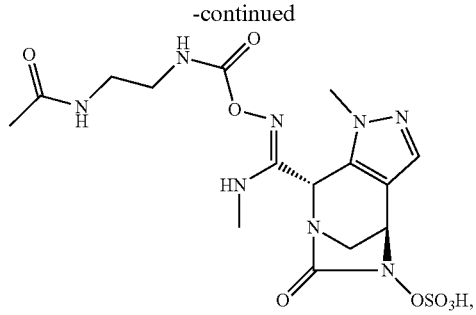
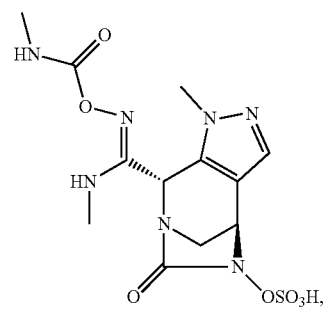
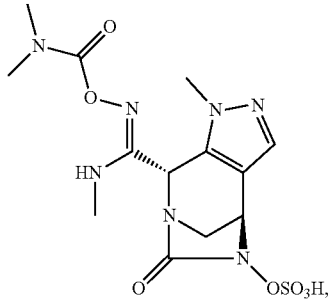
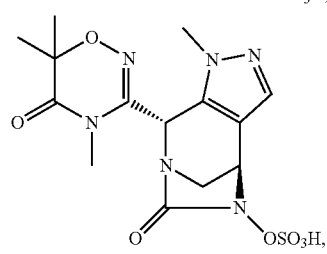
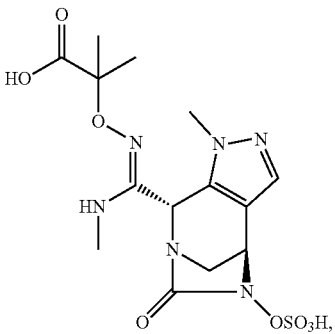
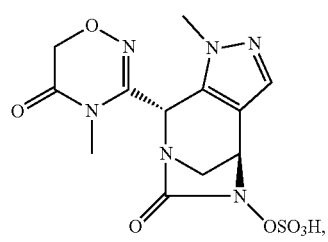
154
-continued
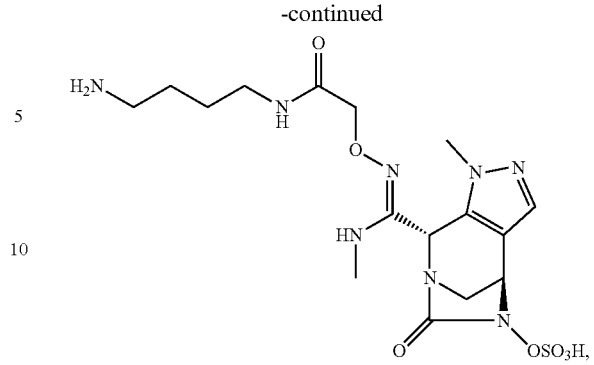
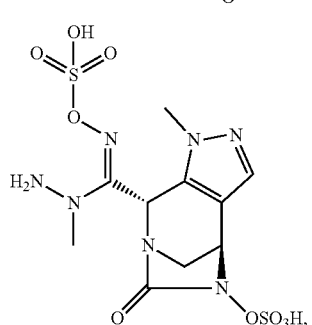
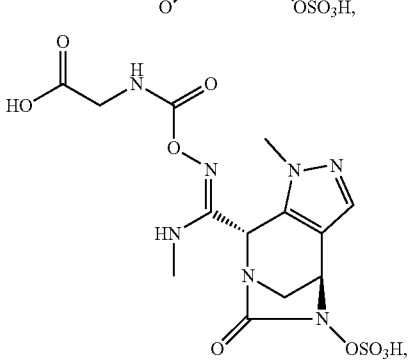
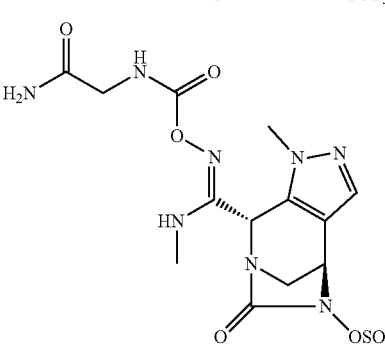
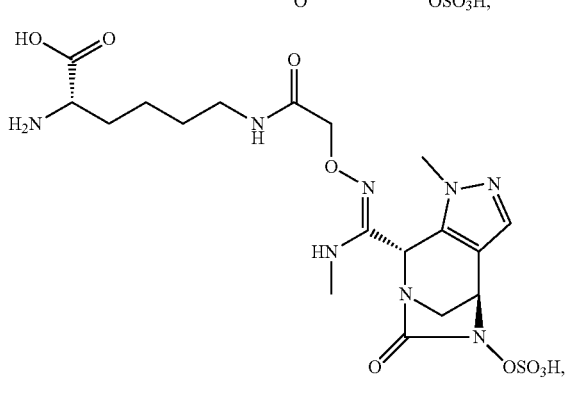

155
-continued
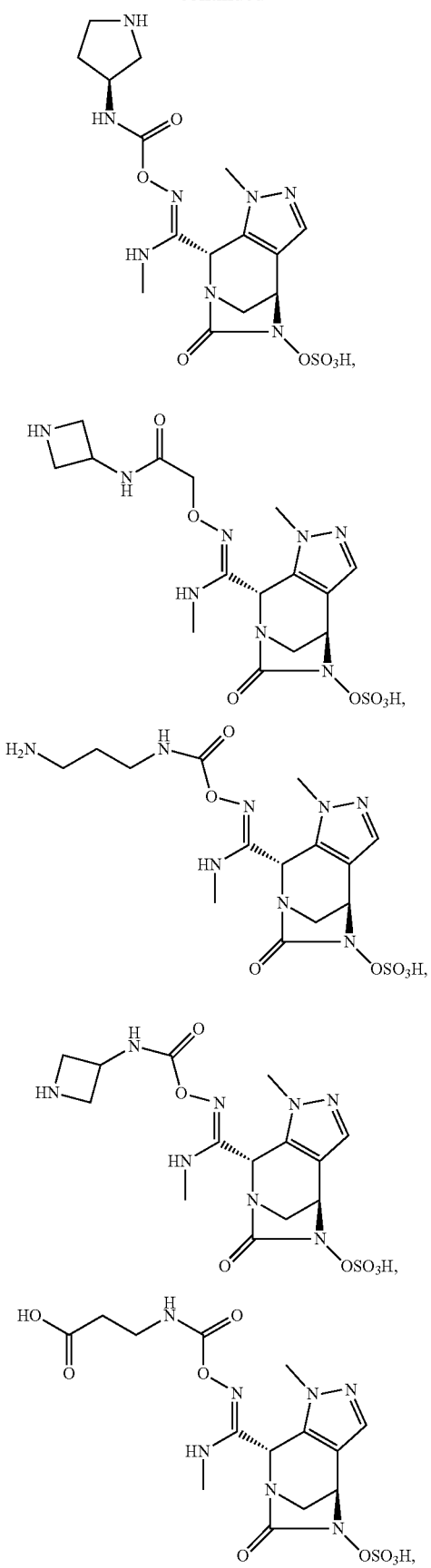
156
-continued
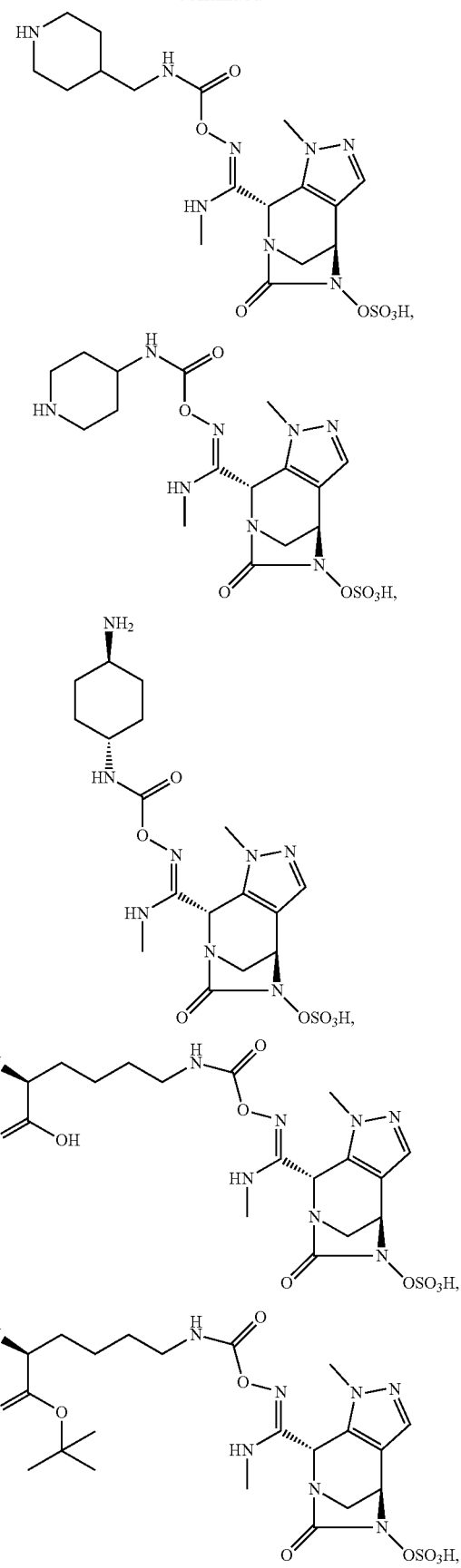

157
-continued
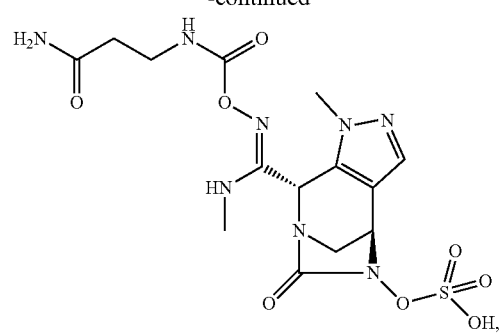
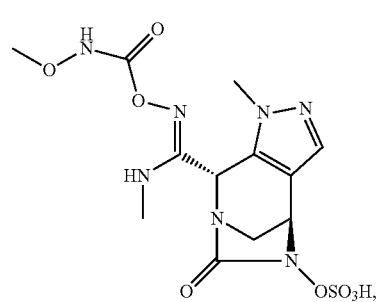
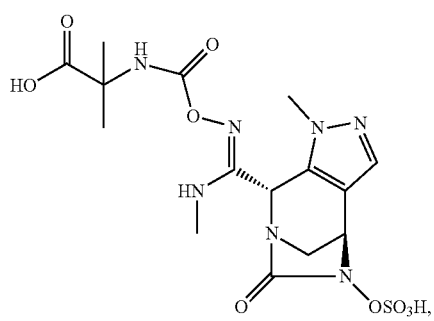
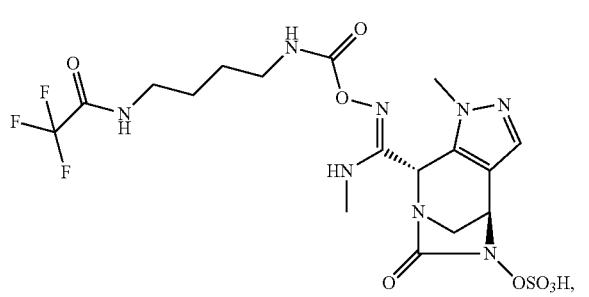
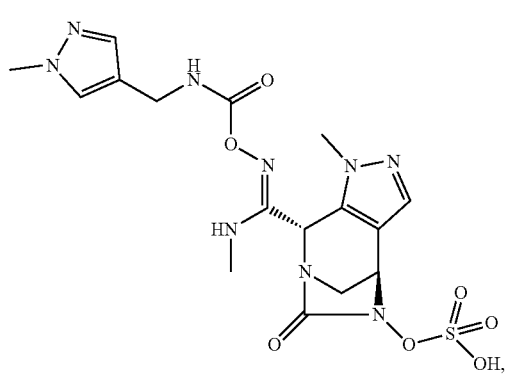
158
-continued
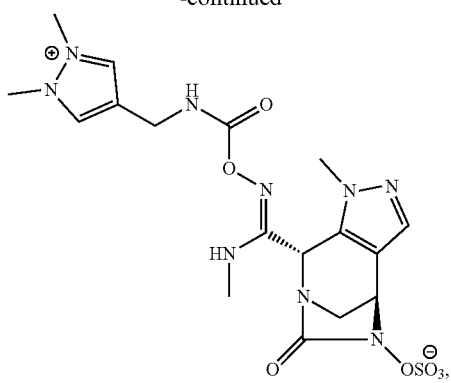
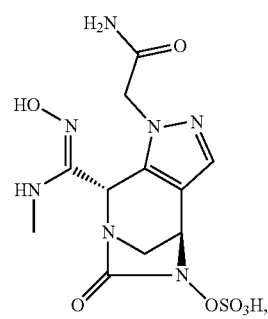
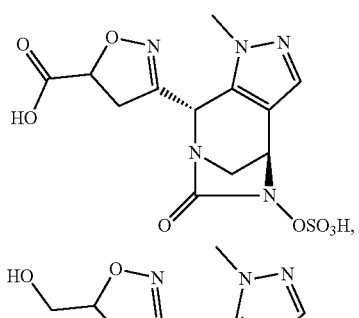
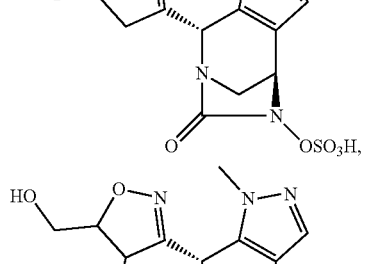
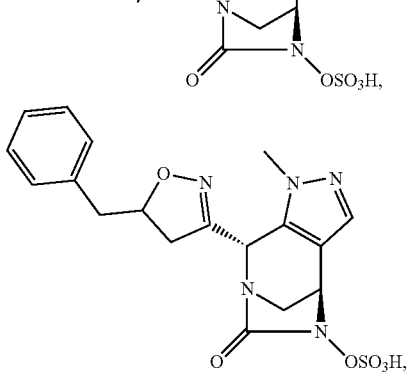

-continued

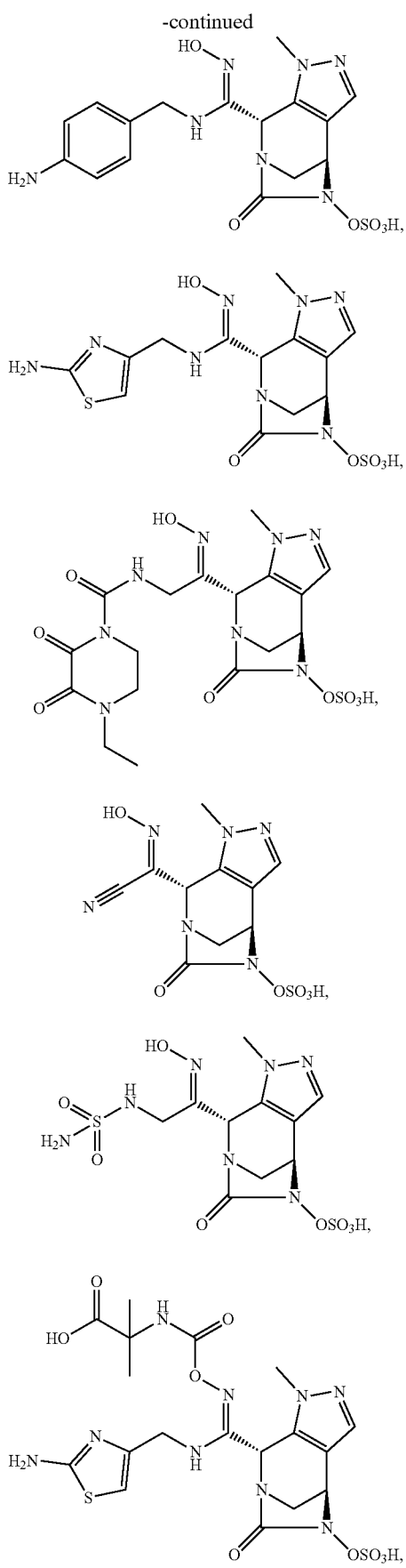

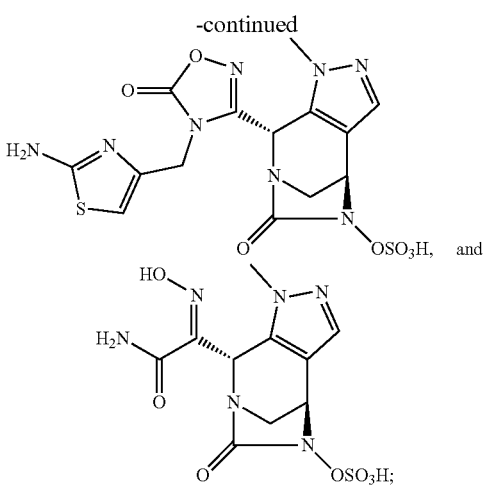

or a pharmaceutically acceptable salt thereof of any of the foregoing.

15. A compound of the Formula:

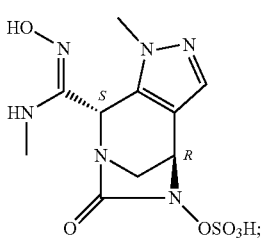

or a pharmaceutically acceptable salt thereof.

16. A pharmaceutical composition comprising a compound of claim 1, or a pharmaceutically acceptable salt thereof; and a pharmaceutically acceptable carrier.

17. A method of treating a bacterial infection in a subject in need thereof comprising administering to the subject an effective amount of a compound of claim 1, or a pharmaceutically acceptable salt thereof.

18. The method of claim 17, wherein the bacterial infection is caused by a Gram-negative bacteria.

19. The method of claim 18, wherein the bacterial infection is caused by *P. aeruginosa*, Enterobacteriaceae, *E. coli, K pneumoniae*, or *Acinetobacter* spp.

20. The method of claim 17, wherein the bacterial infection is caused by a pathogen selected from *Burkholderia* spp., *Burkholderia* spp., B. anthracia, *Y. pestis*, and *F. tularensis*.

21. The compound of claim 1, wherein the compound is of the Formula:

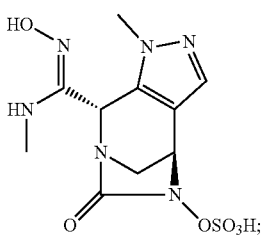

or a pharmaceutically acceptable salt thereof.

22. A pharmaceutical composition comprising the compound of claim 15, or a pharmaceutically acceptable salt thereof; and a pharmaceutically acceptable carrier.

23. A method of treating a bacterial infection in a subject in need thereof comprising administering to the subject an effective amount of the compound of claim 15, or a pharmaceutically acceptable salt thereof.

24. The method of claim 23, wherein the bacterial infection is caused by a Gram-negative bacteria.

25. The method of claim 24, wherein the bacterial infection is caused by *P. aeruginosa*, Enterobacteriaceae, *E. coli, K pneumoniae*, or *Acinetobacter* spp.

26. The method of claim 23, wherein the bacterial infection is caused by a pathogen selected from *Burkholderia* spp., B. anthracia, *Y. pestis*, and *F. tularensis*.

* * * * *